(12) United States Patent
Wampler et al.

(10) Patent No.: US 11,779,911 B2
(45) Date of Patent: Oct. 10, 2023

(54) PRODUCTION OF FATTY OLEFIN DERIVATIVES VIA OLEFIN METATHESIS

(71) Applicant: Provivi, Inc., Santa Monica, CA (US)

(72) Inventors: Keith M. Wampler, Santa Monica, CA (US); Peter Meinhold, Santa Monica, CA (US); Pedro Coelho, Santa Monica, CA (US); Vu Bui, Santa Monica, CA (US); Hasan Mehdi, Budapest (HU)

(73) Assignee: PROVIVI, INC., Santa Monica, CA (US)

( * ) Notice: Subject to any disclaimer, the term of this patent is extended or adjusted under 35 U.S.C. 154(b) by 31 days.

(21) Appl. No.: 17/390,136

(22) Filed: Jul. 30, 2021

(65) Prior Publication Data

US 2022/0032280 A1 Feb. 3, 2022

Related U.S. Application Data

(63) Continuation of application No. 16/798,954, filed on Feb. 24, 2020, now Pat. No. 11,077,433, which is a
(Continued)

(51) Int. Cl.
*B01J 31/22* (2006.01)
*C07C 29/147* (2006.01)
*C07C 67/08* (2006.01)
*C07C 67/343* (2006.01)
*C07C 45/41* (2006.01)
(Continued)

(52) U.S. Cl.
CPC ............ *B01J 31/2278* (2013.01); *C07C 6/04* (2013.01); *C07C 29/147* (2013.01); *C07C 45/41* (2013.01); *C07C 67/08* (2013.01); *C07C 67/293* (2013.01); *C07C 67/343* (2013.01); *B01J 2231/543* (2013.01); *B01J 2531/64* (2013.01); *B01J 2531/66* (2013.01); *C07B 2200/09* (2013.01); *C07C 2531/22* (2013.01)

(58) Field of Classification Search
CPC ............ B01J 31/2278; B01J 2231/543; B01J 2531/64; B01J 2531/66; C07C 6/04; C07C 29/147; C07C 45/41; C07C 67/08; C07C 67/293; C07C 67/343; C07C 2531/22; C07C 33/025; C07C 11/21; C07C 47/21; C07C 69/145; C07C 69/533; C07B 2200/09
See application file for complete search history.

(56) References Cited

U.S. PATENT DOCUMENTS 4,560,792 A 12/1985 Banasiak
4,639,429 A 1/1987 Basset et al.
(Continued)

FOREIGN PATENT DOCUMENTS

CN 1423629 A 6/2003
CN 101558027 A 10/2009
(Continued)

OTHER PUBLICATIONS

Zaragoza Dorwald, ,Side Reactions in Organic Synthesis, ,WILEY-VCH Verlag Gmbh & Co. KGaA,, Weinheim, Preface, p. IX. (Year: 2005).*
Banasiak, "Insect Pheromones from Olefin Metathesis," Journal of Molecular Catalysis, vol. 28, Nos. 1-3, 1985, pp. 107-115.
Chandrasekhar et al., "One Pot Conversion of Carboxylic Acids to Aldehydes with DIBAL-H," Tetrahedron Letters, vol. 39, Feb. 19, 1998, pp. 909-910.
Crisp et al., "Metathesis of Functionalized Alkenes. Synthesis of Insect Pheromones," Australian Journal of Chemistry, vol. 41, No. 6, 1988, pp. 935-942.
(Continued)

*Primary Examiner* — Deborah D Carr
(74) *Attorney, Agent, or Firm* — Kilpatrick Townsend & Stockton LLP

(57) ABSTRACT

In one aspect, the invention provides a method for synthesizing a fatty olefin derivative. The method includes: a) contacting an olefin according to Formula I $$H_3C\underset{z}{\sim\!\!\!\sim\!\!\!\sim}\underset{}{=}\!\!\!\sim\!\!\!\sim R^1, \quad (I)$$

with a metathesis reaction partner according to Formula IIb $$R^1\underset{}{\sim\!\!\!\sim}\underset{y}{=}\!\!\!\sim\!\!\!\sim\underset{}{\overset{O}{\|}}\!\!-\!\!OR^{2b}, \quad (IIb)$$

in the presence of a metathesis catalyst under conditions sufficient to form a metathesis product according to Formula IIIb:

$$H_3C\underset{z}{\sim\!\!\!\sim\!\!\!\sim}\underset{}{=}\!\!\!\sim\!\!\!\sim\underset{y}{\sim\!\!\!\sim}\underset{}{\overset{O}{\|}}\!\!-\!\!OR^{2b}; \quad (IIIb)$$

and
b) converting the metathesis product to the fatty olefin derivative. Each $R^1$ is independently selected from H, $C_{1-18}$ alkyl, and $C_{2-18}$ alkenyl; $R^{2b}$ is $C_{1-8}$ alkyl; subscript y is an integer ranging from 0 to 17; and subscript z is an integer ranging from 0 to 17. In certain embodiments, the metathesis catalyst is a tungsten catalyst or a molybdenum catalyst. In various embodiments, the fatty olefin derivative is a pheromone. Pheromone compositions and methods of using them are also described.

28 Claims, No Drawings

Related U.S. Application Data continuation of application No. 15/721,018, filed on Sep. 29, 2017, now Pat. No. 10,596,562, which is a continuation of application No. 15/354,916, filed on Nov. 17, 2016, now Pat. No. 9,776,179.

(60) Provisional application No. 62/257,148, filed on Nov. 18, 2015.

(51) Int. Cl.
*C07C 6/04* (2006.01)
*C07C 67/293* (2006.01)

(56) References Cited

U.S. PATENT DOCUMENTS

| | | | |
|---|---|---|---|
| 4,792,620 A * | 12/1988 | Paulik | B01J 31/0231 560/232 |
| 4,837,358 A | 6/1989 | Byers et al. | |
| 5,081,287 A | 1/1992 | Peake et al. | |
| 5,831,105 A | 11/1998 | Aulbach et al. | |
| 5,994,590 A | 11/1999 | Tsuda et al. | |
| 6,215,019 B1 | 4/2001 | Pederson et al. | |
| 6,533,960 B2 | 3/2003 | Mimoun | |
| 6,696,597 B2 * | 2/2004 | Pederson | C07F 5/025 560/231 |
| 8,598,400 B2 | 12/2013 | Hoveyda et al. | |
| 8,987,531 B2 | 3/2015 | Grubbs et al. | |
| 9,079,173 B2 | 7/2015 | Schrock et al. | |
| 9,776,179 B2 | 10/2017 | Wampler et al. | |
| 10,596,562 B2 | 3/2020 | Wampler et al. | |
| 11,077,433 B2 | 8/2021 | Wampler et al. | |
| 2002/0022741 A1 | 2/2002 | Pederson et al. | |
| 2012/0302710 A1 | 11/2012 | Hoveyda et al. | |
| 2013/0231499 A1 | 9/2013 | Grubbs et al. | |
| 2013/0274482 A1 | 10/2013 | Schrock et al. | |
| 2014/0031592 A1 | 1/2014 | Shinde | |
| 2014/0275595 A1 | 9/2014 | Wampler et al. | |
| 2014/0288319 A1 | 9/2014 | Grubbs et al. | |
| 2014/0371454 A1 | 12/2014 | Hoveyda et al. | |
| 2014/0378637 A1 | 12/2014 | Schrock et al. | |
| 2015/0240008 A1 | 8/2015 | Schrock et al. | |
| 2015/0307438 A1 | 10/2015 | Abraham et al. | |
| 2017/0137365 A1 | 5/2017 | Wampler et al. | |
| 2018/0099268 A1 | 4/2018 | Wampler et al. | |

FOREIGN PATENT DOCUMENTS

| | | |
|---|---|---|
| CN | 102781888 A | 11/2012 |
| CN | 103319704 A | 9/2013 |
| GB | 2085881 | 5/1982 |
| JP | 2003506663 A | 2/2003 |
| JP | 2003531818 A | 10/2003 |
| JP | 2004035452 A | 2/2004 |
| WO | 2008066754 A1 | 6/2008 |
| WO | 2009094201 A2 | 7/2009 |
| WO | 2011040963 A1 | 4/2011 |
| WO | 2011097642 A1 | 8/2011 |
| WO | 2013070725 A1 | 5/2013 |
| WO | 2013163071 A1 | 10/2013 |
| WO | 2013171302 A1 | 11/2013 |
| WO | 2014052309 A1 | 4/2014 |
| WO | 2014139030 A1 | 9/2014 |
| WO | 2014139679 A2 | 9/2014 |
| WO | 2014152309 A1 | 9/2014 |
| WO | 2014160417 A1 | 10/2014 |
| WO | 2014201300 A1 | 12/2014 |
| WO | 2015127192 A1 | 8/2015 |
| WO | 2015136093 A1 | 9/2015 |
| WO | 2015155593 A1 | 10/2015 |
| WO | 2017/087710 A2 | 5/2017 |
| WO | 2017087710 A3 | 8/2017 |

OTHER PUBLICATIONS

Dorwald, "Side Reactions in Organic Synthesis: A Guide to Successful Synthesis Design," VCH Verlag GmbH & Co. KGaA, Jul. 25, 2005, 4 pages.

Hamasaki et al., "A Highly Efficient Synthesis of Civetone," Tetrahedron, vol. 56, No. 38, Sep. 15, 2000, pp. 7423-7425.

Herbert et al., "Concise Syntheses of Insect Pheromones Using Z-Selective Cross D Metathesis," Angewandte Communications, Olefin Metathesis, vol. 52, Jan. 2, 2013, pp. 310-314.

Herbert et al., "Synthetic Applications of Highly Z-Selective Ruthenium Metathesis Catalysts," Z-Selective Olefin Metathesis Using Chelating Ruthenium Alkylidene Catalysts, Chapter 2, California Institute of Technology, 2014, 58 pages.

Kuepper et al., "Synthese von Insektenpheromonen an Metathesekatalysatoren," Chemiker-Zeitung, vol. 99, 1975, pp. 464-465.

Levisalles et al., "Metathese D'acetates D'alcools ω-Insatures : Synthese De pheromones D'insectes," Tetrahedron, vol. 36, No. 22, 1980, pp. 3181-3185.

Marinescu et al., "Isolation of Pure Disubstituted E Olefins through Mo-Catalyzed Z-Selective Ethenolysis of Stereoisomeric Mixtures," Journal Of The American Chemical Society, vol. 133, No. 30, Aug. 3, 2011, pp. 11512-11514.

Marx et al., "Stereoselective Access to Z and E Macrocycles by Ruthenium-Catalyzed Z-Selective Ring-Closing Metathesis and Ethenolysis," Journal Of The American Chemical Society, vol. 135, Jan. 9, 2013, pp. 94-97.

Matyska et al., "Cometathesis of Methyl Oleate with -α Olefins," Collection of Czchchoslovak Chemical Communications, vol. 54, No. 2, 1989, pp. 455-461.

MIMOUN, "Selective Reduction of Carbonyl Compounds by Polymethylhydrosiloxane in the Presence of Metal Hydride Catalysts," Journal Of The American Chemical Society, vol. 64, No. 7, Mar. 18, 1999, pp. 2582-2589.

Miyazakhi et al., "Z-Selective Ethenolysis with a Ruthenium Metathesis Catalyst: Experiment and Theory," Journal of the American Chemical Society, vol. 135, Apr. 2, 2013, pp. 5848-5858.

PCT/US2016/062595, International Search Report and Written Opinion, dated Jul. 5, 2017, 29 pages.

Pederson et al., "Applications of Olefin Cross Metathesis to Commercial Products," Advanced Synthesis and Catalysis, vol. 344, Nos. 6-7, 2002, pp. 728-735.

Rizzo et al., "Microsomal Fatty Aldehyde Dehydrogenase Catalyzes the Oxidation of Aliphatic Aldehyde Derived from Ether Glycerolipid CatabolismImplications for Sjogren-Larsson Syndrome," Biochimica et Biophysica Acta, vol. 1535, 2000, pp. 1-9.

Rizzo et al., "Sjogren-Larsson Syndrome Deficient Activity of the Fatty Aldehyde Dehydrogenase Component of Fatty Alcohoi:NAD+ Oxidoreductase in Cultured Fibroblasts," Journal of Clinical Investigations, vol. 88, Nov. 1991, pp. 1643-1648.

Shin et al., "Partial Reduction of Esters to Aldehydes Using a Novel Modified Red-Al Reducing Agent," Bulletin of Korean Chemical Society, vol. 35, No. 7, 2014, pp. 2169-2171.

Spasyuk et al., "Chemoselective Hydrogenation of Carbonyl Compounds and Acceptorless Dehydrogenative Coupling of Alcohols," Journal Of The American Chemical Society, vol. 137, No. 11, Mar. 25, 2015, pp. 3743-3746.

Tan et al., "Highly Efficient Tetradentate Ruthenium Catalyst for Ester Reduction: Especially for Hydrogenation of Fatty Acid Esters", Organic Letters, vol. 17, No. 3, Feb. 6, 2015, pp. 454-457.

Baker, et al., "A Comparison of Responses from Olfactory Receptor Neurons of Heliothis subflexa and Heliothis virescens to Components of their Sex Pheromone," Journal of Comparative Physiology A, vol. 190, No. 2, (2004), pp. 155-165.

Yan, et al., "Reexamination of the Female Sex Pheromone of the Sweet Potato Vine Borer Moth: Identification and Field Evaluation of a Tricosatriene," Journal of Chemical Ecology, vol. 40, No. 6, (2014), pp. 590-598.

* cited by examiner

PRODUCTION OF FATTY OLEFIN DERIVATIVES VIA OLEFIN METATHESIS

CROSS-REFERENCES TO RELATED APPLICATIONS

The present application is a continuation of U.S. patent application Ser. No. 16/798,954, filed on Feb. 24, 2020, which is a continuation of U.S. patent application Ser. No. 15/721,018, filed on Sep. 29, 2017 and issued as U.S. Pat. No. 10,596,562 on Mar. 24, 2020, which is a continuation of U.S. patent application Ser. No. 15/354,916, filed on Nov. 17, 2016 and issued as U.S. Pat. No. 9,776,179 on Oct. 3, 2017, which claims priority to U.S. Provisional Pat. Appl. No. 62/257,148, filed on Nov. 18, 2015, which applications are incorporated herein by reference in their entirety.

BACKGROUND OF THE INVENTION

Insect infestation is a primary cause of crop loss throughout the United States. A wide variety of chemical pesticides has been relied upon in the past to control insect pests. However, environmental concerns as well as consumer safety concerns have led to the de-registration of many pesticides and a reluctance to use others on agricultural products which are ultimately consumed as food. As a consequence, there is a desire for the development of alternative biological control agents.

Pheromones are chemicals which are secreted outside the body of insects can be classified according to the type of behavioral reaction they induce. Pheromone classes include aggregation pheromones, sexual pheromones, trail pheromones, and alarm pheromones. Sex pheromones, for example, are typically secreted by insects to attract partners for mating.

When pheromones are dispersed on leaves of a crop plant, or in an orchard environment in small quantities over a continuous period of time, pheromone levels reach thresholds that can modify insect behavior. Maintenance of pheromone levels at or above such thresholds can impact insect reproductive processes and reduce mating. Use of pheromones in conjunction with conventional insecticides can therefore reduce the quantity of insecticide required for effective control and can specifically target pest insects while preserving beneficial insect populations. These advantages can reduce risks to humans and the environment and lower overall insect control costs.

Despite these advantages, pheromones are not widely used today because of the high cost of active ingredient (AI). Even though thousands of insect pheromones have been identified, less than about twenty insect pests worldwide are currently controlled using pheromone strategies, and only 0.05% of global agricultural land employs pheromones. Lepidopteran pheromones, which are naturally occurring compounds, or identical or substantially similar synthetic compounds, are designated by an unbranched aliphatic chain (between 9 and 18 carbons) ending in an alcohol, aldehyde, or acetate functional group and containing up to 3 double bonds in the aliphatic backbone. Improved methods for preparing lepidopteran insect pheromones and structurally related compounds are needed. The present invention meets this and other needs.

BRIEF SUMMARY OF THE INVENTION

In a first aspect, the invention provides a method for synthesizing a fatty olefin derivative. The method includes:

a) contacting an olefin according to Formula I

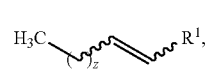

(I)

with a metathesis reaction partner according to Formula II

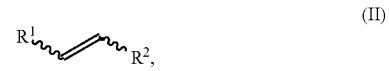

(II)

in the presence of a metathesis catalyst under conditions sufficient to form a metathesis product; and b) optionally converting the metathesis product to the fatty olefin derivative;

wherein:

$R^1$ is selected from H, $C_{1-18}$ alkyl, and $C_{2-18}$ alkenyl;

$R^2$ is selected from $-(CH_2)_xOR^{2a}$ and $-(CH_2)_yCOOR^{2b}$, wherein $R^{2a}$ is an alcohol protecting group and $R^{2b}$ is $C_{1-8}$ alkyl;

subscript x is an integer ranging from 1 to 18;

subscript y is an integer ranging from 0 to 17; and subscript z is an integer ranging from 0 to 17.

In some embodiments, the metathesis catalyst is a tungsten metathesis catalyst, a molybdenum metathesis catalyst, or a ruthenium metathesis catalyst. In certain embodiments, the metathesis catalyst is a tungsten catalyst or a molybdenum catalyst.

In some embodiments, the metathesis reaction partner is a protected alcohol according to Formula IIa:

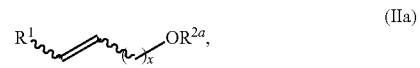

(IIa)

wherein $R^{2a}$ is an alcohol protecting group, and wherein the metathesis product is a compound according to Formula IIIa:

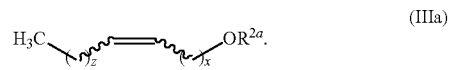

(IIIa)

In some embodiments, converting the metathesis product to the fatty olefin derivative includes removing $R^{2a}$ from the compound of Formula IIIa to form an alkenol according to Formula Va:

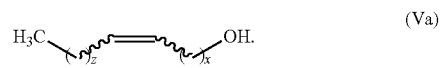

(Va)

In some embodiments, the alkenol of Formula Va is the pheromone. In some embodiments, converting the metathesis product to the fatty olefin derivative further includes acylating the alkenol of Formula Va, thereby forming a fatty olefin derivative according to Formula VIa:

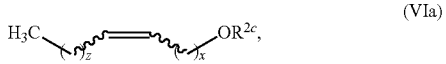

(VIa)

wherein $R^{2c}$ is $C_{1-6}$ acyl.

In some embodiments, converting the metathesis product to the fatty olefin derivative further includes oxidizing the alkenol of Formula Va, thereby forming a fatty olefin derivative according to Formula VIIa:

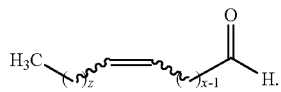

(VIIa)

In some embodiments, the metathesis reaction partner is an ester according to Formula IIb:

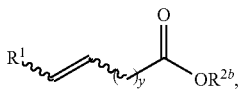

(IIb)

and subscript z is an integer ranging from 1 to 18; and wherein the metathesis product is a compound according to Formula IIIb:

(IIIb)

In some embodiments, converting the metathesis product to the fatty olefin derivative includes reducing the metathesis product of Formula IIIb to form an alkenol according to Formula Vb:

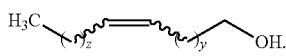

(Vb)

In some embodiments, the metathesis reaction partner is a protected alcohol according to Formula IIa or Formula IIb and the metathesis product is a compound according to Formula IV:

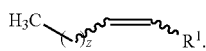

(IV)

In some embodiments, $R^1$ in the compound of Formula IV is $C_{2-18}$ alkenyl.

A number of pheromones and pheromone precursors, including unsaturated fatty alcohols, unsaturated fatty alcohol acetates, unsaturated fatty aldehydes, unsaturated fatty acid esters, and polyenes, can be synthesized using the methods of the invention.

DETAILED DESCRIPTION OF THE INVENTION

I. Introduction

The present invention provides methods for the synthesis of fatty olefin derivatives (such as straight-chain lepidopteran pheromones; SCLPs) through the cross-metathesis of protected fatty alcohols or fatty acid esters with olefins (e.g., α-olefins). Through the use of a variety of fatty alcohols, fatty acid alkyl esters and α-olefin feedstocks in concert with olefin metathesis catalysts (including Group VI Z-selective catalysts), a wide variety of protected unsaturated fatty alcohol precursors with high Z-olefin content can be obtained. These precursor compounds can be converted to pheromones (e.g., long chain Z-alcohols, Z-aldehydes, Z-acetates, and Z-nitrates) and other useful fatty olefin derivatives as described in detail below. Alternatively, non-selective olefin metathesis catalysts (including Group VI non-selective catalysts) can be used to generate cis/trans mixtures of protected long chain fatty alcohols. Such mixtures can be refined to provide pure E-pheromone precursors and other fatty E-olefin derivatives via Z-selective ethenolysis. The methods provide access to valuable products, including SCLPs containing 7-, 9-, or 10-monounsaturation.

II. Definitions

The following definitions and abbreviations are to be used for the interpretation of the invention. The term "invention" or "present invention" as used herein is a non-limiting term and is not intended to refer to any single embodiment but encompasses all possible embodiments.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, and in certain instances, a value from 0.95X to 1.05X or from 0.98X to 1.02X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.99X."

As used herein, the term "pheromone" refers to a substance, or characteristic mixture of substances, that is secreted and released by an organism and detected by a second organism of the same species or a closely related species. Typically, detection of the pheromone by the second organism promotes a specific reaction, such as a definite behavioral reaction or a developmental process. Insect pheromones, for example, can influence behaviors such as mating and aggregation. Examples of pheromones include, but are not limited to, compounds produced by Lepidoptera (i.e., moths and butterflies belonging to the Geometridae, Noctuidae, Arctiidae, and Lymantriidae families) such as $C_{10}$-$C_{18}$ acetates, $C_{10}$-$C_{18}$ alcohols, $C_{10}$-$C_{18}$ aldehydes, and $C_{17}$-$C_{23}$ polyenes. An "unsaturated pheromone" refers to any pheromone having at least one carbon-carbon double bond.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents that can be produced in the reaction mixture.

As used herein, the term "olefin" refers to a straight-chain or branched hydrocarbon compound containing at least one carbon-carbon double bond and derivatives thereof. The olefin can be unsubstituted or substituted with one or more functional groups including alcohol groups, protected alcohol groups, carboxylate groups, and carboxylic acid ester groups. As used herein, the term "olefin" encompasses hydrocarbons having more than one carbon-carbon double bond (e.g., di-olefins, tri-olefins, etc.). Hydrocarbons having more than one carbon-carbon double bond and derivatives thereof are also referred to as "polyenes." The term "fatty olefin" refers to an olefin having at least four carbon atoms; fatty olefins can have, for example, 4, 6, 8, 10, 12, 14, 16, 18, 20, 22, 24, or 28 carbon atoms. A "fatty olefin derivative" refers to a compound obtained from an olefin starting material or a fatty olefin starting material. Examples of fatty olefin derivatives include, but are not limited to, unsaturated fatty alcohols, unsaturated fatty alcohol acetates, unsaturated fatty aldehydes, unsaturated fatty acids, unsaturated fatty acid esters, and polyenes. In certain embodiments, fatty olefins derivatives synthesized according to the methods of the invention have from 8 to 28 carbon atoms.

A $\Delta^9$-unsaturated olefin refers to an olefin wherein the ninth bond from the end of olefin is a double bond. A $\Delta^9$-unsaturated fatty acid refers to an olefinic carboxylic acid wherein the ninth bond from the carboxylic acid group is a double bond. Examples of $\Delta^9$-unsaturated fatty acids include, but are not limited to, 9-decenoic acid, oleic acid (i.e., (Z)-octadec-9-enoic acid), and elaidic acid (i.e., (E)-octadec-9-enoic acid).

As used herein, the term "metathesis reaction" refers to a catalytic reaction which involves the interchange of alkylidene units (i.e., $R_2C=$units) among compounds containing one or more carbon-carbon double bonds (e.g., olefinic compounds) via the formation and cleavage of the carbon-carbon double bonds. Metathesis can occur between two molecules having the same structure (often referred to as self-metathesis) and/or between two molecules having different structures (often referred to as cross-metathesis). The term "metathesis reaction partner" refers to a compound having a carbon-carbon double bond that can react with an olefin in a metathesis reaction to form a new carbon-carbon double bond.

As used herein, the term "metathesis catalyst" refers to any catalyst or catalyst system that catalyzes a metathesis reaction. One of skill in the art will appreciate that a metathesis catalyst can participate in a metathesis reaction so as to increase the rate of the reaction, but is itself not consumed in the reaction. A "tungsten catalyst" refers to a metathesis catalyst having one or more tungsten atoms. A "molybdenum catalyst" refers to a metathesis catalyst having one or more molybdenum atoms.

As used herein, the term "metathesis product" refers to an olefin containing at least one double bond, the bond being formed via a metathesis reaction.

As used herein, the term "converting" refers to reacting a starting material with at least one reagent to form an intermediate species or a product. The converting can also include reacting an intermediate with at least one reagent to form a further intermediate species or a product.

As used herein, the term "oxidizing" refers to the transfer of electron density from a substrate compound to an oxidizing agent. The electron density transfer typically occurs via a process including addition of oxygen to the substrate compound or removal of hydrogen from the substrate compound. The term "oxidizing agent" refers to a reagent which can accept electron density from the substrate compound. Examples of oxidizing agents include, but are not limited to, pyridinium chlorochromate, o-iodoxybenzoic acid, and 2,2,6,6-tetramethylpiperidine 1-oxyl.

As used herein, the term "reducing" refers to the transfer of electron density from a reducing agent to a substrate compound. The electron density transfer typically occurs via a process including addition of hydrogen to the substrate compound. The term "reducing agent" refers to a reagent which can donate electron density to the substrate compound. Examples of reducing agents include, but are not limited to, sodium borohydride and sodium triacetoxyborohydride.

As used herein, the term "acylating" refers to converting a alcohol group (—OH), to an ester group (—OC(O)R), where R is an alkyl group as described below.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. In some embodiments, "cycloaliphatic" (or "carbocycle") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl, or (cycloalkyl)alkenyl. The term "heteroaliphiatic" refers to an aliphatic group wherein at least one carbon atom of the aliphatic group is replaced with a heteroatom (i.e., nitrogen, oxygen, or sulfur, including any oxidized form of nitrogen or sulfur, and any quaternized form of a basic nitrogen).

As used herein, the term "alkyl" is given its ordinary meaning in the art and includes straight-chain alkyl groups and branched-chain alkyl groups having the number of carbons indicated. In certain embodiments, a straight chain or branched chain alkyl has about 1-30 carbon atoms in its backbone (e.g., $C_1$-$C_{30}$ for straight chain, $C_3$-$C_{30}$ for branched chain), and alternatively, about 1-20. In some embodiments, an alkyl group may be a lower alkyl group, wherein a lower alkyl group comprises 1~4 carbon atoms (e.g., $C_1$-$C_4$ for straight chain lower alkyls).

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, and the like.

As used herein, the term "acyl" refers to the functional group —C(O)R), wherein R is an alkyl group as described above.

As used herein, the term "alkoxy" refers to a moiety —OR wherein R is an alkyl group as defined above. The term "silylalkyl" refers to an alkyl group as defined herein wherein as least one carbon atom is replaced with a silicon atom. The term "silyloxy" refers to a moiety —OSiR$_3$, wherein each R is independently selected from the group consisting of H, alkyl, substituted alkyl, aryl, and substituted aryl as described herein.

As used herein, the term "cycloalkyl" refers to a saturated, monocyclic hydrocarbon, bicyclic hydrocarbon, or tricyclic hydrocarbon group that has a single point of attachment to the rest of the molecule. Cycloalkyl groups include alkyl substituted cycloalkyl groups and cycloalkyl substituted alkyl groups. In some embodiments, cycloalkyl rings have from about 3-10 carbon atoms in their ring structure where such rings are monocyclic or bicyclic, and alternatively about 5, 6 or 7 carbons in the ring structure.

As used herein, the term "alkenyl" refers to an alkyl group, as defined herein, having one or more double bonds. The term "heteroalkenyl" refers to an alkenyl group wherein one or more carbon atoms is replaced with a heteroatom (i.e., nitrogen, oxygen, or sulfur, including any oxidized form of nitrogen or sulfur, and any quaternized form of a basic nitrogen).

As used herein, the term "alkenol" refers to a compound having a formula R—OR' wherein R is an alkenyl group and R' is hydrogen or an alcohol protecting group.

As used herein, the term "alkynyl" refers to an alkyl group, as defined herein, having one or more triple bonds.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "aryloxy" refers to a moiety —OR, wherein R is an aryl group as defined above.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 pi electrons shared in a cyclic arrangement; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least one functional group that has sufficient ionic character to coordinate the metal center, such as a biphenolate group, for example.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more heteroatoms (e.g., one to four heteroatoms), as defined above. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl-ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

The terms "halogen" and "halo" are used interchangeably to refer to F, Cl, Br, or I.

As used herein, the term "protecting group" refers to a chemical moiety that renders a functional group unreactive, but is also removable so as to restore the functional group. Examples of "alcohol protecting groups" include, but are not limited to, benzyl; tert-butyl; trityl; tert-butyldimethylsilyl (TBDMS; TBS); 4,5-dimethoxy-2-nitrobenzyloxycarbonyl (Dmnb); propargyloxycarbonyl (Poc); and the like. Examples of "amine protecting groups" include, but are not limited to, benzyloxycarbonyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethyl-chroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other alcohol protecting groups and amine protecting groups are known to those of skill in the art including, for example, those described by Green and Wuts (*Protective Groups in Organic Synthesis*, 4th Ed. 2007, Wiley-Interscience, New York).

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are generally those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}R^\alpha$; $-O(CH_2)_{0-4}R^\alpha$, $-O-(CH_2)_{0-4}C(O)OR^\alpha$; $-(CH_2)_{0-4}CH(OR^\alpha)_2$; $-(CH_2)_{0-4}SR^\alpha$; $-(CH_2)_{0-4}Ph$, which may be substituted with $R^\alpha$; $-(CH_2)_{0-4}O(CH_2)_{0-1}Ph$ which may be substituted with $R^\alpha$; $-CH=CHPh$, which may be substituted with $R^\alpha$; $-(CH_2)_{0-4}O(CH_2)_{0-1}$-pyridyl which may be substituted with $R^\alpha$; $-NO_2$; $-CN$; $-N_3$; $-(CH_2)_{0-4}N(R^\alpha)_2$; $-(CH_2)_{0-4}N(R^\alpha)C(O)R^\alpha$; $-N(R^\alpha)C(S)R^\alpha$; $-(CH_2)_{0-4}N(R^\alpha)C(O)NR^\alpha_2$; $-N(R^\alpha)C(S)NR^\alpha_2$; $-(CH_2)_{0-4}N(R^\alpha)C(O)OR^\alpha$; $-N(R^\alpha)N(R^\alpha)C(O)R^\alpha$; $-N(R^\alpha)N(R^\alpha)C(O)NR^\alpha_2$; $-N(R^\alpha)N(R^\alpha)C(O)OR^\alpha$; $-(CH_2)_{0-4}C(O)R^\alpha$; $-C(S)R^\alpha$; $-(CH_2)_{0-4}C(O)OR^\alpha$; $-(CH_2)_{0-4}C(O)SR^\alpha$; $-(CH_2)_{0-4}C(O)OSiR^\alpha_3$; $-(CH_2)_{0-4}OC(O)R^\alpha$; $-OC(O)(CH_2)_{0-4}SR-SC(S)SR^\alpha$; $-(CH_2)_{0-4}SC(O)R^\alpha$; $-(CH_2)_{0-4}C(O)NR^\alpha_2$; $-C(S)NR^\alpha_2$, $-C(S)SR^\alpha$; $-SC(S)SR^\alpha$, $-(CH_2)_{0-4}OC(O)NR^\alpha_2$; $-C(O)N(OR^\alpha)R^\alpha$; $-C(O)C(O)R^\alpha$; $-C(O)CH_2C(O)R^\alpha$; $-C(NOR^\alpha)R^\alpha$; $-(CH_2)_{0-4}SSR^\alpha$; $-(CH_2)_{0-4}S(O)_2R^\alpha$; $-(CH_2)_{0-4}S(O)_2OR^\alpha$; $-(CH_2)_{0-4}OS(O)_2R^\alpha$; $-S(O)_2NR^\alpha_2$; $-(CH_2)_{0-4}S(O)R^\alpha$; $-N(R^\alpha)S(O)_2NR^\alpha_2$; $-N(R^\alpha)S(O)_2R^\alpha$; $-N(OR^\alpha)R^\alpha$; $-C(NH)NR^\alpha_2$; $-P(O)_2R^\alpha$; $-P(O)R^\alpha_2$; $-OP(O)R^\alpha_2$; $-OP(O)(OR^\alpha)_2$; $SiR^\alpha_3$; $-(C_{1-4}$ straight or branched)alkylene)O$-N(R^\alpha)_2$; or $-(C_{1-4}$ straight or branched)alkylene)C(O)O$-N(R^\alpha)_2$, wherein each $R^\alpha$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aromatic ring having 0-4 heteroatoms independently selected from nitrogen, oxygen, and sulfur, or, notwithstanding the definition above, two independent occurrences of Ra, taken together with their intervening atom(s), form a 3-12-membered saturated, partially unsaturated, or aromatic mono- or bi-cyclic ring having 0-4 heteroatoms independently selected from nitrogen, oxygen, and sulfur, which may be substituted as defined below.

Suitable monovalent substituents on Ra (or the ring formed by taking two independent occurrences of $R^\alpha$ together with their intervening atoms), are independently halogen, $-(CH_2)_{0-2}R^\beta$; -(halo$R^\beta$); $-(CH_2)_{0-2}OH$; $-(CH_2)_{0-2}OR^\beta$; $-(CH_2)_{0-2}CH(OR^\beta)_2$; $-O(haloR^\beta)$; $-CN$; $-N_3$; $-(CH_2)_{0-2}C(O)R^\beta$; $-(CH_2)_{0-2}C(O)OH$; $-(CH_2)_{0-2}C(O)OR^\beta$; $-(CH_2)_{0-2}SR^\beta$; $-(CH_2)_{0-2}SH$; $-(CH_2)_{0-2}NH_2$, $-(CH_2)_{0-2}NHR^\beta$; $-(CH_2)_{0-2}NR^\beta_2$; $-NO_2$; $SiR^\beta$; $-OSiR^\beta$; $-C(O)SR^\beta$; $-(C_{1-4}$ straight or branched alkylene)C(O)OR$^\beta$; or $-SSR^\beta$; wherein each $R^\beta$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aromatic ring having 0-4 heteroatoms independently selected from nitrogen, oxygen, and sulfur. Suitable divalent substituents on a saturated carbon atom of $R^\alpha$ include $=O$ and $=S$.

Suitable divalent substituents on a saturated carbon atom of an "optionally substituted" group include the following: $=O$; $=S$; $=NNR^\gamma_2$; $=NNHC(O)R^\gamma$; $=NNHC(O)OR^\gamma$; $=NNHS(O)_2R^\gamma$; $=NR^\gamma$; $=NOR^\gamma$; $-O(C(R^\gamma_2))_{2-3}O-$; or $-S(C(R^\gamma_2))_{2-3}S-$; wherein each independent occurrence of RY is selected from hydrogen, $C_{1-6}$ aliphatic which may be substituted as defined below, or an unsubstituted 5-6-membered saturated, partially unsaturated, or aromatic ring having 0-4 heteroatoms independently selected from nitrogen, oxygen, and sulfur. Suitable divalent substituents that are bound to vicinal substitutable carbons of an "optionally substituted" group include: $-O(CR^\beta_2)_{2-3}O-$, wherein each independent occurrence of $R^\beta$ is selected from hydrogen, $C_{1-6}$ aliphatic which may be substituted as defined below, or an unsubstituted 5-6-membered saturated, partially unsaturated, or aromatic ring having 0-4 heteroatoms independently selected from nitrogen, oxygen, and sulfur.

Suitable substituents on the aliphatic group of $R^\gamma$ include halogen, $-R^\delta$, -(halo$R^\delta$), $-OH$, $-OR^\delta$, $-O(haloR^\delta)$, $-CN$, $-C(O)OH$, $-C(O)OR^\delta$, $-NH_2$, $-NHR^\delta$, $-NR^\delta_2$, or $-NO_2$, wherein each $R^\delta$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aromatic ring having 0-4 heteroatoms independently selected from nitrogen, oxygen, and sulfur.

Suitable substituents on a substitutable nitrogen of an "optionally substituted" group include $-R^\varepsilon$, $-NR^\varepsilon_2$, $-C(O)R^\varepsilon$, $-C(O)OR^\varepsilon$, $-C(O)C(O)R^\varepsilon$, $-C(O)CH_2C(O)R^\varepsilon$, $-S(O)_2R^\varepsilon$, $-S(O)_2NR^\varepsilon_2$, $-C(S)NR^\varepsilon_2$, $-C(NH)NR^\varepsilon_2$, or $-N(R^\varepsilon)S(O)_2R^\varepsilon$; wherein each $R^\varepsilon$ is independently hydrogen, CM aliphatic which may be substituted as defined below, unsubstituted $-OPh$, or an unsubstituted 5-6-membered saturated, partially unsaturated, or aromatic ring having 0-4 heteroatoms independently selected from nitrogen, oxygen, and sulfur, or, notwithstanding the definition above, two independent occurrences of $R^\varepsilon$, taken together with their intervening atom(s) form an unsubstituted 3-12-membered saturated, partially unsaturated, or aromatic memo- or bicyclic ring having 0-4 heteroatoms independently selected from nitrogen, oxygen, and sulfur.

Suitable substituents on the aliphatic group of $R^\epsilon$ are independently halogen, $-R^\delta$, -(halo$R^\delta$), $-OH$, $-OR^\delta$, $-CN$, $-C(O)OH$, $-C(O)OR^\delta$, $-NH_2$, $-NHR^\delta$, $-NR^\delta_2$, or $-NO_2$, wherein each $R^\delta$ is unsubstituted or where preceded by "halo" is substituted only with one or more halogens, and is independently CM aliphatic, $-CH_2Ph$, $-O(CH_2)_{0-1}Ph$, or a 5-6-membered saturated, partially unsaturated, or aromatic ring having 0-4 heteroatoms independently selected from nitrogen, oxygen, and sulfur.

In some embodiments, the term "substituted" is contemplated to include all permissible substituents of organic compounds, "permissible" being in the context of the chemical rules of valence known to those of ordinary skill in the art. In some cases, "substituted" may generally refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group. In a broad aspect, permissible substituents include acyclic and cyclic, branched and unbranched, carbocyclic and heterocyclic, aromatic and nonaromatic substituents of organic compounds. Illustrative substituents include, for example, those described herein. Permissible substituents can be one or more and the same or different for appropriate organic compounds. For example, a substituted alkyl group may be $CF_3$. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxamido, nitro, acyloxy, aminoalkyl, alkylaminoaryl, alkylaryl, alkylaminoalkyl, alkoxyaryl, arylamino, arylalkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like.

As used herein, the term "natural oil" refers to an oil derived from a plant or animal source. The term "natural oil" includes natural oil derivatives, unless otherwise indicated. The plant or animal sources can be modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

"Natural oil derivatives" refer to compounds (or mixtures of compounds) derived from natural oils using any one or combination of methods known in the art Such methods include but are not limited to saponification, fat splitting, transesterification, esterification, hydrogenation (partial or full), isomerization, oxidation, reduction, and metathesis. Representative non-limiting examples of natural oil derivatives include gums, phospholipids, soapstock, acidulated soapstock, distillate or distillate sludge, fatty acids, and fatty acid alkyl esters (e.g., non-limiting examples such as 2-ethylhexyl ester), and hydroxy substituted variations thereof. For example, the natural oil derivative may be a fatty acid methyl ester ("FAME") derived from the glyceride of the natural oil.

The term "contaminant" refers broadly and without limitation to any impurity, regardless of the amount in which it is present, admixed with a substrate to be used in olefin metathesis. A "catalyst poisoning contaminant" refers to a contaminant having the potential to adversely affect the performance of a metathesis catalyst. Examples of catalyst poisoning contaminants include, but are not limited to, water, peroxides, and hydroperoxides.

As used herein, the term "metal alkyl compound" refers to a compound having the formula $MR_m$ wherein, M is a metal (e.g., a Group II metal or a Group IIIA metal), each R is independently an alkyl radical of 1 to about 20 carbon atoms, and subscript m corresponds to the valence of M. Examples of metal alkyl compounds include $Mg(CH_3)_2$, $Zn(CH_3)_2$, $Al(CH_3)_3$, and the like. Metal alkyl compounds also include substances having one or more halogen or hydride groups, such as Grignard reagents, diisobutylaluminum hydride, and the like.

III. Description of the Embodiments

In one aspect, the invention provides a method for synthesizing a fatty olefin derivative. The method includes:

a) contacting an olefin according to Formula I

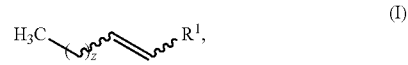

with a metathesis reaction partner according to Formula II

in the presence of a metathesis catalyst under conditions sufficient to form a metathesis product; and
b) optionally converting the metathesis product to the fatty olefin derivative;
wherein:
$R^1$ is selected from H, $C_{1-18}$ alkyl, and $C_{2-18}$ alkenyl;
$R^2$ is selected from $-(CH_2)_xOR^{2a}$ and $-(CH_2)_yCOOR^{2b}$, wherein $R^{2a}$ is an alcohol protecting group and $R^{2b}$ is $C_{1-8}$ alkyl;
subscript x is an integer ranging from 1 to 18;
subscript y is an integer ranging from 0 to 17; and
subscript z is an integer ranging from 0 to 17.

In some embodiments, the invention provides a method for synthesizing a fatty olefin derivative including:

a) contacting an olefin according to Formula I

(I)

with a metathesis reaction partner according to Formula II

(II)

in the presence of a metathesis catalyst under conditions sufficient to form a metathesis product; and
b) optionally converting the metathesis product to the fatty olefin derivative;
wherein:
$R^1$ is selected from H, $C_{1-18}$ alkyl, and $C_{2-18}$ alkenyl;
$R^2$ is selected from $-(CH_2)_xOR^{2a}$ and $-(CH_2)_yCOOR^{2b}$, wherein $R^{2a}$ is an alcohol protecting group and $R^{2b}$ is $C_{1-8}$ alkyl;
subscript x is an integer ranging from 1 to 18;
subscript y is an integer ranging from 0 to 17; and
subscript z is an integer ranging from 0 to 17;
wherein the metathesis catalyst is a tungsten catalyst or a molybdenum catalyst.

In the methods of the invention, olefins can be reacted with a variety of metathesis reaction partners to obtain pheromones, pheromone precursors, and other useful fatty olefin derivatives.

Metathesis of Fatty Alcohols

Certain embodiments of the method are summarized in Scheme 1. A fatly alcohol containing an appropriate protecting group is reacted with an α-olefin in the presence of a group VI olefin metathesis catalyst (e.g., a Z-selective Group VI metathesis catalyst) to produce a statistical mixture of the desired cross-metathesis product and the self-metathesis co-products. The ratio of the feedstocks can be adjusted to vary the ratio of products. For example, feeding the reactants in a 1.5:1 molar ratio of α-olefin to protected fatty alcohol can result in a 3:2.25:1 ratio of the internal olefin, metathesis product, and protected diol products. This process condition results in the efficient utilization of the more costly protected fatty alcohol.

Products obtained from metathesis of protected fatty alcohols can be converted to a number of pheromones, as set forth in Table 1.

TABLE 1

Pheromones accessible from fatty alcohol metathesis products.

| Olefin | Metathesis Reaction Partner | Metathesis Product | Exemplary Pheromone | Pheromone CAS # |
|---|---|---|---|---|
| propylene | oleyl alcohol | protected (Z)-9-undecenol | (Z)-9-undecenyl acetate | 85576-13-2 |
| 1-butene | oleyl alcohol | protected (Z)-9-dodecenol | (Z)-9-dodecenal | 56219-03-5 |
| 1-butene | oleyl alcohol | protected (Z)-9-dodecenol | (Z)-9-dodecenyl acetate | 16974-11-1 |
| 1-pentene | oleyl alcohol | protected (Z)-9-tridecenol | (Z)-9-tridecenyl acetate | 35835-78-0 |
| 1-hexene | oleyl alcohol | protected (Z)-9-tetradecenol | (Z)-9-tetradecenal | 53939-27-8 |
| 1-hexene | oleyl alcohol | protected (Z)-9-tetradecenol | (Z)-9-tetradecenyl acetate | 16725-53-4 |
| 1-hexene | oleyl alcohol | protected (Z)-9-tetradecenol | (Z)-9-tetradecenyl formate | 56776-10-4 |
| 1-hexene | oleyl alcohol | protected (Z)-9-tetradecenol | (Z)-9-tetradecenyl nitrate | 143816-21-1 |
| 1-heptene | oleyl alcohol | protected (Z)-9-pentadecenol | (Z)-9-pentadecenyl acetate | 64437-41-8 |
| 1-octene | oleyl alcohol | protected (Z)-9-hexadecenol | (Z)-9-hexadecenal | 56219-04-6 |
| 1-octene | oleyl alcohol | protected (Z)-9-hexadecenol | (Z)-9-hexadecenyl acetate | 34010-20-3 |
| propylene | 9-decen-1-ol | protected (Z)-9-undecenol | (Z)-9-undecenyl acetate | 85576-13-2 |
| 1-butene | 9-decen-1-ol | protected (Z)-9-dodecenol | (Z)-9-dodecenal | 56219-03-5 |
| 1-butene | 9-decen-1-ol | protected (Z)-9-dodecenol | (Z)-9-dodecenyl acetate | 16974-11-1 |
| 1-pentene | 9-decen-1-ol | protected (Z)-9-tridecenol | (Z)-9-tridecenyl acetate | 35835-78-0 |

Scheme 1

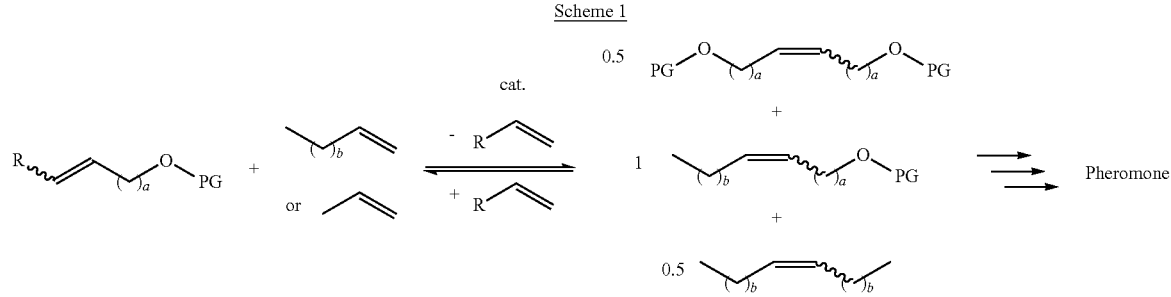

R = H, $C_8H_{17}$ PG = protecting group

TABLE 1-continued

Pheromones accessible from fatty alcohol metathesis products.

| Olefin | Metathesis Reaction Partner | Metathesis Product | Exemplary Pheromone | Pheromone CAS # |
|---|---|---|---|---|
| 1-hexene | 9-decen-1-ol | protected (Z)-9-tetradecenol | (Z)-9-tetradecenal | 53939-27-8 |
| 1-hexene | 9-decen-1-ol | protected (Z)-9-tetradecenol | (Z)-9-tetradecenyl acetate | 16725-53-4 |
| 1-hexene | 9-decen-1-ol | protected (Z)-9-tetradecenol | (Z)-9-tetradecenyl formate | 56776-10-4 |
| 1-hexene | 9-decen-1-ol | protected (Z)-9-tetradecenol | (Z)-9-tetradecenyl nitrate | 143816-21-1 |
| 1-heptene | 9-decen-1-ol | protected (Z)-9-pentadecenol | (Z)-9-pentadecenyl acetate | 64437-41-8 |
| 1-octene | 9-decen-1-ol | protected (Z)-9-hexadecenol | (Z)-9-hexadecenal | 56219-04-6 |
| 1-octene | 9-decen-1-ol | protected (Z)-9-hexadecenol | (Z)-9-hexadecenyl acetate | 34010-20-3 |
| propylene | 10-undecen-1-ol | protected (Z)-10-dodecenol | (Z)-10-dodecenyl acetate | 35148-20-0 |
| 1-butene | 10-undecen-1-ol | protected (Z)-10-tridecenol | (Z)-10-tridecenyl acetate | 64437-24-7 |
| 1-pentene | 10-undecen-1-ol | protected (Z)-10-tetradecenol | (Z)-10-tetradecenyl acetate | 35153-16-3 |
| 1-hexene | 10-undecen-1-ol | protected (Z)-10-pentadecenol | (Z)-10-pentadecenal | 60671-80-9 |
| 1-hexene | 10-undecen-1-ol | protected (Z)-10-pentadecenol | (Z)-10-pentadecenyl acetate | 64437-43-0 |
| 1-heptene | 10-undecen-1-ol | protected (Z)-10-hexadecenol | (Z)-10-hexadecenyl acetate | 56218-71-4 |
| 1-butene | 8-octen-1-ol | protected (Z)-7-decenol | (Z)-7-decenyl acetate | 13857-03-9 |
| 1-pentene | 8-octen-1-ol | protected (Z)-7-undecenol | (Z)-7-undecenyl acetate | — |
| 1-hexene | 8-octen-1-ol | protected (Z)-7-dodecenol | (E)-7-dodecenal | 60671-75-2 |
| 1-hexene | 8-octen-1-ol | protected (Z)-7-dodecenol | (Z)-7-dodecenyl acetate | 14959-86-5 |
| 1-octene | 8-octen-1-ol | protected (Z)-7-tetradecenol | (Z)-7-tetradecenal | 65128-96-3 |
| 1-octene | 8-octen-1-ol | protected (Z)-7-tetradecenol | (Z)-7-tetradecenyl acetate | 16974-10-0 |
| 1-decene | 8-octen-1-ol | protected (Z)-7-hexadecenol | (Z)-7-hexadecenal | 56797-40-1 |
| 1-decene | 8-octen-1-ol | protected (Z)-7-hexadecenol | (Z)-7-hexadecenyl acetate | 23192-42-9 |

Accordingly, some embodiments of the invention provide a method wherein the metathesis reaction partner is a protected alcohol according to Formula IIa:

(IIa)

wherein $R^{2a}$ is an alcohol protecting group,
and wherein the metathesis product is a compound according to Formula IIIa:

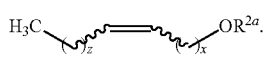
(IIIa)

Any protecting group $R^{2a}$ that is stable under the metathesis reaction conditions can be used in the methods of the invention. Examples of suitable protecting groups include, but are not limited to, silyl, tert-butyl, benzyl, and acetyl. In some embodiments, $R^{2a}$ is acetyl.

In some embodiments, converting the metathesis product to the fatty olefin derivative includes removing $R^{2a}$ from the compound of Formula IIIa to form an alkenol according to Formula Va:

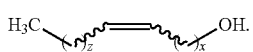
(Va)

In some embodiments, the metathesis reaction partner is a protected alcohol according to Formula IIa:

(IIa)

wherein $R^{2a}$ is an alcohol protecting group,
and the metathesis product is a compound according to Formula IIIc:

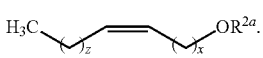
(IIIc)

In some embodiments, the metathesis reaction partner is a protected alcohol according to Formula IIc:

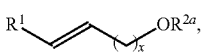
(IIc)

wherein $R^{2a}$ is an alcohol protecting group,
and the metathesis product is a compound according to Formula IIIc:

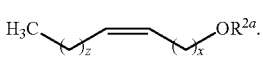
(IIIc)

Metathesis products of Formula IIIc can be prepared using Z-selective metathesis catalysts.

In some embodiments, converting the metathesis product to the fatty olefin derivative includes removing $R^{2a}$ from the compound of Formula IIIc to form an alkenol according to Formula Vc:

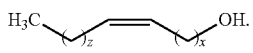
(Vc)

Conversion of Fatty Alcohol Metathesis Products to Fatty Olefin Derivatives

In some embodiments, the alkenol is the fatty olefin derivative. In some embodiments, an alkenol is converted to a desired fatty olefin derivative product via one or more chemical or biochemical transformations. In some such embodiments, the fatty olefin derivative is a pheromone.

In some embodiments, converting the metathesis product to the fatty olefin derivative further includes acylating the alkenol of Formula Va, thereby forming a fatty olefin derivative according to Formula VIa:

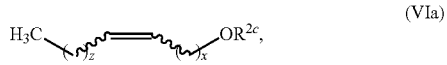

(VIa)

wherein $R^{2c}$ is $C_{1-6}$ acyl.

In some embodiments, converting the metathesis product to the fatty olefin derivative further includes acylating the alkenol of Formula Vc, thereby forming a fatty olefin derivative according to Formula VIc:

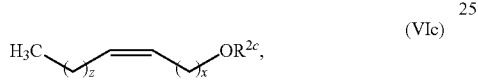

(VIc)

wherein $R^{2c}$ is $C_{1-6}$ acyl.

Any acylating agent suitable for forming the fatty olefin derivative of Formula VIa or Formula VIc can be used in the method of the invention. Examples of suitable acylating agents include acid anhydrides (e.g., acetic anhydride), acid chlorides (e.g., acetyl chloride), activated esters (e.g., pentafluorophenyl esters of carboxylic acids), and carboxylic acids used with coupling agents such as dicyclohexylcarbodiimide or carbonyl diimidazole. Typically, 1-10 molar equivalents of the acylating agent with respect to the alkenol will be used. For example, 1-5 molar equivalents of the acylating agent or 1-2 molar equivalents of the acylating agent can be used. In some embodiments, around 1.0, 1.1, 1.2, 1.3, 1.4, or 1.5 molar equivalents of the acylating agent (e.g., acetic anhydride) with respect to the alkenol is used to form the fatty olefin derivative of Formula VIa or Formula VIc.

A base can be used to promote acylation of the alkenol by the acylating agent. Examples of suitable bases include potassium carbonate, sodium carbonate, sodium acetate, Huenig's base (i.e., N,N-diisopropylethylamine), lutidines including 2,6-lutidine (i.e., 2,6-dimethylpyridine), triethylamine, tributylamine, pyridine, 2,6-di-tert-butylpyridine, 1,8-diazabicycloundec-7-ene (DBU), quinuclidine, and the collidines. Combinations of two or more bases can be used. Typically, less than one molar equivalent of base with respect to the alkenol will be employed in the methods of the invention. For example, 0.05-0.9 molar equivalents or 0.1-0.5 molar equivalents of the base can be used. In some embodiments, around 0.05, 0.1, 0.15, or 0.2 molar equivalents of the base (e.g., sodium acetate) with respect to the alkenol is used in conjunction with the acylating agent (e.g., acetic anhydride) to form the fatty olefin derivative of Formula VIa or Formula VIc.

Any suitable solvent can be used for acylating the alkenol. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. Alternatively, an alkenol such as 7-octen-1-ol can be combined with an acylating agent such as acetic anhydride and a base such as sodium acetate without an additional solvent. The acylation reaction is typically conducted at temperatures ranging from around 25° C. to about 100° C. for a period of time sufficient to form the fatty olefin derivative of Formula VIa or Formula VIc. The reaction can be conducted for a period of time ranging from a few minutes to several hours or longer, depending on the particular alkenol and acylating agent used in the reaction. For example, the reaction can be conducted for around 10 minutes, or around 30 minutes, or around 1 hour, or around 2 hours, or around 4 hours, or around 8 hours, or around 12 hours at around 40° C., or around 50° C., or around 60° C., or around 70° C., or around 80° C.

In some embodiments, converting the metathesis product to the fatty olefin derivative further includes oxidizing the alkenol of Formula Va, thereby forming a fatty olefin derivative according to Formula VIIa:

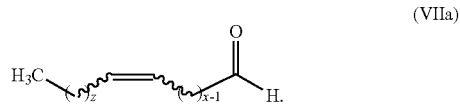

(VIIa)

Many insect pheromones are fatty aldehydes or comprise a fatty aldehyde component. As such, synthesis of certain pheromones includes the conversion of alkenols prepared according to the methods of the invention to fatly aldehydes. In some embodiments, converting the metathesis product to the fatty olefin derivative further includes oxidizing the alkenol of Formula Vc, thereby forming a fatty olefin derivative according to Formula VIIe:

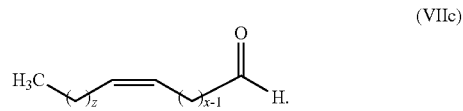

(VIIc)

Any oxidizing agent suitable for converting the alkenol Formula Va to the fatty olefin derivative of Formula VIIa or Formula VIIe can be used in the methods of the invention. Examples of suitable oxidizing agents include, but are not limited to, chromium-based reagents (e.g., chromic acid; Jones reagent-chromium trioxide in aqueous sulfuric acid; Collins reagent-chromium trioxide pyridine complex; pyridinium dichromate; pyridinium chlorochromate and the like); dimethyl sulfoxide (DMSO)-based reagents (e.g., DMSO/oxalyl chloride; DMSO/diycyclohexyl-carbodiimide; DMSO/acetic anhydride; DMSO/phosphorous pentoxide; DMSO/trifluoroacetic anhydride; and the like); hypervalent iodine compounds (e.g., Dess-Martin periodinane; o-iodoxybenzoic acid; and the like); ruthenium-based reagents (e.g., ruthenium tetroxide; tetra-n-propylammonium perruthenate; and the like); and nitroxyl-based reagents (e.g., TEMPO-2,2,6,6-tetramethylpiperidine 1-oxyl-employed with sodium hypochlorite, bromine, or the like).

Oxidation of fatty alcohols is often achieved, for example, via selective oxidation via pyridinium chlorochromate (PCC) (Scheme 2).

Scheme 2

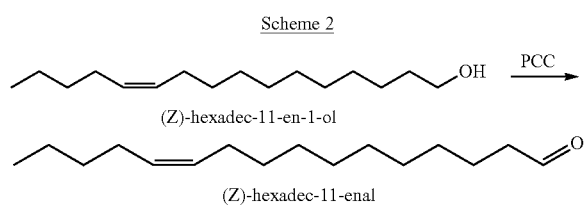

Alternatively, TEMPO (TEMPO=2,2,6,6-tetramethylpiperidinyl-N-oxyl) and related catalyst systems can be used to selectively oxidize alcohols to aldehydes. These methods are described in Ryland and Stahl (2014), herein incorporated by reference in its entirety.

Bio-Oxidation of Terminal Alcohols

The conversion of a fatty alcohol to a fatty aldehyde is known to be catalyzed by alcohol dehydrogenases (ADH) and alcohol oxidases (AOX). Additionally, the conversion of a length $C_n$ fatty acid to a $C_{n-1}$ fatty aldehyde is catalyzed by plant α-dioxygenases (α-DOX) (Scheme 3).

Scheme 3

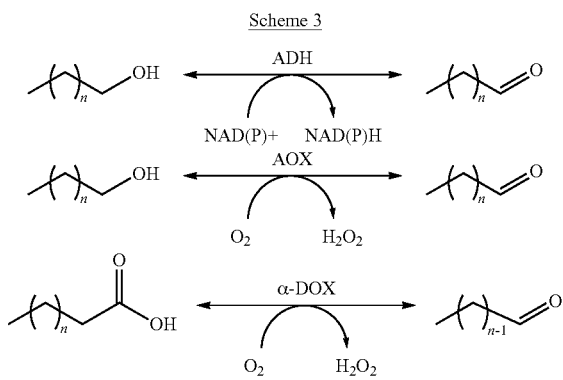

In some embodiments, an alcohol oxidase (AOX) is used to catalyze the conversion of a fatty alcohol to a fatty aldehyde. Alcohol oxidases catalyze the conversion of alcohols into corresponding aldehydes (or ketones) with electron transfer via the use of molecular oxygen to form hydrogen peroxide as a by-product. AOX enzymes utilize flavin adenine dinucleotide (FAD) as an essential cofactor and regenerate with the help of oxygen in the reaction medium. Catalase enzymes may be coupled with the AOX to avoid accumulation of the hydrogen peroxide via catalytic conversion into water and oxygen.

Based on the substrate specificities, AOXs may be categorized into four groups: (a) short chain alcohol oxidase, (b) long chain alcohol oxidase, (c) aromatic alcohol oxidase, and (d) secondary alcohol oxidase (Goswami et al. 2013). Depending on the chain length of the desired substrate, some member of these four groups are better suited for use in the methods of the invention than others.

Short chain alcohol oxidases (including but not limited to those currently classified as EC 1.1.3.13, Table 2) catalyze the oxidation of lower chain length alcohol substrates in the range of C1-C8 carbons (van der Klei et al. 1991) (Ozimek et al. 2005). Aliphatic alcohol oxidases from methylotrophic yeasts such as Candida boidinii and Komagataella pastoris (formerly Pichia pastoris) catalyze the oxidation of primary alkanols to the corresponding aldehydes with a preference for unbranched short-chain aliphatic alcohols. The most broad substrate specificity is found for alcohol oxidase from the Pichia pastoris including propargyl alcohol, 2-chloroethanol, 2-cyanoethanol (Dienys et al. 2003). The major challenge encountered in alcohol oxidation is the high reactivity of the aldehyde product. Utilization of a two liquid phase system (water/solvent) can provide in-situ removal of the aldehyde product from the reaction phase before it is further converted to the acid. For example, hexanal production from hexanol using Pichia pastoris alcohol oxidase coupled with bovine liver catalase was achieved in a biphasic system by taking advantage of the presence of a stable alcohol oxidase in aqueous phase (Karra-Chaabouni et al. 2003). For example, alcohol oxidase from Pichia pastoris was able to oxidize aliphatic alcohols of C6 to C11 when used biphasic organic reaction system (Murray and Duff 1990). Methods for using alcohol oxidases in a biphasic system according to (Karra-Chaabouni et al 2003) and (Murray and Duff 1990) are incorporated by reference in their entirety.

Long chain alcohol oxidases (including but not limited to those currently classified as EC 1.1.3.20; Table 3) include fatty alcohol oxidases, long chain fatty acid oxidases, and long chain fatty alcohol oxidases that oxidize alcohol substrates with carbon chain length of greater than six (Goswami et al 2013). Banthorpe et al reported a long chain alcohol oxidase purified from the leaves of Tanacetum vulgare that was able to oxidize saturated and unsaturated long chain alcohol substrates including hex-trans-2-en-1-ol and octan-1-ol (Banthorpe 1976) (Cardemil 1978). Other plant species, including Simmondsia chinensis (Moreau, R. A., Huang 1979), Arabidopsis thaliana (Cheng et al 2004), and Lotus japonicas (Zhao et al. 2008) have also been reported as sources of long chain alcohol oxidases. Fatty alcohol oxidases are mostly reported from yeast species (Hommel and Rati edge 1990) (Vanhanen et al 2000) (Hommel et al 1994) (Kemp et al 1990) and these enzymes play an important role in long chain fatty acid metabolism (Cheng et al 2005). Fatty alcohol oxidases from yeast species that degrade and grow on long chain alkanes and fatty acid catalyze the oxidation of fatty alcohols. Fatty alcohol oxidase from Candida tropicalis has been isolated as microsomal cell fractions and characterized for a range of substrates (Eirich et al. 2004) (Kemp et al. 1988) (Kemp et al. 1991) (Mauersberger et al. 1992). Significant activity is observed for primary alcohols of length $C_8$ to $C_{1-6}$ with reported KM in the 10-50 μM range (Eirich et al. 2004). Alcohol oxidases described may be used for the conversion of medium chain aliphatic alcohols to aldehydes as described, for example, for whole-cells Candida boidinii (Gabelman and Luzio 1997), and Pichia pastoris (Duff and Murray 1988) (Murray and Duff 1990). Long chain alcohol oxidases from filamentous fungi were produced during growth on hydrocarbon substrates (Kumar and Goswami 2006) (Savitha and Ratledge 1991). The long chain fatty alcohol oxidase (LjFAO1) from Lotus japonicas has been heterologously expressed in E. coli and exhibited broad substrate specificity for alcohol oxidation including 1-dodecanol and 1-hexadecanol (Zhao et al. 2008).

TABLE 2

Alcohol oxidase enzymes capable of oxidizing short chain alcohols (EC 1.1.3.13).

| Organism | Gene names | Accession No. |
|---|---|---|
| Komagataella pastoris (strain ATCC 76273/CBS 7435/CECT 11047/NRRL Y-11430/Wegner 21-1) (Yeast) (Pichia pastoris) | AOX1 PP7435_Chr4-0130 | F2QY27 |
| Komagataella pastoris (strain GS115/ATCC 20864) (Yeast) (Pichia pastoris) | AOX1 PAS_chr4_0821 | P04842 |
| Komagataella pastoris (strain ATCC 76273/CBS 7435/CECT 11047/NRRL Y-11430/Wegner 21-1) (Yeast) (Pichia pastoris) | AOX2 PP7435_Chr4-0863 | F2R038 |
| Komagataella pastoris (strain GS115/ATCC 20864) (Yeast) (Pichia pastoris) | AOX2 PAS_chr4_0152 | C4R702 |
| Candida boidinii (Yeast) | AOD1 | Q00922 |
| Pichia angusta (Yeast) (Hansenula polymorpha) | MOX | P04841 |
| Thanatephorus cucumeris (strain AG1-IB/isolate Jul. 3, 2014) (Lettuce bottom rot fungus) (Rhizoctonia solani) | AOD1 BN14_10802 | M5CC52 |
| Thanatephorus cucumeris (strain AG1-IB/isolate Jul. 3, 2014) (Lettuce bottom rot fungus) (Rhizoctonia solani) | MOX BN14_12214 | M5CF32 |
| Thanatephorus cucumeris (strain AG1-IB/isolate Jul. 3, 2014) (Lettuce bottom rot fungus) (Rhizoctonia solani) | AOD1 BN14_10691 | M5CAV1 |
| Thanatephorus cucumeris (strain AG1-IB/isolate Jul. 3, 2014) (Lettuce bottom rot fungus) (Rhizoctonia solani) | AOD1 BN14_09479 | M5C7F4 |
| Thanatephorus cucumeris (strain AG1-IB/isolate Jul. 3, 2014) (Lettuce bottom rot fungus) (Rhizoctonia solani) | AOD1 BN14_10803 | M5CB66 |
| Thanatephorus cucumeris (strain AG1-IB/isolate Jul. 3, 2014) (Lettuce bottom rot fungus) (Rhizoctonia solani) | AOD1 BN14_09900 | M5C9N9 |
| Thanatephorus cucumeris (strain AG1-IB/isolate Jul. 3, 2014) (Lettuce bottom rot fungus) (Rhizoctonia solani) | AOD1 BN14_08302 | M5C2L8 |
| Thanatephorus cucumeris (strain AG1-IB/isolate Jul. 3, 2014) (Lettuce bottom rot fungus) (Rhizoctonia solani) | MOX BN14_09408 | M5C784 |
| Thanatephorus cucumeris (strain AG1-IB/isolate Jul. 3, 2014) (Lettuce bottom rot fungus) (Rhizoctonia solani) | MOX BN14_09478 | M5C8F8 |
| Thanatephorus cucumeris (strain AG1-IB/isolate Jul. 3, 2014) (Lettuce bottom rot fungus) (Rhizoctonia solani) | AOD1 BN14_11356 | M5CH40 |
| Ogataea henricii | AOD1 | A5LGF0 |
| Candida methanosorbosa | AOD1 | A5LGE5 |
| Candida methanolovescens | AOD1 | A5LGE4 |
| Candida succiphila | AOD1 | A5LGE6 |
| Aspergillus niger (strain CBS 513.88/FGSC A1513) | An15g02200 | A2R501 |
| Aspergillus niger (strain CBS 513.88/FGSC A1513) | An18g05480 | A2RB46 |
| Moniliophthora perniciosa (Witches'-broom disease fungus) (Marasmius perniciosus) | | I7CMK2 |
| Candida cariosilignicola | AOD1 | A5LGE3 |
| Candida pignaliae | AOD1 | A5LGE1 |
| Candida pignaliae | AOD2 | A5LGE2 |
| Candida sonorensis | AOD1 | A5LGD9 |
| Candida sonorensis | AOD2 | A5LGE0 |
| Pichia naganishii | AOD1 | A5LGF2 |
| Ogataea minuta | AOD1 | A5LGF1 |
| Ogataea philodendri | AOD1 | A5LGF3 |
| Ogataea wickerhamii | AOD1 | A5LGE8 |
| Kuraishia capsulata | AOD1 | A5LGE7 |
| Talaromyces stipitatus (strain ATCC 10500/CBS 375.48/QM 6759/NRRL 1006) (Penicillium stipitatum) | TSTA_021940 | B8MHF8 |
| Talaromyces stipitatus (strain ATCC 10500/CBS 375.48/QM 6759/NRRL 1006) (Penicillium stipitatum) | TSTA_065150 | B8LTH7 |
| Talaromyces stipitatus (strain ATCC 10500/CBS 375.48/QM 6759/NRRL 1006) (Penicillium stipitatum) | TSTA_065150 | B8LTH8 |
| Talaromyces stipitatus (strain ATCC 10500/CBS 375.48/QM 6759/NRRL 1006) (Penicillium stipitatum) | TSTA_000410 | B8MSB1 |
| Ogataea glucozyma | AOD1 | A5LGE9 |
| Ogataea parapolymorpha (strain DL-1/ATCC 26012/NRRL Y-7560) (Yeast) (Hansenula polymorpha) | HPODL_03886 | W1QCJ3 |
| Gloeophyllum trabeum (Brown rot fungus) | AOX | A8DPS4 |
| Pichia angusta (Yeast) (Hansenula polymorpha) | mox1 | A6PZG8 |
| Pichia trehalophila | AOD1 | A5LGF4 |
| Pichia angusta (Yeast) (Hansenula polymoipha) | mox1 | A6PZG9 |
| Pichia angusta (Yeast) (Hansenula polymoipha) | mox1 | A6PZG7 |
| Ixodes scapularis (Black-legged tick) (Deer tick) | IscW_ISCW017898 | B7PIZ7 |

TABLE 3

Alcohol oxidate enzymes capable of oxidizing long chain alcohols including fatty alcohols (EC 1.1.3.20).

| Organism | Gene names | Accession No. |
|---|---|---|
| Lotus japonicus (Lotus corniculatus var. japonicus) | FAO1 | B5WWZ8 |
| Arabidopsis thaliana (Mouse-ear cress) | FAO1 At1g03990 F21M11.7 | Q9ZWB9 |
| Lotus japonicus (Lotus corniculatus var. japonicus) | FAO2 | B5WWZ9 |
| Arabidopsis thaliana (Mouse-ear cress) | FAO3 At3g23410 MLM24.14 MLM24.23 | Q9LW56 |
| Arabidopsis thaliana (Mouse-ear cress) | FAO4A At4g19380 T5K18.160 | O65709 |
| Arabidopsis thaliana (Mouse-ear cress) | FAO4B At4g28570 T5F17.20 | Q94BP3 |
| Microbotiyum violaceum (strain p1A1 Lamole) (Anther smut fungus) (Ustilago violacea) | MVLG_06864 | U5HIL4 |
| Ajellomyces dermatitidis ATCC 26199 | BDFG_03507 | T5BNQ0 |
| Gibberella zeae (strain PH-1/ATCC MYA-4620/FGSC 9075/NRRL 31084) (Wheat head blight fungus) (Fusarium graminearum) | FG06918.1 FGSG_06918 | I1RS14 |
| Pichia sorbitophila (strain ATCC MYA-4447/BCRC 22081/CBS 7064/NBRC 10061/NRRL Y-12695) (Hybrid yeast) | Piso0_004410 GNLVRS01_PISOOK16268g GNLVRS01_PISO0L16269g | G8Y5E1 |

TABLE 3-continued

Alcohol oxidate enzymes capable of oxidizing long chain alcohols including fatty alcohols (EC 1.1.3.20).

| Organism | Gene names | Accession No. |
| --- | --- | --- |
| Emericella nidulans (strain FGSC A4/ATCC 38163/CBS 112.46/NRRL 194/M139) (Aspergillus nidulans) | AN0623.2 ANIA_00623 | Q5BFQ7 |
| Pyrenophora tritici-repentis (strain Pt-1C-BFP) (Wheat tan spot fungus) (Drechslera tritici-repentis) | TRPG_10154 | B2WJW5 |
| Paracoccidioides lutzii (strain ATCC MYA-826/Pb01) (Paracoccidioides brasiliensis) | PAAG_09117 | C1HEC6 |
| Candida parapsilosis (strain CDC 317/ATCC MYA-4646) (Yeast) (Monilia parapsilosis) | CPAR2_204420 | G8BG15 |
| Pseudozyma brasiliensis (strain GHG001) (Yeast) | PSEUBRA_SCAF2g03010 | V5GPS6 |
| Candida parapsilosis (strain CDC 317/ATCC MYA-4646) (Yeast) (Monilia parapsilosis) | CPAR2_204430 | G8BG16 |
| Sclerotinia borealis F-4157 | SBOR_5750 | W9CDE2 |
| Sordaria macrospora (strain ATCC MYA-333/DSM 997/K(L3346)/K-hell) | SMAC_06361 | F7W6K4 |
| Sordaria macrospora (strain ATCC MYA-333/DSM 997/K(L3346)/K-hell) | SMAC_01933 | F7VSA1 |
| Meyerozyma guilliermondii (strain ATCC 6260/CBS 566/DSM 6381/JCM 1539/NBRC 10279/NRRL Y-324) (Yeast) (Candida guilliermondii) | PGUG_03467 | A5DJL6 |
| Trichophyton rubrum CBS 202.88 | H107_00669 | A0A023ATC5 |
| Arthrobotrys oligospora (strain ATCC 24927/CBS 115.81/DSM 1491) (Nematode-trapping fungus) (Didymozoophaga oligospora) | AOL_s00097g516 | G1XJI9 |
| Scheffersomyces stipitis (strain ATCC 58785/CBS 6054/NBRC 10063/NRRL Y-11545) (Yeast) (Pichia stipitis) | FAO1 PICST_90828 | A3LYX9 |
| Scheffersomyces stipitis (strain ATCC 58785/CBS 6054/NBRC 10063/NRRL Y-11545) (Yeast) (Pichia stipitis) | FAO2 PICST_32359 | A3LW61 |
| Aspergillus oryzae (strain 3.042) (Yellow koji mold) | Ao3042_09114 | I8TL25 |
| Fusarium oxysporum (strain Fo5176) (Fusarium vascular wilt) | FOXB_17532 | F9GFU8 |
| Rhizopus delemar (strain RA 99-880/ATCC MYA-4621/FGSC 9543/NRRL 43880) (Mucormycosis agent) (Rhizopus arrhizus var. delemar) | RO3G_08271 | I1C536 |
| Rhizopus delemar (strain RA 99-880/ATCC MYA-4621/FGSC 9543/NRRL 43880) (Mucormycosis agent) (Rhizopus arrhizus var. delemar) | RO3G_00154 | I1BGX0 |
| Fusarium oxysporum (strain Fo5176) (Fusarium vascular wilt) | FOXB_07532 | F9FMA2 |
| Penicillium roqueforti | PROQFM164_S02g001772 | W6QPY1 |
| Aspergillus clavatus (strain ATCC 1007/CBS 513.65/DSM 816/NCTC 3887/NRRL 1) | ACLA_018400 | A1CNB5 |
| Arthroderma otae (strain ATCC MYA-4605/CBS 113480) (Microsporum canis) | MCYG_08732 | C5G1B0 |
| Trichophyton tonsurans (strain CBS 112818) (Scalp ringworm fungus) | TESG_07214 | F2S8I2 |
| Colletotrichum higginsianum (strain IMI 349063) (Crucifer anthracnose fungus) | CH063_13441 | H1VUE7 |
| Ajellomyces capsulatus (strain H143) (Darling's disease fungus) (Histoplasma capsulatum) | HCDG_07658 | C6HN77 |
| Trichophyton rubrum (strain ATCC MYA-4607/CBS 118892) (Athlete's foot fungus) | TERG_08235 | F2T096 |
| Cochliobolus heterostrophus (strain C5/ATCC 48332/race O) (Southern corn leaf blight fungus) (Bipolaris maydis) | COCHEDRAFT_1201414 | M2UMT9 |
| Candida orthopsilosis (strain 90-125) (Yeast) | CORT_0D04510 | H8X643 |
| Candida orthopsilosis (strain 90-125) (Yeast) | CORT_0D04520 | H8X644 |
| Candida orthopsilosis (strain 90-125) (Yeast) | CORT_0D04530 | H8X645 |
| Pseudozyma aphidis DSM 70725 | PaG_03027 | W3VP49 |
| Coccidioides posadasii (strain C735) (Valley fever fungus) | CPC735_000380 | C5P005 |
| Magnaporthe olyzae (strain P131) (Rice blast fungus) (Pyricularia olyzae) | OOW_P131scaffold01214g15 | L7IZ92 |
| Neurospora tetrasperma (strain FGSC 2508/ATCC MYA-4615/P0657) | NEUTE1DRAFT_82541 | F8MKD1 |
| Hypocrea virens (strain Gv29-8/FGSC 10586) (Gliocladium virens) (Trichoderma virens) | TRIVIDRAFT_54537 | G9MMY7 |
| Hypocrea virens (strain Gv29-8/FGSC 10586) (Gliocladium virens) (Trichoderma virens) | TRIVIDRAFT_53801 | G9MT89 |
| Aspergillus niger (strain CBS 513.88/FGSC A1513) | An01g09620 | A2Q9Z3 |
| Verticillium dahliae (strain VdLs.17/ATCC MYA-4575/FGSC 10137) (Verticillium wilt) | VDAG_05780 | G2X6J8 |

TABLE 3-continued

Alcohol oxidate enzymes capable of oxidizing long chain alcohols including fatty alcohols (EC 1.1.3.20).

| Organism | Gene names | Accession No. |
| --- | --- | --- |
| Ustilago maydis (strain 521/FGSC 9021) (Corn smut fungus) | UM02023.1 | Q4PCZ0 |
| Fusarium oxysporum f. sp. lycopersici MN25 | FOWG_13006 | W9LNI9 |
| Fusarium oxysporum f. sp. lycopersici MN25 | FOWG_02542 | W9N9Z1 |
| Candida tropicalis (Yeast) | FAO1 | Q6QIR6 |
| Magnaporthe olyzae (strain 70-15/ATCC MYA-4617/FGSC 8958) (Rice blast fungus) (Pyricularia oryzae) | MGG_11317 | G4MVK1 |
| Candida tropicalis (Yeast) | faot | Q9P8D9 |
| Candida tropicalis (Yeast) | FAO2a | Q6QIR5 |
| Phaeosphaeria nodorum (strain SN15/ATCC MYA-4574/FGSC 10173) (Glume blotch fungus) (Septoria nodorum) | SNOG_02371 | Q0V0U3 |
| Candida tropicalis (Yeast) | FAO2b | Q6QIR4 |
| Pestalotiopsis fici W106-1 | PFICI_11209 | W3WU04 |
| Magnaporthe olyzae (strain Y34) (Rice blast fungus) (Pyricularia olyzae) | OOU_Y34scaffold00240g57 | L7IFT5 |
| Pseudogymnoascus destructans (strain ATCC MYA-4855/20631-21) (Bat white-nose syndrome fungus) (Geomyces destructans) | GMDG_01756 | L8G0G6 |
| Pseudogymnoascus destructans (strain ATCC MYA-4855/20631-21) (Bat white-nose syndrome fungus) (Geomyces destructans) | GMDG_04950 | L8GCY2 |
| Mycosphaerella fijiensis (strain CIRAD86) (Black leaf streak disease fungus) (Pseudocercospora fijiensis) | MYCFIDRAFT_52380 | M2Z831 |
| Bipolaris oryzae ATCC 44560 | COCMIDRAFT_84580 | W7A0I8 |
| Cladophialophora psammophila CBS 110553 | A1O5_08147 | W9WTM9 |
| Fusarium oxysporum f. sp. melonis 26406 | FOMG_05173 | X0AEE6 |
| Fusarium oxysporum f. sp. melonis 26406 | FOMG_17829 | W9ZBB7 |
| Cyphellophora europaea CBS 101466 | HMPREF1541_02174 | W2S2S5 |
| Aspergillus kawachii (strain NBRC 4308) (White koji mold) (Aspergillus awamori var. kawachi) | AKAW_00147 | G7X626 |
| Aspergillus terreus (strain NIH 2624/FGSC A1156) | ATEG_05086 | Q0CMJ8 |
| Coccidioides immitis (strain RS) (Valley fever fungus) | CIMG_02987 | J3KAI8 |
| Ajellomyces dermatitidis (strain ER-3/ATCC MYA-2586) (Blastomyces dermatitidis) | BDCG_04701 | C5GLS5 |
| Fusarium oxysporum f. sp. cubense (strain race 1) (Panama disease fungus) | FOC1_g10013865 | N4U732 |
| Rhodotorula glutinis (strain ATCC 204091/IIP 30/MTCC 1151) (Yeast) | RTG_00643 | G0SVU8 |
| Aspergillus niger (strain ATCC 1015/CBS 113.46/FGSC A1144/LSHB Ac4/NCTC 3858a/NRRL 328/USDA 3528.7) | ASPNIDRAFT_35778 | G3XTM6 |
| Candida cloacae | fao1 | Q9P8D8 |
| Candida cloacae | fao2 | Q9P8D7 |
| Fusarium oxysporum f. sp. cubense (strain race 1) (Panama disease fungus) | FOC1_g10006358 | N4TUH3 |
| Candida albicans (strain SC5314/ATCC MYA-2876) (Yeast) | FAO1 CaO19.13562 orf19.13562 | Q59RS8 |
| Candida albicans (strain SC5314/ATCC MYA-2876) (Yeast) | FAO1 CaO19.6143 orf19.6143 | Q59RP0 |
| Chaetomium thermophilum (strain DSM 1495/CBS 144.50/IMI 039719) | CTHT_0018560 | G0S2U9 |
| Mucor circinelloides f. circinelloides (strain 1006PhL) (Mucormycosis agent) (Calyptromyces circinelloides) | HMPREF1544_05296 | S2JDN0 |
| Mucor circinelloides f. circinelloides (strain 1006PhL) (Mucormycosis agent) (Calyptromyces circinelloides) | HMPREF1544_05295 | S2JYP5 |
| Mucor circinelloides f. circinelloides (strain 1006PhL) (Mucormycosis agent) (Calyptromyces circinelloides) | HMPREF1544_06348 | S2JVK9 |
| Botryotinia fuckeliana (strain BcDW1) (Noble rot fungus) (Botrytis cinerea) | BcDW1_6807 | M7UD26 |
| Podospora anserina (strain S/ATCC MYA-4624/DSM 980/FGSC 10383) (Pleurage anserina) | PODANS_5_13040 | B2AFD8 |
| Neosartorya fumigata (strain ATCC MYA-4609/Af293/CBS 101355/FGSC A1100) (Aspergillus fumigatus) | AFUA_1G17110 | Q4WR91 |
| Fusarium oxysporum f. sp. vasinfectum 25433 | FOTG_00686 | X0MEE6 |
| Fusarium oxysporum f. sp. vasinfectum 25433 | FOTG_12485 | X0LE98 |
| Trichophyton interdigitale H6 | H101_06625 | A0A022U717 |

TABLE 3-continued

Alcohol oxidate enzymes capable of oxidizing long chain alcohols including fatty alcohols (EC 1.1.3.20).

| Organism | Gene names | Accession No. |
|---|---|---|
| Beauveria bassiana (strain ARSEF 2860) (White muscardine disease fungus) (Tritirachium shiotae) | BBA_04100 | J4UNY3 |
| Fusarium oxysporum f. sp. radicis-lycopersici 26381 | FOCG_00843 | X0GQ62 |
| Fusarium oxysporum f. sp. radicis-lycopersici 26381 | FOCG_15170 | X0F4T1 |
| Neurospora tetrasperma (strain FGSC 2509/P0656) | NEUTE2DRAFT_88670 | G4UNN6 |
| Pseudozyma hubeiensis (strain SY62) (Yeast) | PHSY_000086 | R9NVU1 |
| Lodderomyces elongisporus (strain ATCC 11503/CBS 2605/JCM 1781/NBRC 1676/NRRL YB-4239) (Yeast) (Saccharomyces elongisporus) | LELG_03289 | A5E102 |
| Malassezia globosa (strain ATCC MYA-4612/CBS 7966) (Dandruff-associated fungus) | MGL_3855 | A8QAY8 |
| Byssochlamys spectabilis (strain No. 5/NBRC 109023) (Paecilomyces variotii) | PVAR5_7014 | V5GBL6 |
| Ajellomyces capsulatus (strain H88) (Darling's disease fungus) (Histoplasma capsulatum) | HCEG_03274 | F0UF47 |
| Trichosporon asahii var. asahii (strain ATCC 90039/CBS 2479/JCM 2466/KCTC 7840/NCYC 2677/UAMH 7654) (Yeast) | A1Q1_03669 | J6FBP4 |
| Penicillium oxalicum (strain 114-2/CGMCC 5302) (Penicillium decumbens) | PDE_00027 | S7Z8U8 |
| Fusarium oxysporum f. sp. conglutinans race 2 54008 | FOPG_02304 | X0IBE3 |
| Fusarium oxysporum f. sp. conglutinans race 2 54008 | FOPG_13066 | X0H540 |
| Fusarium oxysporum f. sp. raphani 54005 | FOQG_00704 | X0D1G8 |
| Fusarium oxysporum f. sp. raphani 54005 | FOQG_10402 | X0C482 |
| Metarhizium acridum (strain CQMa 102) | MAC_03115 | E9DZR7 |
| Arthroderma benhamiae (strain ATCC MYA-4681/CBS 112371) (Trichophyton mentagrophytes) | ARB_02250 | D4B1C1 |
| Fusarium oxysporum f. sp. cubense tropical race 4 54006 | FOIG_12161 | X0JFI6 |
| Fusarium oxysporum f. sp. cubense tropical race 4 54006 | FOIG_12751 | X0JDU5 |
| Cochliobolus heterostrophus (strain C4/ATCC 48331/race T) (Southern corn leaf blight fungus) (Bipolaris maydis) | COCC4DRAFT_52836 | N4WZZ0 |
| Trichosporon asahii var. asahii (strain CBS 8904) (Yeast) | A1Q2_00631 | K1VZW1 |
| Mycosphaerella graminicola (strain CBS 115943/IPO323) (Speckled leaf blotch fungus) (Septoria tritici) | MYCGRDRAFT_37086 | F9X375 |
| Botryotinia fuckeliana (strain T4) (Noble rot fungus) (Bonytis cinerea) | BofuT4_P072020.1 | G2XQ18 |
| Metarhizium anisopliae (strain ARSEF 23/ATCC MYA-3075) | MAA_05783 | E9F0I4 |
| Cladophialophora carrionii CBS 160.54 | G647_05801 | V9DAR1 |
| Coccidioides posadasii (strain RMSCC 757/Silveira) (Valley fever fungus) | CPSG_09174 | E9DH75 |
| Rhodosporidium toruloides (strain NP11) (Yeast) (Rhodotorula gracilis) | RHTO_06879 | M7X159 |
| Puccinia graminis f. sp. tritici (strain CRL 75-36-700-3/race SCCL) (Black stem rust fungus) | PGTG_10521 | E3KIL8 |
| Trichophyton rubrum CBS 288.86 | H103_00624 | A0A022WG28 |
| Colletotrichum fioriniae PJ7 | CFIO01_08202 | A0A010RKZ4 |
| Trichophyton rubrum CBS 289.86 | H104_00611 | A0A022XB46 |
| Cladophialophora yegresii CBS 114405 | A1O7_02579 | W9WC55 |
| Colletotrichum orbiculare (strain 104-T/ATCC 96160/CBS 514.97/LARS 414/MAFF 240422) (Cucumber anthracnose fungus) (Colletotrichum lagenarium) | Cob_10151 | N4VFP3 |
| Drechslerella stenobrocha 248 | DRE_03459 | W7IDL6 |
| Neosartorya fumigata (strain CEA10/CBS 144.89/FGSC A1163) (Aspergillus fumigatus) | AFUB_016500 | B0XP90 |
| Thielavia terrestris (strain ATCC 38088/NRRL 8126) (Acremonium alabamense) | THITE_2117674 | G2R8H9 |
| Gibberella fujikuroi (strain CBS 195.34/IMI 58289/NRRL A-6831) (Bakanae and foot rot disease fungus) (Fusarium fujikuroi) | FFUJ_02948 | S0DZP7 |
| Gibberella fujikuroi (strain CBS 195.34/IMI 58289/NRRL A-6831) (Bakanae and foot rot disease fungus) (Fusarium fujikuroi) | FFUJ_12030 | S0EMC6 |
| Aspergillus flavus (strain ATCC 200026/FGSC A1120/NRRL 3357/JCM 12722/SRRC 167) | AFLA_109870 | B8N941 |
| Togninia minima (strain UCR-PA7) (Esca disease fungus) (Phaeoacremonium aleophilum) | UCRPA7_1719 | R8BTZ6 |

TABLE 3-continued

Alcohol oxidate enzymes capable of oxidizing long chain alcohols including fatty alcohols (EC 1.1.3.20).

| Organism | Gene names | Accession No. |
| --- | --- | --- |
| Ajellomyces dermatitidis (strain ATCC 18188/ CBS 674.68) (Blastomyces dermatitidis) | BDDG_09783 | F2TUC0 |
| Macrophomina phaseolina (strain MS6) (Charcoal rot fungus) | MPH_10582 | K2RHA5 |
| Neurospora crassa (strain ATCC 24698/74-OR23-1A/CBS 708.71/DSM 1257/FGSC 987) | NCU08977 | Q7S2Z2 |
| Neosartorya fischeri (strain ATCC 1020/DSM 3700/FGSC A1164/NRRL 181) (Aspergillus fischerianus) | NFIA_008260 | A1D1S6 |
| Fusarium pseudograminearum (strain CS3096) (Wheat and barley crown-rot fungus) | FPSE_11742 | K3U9J5 |
| Spathaspora passalidarum (strain NRRL Y-27907/ 11-Y1) | SPAPADRAFT_54193 | G3AJP0 |
| Spathaspora passalidarum (strain NRRL Y-27907/ 11-Y1) | SPAPADRAFT_67198 | G3ANX7 |
| Trichophyton verrucosum (strain HKI 0517) | TRV_07960 | D4DL86 |
| Arthroderma gypseum (strain ATCC MYA-4604/ CBS 118893) (Microsporum gypseum) | MGYG_07264 | E4V2J0 |
| Hypocrea jecorina (strain QM6a) (Trichoderma reesei) | TRIREDRAFT_43893 | G0R7P8 |
| Trichophyton rubrum MR1448 | H110_00629 | A0A022Z1G4 |
| Aspergillus ruber CBS 135680 | EURHEDRAFT_512125 | A0A017SPR0 |
| Glarea lozoyensis (strain ATCC 20868/MF5171) | GLAREA_04397 | S3D6C1 |
| Setosphaeria turcica (strain 28A) (Northern leaf blight fungus) (Exserohilum turcicum) | SETTUDRAFT_20639 | R0K6H8 |
| Paracoccidioides brasiliensis (strain Pb18) | PADG_06552 | C1GH16 |
| Fusarium oxysporum Fo47 | FOZG_13577 | W9JPG9 |
| Fusarium oxysporum Fo47 | FOZG_05344 | W9KPH3 |
| Trichophyton rubrum MR1459 | H113_00628 | A0A022ZY09 |
| Penicillium marneffei (strain ATCC 18224/CBS 334.59/QM 7333) | PMAA_075740 | B6QBY3 |
| Sphaerulina musiva (strain SO2202) (Poplar stem canker fungus) (Septoria musiva) | SEPMUDRAFT_154026 | M3DAK6 |
| Gibberella moniliformis (strain M3125/FGSC 7600) (Maize ear and stalk rot fungus) (Fusarium verticillioides) | FVEG_10526 | W7N4P8 |
| Gibberella moniliformis (strain M3125/FGSC 7600) (Maize ear and stalk rot fungus) (Fusarium verticillioides) | FVEG_08281 | W7MVR9 |
| Pseudozyma antarctica (strain T-34) (Yeast) (Candida antarctica) | PANT_22d00298 | M9MGF2 |
| Paracoccidioides brasiliensis (strain Pb03) | PABG_07795 | C0SJD4 |
| Rhizophagus irregularis (strain DAOM 181602/ DAOM 197198/MUCL 43194) (Arbuscular mycorrhizal fungus) (Glomus intraradices) | GLOINDRAFT_82554 | U9TF61 |
| Penicillium chrysogenum (strain ATCC 28089/ DSM 1075/Wisconsin 54-1255) (Penicillium notatum) | Pc21g23700 PCH_Pc21g23700 | B6HJ58 |
| Baudoinia compniacensis (strain UAMH 10762) (Angels' share fungus) | BAUCODRAFT_274597 | M2M6Z5 |
| Hypocrea atroviridis (strain ATCC 20476/IMI 206040) (Trichoderma atroviride) | TRIATDRAFT_280929 | G9NJ32 |
| Colletotrichum gloeosporioides (strain Cg-14) (Anthracnose fungus) (Glomerella cingulata) | CGLO_06642 | T0LPH0 |
| Cordyceps militaris (strain CM01) (Caterpillar fungus) | CCM_02665 | G3JB34 |
| Pyronema omphalodes (strain CBS 100304) (Pyronema confluens) | PCON_13062 | U4LKE9 |
| Colletotrichum graminicola (strain M1.001/M2/ FGSC 10212) (Maize anthracnose fungus) (Glomerella graminicola) | GLRG_08499 | E3QR67 |
| Glarea lozoyensis (strain ATCC 74030/MF5533) | M7I_2117 | H0EHX4 |
| Fusarium oxysporum f. sp. cubense (strain race 4) (Panama disease fungus) | FOC4_g10002493 | N1S969 |
| Fusarium oxysporum f. sp. cubense (strain race 4) (Panama disease fungus) | FOC4_g10011461 | N1RT80 |
| Cochliobolus sativus (strain ND90Pr/ATCC 201652) (Common root rot and spot blotch fungus) (Bipolaris sorokiniana) | COCSADRAFT_295770 | M2TBE4 |
| Mixia osmundae (strain CBS 9802/IAM 14324/ JCM 22182/KY 12970) | Mo05571 E5Q_05571 | G7E7S3 |
| Mycosphaerella pini (strain NZE10/CBS 128990) (Red band needle blight fungus) (Dothistroma septosporum) | DOTSEDRAFT_69651 | N1PXR0 |
| Grosmannia clavigera (strain kw1407/UAMH 11150) (Blue stain fungus) (Graphiocladiella clavigera) | CMQ_1113 | F0XC64 |

TABLE 3-continued

Alcohol oxidate enzymes capable of oxidizing long chain alcohols including fatty alcohols (EC 1.1.3.20).

| Organism | Gene names | Accession No. |
| --- | --- | --- |
| Fusarium oxysporum FOSC 3-a | FOYG_03004 | W9IUE5 |
| Fusarium oxysporum FOSC 3-a | FOYG_16040 | W9HNP0 |
| Fusarium oxysporum FOSC 3-a | FOYG_17058 | W9HB31 |
| Nectria haematococca (strain 77-13-4/ATCC MYA-4622/FGSC 9596/MPVI) (Fusarium solani subsp. pisi) | NECHADRAFT_37686 | C7YQL1 |
| Nectria haematococca (strain 77-13-4/ATCC MYA-4622/FGSC 9596/MPVI) (Fusarium solani subsp. pisi) | NECHADRAFT_77262 | C7ZJI0 |
| Tuber melanosporum (strain Me128) (Perigord black truffle) | GSTUM_00010376001 | D5GLS0 |
| Ajellomyces dermatitidis (strain SLH14081) (Blastomyces dermatitidis) | BDBG_07633 | C5JYI9 |
| Chaetomium globosum (strain ATCC 6205/CBS 148.51/DSM 1962/NBRC 6347/NRRL 1970) (Soil fungus) | CHGG_09885 | Q2GQ69 |
| Candida tenuis (strain ATCC 10573/BCRC 21748/CBS 615/JCM 9827/NBRC 10315/NRRL Y-1498/VKM Y-70) (Yeast) | CANTEDRAFT_108652 | G3B9Z1 |
| Trichophyton rubrum CBS 100081 | H102_00622 | A0A022VKY4 |
| Pyrenophora teres f. teres (strain 0-1) (Barley net blotch fungus) (Drechslera teres f. teres) | PTT_09421 | E3RLZ3 |
| Colletotrichum gloeosporioides (strain Nara gc5) (Anthracnose fungus) (Glomerella cingulata) | CGGC5_4608 | L2GB29 |
| Gibberella zeae (Wheat head blight fungus) (Fusarium graminearum) | FG05_06918 | A0A016PCS4 |
| Trichophyton soudanense CBS 452.61 | H105_00612 | A0A022Y6A6 |
| Sclerotinia sclerotiorum (strain ATCC 18683/1980/Ss-1) (White mold) (Whetzelinia sclerotiorum) | SS1G_07437 | A7EQ37 |
| Fusarium oxysporum f. sp. pisi HDV247 | FOVG_14401 | W9NWU8 |
| Fusarium oxysporum f. sp. pisi HDV247 | FOVG_02874 | W9Q5V3 |
| Ustilago hordei (strain Uh4875-4) (Barley covered smut fungus) | UHOR_03009 | I2G1Z4 |
| Sporisorium reilianum (strain SRZ2) (Maize head smut fungus) | sr12985 | E6ZYF7 |
| Bipolaris zeicola 26-R-13 | COCCADRAFT_81154 | W6YIP8 |
| Melampsora larici-populina (strain 98AG31/pathotype 3-4-7) (Poplar leaf rust fungus) | MELLADRAFT_78490 | F4RUZ8 |
| Fusarium oxysporum f. sp. lycopersici (strain 4287/CBS 123668/FGSC 9935/NRRL 34936) (Fusarium vascular wilt of tomato) | FOXG_01901 | J9MG95 |
| Fusarium oxysporum f. sp. lycopersici (strain 4287/CBS 123668/FGSC 9935/NRRL 34936) (Fusarium vascular wilt of tomato) | FOXG_11941 | J9N954 |
| Bipolaris victoriae FI3 | COCVIDRAFT_39053 | W7EMJ8 |
| Debaryomyces hansenii (strain ATCC 36239/CBS 767/JCM 1990/NBRC 0083/IGC 2968) (Yeast) (Torulaspora hansenii) | DEHA2E04268g | Q6BQL4 |
| Clavispora lusitaniae (strain ATCC 42720) (Yeast) (Candida lusitaniae) | CLUG_01505 | C4XZX3 |
| Candida albicans (strain WO-1) (Yeast) | CAWG_02023 | C4YME4 |
| Trichophyton rubrum MR850 | H100_00625 | A0A022U0Q2 |
| Candida dubliniensis (strain CD36/ATCC MYA-646/CBS 7987/NCPF 3949/NRRL Y-17841) (Yeast) | CD36_32890 | B9WMC7 |
| Starmerella bombicola | AOX1 | A0A024FB95 |
| Thielavia heterothallica (strain ATCC 42464/BCRC 31852/DSM 1799) (Myceliophthora thermophila) | MYCTH_103590 | G2QJL7 |
| Claviceps purpurea (strain 20.1) (Ergot fungus) (Sphacelia segetum) | CPUR_07614 | M1WFI4 |
| Aspergillus oryzae (strain ATCC 42149/RIB 40) (Yellow koji mold) | AO090023000571 | Q2UH61 |
| Dictyostelium discoideum (Slime mold) | DDB_0184181 DDB_G0292042 | Q54DT6 |
| Triticum urartu (Red wild einkorn) (Crithodium urartu) | TRIUR3_22733 | M7YME5 |
| Solanum tuberosum (Potato) | PGSC0003DMG400017211 | M1BG07 |
| Oryza sativa subsp. japonica (Rice) | OSJNBb0044B19.5 LOC_Os10g33540 | Q8W5P8 |
| Oryza sativa subsp. japonica (Rice) | OJ1234_B11.20 Os02g0621800 | Q6K9N5 |
| Oryza sativa subsp. japonica (Rice) | OSJNBa0001K12.5 LOC_Os10g33520 | Q8W5P3 |
| Zea mays (Maize) | ZEAMB73_809149 | C0P3J6 |
| Citrus clementina | CICLE_v10011111mg | V4S9P4 |
| Citrus clementina | CICLE_v10018992mg | V4U4C9 |

TABLE 3-continued

Alcohol oxidate enzymes capable of oxidizing long chain alcohols including fatty alcohols (EC 1.1.3.20).

| Organism | Gene names | Accession No. |
|---|---|---|
| Citrus clementina | CICLE_v10004405mg | V4S9D3 |
| Citrus clementina | CICLE_v10004403mg | V4RZZ6 |
| Moms notabilis | L484_011703 | W9RIK0 |
| Moms notabilis | L484_005930 | W9RET7 |
| Medicago truncatula (Barrel medic) (Medicago tribuloides) | MTR_1g075650 | G7I4U3 |
| Arabidopsis thaliana (Mouse-ear cress) | | Q8LDP0 |
| Medicago truncatula (Barrel medic) (Medicago tribuloides) | MTR_4g081080 | G7JF07 |
| Simmondsia chinensis (Jojoba) (Buxus chinensis) | | L7VFV2 |
| Prunus persica (Peach) (Amygdalus persica) | PRUPE_ppa018458mg | M5VXL1 |
| Aphanomyces astaci | H257_07411 | W4GI89 |
| Aphanomyces astaci | H257_07412 | W4GI44 |
| Aphanomyces astaci | H257_07411 | W4GKE3 |
| Aphanomyces astaci | H257_07411 | W4GK29 |
| Aphanomyces astaci | H257_07411 | W4GJ79 |
| Aphanomyces astaci | H257_07411 | W4GI38 |
| Phaeodactylum tricornutum (strain CCAP 1055/1) | PHATRDRAFT_48204 | B7G6C1 |
| Hordeum vulgare var. distichum (Two-rowed barley) | | F2E4R4 |
| Hordeum vulgare var. distichum (Two-rowed barley) | | F2DZG1 |
| Hordeum vulgare var. distichum (Two-rowed barley) | | M0YPG7 |
| Hordeum vulgare var. distichum (Two-rowed barley) | | M0YPG6 |
| Hordeum vulgare var. distichum (Two-rowed barley) | | F2CUY4 |
| Ricinus communis (Castor bean) | RCOM_0867830 | B9S1S3 |
| Brassica rapa subsp. pekinensis (Chinese cabbage) (Brassica pekinensis) | BRA014947 | M4DEM5 |
| Ricinus communis (Castor bean) | RCOM_0258730 | B9SV13 |
| Brassica rapa subsp. pekinensis (Chinese cabbage) (Brassica pekinensis) | BRA001912 | M4CCI2 |
| Brassica rapa subsp. pekinensis (Chinese cabbage) (Brassica pekinensis) | BRA012548 | M4D7T8 |
| Brassica rapa subsp. pekinensis (Chinese cabbage) (Brassica pekinensis) | BRA024190 | M4E5Y6 |
| Brassica rapa subsp. pekinensis (Chinese cabbage) (Brassica pekinensis) | BRA015283 | M4DFL0 |
| Ricinus communis (Castor bean) | RCOM_1168730 | B9SS54 |
| Zea mays (Maize) | | C4J691 |
| Oryza glaberrima (African rice) | | I1P2B7 |
| Zea mays (Maize) | | B6SXM3 |
| Zea mays (Maize) | | C0HFU4 |
| Aegilops tauschii (Tausch's goatgrass) (Aegilops squarrosa) | F775_19577 | R7W4J3 |
| Solanum habrochaites (Wild tomato) (Lycopersicon hirsutum) | | R9R6T0 |
| Physcomitrella patens subsp. patens (Moss) | PHYPADRAFT_124285 | A9S535 |
| Physcomitrella patens subsp. patens (Moss) | PHYPADRAFT_113581 | A9RG13 |
| Physcomitrella patens subsp. patens (Moss) | PHYPADRAFT_182504 | A9S9A5 |
| Solanum pennellii (Tomato) (Lycopersicon pennellii) | | R9R6Q1 |
| Vitis vinifera (Grape) | VIT_02s0087g00630 | F6HJ27 |
| Vitis vinifera (Grape) | VIT_07s0005g03780 | F6HZM3 |
| Vitis vinifera (Grape) | VIT_05s0049g01400 | F6H8T4 |
| Vitis vinifera (Grape) | VITISV_019349 | A5AH38 |
| Capsella rubella | CARUB_v10013046mg | R0HIT3 |
| Capsella rubella | CARUB_v10004212mg | R0GUX4 |
| Capsella rubella | CARUB_v10004208mg | R0F3X6 |
| Capsella rubella | CARUB_v10012453mg | R0ILD0 |
| Capsella rubella | CARUB_v10004208mg | R0GUX1 |
| Eutrema salsugineum (Saltwater cress) (Sisymbrium salsugineum) | EUTSA_v10024496mg | V4MD54 |
| Eutrema salsugineum (Saltwater cress) (Sisymbrium salsugineum) | EUTSA_v10020141mg | V4NM59 |
| Eutrema salsugineum (Saltwater cress) (Sisymbrium salsugineum) | EUTSA_v10024496mg | V4LUR9 |
| Eutrema salsugineum (Saltwater cress) (Sisymbrium salsugineum) | EUTSA_v10024528mg | V4P767 |
| Eutrema salsugineum (Saltwater cress) (Sisymbrium salsugineum) | EUTSA_v10006882mg | V4L2P6 |
| Selaginella moellendorffii (Spikemoss) | SELMODRAFT_87684 | D8R6Z6 |
| Selaginella moellendorffii (Spikemoss) | SELMODRAFT_87621 | D8R6Z5 |
| Selaginella moellendorffii (Spikemoss) | SELMODRAFT_74601 | D8QN81 |

TABLE 3-continued

Alcohol oxidate enzymes capable of oxidizing long chain alcohols including fatty alcohols (EC 1.1.3.20).

| Organism | Gene names | Accession No. |
| --- | --- | --- |
| Selaginella moellendorffii (Spikemoss) | SELMODRAFT_73531 | D8QN82 |
| Sorghum bicolor (Sorghum) (Sorghum vulgare) | Sb04g026390 SORBIDRAFT_04g026390 | C5XXS4 |
| Sorghum bicolor (Sorghum) (Sorghum vulgare) | Sb04g026370 SORBIDRAFT_04g026370 | C5XXS1 |
| Sorghum bicolor (Sorghum) (Sorghum vulgare) | Sb01g019470 SORBIDRAFT_01g019470 | C5WYH6 |
| Sorghum bicolor (Sorghum) (Sorghum vulgare) | Sb01g019480 SORBIDRAFT_01g019480 | C5WYH7 |
| Sorghum bicolor (Sorghum) (Sorghum vulgare) | Sb01g019460 SORBIDRAFT_01g019460 | C5WYH5 |
| Solanum pimpinellifolium (Currant tomato) (Lycopersicon pimpinellifolium) | | R9R6J2 |
| Phaseolus vulgaris (Kidney bean) (French bean) | PHAVU_007G124200g | V7BGM7 |
| Phaseolus vulgaris (Kidney bean) (French bean) | PHAVU_011G136600g | V7AI35 |
| Phaseolus vulgaris (Kidney bean) (French bean) | PHAVU_001G162800g | V7D063 |
| Solanum tuberosum (Potato) | PG5C0003DMG400024294 | M1C923 |
| Solanum tuberosum (Potato) | PGSC0003DMG400018458 | M1BKV4 |
| Solanum tuberosum (Potato) | PGSC0003DMG400018458 | M1BKV3 |
| Glycine max (Soybean) (Glycine hispida) | | K7LK61 |
| Glycine max (Soybean) (Glycine hispida) | | K7KXQ9 |
| Populus trichocarpa (Western balsam poplar) (Populus balsamifera subsp. trichocarpa) | POPTR_0008s16920g | B9HKS3 |
| Picea sitchensis (Sitka spruce) (Pinus sitchensis) | | B8LQ84 |
| Populus trichocarpa (Western balsam poplar) (Populus balsamifera subsp. trichocarpa) | POPTR_0004s24310g | U5GKQ5 |
| Populus trichocarpa (Western balsam poplar) (Populus balsamifera subsp. trichocarpa) | POPTR_0010s07980g | B9HSG9 |
| Glycine max (Soybean) (Glycine hispida) | | I1N9S7 |
| Glycine max (Soybean) (Glycine hispida) | | I1LSK5 |
| Setaria italica (Foxtail millet) (Panicum italicum) | Si034362m.g | K4A658 |
| Solanum lycopersicum (Tomato) (Lycopersicon esculentum) | Solyc09g072610.2 | K4CUT7 |
| Setaria italica (Foxtail millet) (Panicum italicum) | Si016380m.g | K3YQ38 |
| Solanum lycopersicum (Tomato) (Lycopersicon esculentum) | | R9R6I9 |
| Solanum lycopersicum (Tomato) (Lycopersicon esculentum) | Solyc09g090350.2 | K4CW61 |
| Solanum lycopersicum (Tomato) (Lycopersicon esculentum) | Solyc08g005630.2 | K4CI54 |
| Solanum lycopersicum (Tomato) (Lycopersicon esculentum) | Solyc08g075240.2 | K4CMP1 |
| Setaria italica (Foxtail millet) (Panicum italicum) | Si034359m.g | K4A655 |
| Setaria italica (Foxtail millet) (Panicum italicum) | Si034354m.g | K4A650 |
| Mimulus guttatus (Spotted monkey flower) (Yellow monkey flower) | MIMGU_mgv1a001896mg | A0A022PU07 |
| Mimulus guttatus (Spotted monkey flower) (Yellow monkey flower) | MIMGU_mgv1a022390mg | A0A022RAV4 |
| Mimulus guttatus (Spotted monkey flower) (Yellow monkey flower) | MIMGU_mgv1a001868mg | A0A022S2E6 |
| Mimulus guttatus (Spotted monkey flower) (Yellow monkey flower) | MIMGU_mgv1a001883mg | A0A022S275 |
| Mimulus guttatus (Spotted monkey flower) (Yellow monkey flower) | MIMGU_mgv1a001761mg | A0A022QNF0 |
| Musa acuminata subsp. malaccensis (Wild banana) (Musa malaccensis) | | M0SNA8 |
| Musa acuminata subsp. malaccensis (Wild banana) (Musa malaccensis) | | M0RUT7 |
| Musa acuminata subsp. malaccensis (Wild banana) (Musa malaccensis) | | M0RUK3 |
| Saprolegnia diclina VS20 | SDRG_10901 | T0RG89 |
| Brachypodium distachyon (Purple false brome) (Trachynia distachya) | BRADI3G49085 | I1IBP7 |
| Brachypodium distachyon (Purple false brome) (Trachynia distachya) | BRADI3G28677 | I1I4N2 |
| Brachypodium distachyon (Purple false brome) (Trachynia distachya) | BRADI3G28657 | I1I4N0 |
| Oryza sativa subsp. indica (Rice) | OsI_34012 | B8BHG0 |
| Oryza sativa subsp. indica (Rice) | OsI_08118 | B8AFT8 |
| Oryza sativa subsp. indica (Rice) | OsI_34008 | A2Z8H1 |
| Oryza sativa subsp. indica (Rice) | OsI_34014 | B8BHG1 |
| Oryza sativa subsp. japonica (Rice) | LOC_Os10g33460 | Q7XDG3 |
| Oryza sativa subsp. japonica (Rice) | Os10g0474800 | Q0IX12 |
| Oryza sativa subsp. japonica (Rice) | Os10g0474966 | C7J7R1 |
| Oryza sativa subsp. japonica (Rice) | OSJNBa0001K12.13 | Q8W5N7 |
| Oryza sativa subsp. japonica (Rice) | OsJ_31873 | B9G683 |

TABLE 3-continued

Alcohol oxidate enzymes capable of oxidizing long chain alcohols including fatty alcohols (EC 1.1.3.20).

| Organism | Gene names | Accession No. |
| --- | --- | --- |
| Oryza sativa subsp. japonica (Rice) | OsJ_31875 | B9G684 |
| Oryza sativa subsp. japonica (Rice) | OSJNBa0001K12.3 | Q8W5P5 |
| Arabidopsis lyrata subsp. lyrata (Lyre-leaved rock-cress) | ARALYDRAFT_470376 | D7KDA3 |
| Arabidopsis lyrata subsp. lyrata (Lyre-leaved rock-cress) | ARALYDRAFT_479855 | D7L3B6 |
| Arabidopsis lyrata subsp. lyrata (Lyre-leaved rock-cress) | ARALYDRAFT_491906 | D7MDA9 |
| Arabidopsis lyrata subsp. lyrata (Lyre-leaved rock-cress) | ARALYDRAFT_914728 | D7MGS9 |

In some embodiments, an alcohol dehydrogenase (ADH, Table 4) is used to catalyze the conversion of a fatty alcohol to a fatty aldehyde. A number of ADHs identified from alkanotrophic organisms, *Pseudomonas fluorescens* NRRL B-1244 (Hou et al. 1983), *Pseudomonas butanovora* ATCC 43655 (Vangnai and Arp 2001), and *Acinetobacter* sp. strain M-1 (Tani et al. 2000), have shown to be active on short to medium-chain alkyl alcohols ($C_2$ to $C_{14}$). Additionally, commercially available ADHs from Sigma, Horse liver ADH and Baker's yeast ADH have detectable activity for substrates with length $C_{10}$ and greater. The reported activities for the longer fatty alcohols may be impacted by the difficulties in solubilizing the substrates. For the yeast ADH from Sigma, little to no activity is observed for $C_{12}$ to $C_{14}$ aldehydes by (Tani et al. 2000), however, activity for $C_{12}$ and $C_{16}$ hydroxy-co-fatty acids has been observed (Lu et al. 2010). Recently, two ADHs were characterized from *Geobacillus thermodenitrifleans* NG80-2, an organism that degrades $C_{15}$ to $C_{36}$ alkanes using the LadA hydroxylase. Activity was detected from methanol to 1-triacontanol ($C_{30}$) for both ADHs, with 1-octanol being the preferred substrate for ADH2 and ethanol for ADH1 (Liu et al. 2009).

The use of ADHs in whole-cell bioconversions has been mostly focused on the production of chiral alcohols from ketones (Ernst et al. 2005) (Schroer et al. 2007). Using the ADH from *Lactobacillus brevis* and coupled cofactor regeneration with isopropanol, Schroer et al. reported the production of 797 g of (R)-methyl-3 hydroxybutanoate from methyl acetoacetate, with a space time yield of 29 g/L/h (Schroer et al. 2007). Examples of aliphatic alcohol oxidation in whole-cell transformations have been reported with commercially obtained *S. cerevisiae* for the conversion of hexanol to hexanal (Presecki et al. 2012) and 2-heptanol to 2-heptanone (Cappaert and Larroche 2004).

TABLE 4

Exemplary alcohol dehydrogenase enzymes.

| Organism | Gene Name | Accession No. |
| --- | --- | --- |
| Bactrocera oleae (Olive fruit fly) (Dacus oleae) | ADH | Q9NAR7 |
| Cupriavidus necator (Alcaligenes eutrophus) (Ralstonia eutropha) | adh | P14940 |
| Drosophila adiastola (Fruit fly) (Idiomyia adiastola) | Adh | Q00669 |
| Drosophila affinidisjuncta (Fruit fly) (Idiomyia affinidisjuncta) | Adh | P21518 |
| Drosophila ambigua (Fruit fly) | Adh | P25139 |
| Drosophila borealis (Fruit fly) | Adh | P48584 |
| Drosophila differens (Fruit fly) | Adh | P22245 |
| Drosophila equinoxialis (Fruit fly) | Adh | Q9NG42 |
| Drosophila flavomontana (Fruit fly) | Adh | P48585 |
| Drosophila guanche (Fruit fly) | Adh | Q09009 |
| Drosophila hawaiiensis (Fruit fly) | Adh | P51549 |
| Drosophila heteroneura (Fruit fly) | Adh | P21898 |
| Drosophila immigrans (Fruit fly) | Adh | Q07588 |
| Drosophila insularis (Fruit fly) | Adh | Q9NG40 |
| Drosophila lebanonensis (Fruit fly) (Scaptodrosophila lebanonensis) | Adh | P10807 |
| Drosophila mauritiana (Fruit fly) | Adh | P07162 |
| Drosophila madeirensis (Fruit fly) | Adh | Q09010 |
| Drosophila mimica (Fruit fly) (Idiomyia mimica) | Adh | Q00671 |
| Drosophila nigra (Fruit fly) (Idiomyia nigra) | Adh | Q00672 |
| Drosophila orena (Fruit fly) | Adh | P07159 |
| Drosophila pseudoobscura bogotana (Fruit fly) | Adh | P84328 |
| Drosophila picticornis (Fruit fly) (Idiomyia picticornis) | Adh | P23361 |
| Drosophila planitibia (Fruit fly) | Adh | P23277 |
| Drosophila paulistorum (Fruit fly) | Adh | Q9U8S9 |
| Drosophila silvestris (Fruit fly) | Adh | P23278 |
| Drosophila subobscura (Fruit fly) | Adh | Q03384 |
| Drosophila teissieri (Fruit fly) | Adh | P28484 |
| Drosophila tsacasi (Fruit fly) | Adh | P51550 |
| Fragaria ananassa (Strawberry) | ADH | P17648 |
| Malus domestica (Apple) (Pyrus malus) | ADH | P48977 |
| Scaptomyza albovittata (Fruit fly) | Adh | P25988 |
| Scaptomyza crassifemur (Fruit fly) (Drosophila crassifemur) | Adh | Q00670 |

TABLE 4-continued

Exemplary alcohol dehydrogenase enzymes.

| Organism | Gene Name | Accession No. |
|---|---|---|
| Sulfolobus sp. (strain RC3) | adh | P50381 |
| Zaprionus tuberculatus (Vinegar fly) | Adh | P51552 |
| Geobacillus stearothermophilus (Bacillus stearothermophilus) | adh | P42327 |
| Drosophila mayaguana (Fruit fly) | Adh, Adh2 | P25721 |
| Drosophila melanogaster (Fruit fly) | Adh, CG3481 | P00334 |
| Drosophila pseudoobscura pseudoobscura (Fruit fly) | Adh, GA17214 | Q6LCE4 |
| Drosophila simulans (Fruit fly) | Adh, GD23968 | Q24641 |
| Drosophila yakuba (Fruit fly) | Adh, GE19037 | P26719 |
| Drosophila ananassae (Fruit fly) | Adh, GF14888 | Q50L96 |
| Drosophila erecta (Fruit fly) | Adh, GG25120 | P28483 |
| Drosophila grimshawi (Fruit fly) (Idiomyia grimshawi) | Adh, GH13025 | P51551 |
| Drosophila willistoni (Fruit fly) | Adh, GK18290 | Q05114 |
| Drosophila persimilis (Fruit fly) | Adh, GL25993 | P37473 |
| Drosophila sechellia (Fruit fly) | Adh, GM15656 | Q9GN94 |
| Cupriavidus necator (strain ATCC 17699/H16/DSM 428/ Stanier 337) (Ralstonia eutropha) | adh, H16_A0757 | Q0KDL6 |
| Mycobacterium tuberculosis (strain CDC 1551/Oshkosh) | adh, MT1581 | P9WQC2 |
| Staphylococcus aureus (strain MW2) | adh, MW0568 | Q8NXU1 |
| Mycobacterium tuberculosis (strain ATCC 25618/H37Rv) | adh, Rv1530 | P9WQC3 |
| Staphylococcus aureus (strain N315) | adh, SA0562 | Q7A742 |
| Staphylococcus aureus (strain bovine RF122/ET3-1) | adh, SAB0557 | Q2YSX0 |
| Sulfolobus acidocaldarius (strain ATCC 33909/DSM 639/ JCM 8929/NBRC 15157/NCIMB 11770) | adh, Saci_2057 | Q4J781 |
| Staphylococcus aureus (strain COL) | adh, SACOL0660 | Q5HI63 |
| Staphylococcus aureus (strain NCTC 8325) | adh, SAOUHSC_00608 | Q2G0G1 |
| Staphylococcus aureus (strain MRSA252) | adh, SAR0613 | Q6GJ63 |
| Staphylococcus aureus (strain MSSA476) | adh, SAS0573 | Q6GBM4 |
| Staphylococcus aureus (strain USA300) | adh, SAUSA300_0594 | Q2FJ31 |
| Staphylococcus aureus (strain Mu50/ATCC 700699) | adh, SAV0605 | Q99W07 |
| Staphylococcus epidermidis (strain ATCC 12228) | adh, SE_0375 | Q8CQ56 |
| Staphylococcus epidermidis (strain ATCC 35984/RP62A) | adh, SERP0257 | Q5HRD6 |
| Sulfolobus solfataricus (strain ATCC 35092/DSM 1617/ JCM 11322/P2) | adh, SSO2536 | P39462 |
| Sulfolobus tokodaii (strain DSM 16993/JCM 10545/NBRC 100140/7) | adh, STK 25770 | Q96XE0 |
| Anas platyrhynchos (Domestic duck) (Arias boschas) | ADH1 | P30350 |
| Apteryx australis (Brown kiwi) | ADH1 | P49645 |
| Ceratitis capitata (Mediterranean fruit fly) (Tephritis capitata) | ADH1 | P48814 |
| Ceratitis cosyra (Mango fruit fly) (Trypeta cosyra) | ADH1 | Q70UN9 |
| Gallus gallus (Chicken) | ADH1 | P23991 |
| Columba livia (Domestic pigeon) | ADH1 | P86883 |
| Coturnix coturnix japonica (Japanese quail) (Coturnix japonica) | ADH1 | P19631 |
| Drosophila hydei (Fruit fly) | Adh1 | P23236 |
| Drosophila montana (Fruit fly) | Adh1 | P48586 |
| Drosophila mettleri (Fruit fly) | Adh1 | P22246 |
| Drosophila mulleri (Fruit fly) | Adh1 | P07161 |
| Drosophila navojoa (Fruit fly) | Adh1 | P12854 |
| Geomys attwateri (Attwater's pocket gopher) (Geomys bursarius attwateri) | ADH1 | Q9Z2M2 |
| Geomys bursarius (Plains pocket gopher) | ADH1 | Q64413 |
| Geomys knoxjonesi (Knox Jones's pocket gopher) | ADH1 | Q64415 |
| Hordeum vulgare (Barley) | ADH1 | P05336 |
| Kluyveromyces marxianus (Yeast) (Candida kefyr) | ADH1 | Q07288 |
| Zea mays (Maize) | ADH1 | P00333 |
| Mesocricetus auratus (Golden hamster) | ADH1 | P86885 |
| Pennisetum americanum (Pearl millet) (Pennisetum glaucum) | ADH1 | P14219 |
| Petunia hybrida (Petunia) | ADH1 | P25141 |
| Oryctolagus cuniculus (Rabbit) | ADH1 | Q03505 |
| Solanum tuberosum (Potato) | ADH1 | P14673 |
| Struthio camelus (Ostrich) | ADH1 | P80338 |
| Trifolium repens (Creeping white clover) | ADH1 | P13603 |
| Zea luxurians (Guatemalan teosinte) (Euchlaena luxurians) | ADH1 | Q07264 |
| Saccharomyces cerevisiae (strain ATCC 204508/S288c) (Baker's yeast) | ADH1, ADC1, YOL086C, O0947 | P00330 |
| Arabidopsis thaliana (Mouse-ear cress) | ADH1, ADH, At1g77120, F22K20.19 | P06525 |
| Schizosaccharomyces pombe (strain 972/ATCC 24843) (Fission yeast) | adh1, adh, SPCC13B11.01 | P00332 |
| Drosophila lacicola (Fruit fly) | Adh1, Adh-1 | Q27404 |
| Mus musculus (Mouse) | Adh1, Adh-1 | P00329 |
| Peromyscus maniculatus (North American deer mouse) | ADH1, ADH-1 | P41680 |

TABLE 4-continued

Exemplary alcohol dehydrogenase enzymes.

| Organism | Gene Name | Accession No. |
|---|---|---|
| Rattus norvegicus (Rat) | Adh1, Adh-1 | P06757 |
| Drosophila virilis (Fruit fly) | Adh1, Adh-1, GJ18208 | B4M8Y0 |
| Scheffersomyces stipitis (strain ATCC 58785/CBS 6054/ NBRC 10063/NRRL Y-11545) (Yeast) (Pichia stipitis) | ADH1, ADH2, PICST_68558 | O00097 |
| Aspergillus flavus (strain ATCC 200026/FGSC A1120/ NRRL 3357/JCM 12722/SRRC 167) | adh1, AFLA_048690 | P41747 |
| Neurospora crassa (strain ATCC 24698/74-OR23-1A/CBS 708.71/DSM 1257/FGSC 987) | adh-1, B17C10.210, NCU01754 | Q9P6C8 |
| Candida albicans (Yeast) | ADH1, CAD | P43067 |
| Olyza sativa subsp. japonica (Rice) | ADH1, DUPR11.3, Os11g0210300, LOC_Os11g10480, OsJ_032001 | Q2R8Z5 |
| Drosophila mojavensis (Fruit fly) | Adh1, GI17644 | P09370 |
| Kluyveromyces lactis (strain ATCC 8585/CBS 2359/DSM 70799/NBRC 1267/NRRL Y-1140/WM37) (Yeast) (Candida sphaerica) | ADH1, KLLA0F21010g | P20369 |
| Olyza sativa subsp. indica (Rice) | ADH1, OsI_034290 | Q75ZX4 |
| Pongo abelii (Sumatran orangutan) (Pongo pygmaeus abelii) | ADH1A | Q5RBP7 |
| Homo sapiens (Human) | ADH1A, ADH1 | P07327 |
| Macaca mulatta (Rhesus macaque) | ADH1A, ADH1 | P28469 |
| Pan troglodytes (Chimpanzee) | ADH1B | Q5R1W2 |
| Papio hamathyas (Hamathyas baboon) | ADH1B | P14139 |
| Homo sapiens (Human) | ADH1B, ADH2 | P00325 |
| Homo sapiens (Human) | ADH1C, ADH3 | P00326 |
| Papio hamathyas (Hamathyas baboon) | ADH1C, ADH3 | O97959 |
| Ceratitis capitata (Mediterranean fruit fly) (Tephritis capitata) | ADH2 | P48815 |
| Ceratitis cosyra (Mango fruit fly) (Trypeta cosyra) | ADH2 | Q70UP5 |
| Ceratitis rosa (Natal fruit fly) (Pterandrus rosa) | ADH2 | Q70UP6 |
| Drosophila arizonae (Fruit fly) | Adh2 | P27581 |
| Drosophila buzzatii (Fruit fly) | Adh2 | P25720 |
| Drosophila hydei (Fruit fly) | Adh2 | P23237 |
| Drosophila montana (Fruit fly) | Adh2 | P48587 |
| Drosophila mulleri (Fruit fly) | Adh2 | P07160 |
| Drosophila wheeleri (Fruit fly) | Adh2 | P24267 |
| Entamoeba histolytica | ADH2 | Q24803 |
| Hordeum vulgare (Barley) | ADH2 | P10847 |
| Kluyveromyces marxianus (Yeast) (Candida kefyr) | ADH2 | Q9P4C2 |
| Zea mays (Maize) | ADH2 | P04707 |
| Olyza sativa subsp. indica (Rice) | ADH2 | Q4R1E8 |
| Solanum lycopersicum (Tomato) (Lycopersicon esculentum) | ADH2 | P28032 |
| Solanum tuberosum (Potato) | ADH2 | P14674 |
| Scheffersomyces stipitis (strain ATCC 58785/CBS 6054/ NBRC 10063/NRRL Y-11545) (Yeast) (Pichia stipitis) | ADH2, ADH1, PICST_27980 | O13309 |
| Arabidopsis thaliana (Mouse-ear cress) | ADH2, ADHIII, FDH1, At5g43940, MRH10.4 | Q96533 |
| Saccharomyces cerevisiae (strain ATCC 204508/S288c) (Baker's yeast) | ADH2, ADR2, YMR303C, YM9952.05C | P00331 |
| Candida albicans (strain SC5314/ATCC MYA-2876) (Yeast) | ADH2, Ca41C10.04, CaO19.12579, CaO19.5113 | O94038 |
| Oryza sativa subsp. japonica (Rice) | ADH2, DUPR11.1, Os11g0210500, LOC Os11g10510 | Q0ITW7 |
| Drosophila mojavensis (Fruit fly) | Adh2, GI17643 | P09369 |
| Kluyveromyces lactis (strain ATCC 8585/CBS 2359/DSM 70799/NBRC 1267/NRRL Y-1140/WM37) (Yeast) (Candida sphaerica) | ADH2, KLLA0F18260g | P49383 |
| Oryctolagus cuniculus (Rabbit) | ADH2-1 | O46649 |
| Oryctolagus cuniculus (Rabbit) | ADH2-2 | O46650 |
| Hordeum vulgare (Barley) | ADH3 | P10848 |
| Solanum tuberosum (Potato) | ADH3 | P14675 |
| Kluyveromyces lactis (strain ATCC 8585/CBS 2359/DSM 70799/NBRC 1267/NRRL Y-1140/WM37) (Yeast) (Candida sphaerica) | ADH3, KLLA0B09064g | P49384 |
| Saccharomyces cerevisiae (strain ATCC 204508/S288c) (Baker's yeast) | ADH3, YMR083W, YM9582.08 | P07246 |
| Homo sapiens (Human) | ADH4 | P08319 |
| Mus musculus (Mouse) | Adh4 | Q9QYY9 |
| Rattus norvegicus (Rat) | Adh4 | Q64563 |
| Struthio camelus (Ostrich) | ADH4 | P80468 |
| Kluyveromyces lactis (strain ATCC 8585/CBS 2359/DSM | ADH4, | P49385 |

TABLE 4-continued

Exemplary alcohol dehydrogenase enzymes.

| Organism | Gene Name | Accession No. |
|---|---|---|
| 70799/NBRC 1267/NRRL Y-1140/WM37) (Yeast) (Candida sphaerica) | KLLA0F13530g | |
| Schizosaccharomyces pombe (strain 972/ATCC 24843) (Fission yeast) | adh4, SPAC5H10.06c | Q09669 |
| Saccharomyces cerevisiae (strain YJM789) (Baker's yeast) | ADH4, ZRG5, SCY_1818 | A6ZTT5 |
| Saccharomyces cerevisiae (strain ATCC 204508/S288c) (Baker's yeast) | ADH4, ZRG5, YGL256W, NRC465 | P10127 |
| Saccharomyces pastorianus (Lager yeast) (Saccharomyces cerevisiae x Saccharomyces eubayanus) | ADH5 | Q6XQ67 |
| Bos taurus (Bovine) | ADH5 | Q3ZC42 |
| Equus caballus (Horse) | ADH5 | P19854 |
| Mus musculus (Mouse) | Adh5, Adh-2, Adh2 | P28474 |
| Rattus norvegicus (Rat) | Adh5, Adh-2, Adh2 | P12711 |
| Oryctolagus cuniculus (Rabbit) | ADH5, ADH3 | O19053 |
| Homo sapiens (Human) | ADH5, ADHX, FDH | P11766 |
| Dictyostelium discoideum (Slime mold) | adh5, DDB_G0281865 | Q54TC2 |
| Saccharomyces cerevisiae (strain ATCC 204508/S288c) (Baker's yeast) | ADH5, YBR145W, YBR1122 | P38113 |
| Homo sapiens (Human) | ADH6 | P28332 |
| Peromyscus maniculatus (North American deer mouse) | ADH6 | P41681 |
| Pongo abelii (Sumatran orangutan) (Pongo pygmaeus abelii) | ADH6 | Q5R7Z8 |
| Rattus norvegicus (Rat) | Adh6 | Q5XI95 |
| Homo sapiens (Human) | ADH7 | P40394 |
| Rattus norvegicus (Rat) | Adh7 | P41682 |
| Mus musculus (Mouse) | Adh7, Adh-3, Adh3 | Q64437 |
| Mycobacterium tuberculosis (strain CDC 1551/Oshkosh) | adhA, MT1911 | P9WQC0 |
| Rhizobium meliloti (strain 1021) (Ensifer meliloti) (Sinorhizobium meliloti) | adhA, RA0704, SMa1296 | O31186 |
| Mycobacterium tuberculosis (strain ATCC 25618/H37Rv) | adhA, Rv1862 | P9WQC1 |
| Zymomonas mobilis subsp. mobilis (strain ATCC 31821/ZM4/CP4) | adhA, ZMO1236 | P20368 |
| Mycobacterium bovis (strain ATCC BAA-935/AF2122/97) | adhB, Mb0784c | Q7U1B9 |
| Mycobacterium tuberculosis (strain CDC 1551/Oshkosh) | adhB, MT0786 | P9WQC6 |
| Mycobacterium tuberculosis (strain ATCC 25618/H37Rv) | adhB, Rv0761c, MTCY369.06c | P9WQC7 |
| Zymomonas mobilis subsp. mobilis (strain ATCC 31821/ZM4/CP4) | adhB, ZM01596 | P0DJA2 |
| Zymomonas mobilis subsp. mobilis (strain ATCC 10988/DSM 424/LMG 404/NCIMB 8938/NRRL B-806/ZM1) | adhB, Zmob_1541 | F8DVL8 |
| Mycobacterium tuberculosis (strain CDC 1551/Oshkosh) | adhD, MT3171 | P9WQB8 |
| Mycobacterium tuberculosis (strain ATCC 25618/H37Rv) | adhD, Rv3086 | P9WQB9 |
| Clostridium acetobutylicum (strain ATCC 824/DSM 792/JCM 1419/LMG 5710/VKM B-1787) | adhE, aad, CA_P0162 | P33744 |
| Escherichia coli (strain K12) | adhE, ana, b1241, JW1228 | P0A9Q7 |
| Escherichia coli O157:H7 | adhE, Z2016, ECs1741 | P0A9Q8 |
| Rhodobacter sphaeroides (strain ATCC 17023/2.4.1/NCIB 8253/DSM 158) | adhI, RHOS4_11650, RSP_2576 | P72324 |
| Olyza sativa subsp. indica (Rice) | ADHIII, OsI_009236 | A2XAZ3 |
| Escherichia coli (strain K12) | adhP, yddN, b1478, JW1474 | P39451 |
| Geobacillus stearothermophilus (Bacillus stearothermophilus) | adhT | P12311 |
| Emericella nidulans (strain FGSC A4/ATCC 38163/CBS 112.46/NRRL 194/M139) (Aspergillus nidulans) | alcA, AN8979 | P08843 |
| Emericella nidulans (strain FGSC A4/ATCC 38163/CBS 112.46/NRRL 194/M139) (Aspergillus nidulans) | alc, AN3741 | P54202 |
| Emericella nidulans (strain FGSC A4/ATCC 38163/CBS 112.46/NRRL 194/M139) (Aspergillus nidulans) | alcC, adh3, AN2286 | P07754 |
| Arabidopsis thaliana (Mouse-ear cress) | At1g22430, F12K8.22 | Q9SK86 |
| Arabidopsis thaliana (Mouse-ear cress) | At1g22440, F12K8.21 | Q9SK87 |
| Arabidopsis thaliana (Mouse-ear cress) | At1g32780, F6N18.16 | A1L4Y2 |
| Arabidopsis thaliana (Mouse-ear cress) | At1g64710, F13O11.3 | Q8VZ49 |
| Arabidopsis thaliana (Mouse-ear cress) | At4g22110, F1N20.210 | Q0V7W6 |
| Arabidopsis thaliana (Mouse-ear cress) | At5g24760, T4C12_30 | Q8LEB2 |
| Arabidopsis thaliana (Mouse-ear cress) | At5g42250, K5J14.5 | Q9FH04 |
| Zea mays (Maize) | FDH | P93629 |
| Drosophila melanogaster (Fruit fly) | Fdh, gfd, ODH, CG6598 | P46415 |
| Bacillus subtilis (strain 168) | gbsB, BSU31050 | P71017 |
| Caenorhabditis elegans | H24K24.3 | Q17335 |
| Olyza sativa subsp. japonica (Rice) | Os02g0815500, LOC_Os02g57040, | Q0DWH1 |

TABLE 4-continued

Exemplary alcohol dehydrogenase enzymes.

| Organism | Gene Name | Accession No. |
|---|---|---|
| | OsJ_008550, P0643F09.4 | |
| Mycobacterium tuberculosis (strain ATCC 25618/H37Rv) | Rv1895 | O07737 |
| Caenorhabditis elegans | sodh-1, K12G11.3 | Q17334 |
| Caenorhabditis elegans | sodh-2, K12G11.4 | O45687 |
| Pseudomonas sp. | terPD | P33010 |
| Escherichia coli (strain K12) | yiaY, b3589, JW5648 | P37686 |
| Moraxella sp. (strain TAE123) | | P81786 |
| Alligator mississippiensis (American alligator) | | P80222 |
| Catharanthus roseus (Madagascar periwinkle) (Vinca rosea) | | P85440 |
| Gadus morhua subsp. callarias (Baltic cod) (Gadus callarias) | | P26325 |
| Naja naja (Indian cobra) | | P80512 |
| Pisum sativum (Garden pea) | | P12886 |
| Pelophylax perezi (Perez's frog) (Rana perezi) | | P22797 |
| Saara hardwickii (Indian spiny-tailed lizard) (Uromastyx hardwickii) | | P25405 |
| Saara hardwickii (Indian spiny-tailed lizard) (Uromastyx hardwickii) | | P25406 |
| Equus caballus (Horse) | | P00327 |
| Equus caballus (Horse) | | P00328 |
| Geobacillus stearothermophilus (Bacillus stearothermophilus) | | P42328 |
| Gadus morhua (Atlantic cod) | | P81600 |
| Gadus morhua (Atlantic cod) | | P81601 |
| Myxine glutinosa (Atlantic hagfish) | | P80360 |
| Octopus vulgaris (Common octopus) | | P81431 |
| Pisum sativum (Garden pea) | | P80572 |
| Saara hardwickii (Indian spiny-tailed lizard) (Uromastyx hardwickii) | | P80467 |
| Scyliorhinus canicula (Small-spotted catshark) (Squalus canicula) | | P86884 |
| Sparus aurata (Gilthead sea bream) | | P79896 |

In some embodiments, an α-dioxygenase is used to catalyze the conversion of a fatty acid to a fatty aldehyde (Hamberg et al. 2005). Alpha-dioxygenases catalyze the conversion of a $C_n$ fatty acid to a $C_{n-1}$ aldehyde and may serve as an alternative to both ADH and AOX for fatty aldehyde production if a fatty acid is used as a biotransformation substrate. Due to the chain shortening of the dioxygenase reaction, this route requires a different synthesis pathway compared to the ADH and AOX routes. Biotransformations of E. coli cells expressing a rice α-dioxygenase exhibited conversion of C10, C12, C14 and C16 fatly acids to the corresponding $C_{n-1}$ aldehydes. With the addition of the detergent Triton X 100, 3.7 mM of pentadecanal (0.8 g/L) was obtained after 3 hours from hexadecanoic acid with 74% conversion (Kaehne et al. 2011). Exemplary α-dioxygenases are shown in Table 5.

Synthesis of Polyenes Via Metathesis Reactions

In some embodiments, the metathesis reaction partner is a protected alcohol according to Formula IIa:

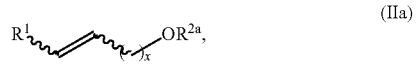

(IIa)

wherein $R^{2a}$ is an alcohol protecting group, and the metathesis product is a compound according to Formula IV:

TABLE 5

Exemplary alpha-dioxygenases.

| Entry | Organism | Gene names |
|---|---|---|
| Q9SGH6 | Arabidopsis thaliana (Mouse-ear cress) | DOX1 DIOX1 PADOX-1 PIOX At3g01420 T13O15.6 |
| Q9C9U3 | Arabidopsis thaliana (Mouse-ear cress) | DOX2 DIOX2 At1g73680 F25P22.10 |
| P14550 | Homo sapiens (Human) | AKR1A1 ALDR1 ALR |
| Q69EZ9 | Solanum lycopersicum (Tomato) (Lycopersicon esculentum) | LOC543896 |
| Q5WM33 | Solanum lycopersicum (Tomato) (Lycopersicon esculentum) | alpha-DOX2 |
| Q69F00 | Solanum lycopersicum (Tomato) (Lycopersicon esculentum) | |
| D7LAG3 | Arabidopsis lyrata subsp. lyrata (Lyre-leaved rock-cress) | ALPHA-DOX1 ARALYDRAFT_317048 |
| D8LJL3 | Ectocarpus siliculosus (Brown alga) | DOX Esi_0026_0091 |
| E3U9P5 | Nicotiana attenuata (Coyote tobacco) | adox2 |

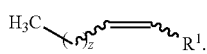

(IV)

In some embodiments, $R^1$ is $C_{2-8}$ alkenyl. Such embodiments can provide polyene pheromones as described in more detail below.

In some embodiments, the metathesis reaction partner is a protected alcohol according to Formula IIa:

(IIa)

wherein $R^{2a}$ is an alcohol protecting group,
and the metathesis product is a compound according to Formula IVc:

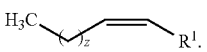

(IVc)

In some embodiments, the metathesis reaction partner is a protected alcohol according to Formula IIc:

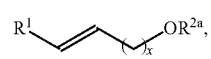

(IIc)

wherein $R^{2a}$ is an alcohol protecting group,
and the metathesis product is a compound according to Formula IVc:

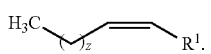

(IVc)

Metathesis of Fatty Acid Esters

Fatty acid alkyl esters (FAAE) can be reduced to either aldehydes or alcohols by the use of well-defined homogenous and heterogeneous methodologies. Therefore, in some cases it can be useful to produce fatty olefin derivatives via Z-selective cross-metathesis of a FAAE with an olefin as shown in Scheme 4.

Scheme 4

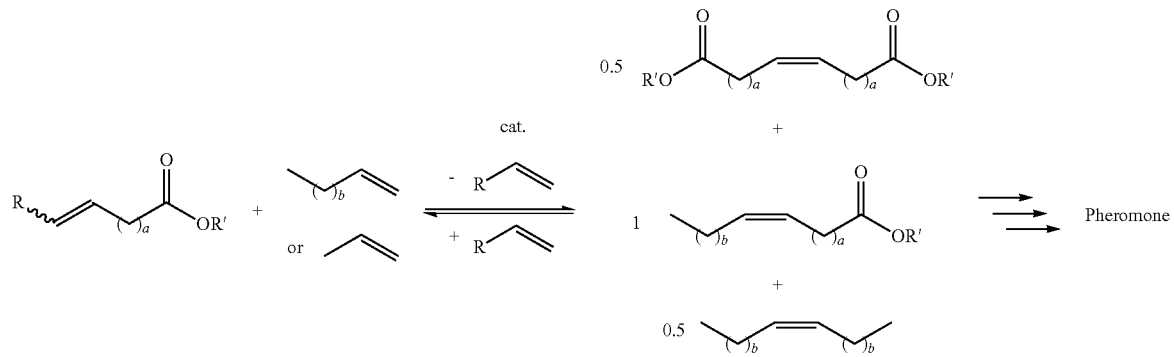

R = H, $C_8H_{17}$  R' = Me, Et

Products obtained from metathesis of protected fatty acid alkyl esters can be converted to a number of pheromones, as set forth in Table 6.

TABLE 6

Pheromones accessible from fatty acid alkyl ester metathesis products.

| Olefin | Metathesis Reaction Partner | Metathesis Product | Exemplary Pheromone derived from Metathesis Product | Pheromone CAS # |
|---|---|---|---|---|
| propylene | oleate | (Z)-9-undecenoate | (Z)-9-undecenyl acetate | 85576-13-2 |
| 1-butene | oleate | (Z)-9-dodecenoate | (Z)-9-dodecenal | 56219-03-5 |
| 1-butene | oleate | (Z)-9-dodecenoate | (Z)-9-dodecenyl acetate | 16974-11-1 |
| 1-pentene | oleate | (Z)-9-tridecenoate | (Z)-9-tridecenyl acetate | 35835-78-0 |
| 1-hexene | oleate | (Z)-tetradec-9-enoate | (Z)-9-tetradecenal | 53939-27-8 |
| 1-hexene | oleate | (Z)-tetradec-9-enoate | (Z)-9-tetradecenyl acetate | 16725-53-4 |
| 1-hexene | oleate | (Z)-tetradec-9-enoate | (Z)-9-tetradecenyl formate | 56776-10-4 |
| 1-hexene | oleate | (Z)-tetradec-9-enoate | (Z)-9-tetradecenyl nitrate | 143816-21-1 |

TABLE 6-continued

Pheromones accessible from fatty acid alkyl ester metathesis products.

| Olefin | Metathesis Reaction Partner | Metathesis Product | Exemplary Pheromone derived from Metathesis Product | Pheromone CAS # |
|---|---|---|---|---|
| 1-heptene | oleate | (Z)-9-pentadecenoate | (Z)-9-pentadecenyl acetate | 64437-41-8 |
| 1-octene | oleate | (Z)-9-hexadecenoate | (Z)-9-hexadecenal | 56219-04-6 |
| 1-octene | oleate | (Z)-9-hexadecenoate | (Z)-9-hexadecenyl acetate | 34010-20-3 |
| propylene | 9-decenoate | (Z)-9-undecenoate | (Z)-9-undecenyl acetate | 85576-13-2 |
| 1-butene | 9-decenoate | (Z)-9-dodecenoate | (Z)-9-dodecenal | 56219-03-5 |
| 1-butene | 9-decenoate | (Z)-9-dodecenoate | (Z)-9-dodecenyl acetate | 16974-11-1 |
| 1-pentene | 9-decenoate | (Z)-9-tridecenoate | (Z)-9-tridecenyl acetate | 35835-78-0 |
| 1-hexene | 9-decenoate | (Z)-tetradec-9-enoate | (Z)-9-tetradecenal | 53939-27-8 |
| 1-hexene | 9-decenoate | (Z)-tetradec-9-enoate | (Z)-9-tetradecenyl acetate | 16725-53-4 |
| 1-hexene | 9-decenoate | (Z)-tetradec-9-enoate | (Z)-9-tetradecenyl formate | 56776-10-4 |
| 1-hexene | 9-decenoate | (Z)-tetradec-9-enoate | (Z)-9-tetradecenyl nitrate | 143816-21-1 |
| 1-heptene | 9-decenoate | (Z)-9-pentadecenoate | (Z)-9-pentadecenyl acetate | 64437-41-8 |
| 1-octene | 9-decenoate | (Z)-9-hexadecenoate | (Z)-9-hexadecenal | 56219-04-6 |
| 1-octene | 9-decenoate | (Z)-9-hexadecenoate | (Z)-9-hexadecenyl acetate | 34010-20-3 |
| propylene | 10-undecenoate | (Z)-10-dodecenoate | (Z)-10-dodecenyl acetate | 35148-20-0 |
| 1-butene | 10-undecenoate | (Z)-10-tridecenoate | (Z)-10-tridecenyl acetate | 64437-24-7 |
| 1-pentene | 10-undecenoate | (Z)-10-tetradecenoate | (Z)-10-tetradecenyl acetate | 35153-16-3 |
| 1-hexene | 10-undecenoate | (Z)-10-pentadecenoate | (Z)-10-pentadecenal | 60671-80-9 |
| 1-hexene | 10-undecenoate | (Z)-10-pentadecenoate | (Z)-10-pentadecenyl acetate | 64437-43-0 |
| 1-heptene | 10-undecenoate | (Z)-10-hexadecenoate | (Z)-10-hexadecenyl acetate | 56218-71-4 |

Accordingly, some embodiments of the invention provide methods wherein the metathesis reaction partner is an ester according to Formula IIb:

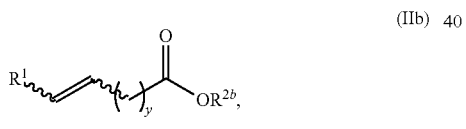
(IIb)

wherein $R^{2b}$ is $C_{1-8}$ alkyl and subscript y is an integer ranging from 0 to 17; and
wherein the metathesis product is a compound according to Formula IIIb:

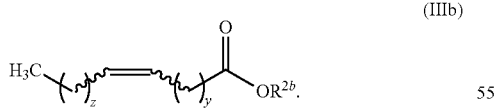
(IIIb)

In some embodiments, the metathesis reaction partner is an ester according to Formula IIb:

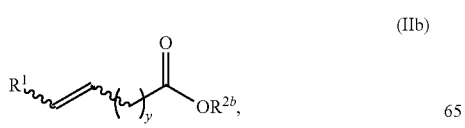
(IIb)

wherein $R^{2b}$ is $C_{1-8}$ alkyl and subscript y is an integer ranging from 0 to 17; and the metathesis product is a compound according to Formula IIIc:

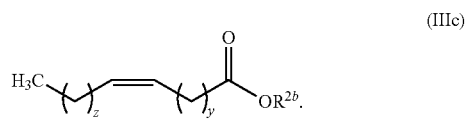
(IIIc)

In some embodiments, the metathesis reaction partner is an ester according to Formula IIc:

(IIc)

wherein $R^{2b}$ is $C_{1-8}$ alkyl and subscript y is an integer ranging from 0 to 17; and the metathesis product is a compound according to Formula IIIc:

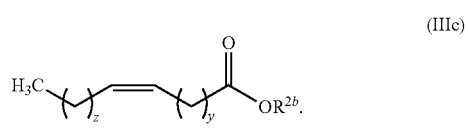
(IIIc)

Metathesis products according to Formula IIIc can be prepared using a number of Z-selective catalysts as described below.

In some embodiments, the methods can be used to prepare products according to Formula IIIb or IIIc wherein y is 0 and z is 4; or y is 1 and z is 3; or y is 3 and z is 1; or y is 4 and z is 0; or y is 0 and z is 5; or y is 1 and z is 4; or y is 2 and z is 3; or y is 3 and z is 2; or y is 4 and z is 1; or y is 5 and z is 0; or y is 0 and z is 6; or y is 1 and z is 5; or y is 2 and z is 4; or y is 4 and z is 2; or y is 5 and z is 1; or y is 6 and z is 0; or y is 0 and z is 7; or y is 1 and z is 6; or y is 2 and z is 5; or y is 3 and z is 4; or y is 4 and z is 3; or y is 5 and z is 2; or y is 6 and z is 1; or y is 7 and z is 0; or y is 0 and z is 8; or y is 1 and z is 7; or y is 2 and z is 6; or y is 3 and z is 5; or y is 5 and z is 3; or y is 6 and z is 2; or y is 7 and z is 1; or y is 8 and z is 0; or y is 0 and z is 9; or y is 1 and z is 8; or y is 2 and z is 7; or y is 3 and z is 6; or y is 4 and z is 5; or y is 5 and z is 4; or y is 6 and z is 3; or y is 7 and z is 2; or y is 8 and z is 1; or y is 9 and z is 0; or y is 0 and z is 10; or y is 1 and z is 9; or y is 2 and z is 8; or y is 3 and z is 7; or y is 4 and z is 6; or y is 6 and z is 4; or y is 7 and z is 3; or y is 8 and z is 2; or y is 9 and z is 1; or y is 10 and z is 0; or y is 0 and z is 11; or y is 1 and z is 10; or y is 2 and z is 9; or y is 3 and z is 8; or y is 4 and z is 7; or y is 5 and z is 6; or y is 6 and z is 5; or y is 7 and z is 4; or y is 8 and z is 3; or y is 9 and z is 2; or y is 10 and z is 1; or y is 11 and z is 0; or y is 0 and z is 12; or y is 1 and z is 11; or y is 2 and z is 10; or y is 3 and z is 9; or y is 4 and z is 8; or y is 5 and z is 7; or y is 7 and z is 5; or y is 8 and z is 4; or y is 9 and z is 3; or y is 10 and z is 2; or y is 11 and z is 1; or y is 12 and z is 0; or y is 0 and z is 13; or y is 1 and z is 12; or y is 2 and z is 11; or y is 3 and z is 10; or y is 4 and z is 9; or y is 5 and z is 8; or y is 6 and z is 7; or y is 7 and z is 6; or y is 8 and z is 5; or y is 9 and z is 4; or y is 10 and z is 3; or y is 11 and z is 2; or y is 12 and z is 1; or y is 13 and z is 0; or y is 0 and z is 14; or y is 1 and z is 13; or y is 2 and z is 12; or y is 3 and z is 11; or y is 4 and z is 10; or y is 5 and z is 9; or y is 6 and z is 8; or y is 8 and z is 6; or y is 9 and z is 5; or y is 10 and z is 4; or y is 11 and z is 3; or y is 12 and z is 2; or y is 13 and z is 1; or y is 14 and z is 0; or y is 0 and z is 15; or y is 1 and z is 14; or y is 2 and z is 13; or y is 3 and z is 12; or y is 4 and z is 11; or y is 5 and z is 10; or y is 6 and z is 9; or y is 7 and z is 8; or y is 8 and z is 7; or y is 9 and z is 6; or y is 10 and z is 5; or y is 11 and z is 4; or y is 12 and z is 3; or y is 13 and z is 2; or y is 14 and z is 1; or y is 15 and z is 0; or y is 0 and z is 16; or y is 1 and z is 15; or y is 2 and z is 14; or y is 3 and z is 13; or y is 4 and z is 12; or y is 5 and z is 11; or y is 6 and z is 10; or y is 7 and z is 9; or y is 9 and z is 7; or y is 10 and z is 6; or y is 11 and z is 5; or y is 12 and z is 4; or y is 13 and z is 3; or y is 14 and z is 2; or y is 15 and z is 1; or y is 16 and z is 0; or y is 1 and z is 16; or y is 2 and z is 15; or y is 3 and z is 14; or y is 4 and z is 13; or y is 5 and z is 12; or y is 6 and z is 11; or y is 7 and z is 10; or y is 8 and z is 9; or y is 9 and z is 8; or y is 10 and z is 7; or y is 11 and z is 6; or y is 12 and z is 5; or y is 13 and z is 4; or y is 14 and z is 3; or y is 15 and z is 2; or y is 16 and z is 1; or y is 17 and z is 0; or y is 0 and z is 17; or y is 1 and z is 17; or y is 2 and z is 16; or y is 3 and z is 15; or y is 4 and z is 14; or y is 5 and z is 13; or y is 6 and z is 12; or y is 7 and z is 11; or y is 8 and z is 10; or y is 10 and z is 8; or y is 11 and z is 7; or y is 12 and z is 6; or y is 13 and z is 5; or y is 14 and z is 4; or y is 15 and z is 3; or y is 16 and z is 2; or y is 17 and z is 1. In some embodiments, both y and z are 0, 1, 2, 3, 4, 5, 6, 7, 8, 9, 10, 11, 12, 13, 14, 15, 16, or 17.

Conversion of Fatty Acid Ester Metathesis Products to Fatty Olefin Derivatives

In some embodiments, converting the metathesis product to the fatty olefin derivative includes reducing the metathesis product of Formula IIIb to form an alkenol according to Formula Vb:

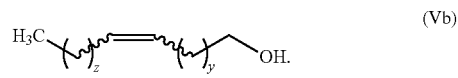

In some embodiments, converting the metathesis product to the fatty olefin derivative includes reducing the metathesis product of Formula IIIc to form an alkenol according to Formula Vc:

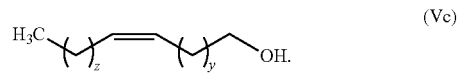

Any suitable conditions for converting the product of Formula IIIb to the alkenol of Formula Vb can be used in conjunction with the method of the invention. Homogenous or heterogenous conditions can be used. Examples of homogenous conditions include, but are not limited to: hydrogenolysis using ligated precious metal catalysts (Tan, et al. *Org. Lett.* 2015, 17(3), 454; Spasyuk, D. et al. *J. Am. Chem. Soc.* 2015, 137, 3743; WO 2014/139030), metal hydride-catalyzed reduction using silane reagents (Mimoun, H. *J. Org. Chem.* 1999, 64, 2582; U.S. Pat. No. 6,533,960); and reduction using aluminum reagents such as lithium aluminum hydride, sodium bis(2-methoxyethoxy)aluminumhydride (also known by the tradename RED-AL), or diisobutyl aluminum hydride (CN 103319704; Chandrasekhar, et al. *Tetrahedron Lett.* 1998, 39, 909). Unsaturated fatty alcohols can also be prepared via hydrogenolysis with heterogeneous catalysts, such as ZnO or CuO/ZnO supported CHI chromite, alumina, or other material. Typically, 1-2 molar equivalents of the reducing agent with respect to the fatty acid ester metathesis product will be used. In some embodiments, around 1.0, 1.1, 1.2, 1.3, 1.4, or 1.5 molar equivalents of the reducing agent with respect to the fatty acid ester is used to form the corresponding alkenol.

Any suitable solvent can be used for reducing the fatty acid ester metathesis product. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. The reduction reaction is typically conducted at temperatures ranging from around −78° C. to about 25° C. for a period of time sufficient to form the alkenol. The reaction can be conducted for a period of time ranging from a few minutes to several hours or longer, depending on the particular fatty acid ester and reducing agent used in the reaction. For example, the reduction of a methyl (Z)-tetradec-9-enoate with an aluminum reagent (e.g., sodium bis(2-methoxyethoxy)-aluminumhydride) can be conducted for 1-2 hours at a temperature ranging from around 0° C. to around 20° C.

In some embodiments, the alkenol is the fatty olefin derivative. In some embodiments, the alkenol is a pheromone.

In some embodiments, converting the metathesis product to the fatty olefin derivative further includes acylating the alkenol of Formula Vb, thereby forming a fatty olefin derivative according to Formula VIb:

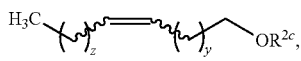
(VIb)

wherein $R^{2c}$ is $C_{1-6}$ acyl. The acylation step can be conducted as described above.

In some embodiments, converting the metathesis product to the fatty olefin derivative further includes acylating the alkenol of Formula Vc, thereby forming a fatty olefin derivative according to Formula VIc:

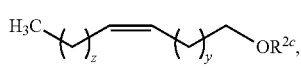
(VIc)

wherein $R^{2c}$ is $C_{1-6}$ acyl. The acylation step can be conducted as described above.

In some embodiments, converting the metathesis product to the fatty olefin derivative further includes oxidizing the alkenol of Formula Vb, thereby forming a fatty olefin derivative according to Formula VIIb:

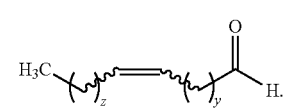
(VIIb)

In some embodiments, converting the metathesis product to the fatty olefin derivative further includes oxidizing the alkenol of Formula Vc, thereby forming a fatty olefin derivative according to Formula VIIc:

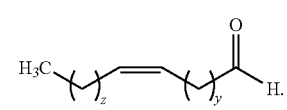
(VIIc)

In some embodiments, the metathesis reaction partner is an ester according to Formula IIb or Formula IIc as described above, and the metathesis product is a compound according to Formula IV:

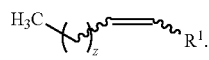
(IV)

In some embodiments, the metathesis reaction partner is an ester according to Formula IIb or Formula IIc as described above, and the metathesis product is a compound according to Formula IVc:

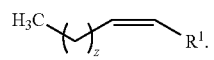
(IVc)

In some embodiments, $R^1$ in Formula IV or Formula IVc is $C_{2-18}$ alkenyl.

In another embodiment, the invention provides a method for synthesizing a fatty olefin derivative, the method comprising:

a) contacting an olefin according to Formula I

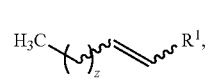
(I)

with a methathesis reaction partner according to formula IIb

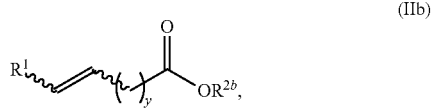
(IIb)

in the presence of a metathesis catalyst under conditions sufficient to form a metathesis product according to Formula IIIb:

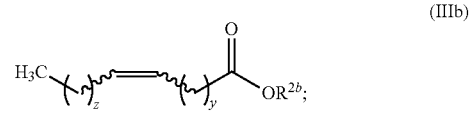
(IIIb)

b) converting the metathesis product to the fatty olefin derivative;
wherein:
each $R^1$ is independently selected from the group consisting of H, $C_{1-18}$ alkyl, and $C_{2-18}$ alkenyl;
$R^{2b}$ is $C_{1-8}$ alkyl;
subscript y is an integer ranging from 0 to 17; and
subscript z is an integer ranging from 0 to 17.

In some embodiments where the metathesis reaction partner according to Formula IIb is employed, converting the metathesis product to the fatty olefin derivative comprises reducing the metathesis product to form an alkenol according to Formula Vb:

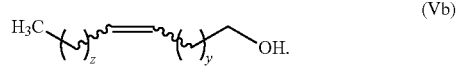
(Vb)

In some embodiments where the metathesis reaction partner according to Formula IIb is employed, the alkenol is the fatty olefin derivative.

In some embodiments where the metathesis reaction partner according to Formula IIb is employed, converting the metathesis product to the fatly olefin derivative further comprises acylating the alkenol, thereby forming a fatty olefin derivative according to Formula VIb:

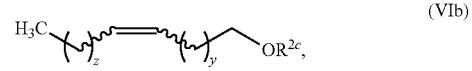
(VIb)

wherein $R^{26}$ is $C_{1-6}$ acyl.

In some embodiments where the metathesis reaction partner according to Formula IIb is employed, $R^1$ is H, $R^{2b}$ is methyl, subscript y is 7, and subscript z is 3. In some such embodiments, $R^1$ is H, $R^{2b}$ is methyl, subscript y is 7, subscript z is 3, and $R^{2c}$ is acetyl.

In some embodiments where the metathesis reaction partner according to Formula IIb is employed, converting the metathesis product to the fatty olefin derivative further comprises oxidizing the alkenol, thereby forming a fatty olefin derivative according to Formula VIIb:

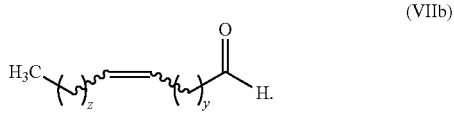
(VIIb)

In some embodiments where the metathesis reaction partner according to Formula IIb is employed, converting the metathesis product to the fatty olefin derivative further comprises reducing the metathesis product, thereby forming a fatty olefin derivative according to Formula VIIb:

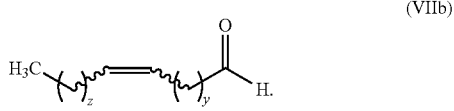
(VIIb)

In some embodiments, $R^1$ is H, $R^{2b}$ is methyl, subscript y is 7, and subscript z is 3 in the fatty olefin derivative according to Formula VIIb.

In some embodiments where the metathesis reaction partner according to Formula IIb is employed, the olefin has a structure according to Formula Ia:

(Ia)

In some embodiments, subscript z is 3 in the olefin according to Formula Ia.

In some embodiments where the metathesis reaction partner according to Formula IIb is employed, the metathesis product comprises a Z olefin. In some embodiments, at least about 90% of the olefin is a Z olefin. In some embodiments, the metathesis catalyst is a Z-selective molybdenum catalyst or a Z-selective tungsten catalyst as described below. In some embodiments, the metathesis catalyst has a structure according to Formula 2 as described below. In some embodiments, the metathesis catalyst has a structure according to Formula 2a as described below.

In another embodiment, the invention provides a method for synthesizing a fatty olefin derivative as described above wherein the olefin according to Formula I is a linear $C_3$-$C_{12}$ alpha olefin, the metathesis reaction partner according to Formula IIb is a $\Delta^9$-unsaturated fatty acid alkyl ester, the metathesis catalyst is a Z-selective metathesis catalyst, and the metathesis product according to Formula IIIb is a $C_{11}$-$C_{20}$ (Z)-9-unsaturated fatty acid alkyl ester. In some such embodiments, converting the metathesis product to the fatty olefin derivative comprises contacting the $C_{11}$-$C_{20}$ (Z)-9-unsaturated fatty acid alkyl ester with a reducing agent under conditions sufficient to form a $C_{11}$-$C_{20}$ (Z)-9-fatty alcohol. In some such embodiments, the reducing agent is sodium bis(2-methoxyethoxy)aluminum hydride.

In some embodiments, converting the metathesis product to the fatty olefin derivative further comprises contacting the $C_{11}$-$C_{20}$ (Z)-9-fatty alcohol with an acylating agent in the presence of a base under conditions sufficient to form an acetate ester of the $C_{11}$-$C_{20}$ (Z)-9-fatty alcohol. In some such embodiments, the acylating agent is acetic anhydride.

In some embodiments, converting the metathesis product to the fatty olefin derivative further comprises oxidizing the $C_{11}$-$C_{20}$ (Z)-9-fatty alcohol to form a $C_{11}$-$C_{20}$ (Z)-9-alkenal.

In some embodiments, converting the metathesis product to the fatty olefin derivative comprises contacting the $C_{11}$-$C_{20}$ (Z)-9-fatty acid alkyl ester with a reducing agent under conditions sufficient to form a $C_{11}$-$C_{20}$ (Z)-9-alkenal. In some such embodiments, the reducing agent is amine-modified sodium bis(2-methoxyethoxy)aluminumhydride. The amine-modified sodium bis(2-methoxyethoxy)aluminumhydride can be generated in situ via reaction of the sodium bis(2-methoxyethoxy)aluminumhydride with either a primary amine or secondary amine (as described, for example, by Shin, et al. *Bull. Korean Chem. Soc.* 2014, 35, 2169, which is incorporated herein by reference). In some such embodiments, the metathesis catalyst has a structure according to Formula 2a as described below.

In another embodiment, the invention provides a method for synthesizing a fatty olefin derivative as described above wherein: the fatty acid derivative is (Z)-tetradec-9-en-1-yl acetate; the olefin according to Formula I is hex-1-ene, the metathesis reaction partner according to Formula IIb is a $\Delta^9$-unsaturated fatty acid alkyl ester, the metathesis catalyst is a Z-selective metathesis catalyst, and the metathesis product according to Formula IIIb is an alkyl ester of (Z)-9-tetradec-9-enoate; and wherein converting the metathesis product to the fatty olefin derivative comprises: contacting the alkyl ester of (Z)-9-tetradec-9-enoate with a reducing agent under conditions sufficient to form (Z)-tetradec-9-en-1-ol, and acylating the (Z)-tetradec-9-en-1-ol to form the (Z)-tetradec-9-en-1-yl acetate.

In some such embodiments, the metathesis reaction partner according to Formula IIb is methyl 9-decenoate and the metathesis product is methyl (Z)-tetradec-9-enoate. In some such embodiments, the reducing agent is sodium bis(2-methoxyethoxy)aluminumhydride. In some such embodiments, acylating the (Z)-tetradec-9-en-1-ol comprises contacting the (Z)-tetradec-9-en-1-ol with an acylating agent in the presence of a base under conditions sufficient to form (Z)-tetradec-9-en-1-yl acetate. In some such embodiments, the acylating agent is acetic anhydride. In some such embodiments, the metathesis catalyst has a structure according to Formula 2a as described below.

In another embodiment, the invention provides a method for synthesizing a fatty olefin derivative as described above, wherein the fatty acid derivative is (Z)-tetradec-9-enal, the olefin according to Formula I is hex-1-ene, the metathesis reaction partner according to Formula IIb is a $\Delta^9$-unsaturated fatty acid alkyl ester, the metathesis catalyst is a Z-selective metathesis catalyst, and the metathesis product according to Formula IIIb is an alkyl ester of (Z)-9-tetradec-9-enoate; and wherein converting the metathesis product to the fatty olefin derivative comprises contacting the alkyl ester of (Z)-9-tetradec-9-enoate with a reducing agent under conditions sufficient to form the (Z)-tetradec-9-enal. In some embodiments, the reducing agent is amine-modified sodium bis(2-methoxyethoxy) aluminumhydride. The amine-modified sodium bis(2-methoxyethoxy) aluminumhydride can be generated as described above. In some such embodiments, the Δ⁹-unsaturated fatty acid alkyl ester according to Formula IIg is methyl 9-decenoate and the metathesis product is methyl (Z)-tetradec-9-enoate. In some such embodiments, the metathesis catalyst has a structure according to Formula 2a as described below.

In another embodiment, the invention provides a method for synthesizing a fatty olefin derivative as described above wherein the fatty acid derivative is (Z)-tetradec-9-enal, the olefin according to Formula I is hex-1-ene, the metathesis reaction partner according to Formula IIb is a Δ⁹-unsaturated fatty acid alkyl ester, the metathesis catalyst is a Z-selective metathesis catalyst, and the metathesis product according to Formula IIIb is an alkyl ester of (Z)-tetradec-9-enoate; and wherein converting the metathesis product to the fatty olefin derivative comprises contacting the alkyl ester of (Z)-tetradec-9-enoate with a reducing agent under conditions sufficient to form (Z)-tetradec-9-en-1-ol, and oxidizing the (Z)-tetradec-9-en-1-ol to form the (Z)-tetradec-9-enal. In some such embodiments, the reducing agent is sodium bis(2-methoxyethoxy)aluminumhydride. In some such embodiments, the Δ⁹-unsaturated fatty acid alkyl ester according to Formula IIg is methyl 9-decenoate and the metathesis product is methyl (Z)-tetradec-9-enoate. In some such embodiments, the metathesis catalyst has a structure according to Formula 2a as described below.

In another embodiment, the invention provides a method for synthesizing a fatty olefin derivative according to Formula VIb:

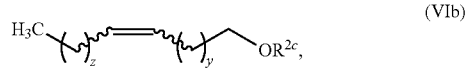
(VIb)

the method comprising:
i) reducing an alkyl ester according to Formula IIb

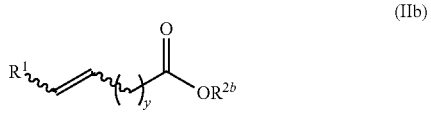
(IIb)

to form an alkenol according to Formula VIII

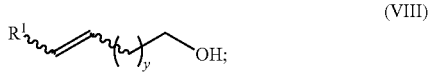
(VIII)

ii) acylating the alkenol to form an acylated alkenol according to Formula IX

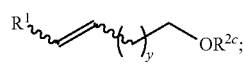

and iii) contacting the acylated alkenol with an olefin according to Formula I

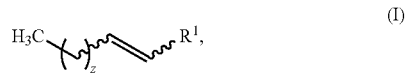
(I)

in the presence of a metathesis catalyst under conditions sufficient to form the fatty olefin derivative; wherein:
$R^1$ is selected from the group consisting of H, $C_{1-18}$ alkyl, and $C_{2-18}$ alkenyl;
$R^{2b}$ is $C_{1-8}$ alkyl,
$R^{2c}$ is $C_{1-6}$ acyl,
subscript y is an integer ranging from 0 to 17;
subscript z is an integer ranging from 0 to 17; and
the metathesis catalyst is a tungsten catalyst or a molybdenum catalyst.

In some embodiments, $R^1$ is H, $R^{2b}$ is methyl, $R^{2c}$ is acetyl, subscript y is 7, and subscript z is 3 in the method for synthesizing a fatty olefin derivative according to Formula VIb. In some embodiments, the metathesis product comprises an E olefin. In some embodiments, the metathesis product comprises a Z-olefin. In some embodiments, the metathesis catalyst is a Z-selective molybdenum catalyst or a Z-selective tungsten catalyst. In some embodiments, the metathesis catalyst has a structure according to Formula 2 as described below. In some embodiments, the metathesis catalyst has a structure according to Formula 2a as described below.

Metathesis Catalysts

The catalysts employed in the present invention generally employ metals which can mediate a particular desired chemical reaction. In general, any transition metal (e.g., having d electrons) can be used to form the catalyst, e.g., a metal selected from one of Groups 3-12 of the periodic table or from the lanthanide series. In some embodiments, the metal is selected from Groups 3-8, or, in some cases, from Groups 4-7. In some embodiments, the metal is selected from Group 6. The term "Group 6" refers to the transition metal group comprising chromium, molybdenum, and tungsten. Additionally, the present invention may also include the formation of heterogeneous catalysts containing forms of these elements (e.g., by immobilizing a metal complex on an insoluble substrate, for example, silica).

The methods of the invention can be assessed in terms of the selectivity of the metathesis reaction—that is, the extent to which the reaction produces a particular olefin isomer, whether a Z olefin (i.e., a cis olefin) or an E olefin (i.e., a trans olefin).

In general, Z-selective catalysts provide metathesis products wherein greater than 15% (w/w) of the olefin is a Z olefin. For example, the metathesis product can contain the Z olefin in an amount ranging from about 20% to about 100%. The metathesis product can contain the Z olefin in an amount ranging from about 25% to about 95%, or from about 30% to about 90%, or from about 35% to about 85%, or from about 40% to about 80%, or from about 45% to about 75%, or from about 50% to about 70%, or from about 55% to about 65%. The metathesis product can contain the Z olefin in an amount ranging from about 15% to about 20%, or from about 20% to about 25%, or from about 25% to about 30%, or from about 30% to about 35%, or from about 35% to about 40%, or from about 40% to about 45%, or from about 45% to about 50%, or from about 50% to about 60%, or from about 60% to about 65%, or from about 65% to about 70%, or from about 70% to about 75%, or from about 75% to about 80%, or from about 80% to about 85%, or from about 85% to about 90%, or from about 90% to about 95%, or from about 95% to about 99%. The metathesis product can contain the Z olefin in an amount of about 55%, 60%, 65%, 70%, 75%, 80%, 85%, 86%, 87%, 88%, 89%, 90%, 91%, 92%, 93%, 94%, 95%, %%, 97%, 98%, 99%, or 100% (w/w).

In general, E-selective catalysts provide metathesis products at least about 85% (w/w) of the olefin is an E olefin. For example, the metathesis product can contain the E olefin in an amount ranging from about 86% to about 100%. The metathesis product can contain the E olefin in an amount ranging from about 86% to about 99%, or from about 88% to about 98%, or from about 90% to about 96%, or from about 92% to about 94%. The metathesis product can contain the E olefin in an amount ranging from about 86% to about 89%, or from about 89% to about 92%, or from about 92% to about 95%, or from about 95% to about 98%. The metathesis product can contain the E olefin in an amount of about 86%, 87%, 88%, 89%, 90%, 91%, 92%, 93%, 94%, 95%, %%, 97%, 98%, 99%, or 100% (w/w).

In some embodiments, the metathesis catalyst has a structure according to Formula 1:

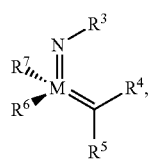

(1)

wherein:
M is Mo or W;
$R^3$ is selected from optionally substituted aryl, optionally substituted heteroaryl, optionally substituted aliphatic, and optionally substituted heteroaliphatic;
each of $R^4$ and $R^5$ is independently selected from hydrogen, optionally substituted aliphatic, optionally substituted heteroaliphatic, optionally substituted aryl, and optionally substituted heteroacyl;
$R^6$ is selected from —O-alkyl, —O-heteroalkyl, —O-aryl, —O-heteroaryl, —N(R″)-alkyl, —N(R″)-heteroalkyl, —N(R″)-aryl, and —N(R″)-heteroaryl, wherein each R″ is independently selected from hydrogen, an amino protecting group, and optionally substituted alkyl,
and wherein $R^6$ is optionally substituted; and
$R^7$ is selected from aryl, heteroaryl, alkyl, heteroalkyl, cycloalkyl, heterocycloalkyl, —O-alkyl, —O-heteroalkyl, —O-aryl, and —O-heteroaryl, each of which is optionally substituted, or
$R^7$ is halogen.

In some embodiments, the metathesis catalyst has a structure according to Formula 1 and the metathesis product comprises a Z olefin.

In some embodiments, $R^6$ is an optionally substituted asymmetric —O-aryl group and $R^7$ is an optionally substituted heteroaryl group.

In some cases, the metal complex includes one or more oxygen-containing ligands lacking a plane of symmetry or nitrogen-containing ligands lacking a plane of symmetry (i.e., asymmetric ligands). In some embodiments, such ligands can coordinate the metal atom via an oxygen atom (e.g., via a hydroxyl group), or other atom of the ligand. The oxygen-containing ligand can coordinate the metal atom via one site of the ligand, i.e., the ligand may be a monodentate ligand.

In some embodiments, a ligand can comprise two sites capable of binding the metal center, wherein a first site is bonded to a protecting group, or other group, that may reduce the ability of the first site to coordinate the metal, and the second site coordinates the metal center. For example, the ligand can be a [1,1'-binaphthalene]-2,2'-diol (BINOL) derivative having two hydroxyl groups, wherein one hydroxyl group is bonded to a protecting group (e.g., a silyl protecting group) and another hydroxyl group coordinates the metal center.

In some embodiments, an asymmetric oxygen-containing ligand is of the following structure:

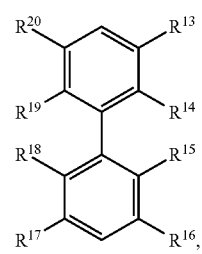

wherein:
$R^{13}$ is an optionally substituted group selected from aryl, heteroaryl, alkyl, or heteroalkyl;
$R^{14}$ is hydrogen, —OH, halogen, —OPG, or an optionally substituted group selected from aliphatic, heteroaliphatic, aryl, aryloxy, heteroaryl, heteroaryloxy, acyl, and acyloxy;
or, together $R^{13}$ and $R^{14}$ are joined to form an optionally substituted partially unsaturated or aryl ring;
$R^{15}$ is —OH, —OPG, or an optionally substituted amino group;
$R^{16}$ is hydrogen, halogen, an optionally substituted group selected from aliphatic, heteroaliphatic, aryl, heteroaryl, or acyl;
each of $R^{17}$, $R^{18}$, $R^{19}$, and $R^{20}$ is independently aryl, heteroaryl, aliphatic, heteroaliphatic, or acyl, optionally substituted;
or, together $R^{17}$ and $R^{18}$ are joined to form an optionally substituted partially unsaturated or aryl ring;
or, together $R^{19}$ and $R^{20}$ are joined to form an optionally substituted partially unsaturated or aryl ring; and
each PG is independently a hydroxyl protecting group.

In some embodiments, $R^3$ is an optionally substituted group selected from aryl and aliphatic.

In some embodiments, $R^3$ is selected from

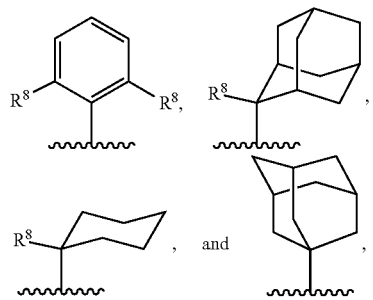

wherein each $R^8$ is independently hydrogen or a monovalent substituent.

In some embodiments, $R^7$ is an optionally substituted group selected from
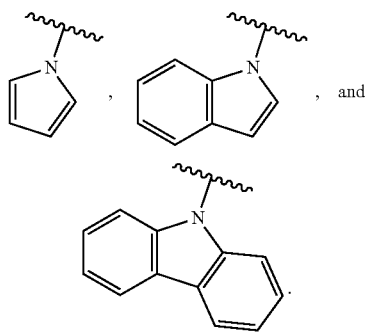
In some embodiments, $R^6$ is an optionally substituted group selected from
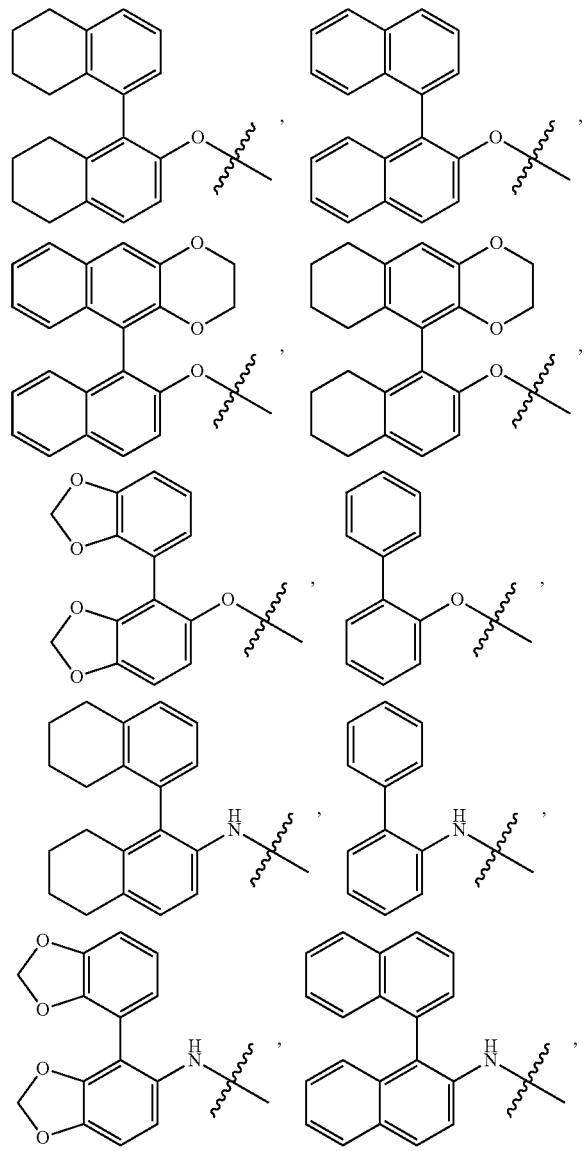
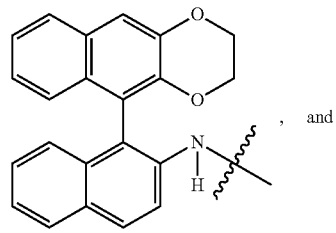
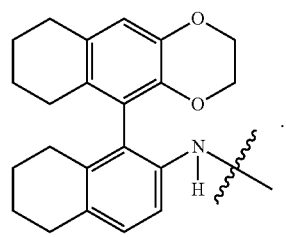 [SMILES: *Nc1ccc2c(c1-c1c3c(cc4c1OCCO4)CCCC3)CCCC2]
In some embodiments, $R^6$ is
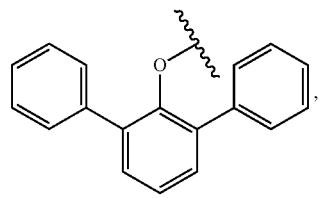 [SMILES: *Oc1c(-c2ccccc2)cccc1-c1ccccc1]
which is optionally substituted.
In some embodiments, the metathesis catalyst is selected from
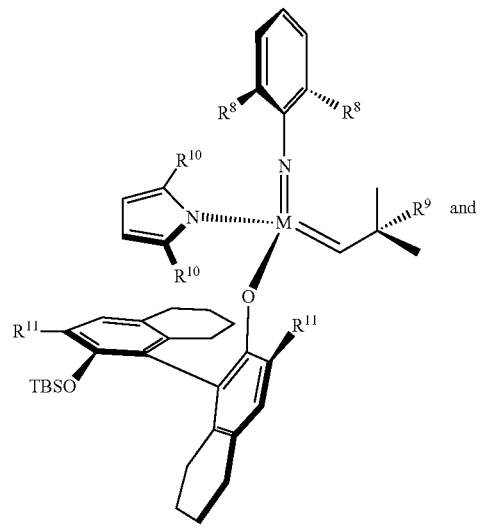

-continued

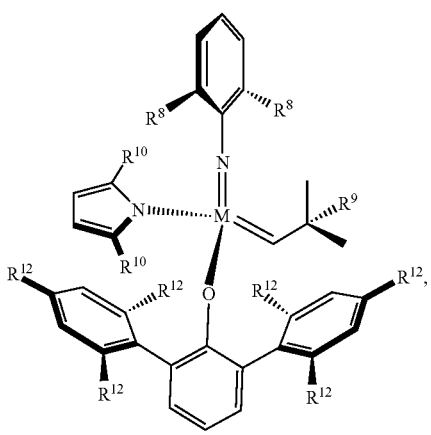

wherein M is Mo or W;

each $R^8$ is independently selected from halo and alkyl;

$R^9$ is selected from the group of consisting of alkyl, aryl, alkenyl, and heteroaryl;

each $R^{10}$ is independently selected from hydrogen, halo, alkyl, aryl, and heteroaryl;

each $R^{11}$ is independently selected from halo, alkyl, aryl, and heteroaryl; and each $R^{12}$ is independently an optionally substituted alkyl.

In some embodiments, the metathesis catalyst is selected from:

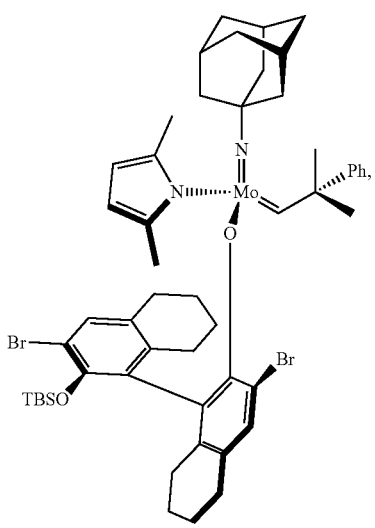

-continued

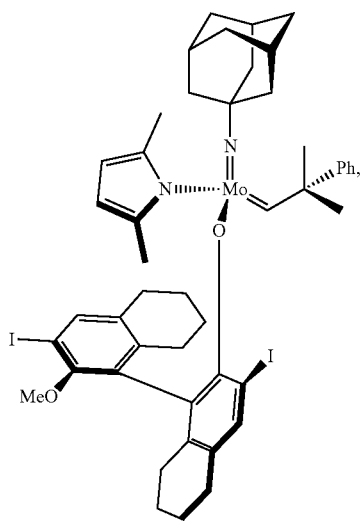

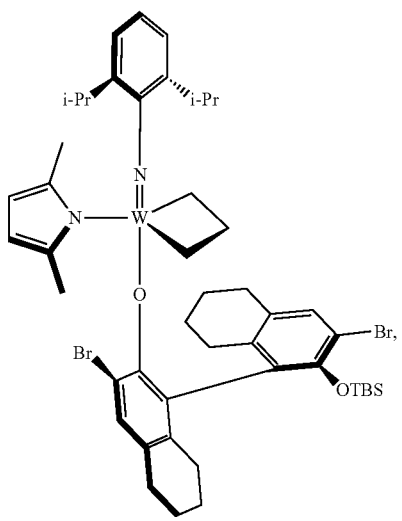

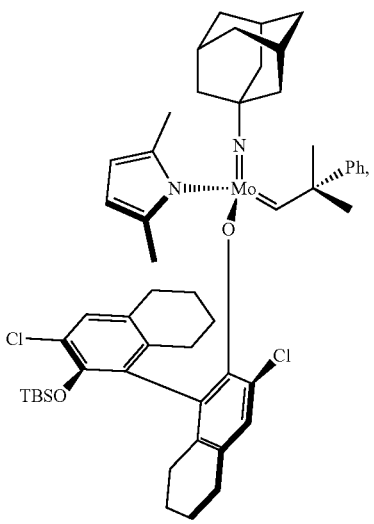

65
-continued
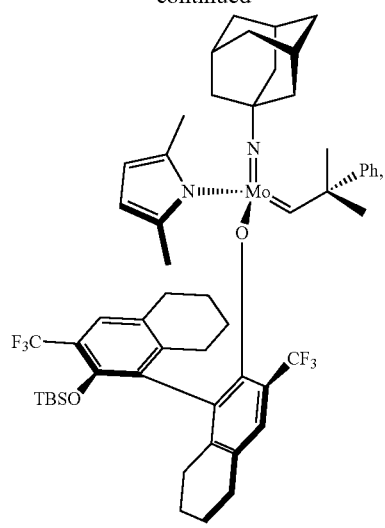
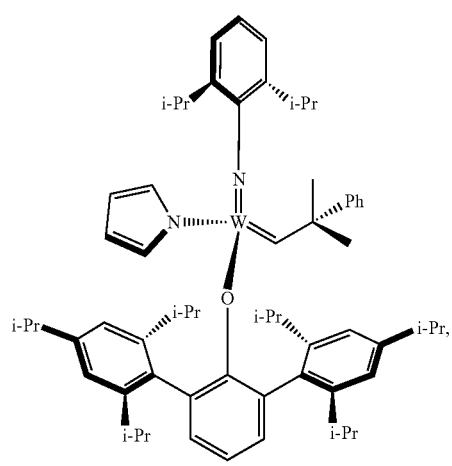
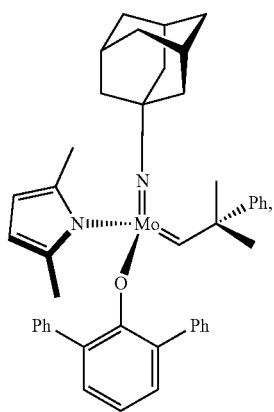
66
-continued
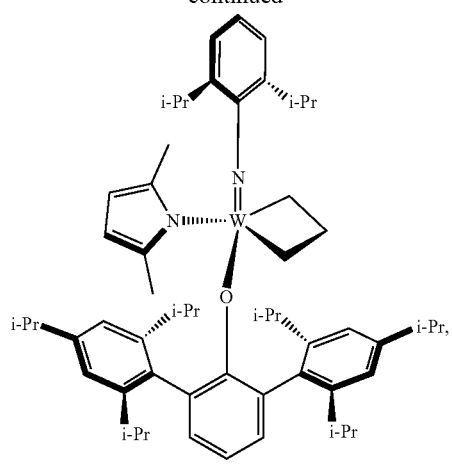
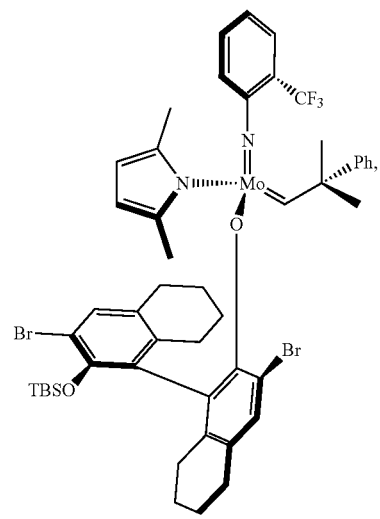
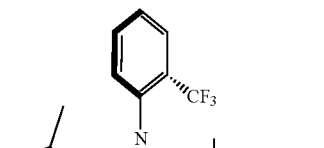
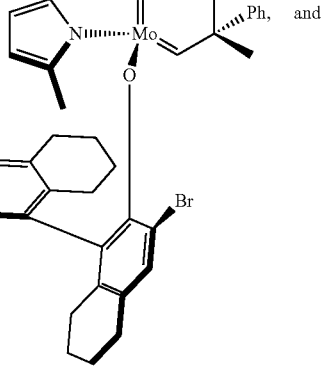

-continued

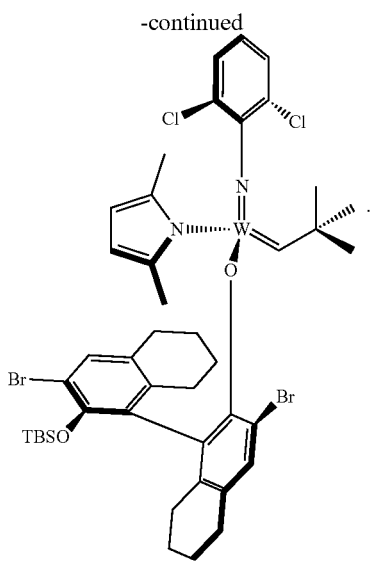

In some embodiments, the metathesis catalyst has a structure according to Formula 2:

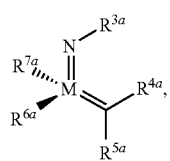

(2)

wherein:

M is Mo or W;

$R^{3a}$ is selected from optionally substituted aryl, optionally substituted heteroaryl, optionally substituted alkyl, optionally substituted heteroalkyl, optionally substituted cycloalkyl, and optionally substituted heterocycloalkyl, and $R^{4a}$ and $R^{5a}$ are independently selected from hydrogen, optionally substituted alkyl, optionally substituted alkenyl, optionally substituted heteroalkyl, optionally substituted heteroalkenyl, optionally substituted aryl, and optionally substituted heteroaryl;

$R^{7a}$ is selected from optionally substituted alkyl, optionally substituted alkoxy, optionally substituted heteroalkyl, optionally substituted aryl, optionally substituted aryloxy, optionally substituted heteroaryl, optionally substituted silylalkyl, and optionally substituted silyloxy; and $R^{6a}$ is $R^{8a}$—X—, wherein X is O or S and $R^{8a}$ is optionally substituted aryl; or X is O and $R^{8a}$ is $SiR^{9a}R^{10a}R^{11a}$ or $CR^{12a}R^{13a}R^{14a}$, wherein $R^{9a}$, $R^{10a}$, $R^{11a}$, $R^{12a}$, $R^{13a}$, and $R^{14a}$ are independently selected from optionally substituted alkyl and optionally substituted phenyl; or $R^{6a}$ and $R^{7a}$ are linked together and are bonded to M via oxygen.

In some embodiments, the metathesis catalyst has a structure according to Formula 2 and the metathesis product comprises a Z olefin.

In some embodiments, the catalyst is a compound of Formula 2 wherein:

$R^{7a}$ is selected from the group consisting of alkyl, alkoxy, heteroalkyl, aryl, aryloxy, and heteroaryl, each of which is optionally substituted; and X is O or S and $R^{8a}$ is optionally substituted aryl; or X is O and $R^{8a}$ is $CR^{12a}R^{13a}R^{14a}$.

In some embodiments, the catalyst is a compound of Formula 2 wherein:

$R^{3a}$ is selected from the group consisting of 2,6-dimethylphenyl; 2,6-diisopropylphenyl; 2,6-dichlorophenyl; and adamant-1-yl;

$R^{4a}$ is selected from the group consisting of —C(CH$_3$)$_2$C$_6$H$_5$ and —C(CH$_3$)$_3$;

$R^{5a}$ is H;

$R^{7a}$ is selected from the group consisting of pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenyl-phenoxy; and t-butyloxy; and $R^{6a}$ is $R^{8a}$—X—, wherein X═O and $R^{8a}$ is phenyl which bears two substituents in the ortho positions with respect to O, or which bears at least three substituents, from which two substituents are in the ortho positions with respect to O and one substituent is in the para position with respect to O; or $R^{8a}$ is selected from the group consisting of optionally substituted 8-(naphthalene-1-yl)-naphthalene-1-yl; optionally substituted 8-phenyl naphthalene-1-yl; optionally substituted quinoline-8-yl; triphenylsilyl; triisopropylsilyl; triphenylmethyl; tri(4-methylphenyl)methyl; 9-phenyl-fluorene-9-yl; 2-phenyl-1,1,1,3,3,3-hexafluoro-prop-2-yl; 2-methyl-1,1,1,3,3,3-hexafluoro-prop-2-yl; and t-butyl.

In some embodiments, the catalyst is a compound of Formula 2 wherein:

$R^{7a}$ is selected from the group consisting of pyrrol-1-yl; 2,5-dimethyl-pyrrol-1-yl; and $R^{8a}$ is phenyl which bears two substituents in the ortho positions with respect to O, or which bears at least three substituents, from which two substituents are in the ortho positions with respect to O and one substituent is in the para position with respect to O; or $R^{8a}$ is selected from the group consisting of optionally substituted 8-(naphthalene-1-yl)-naphthalene-1-yl and optionally substituted 8-phenlynaphthalene-1-yl.

In some embodiments, the catalyst is a compound of Formula 2 wherein $R^4$ is selected from 4-bromo-2,6-diphenylphenoxy; 4-fluoro-2,6-diphenylphenoxy; 4-methyl-2,6-diphenylphenoxy; 4-methoxy-2,6-diphenylphenoxy; 4-dimethylamino-2,6-diphenylphenoxy; 2,4,6-triphenylphenoxy; 4-fluoro-2,6-dimesitylphenoxy; 4-bromo-2,6-di-tert-butylphenoxy; 4-methoxy-2,6-di-tert-butylphenoxy; 4-methyl-2,6-di-tert-butylphenoxy; 2,4,6-tri-tert-butylphenoxy; 4-bromo-2,3,5,6-tetraphenylphenoxy; 4-bromo-2,6-di(4-bromophenyl)-3,5-diphenylphenoxy; 2,6-diphenylphenoxy; 2,3,5,6-tetraphenylphenoxy; 2,6-di(tert-butyl)phenoxy; 2,6-di(2,4,6-triisopropylphenyl)phenoxy; triphenylsilyloxy; triisopropylsilyloxy; triphenylmethyloxy; tri(4-methyphenyl)methyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; t-butyloxy;

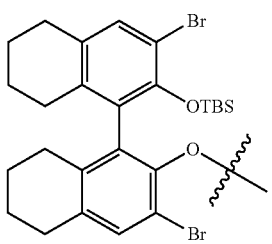 [SMILES: *Oc1c(Br)cc2c(c1-c1c3c(cc(Br)c1O[Si](C)(C)C(C)(C)C)CCCC3)CCCC2]

wherein TBS is t-butyldimethylsilyl; or

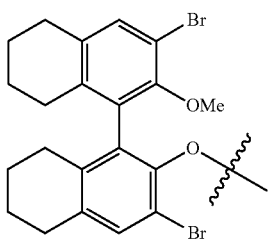

wherein Me=methyl.

In some embodiments, the metathesis catalyst has a structure according to Formula 2a:

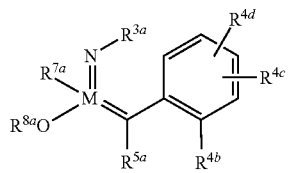

(2a)

wherein:

$R^{3a}$ is aryl, heteroaryl, alkyl, or cycloalkyl, each of which is optionally substituted;

$R^{7a}$ is pyrrolyl, imidazolyl, indolyl, pyrazolyl, azaindolyl, or indazolyl, each of which is optionally substituted;

$R^{8a}$ is optionally substituted aryl;

$R^{5a}$ is a hydrogen atom, alkyl, or alkoxy;

$R^{4b}$ is a hydrogen atom, —O—($C_{1-6}$ alkyl), —$CH_2$—O—($C_{1-6}$ alkyl), heteroalkoxy, or —N($C_{1-6}$ alkyl)$_2$; and $R^{4c}$ and $R^{4d}$ are independently a hydrogen atom, $C_{1-6}$ alkyl, $C_{1-6}$ alkoxy, a halogen atom, —$NO_2$, an amide, or a sulfonamide.

In some embodiments, the metathesis catalyst has a structure according to Formula 2a and the metathesis product comprises a Z olefin.

In some embodiments, $R^{3a}$ in the metathesis catalyst according to Formula 2a is phenyl, 2,6-dichlorophenyl, 2,6-dimethylphenyl, 2,6-diisopropylphenyl, 2-trifluoromethylphenyl, pentafluorophenyl, tert-butyl, or 1-adamantyl.

In some embodiments, $R^{8a}$ is

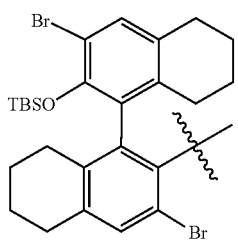

In some embodiments, $R^{4a}$ is methoxy, $R^{4c}$ is hydrogen, and $R^{4d}$ is hydrogen.

In some embodiments, the metathesis catalyst is selected from the group consisting of:

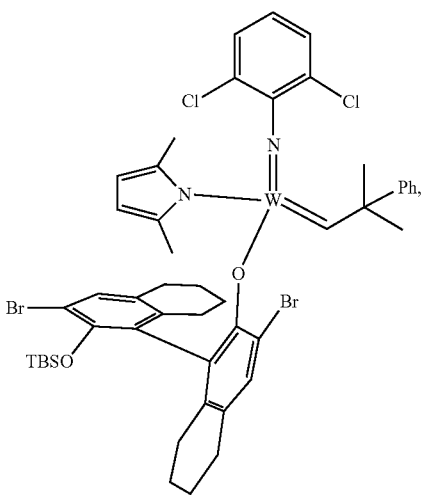

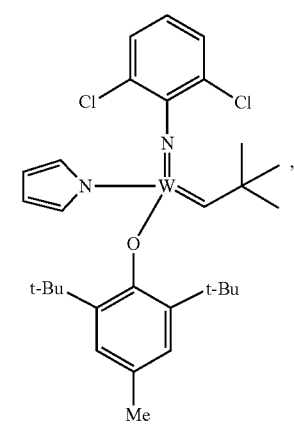

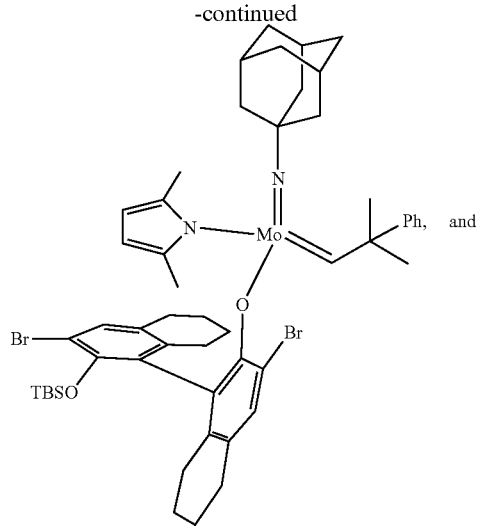
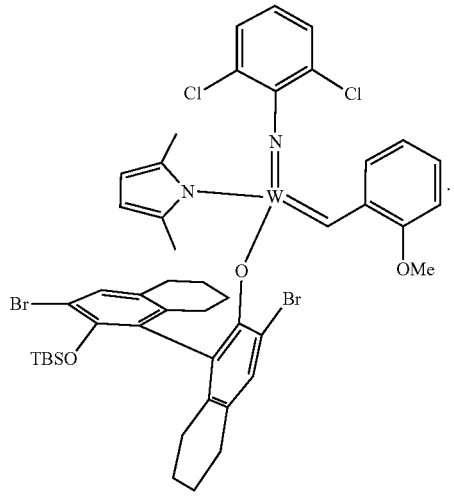
In some embodiments, the metathesis catalyst is
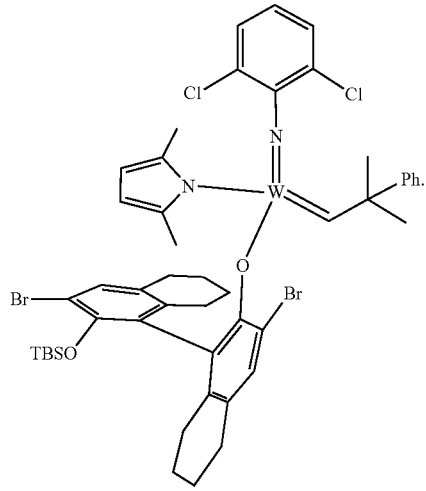
In some embodiments, the metathesis catalyst is
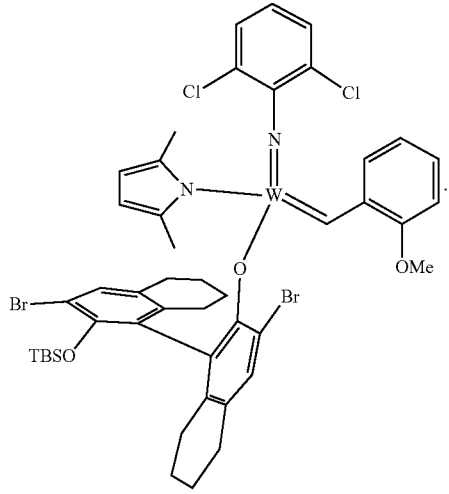
In some embodiments, the metathesis catalyst is selected from:
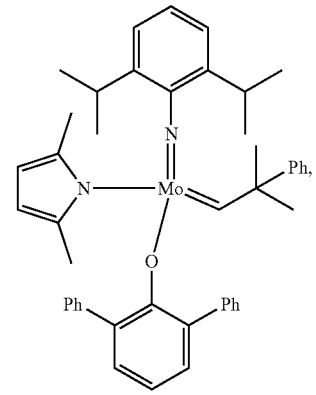
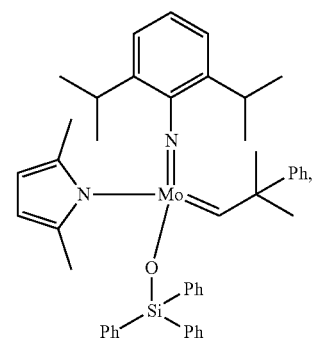

-continued
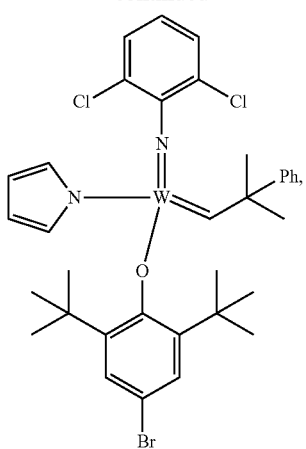
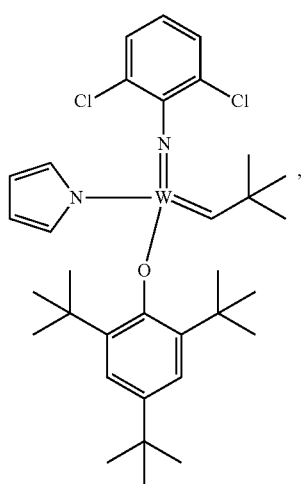
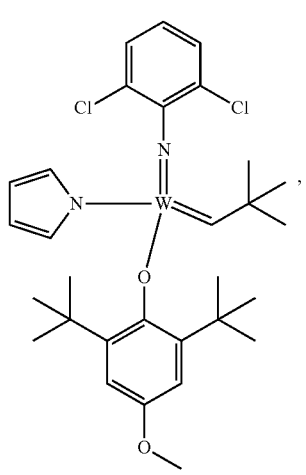
-continued
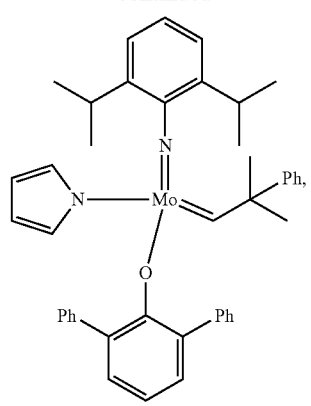
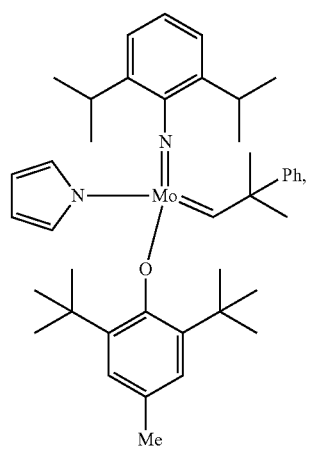
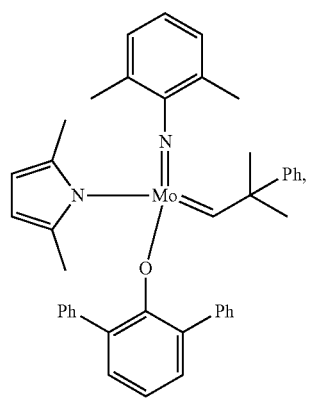
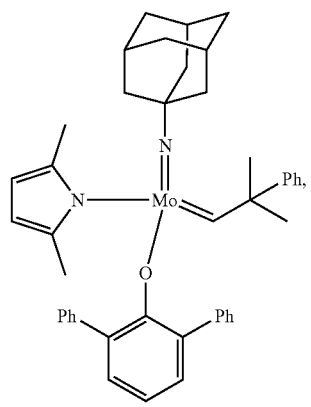

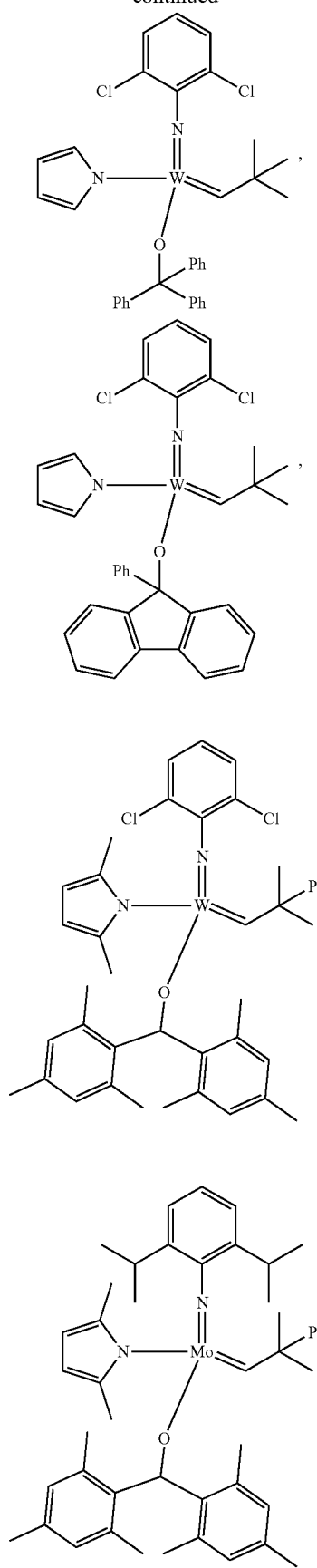

-continued
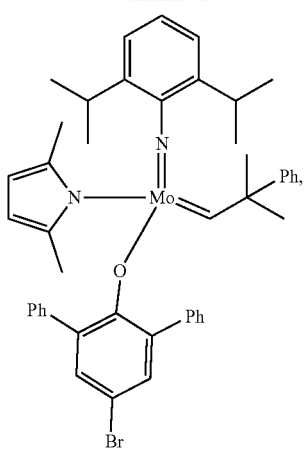
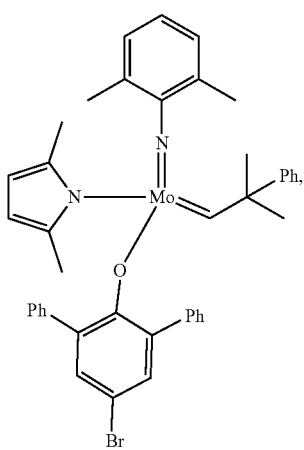
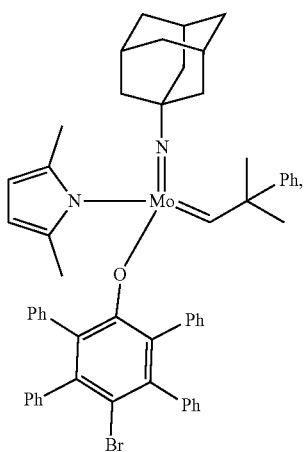
-continued
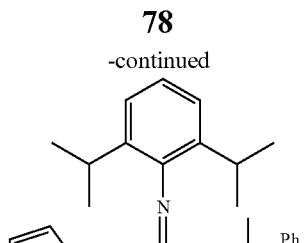
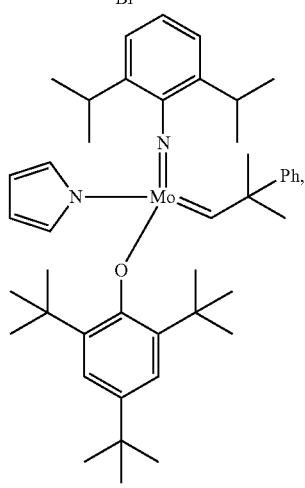
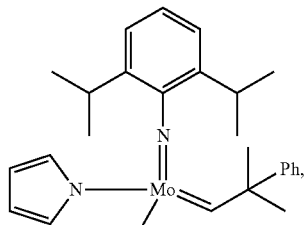
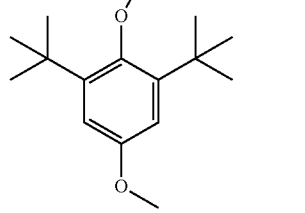
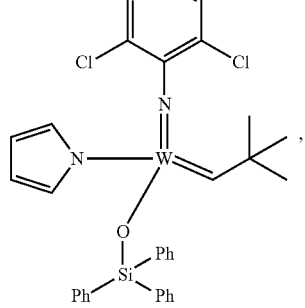

-continued
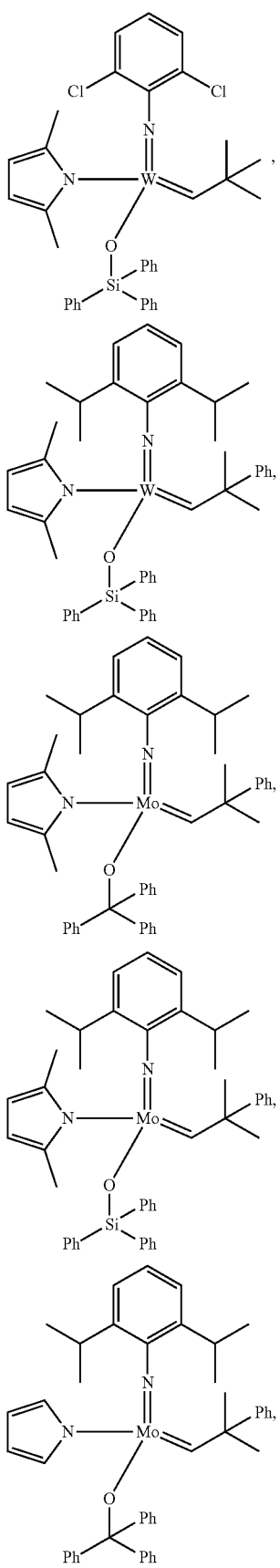
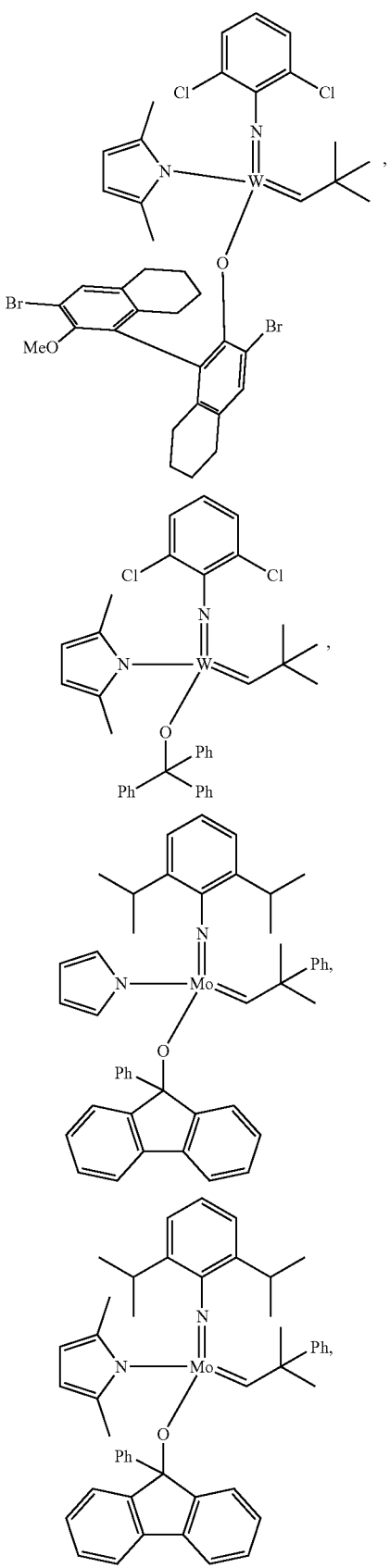

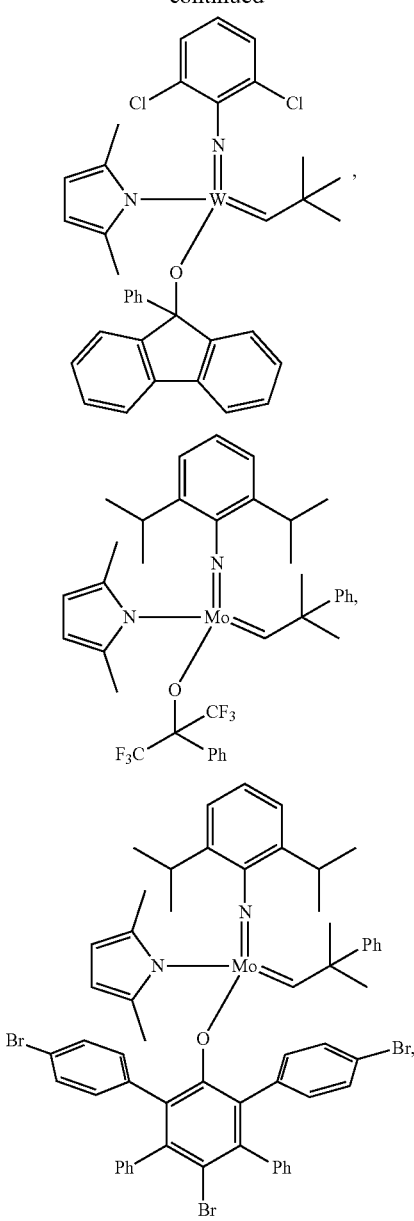
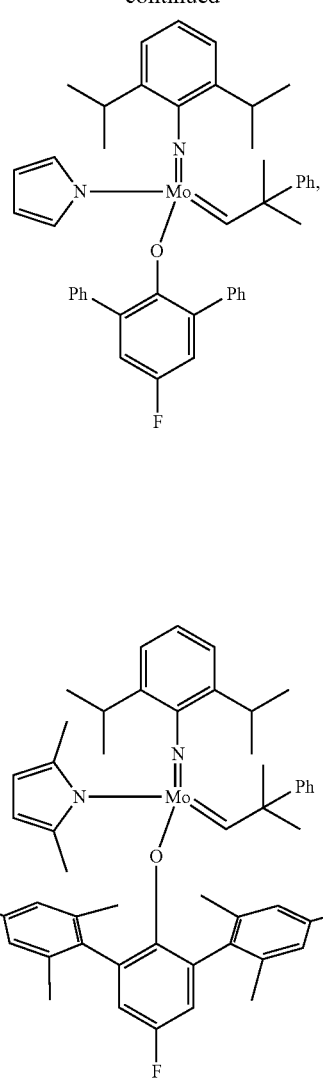
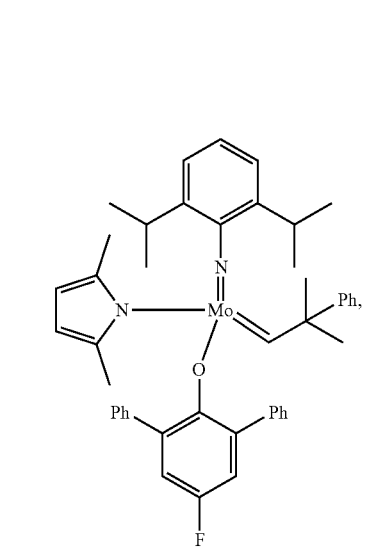

83
-continued
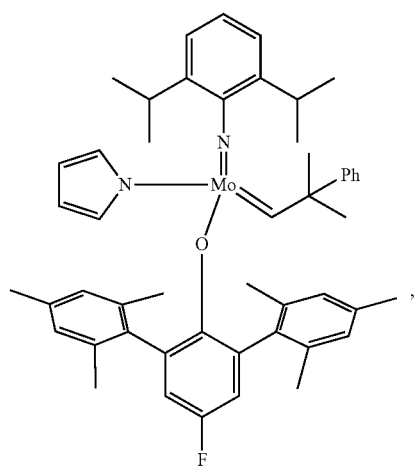
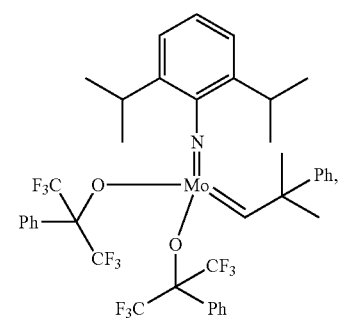
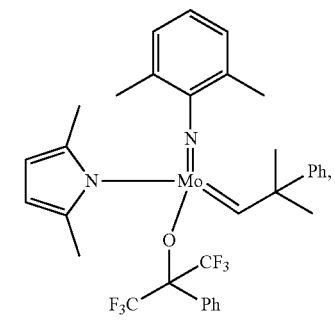
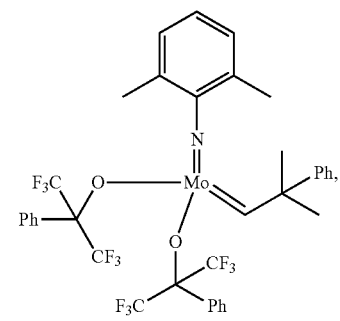
84
-continued
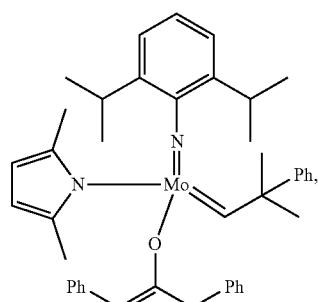
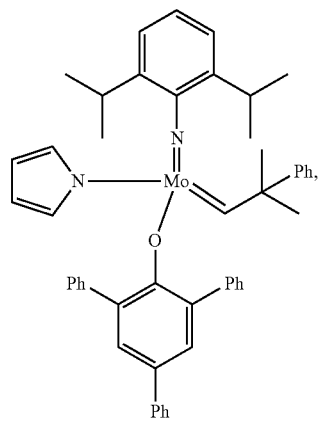
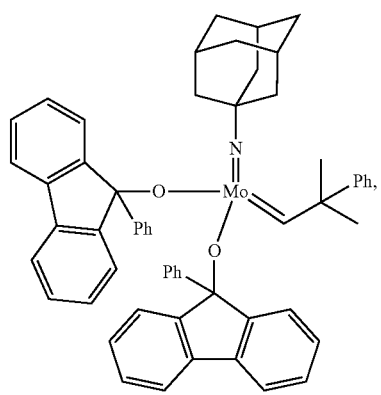

-continued
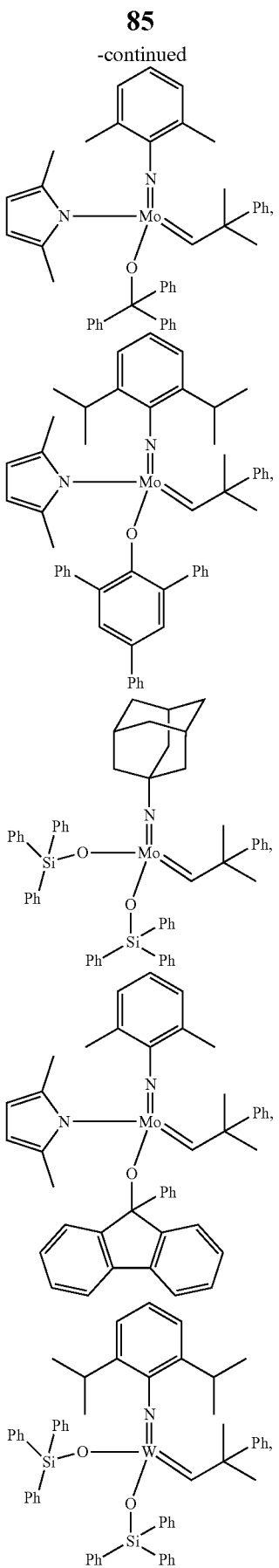
-continued
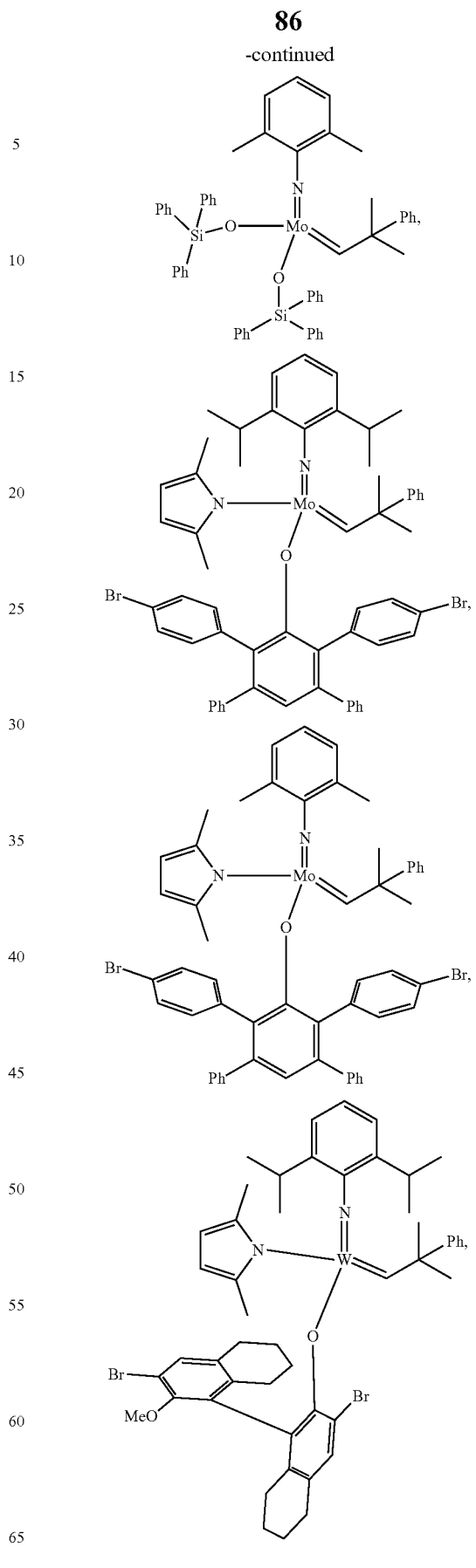

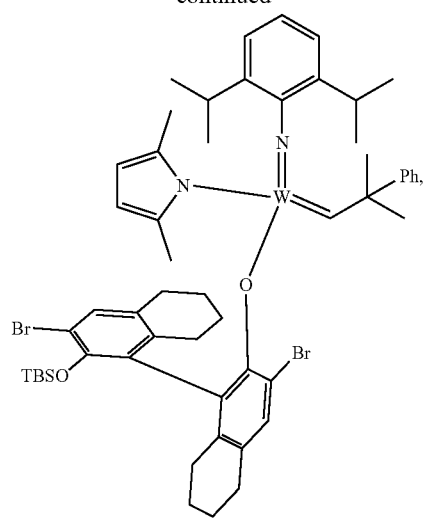
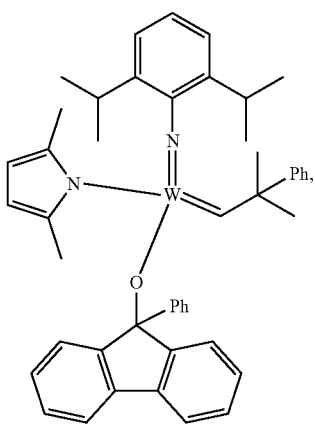
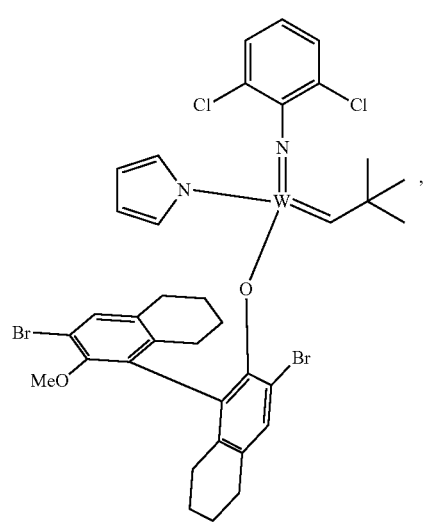
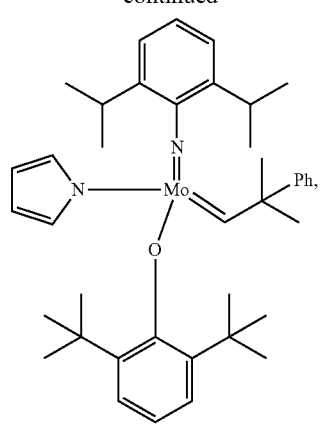
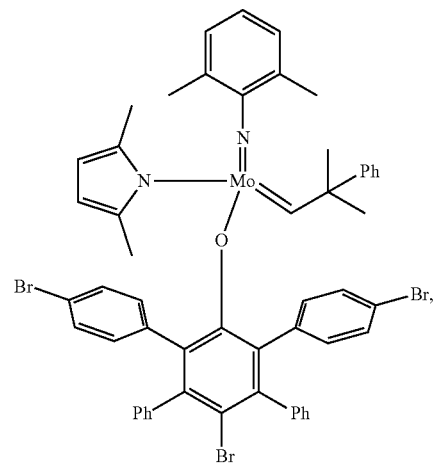
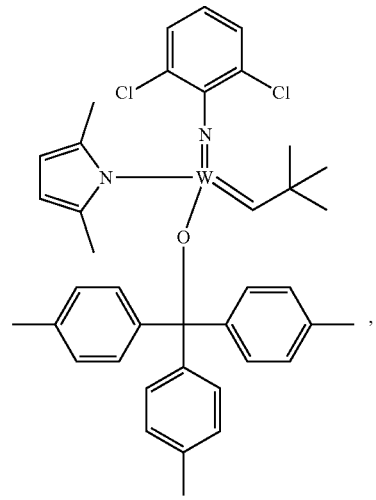

-continued
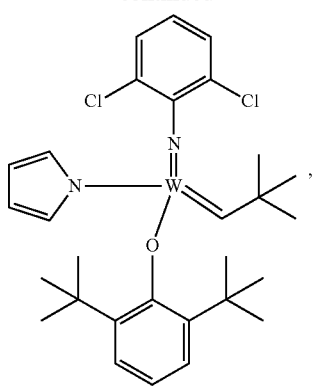
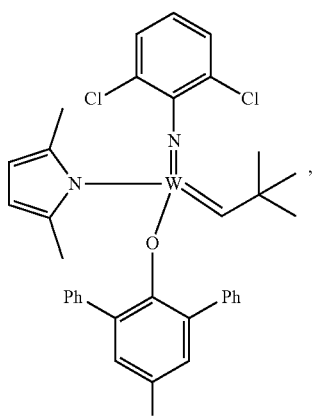
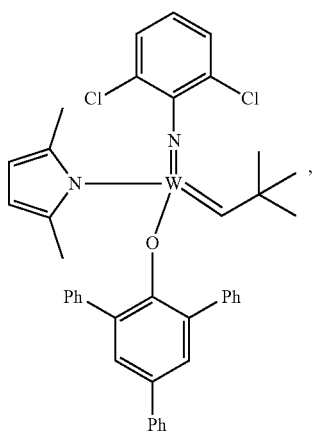
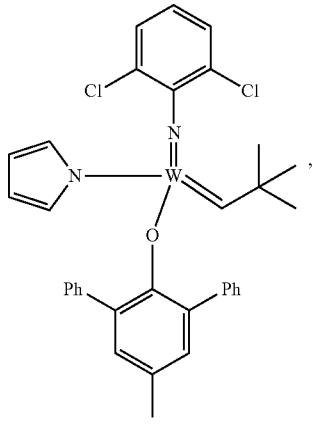
-continued
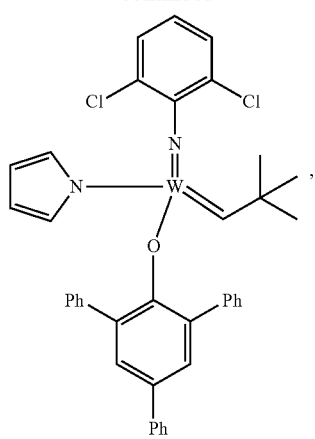
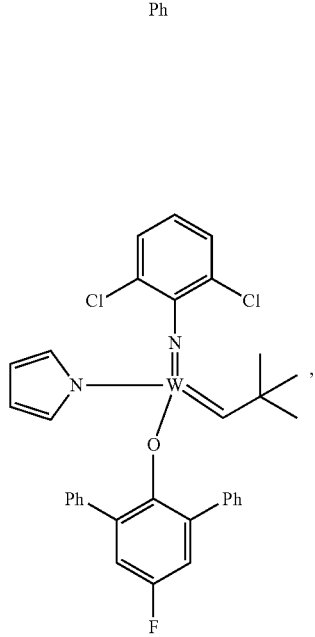
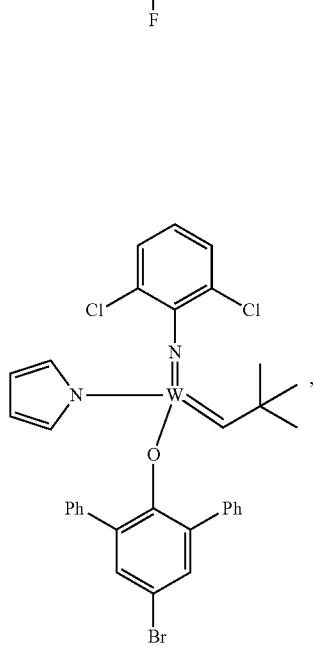

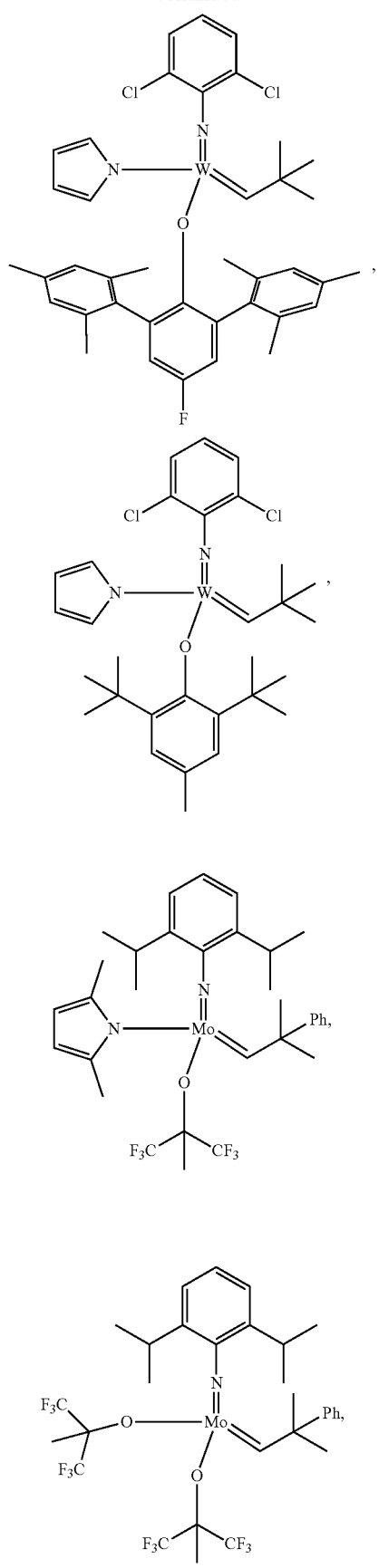

93
-continued
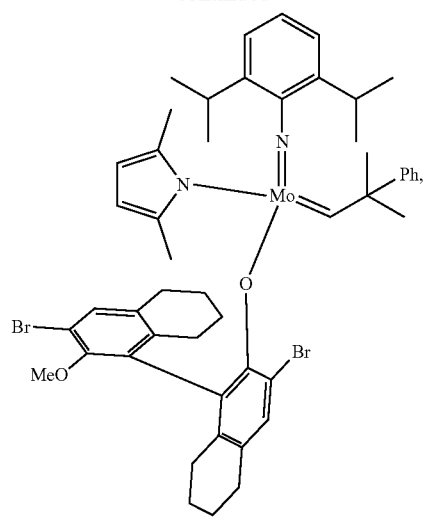
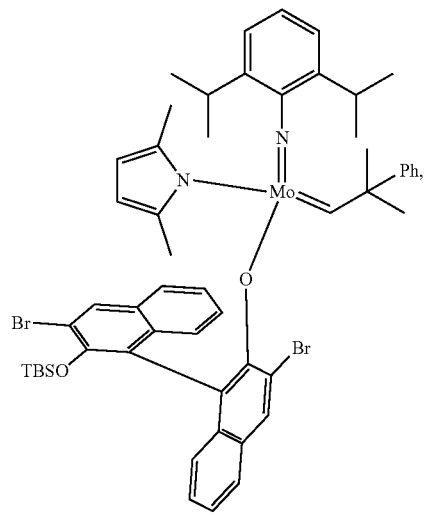
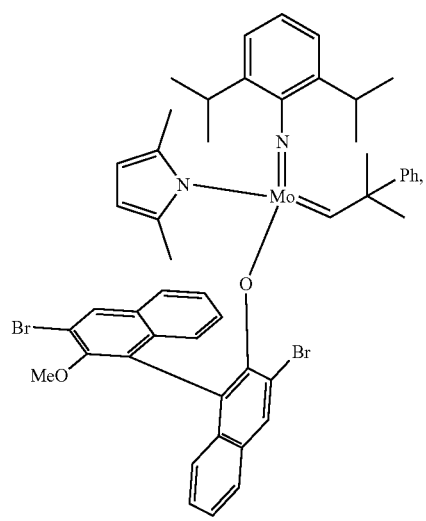
94
-continued
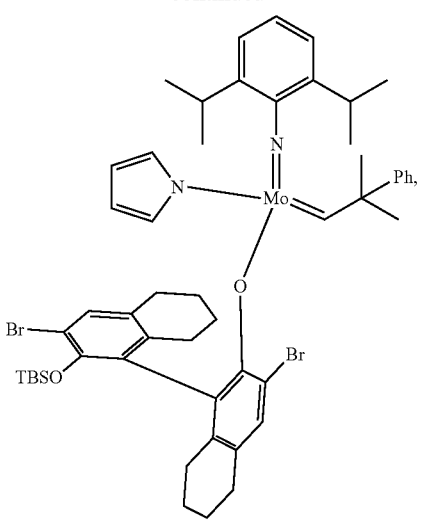
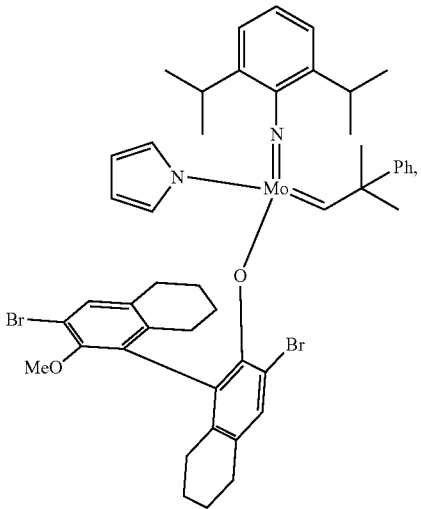
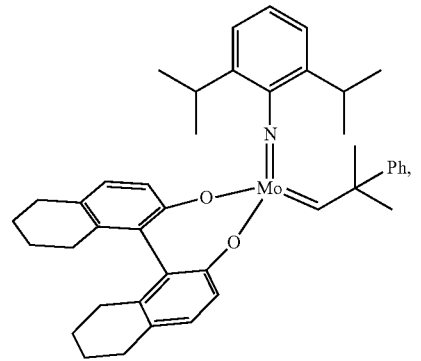

95
-continued
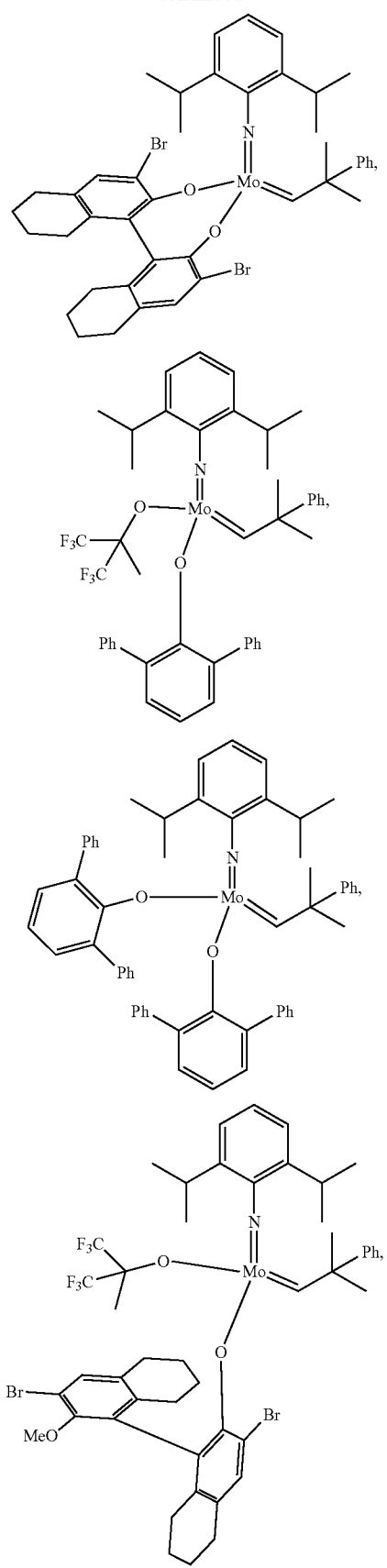
96
-continued
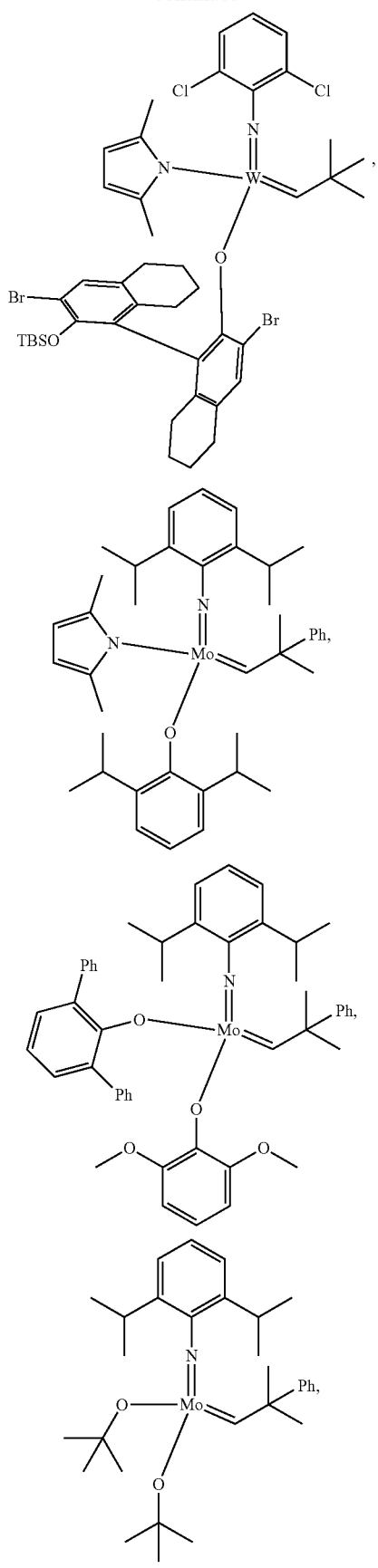

-continued
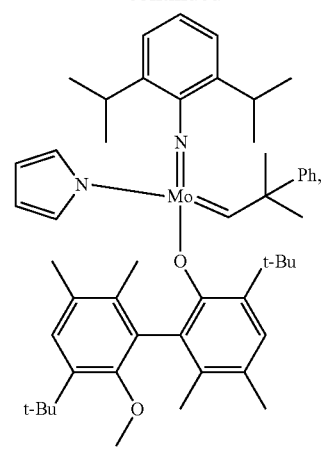
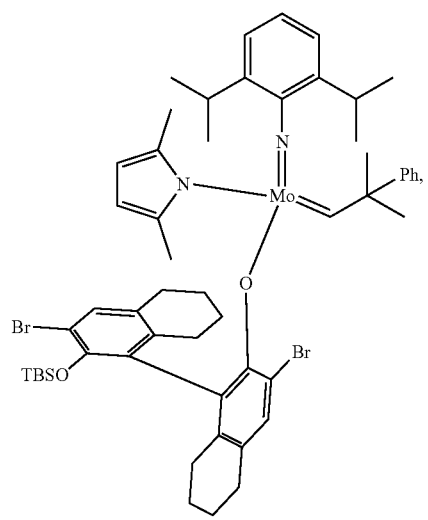
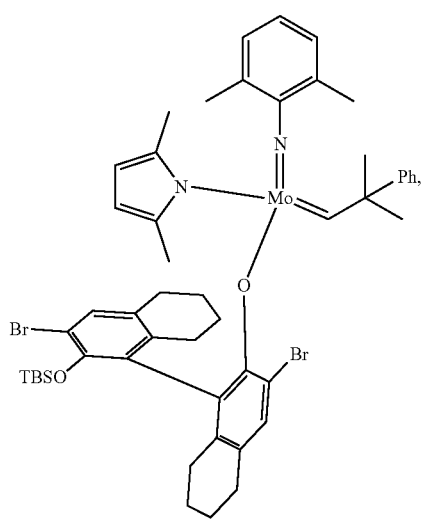
-continued
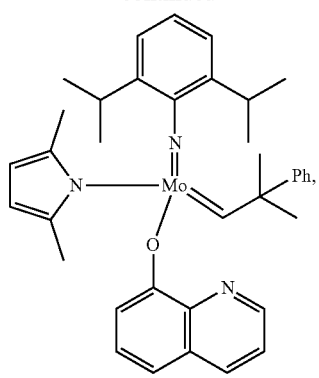
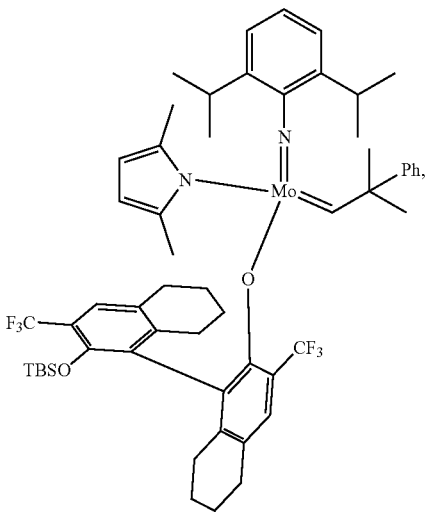
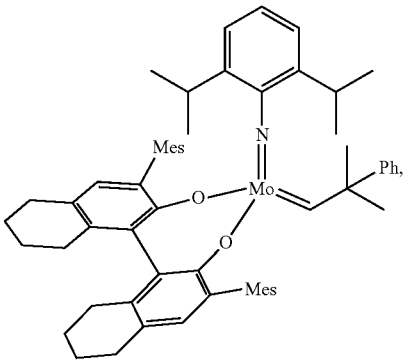
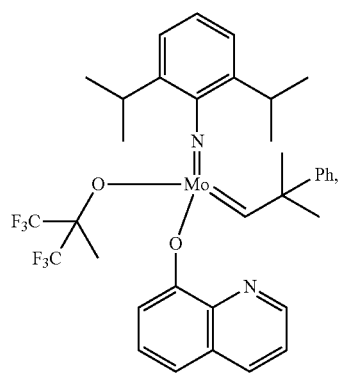

99
-continued
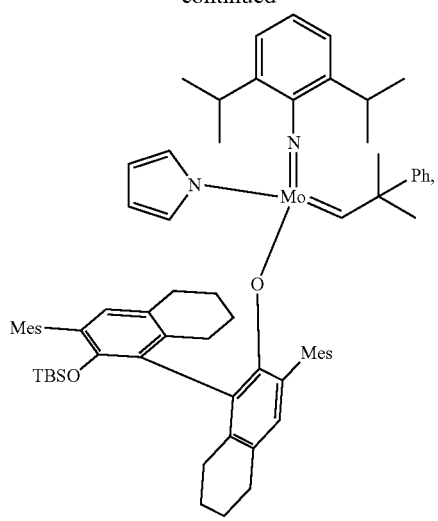
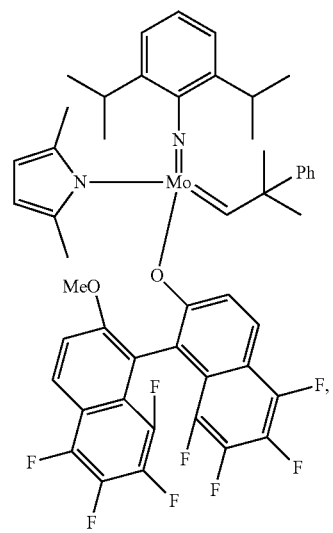
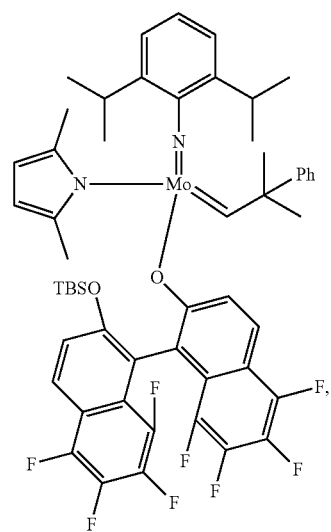
100
-continued
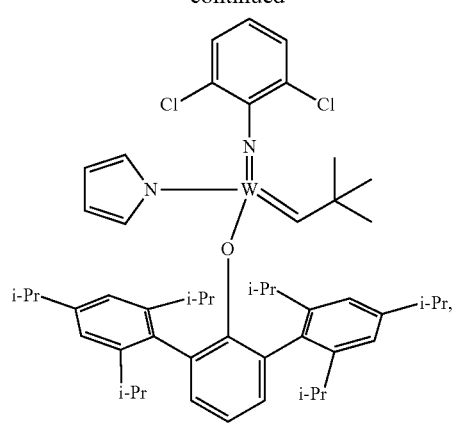
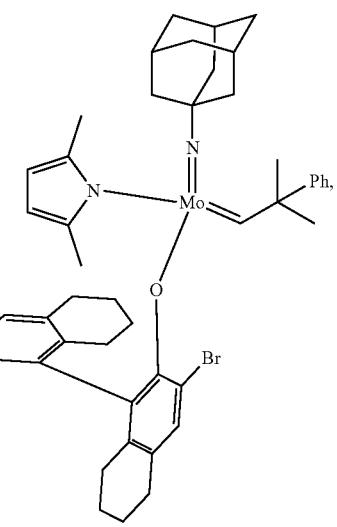
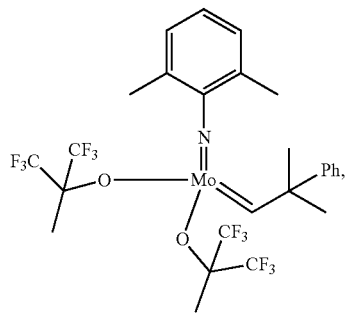

101
-continued
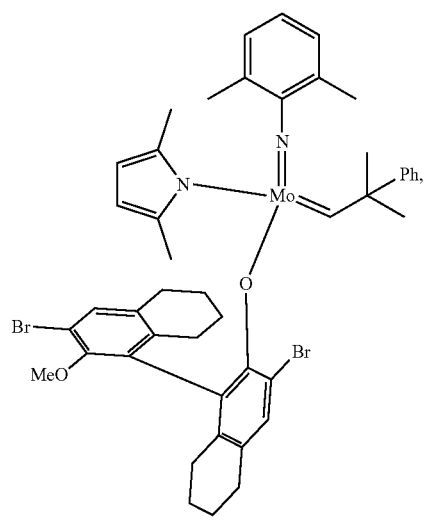
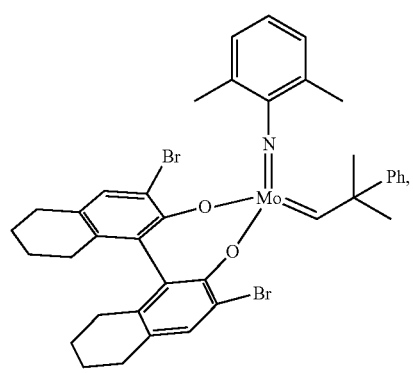
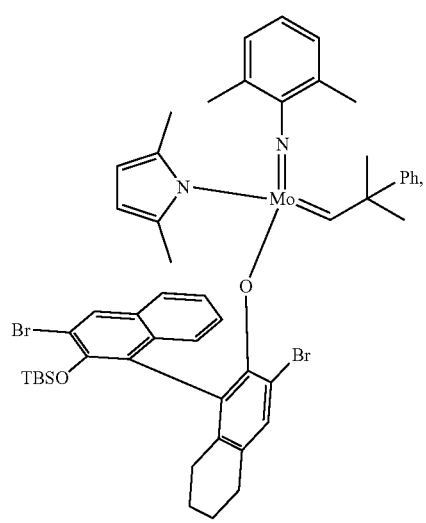
102
-continued
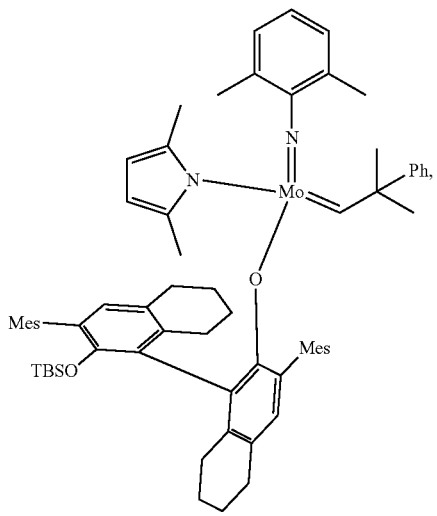
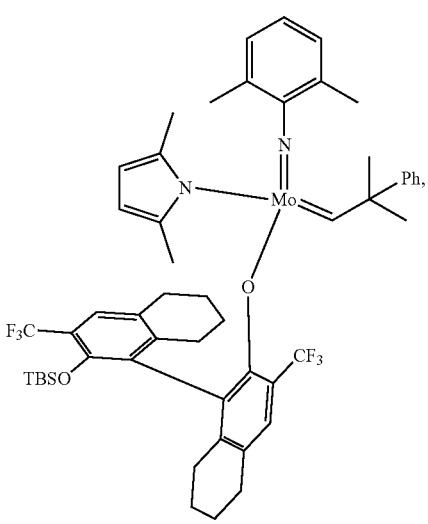
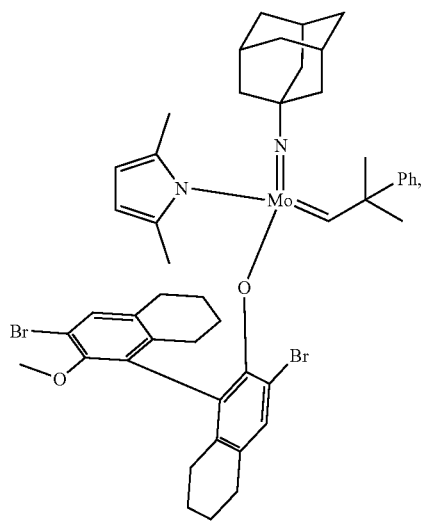

103
-continued
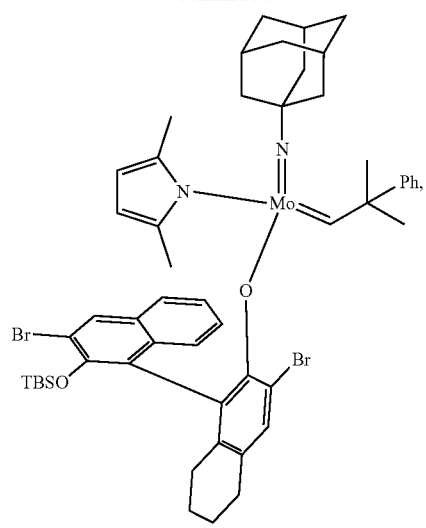
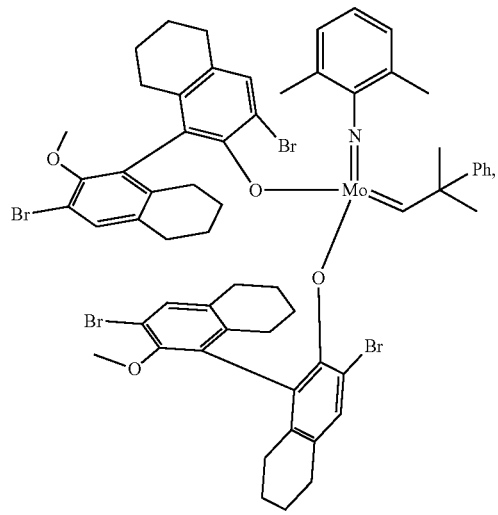
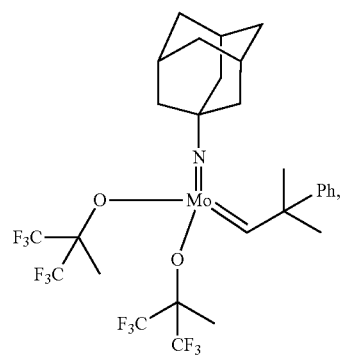
104
-continued
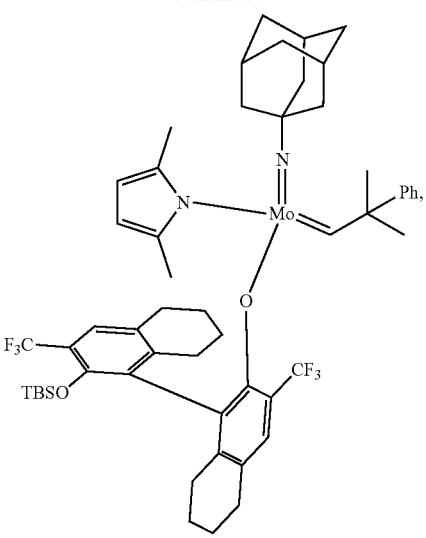
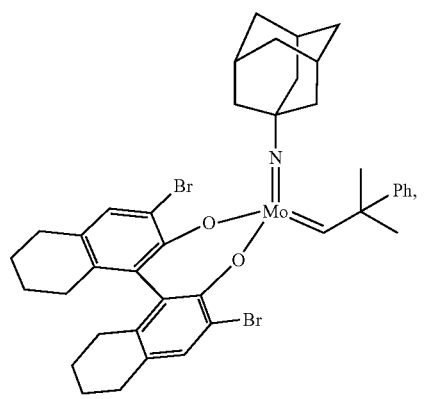
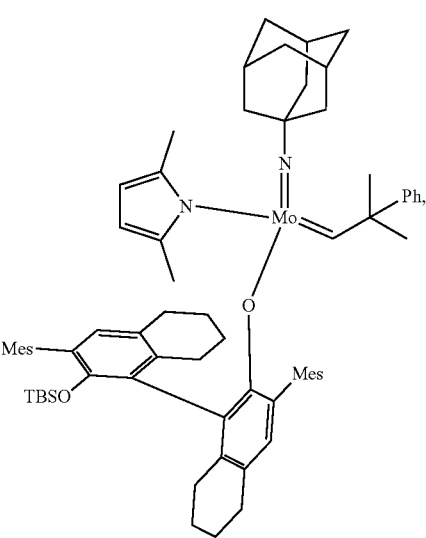

105
-continued
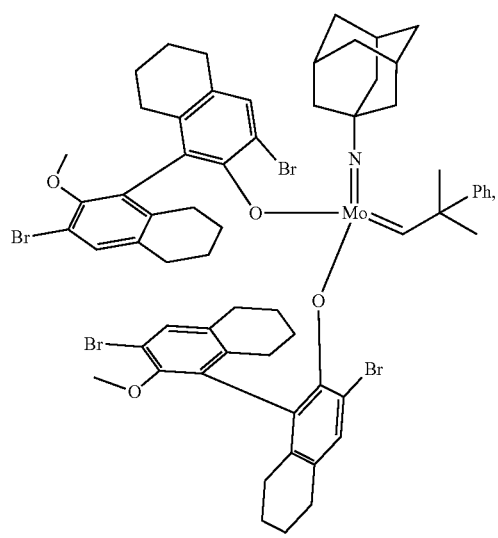
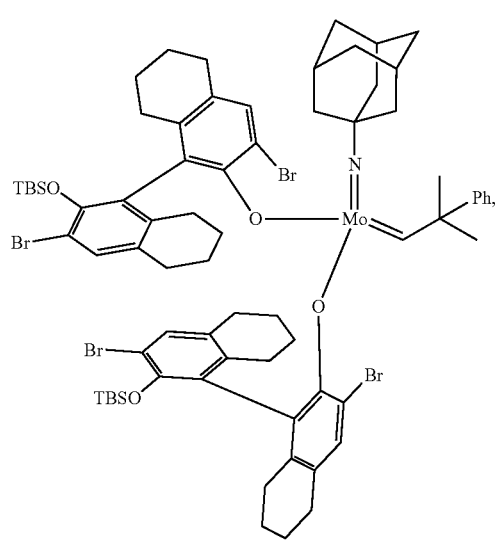
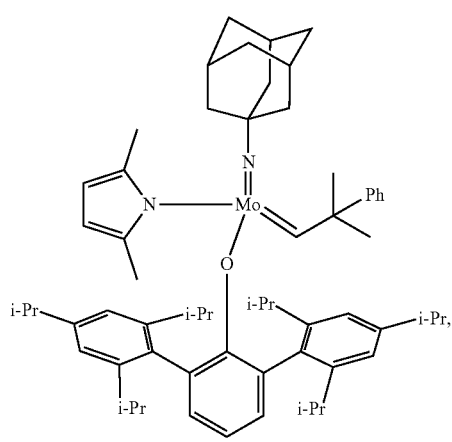
106
-continued
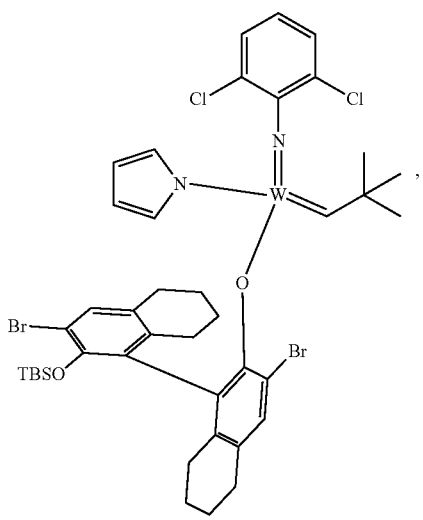
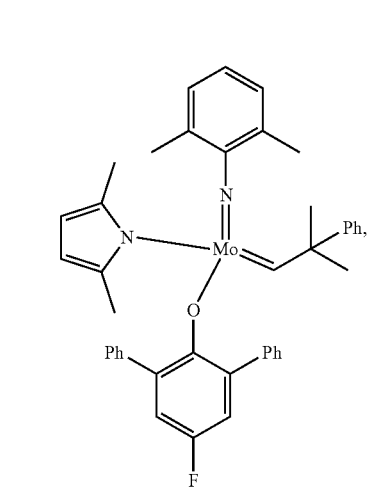
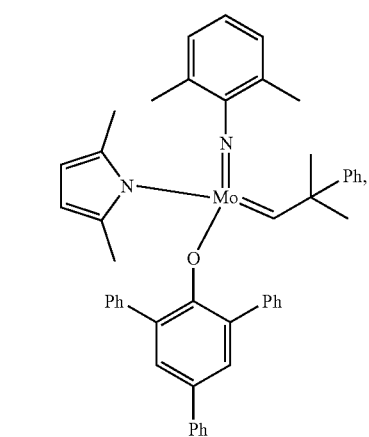

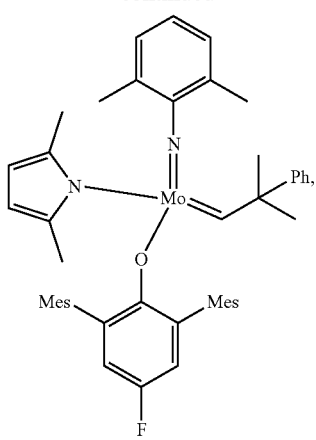
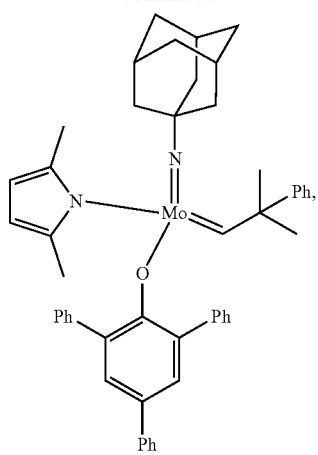
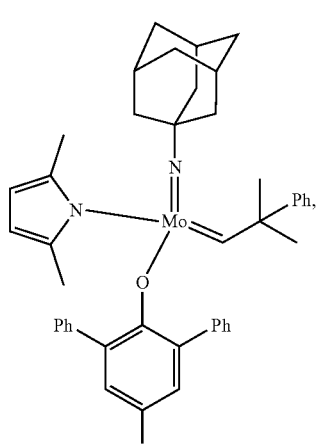
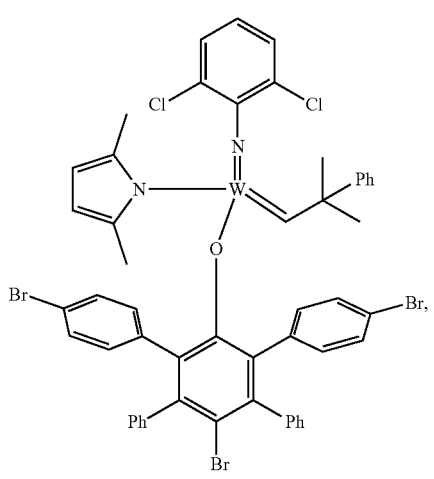
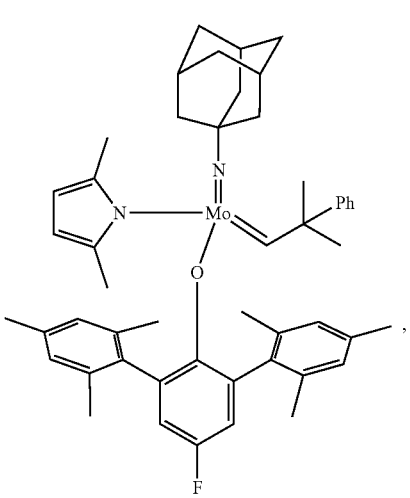

-continued
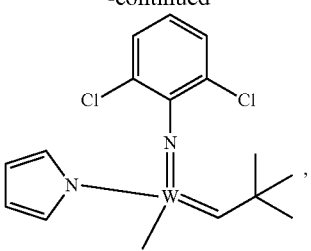
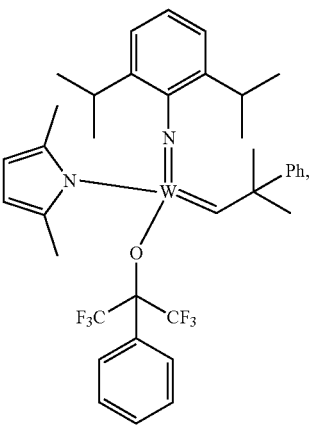
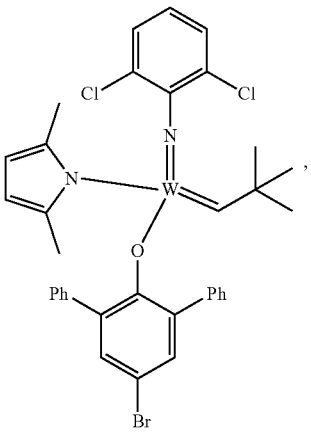
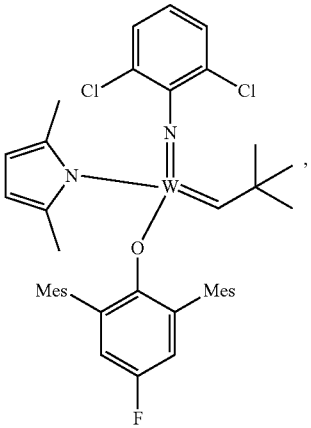
-continued
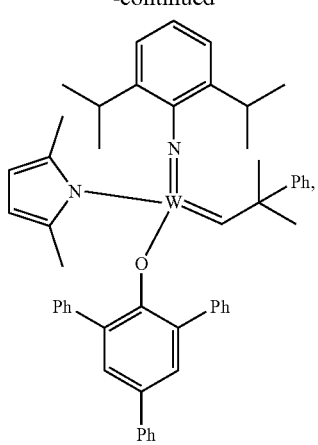
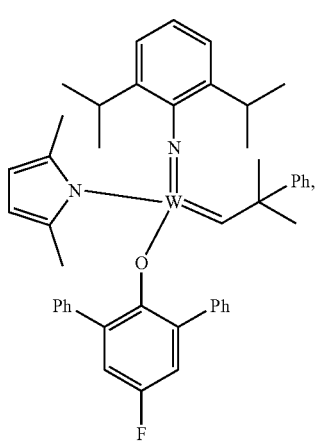
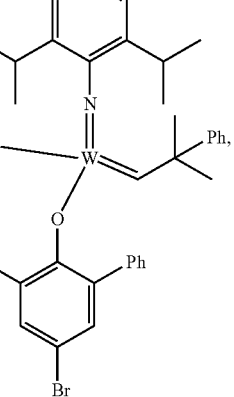

-continued
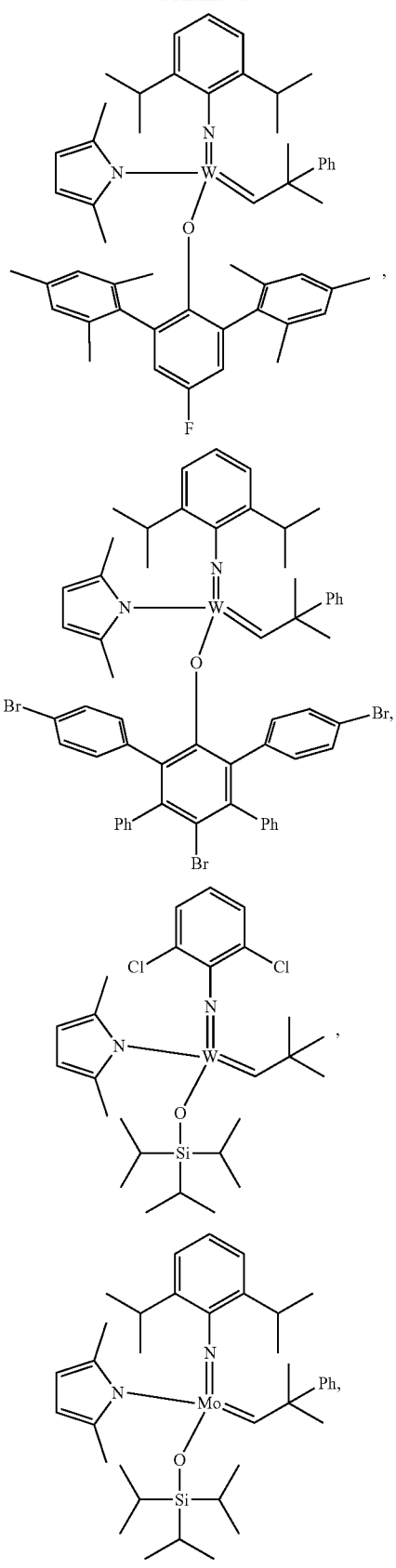
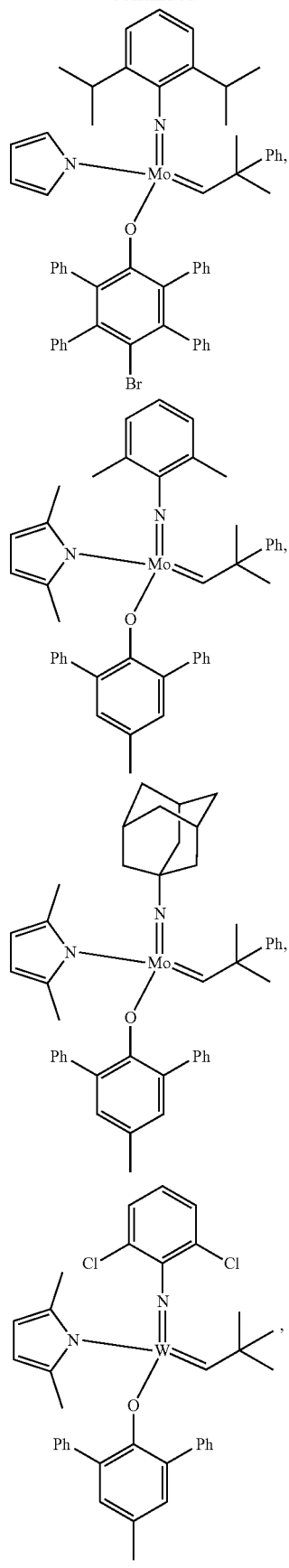

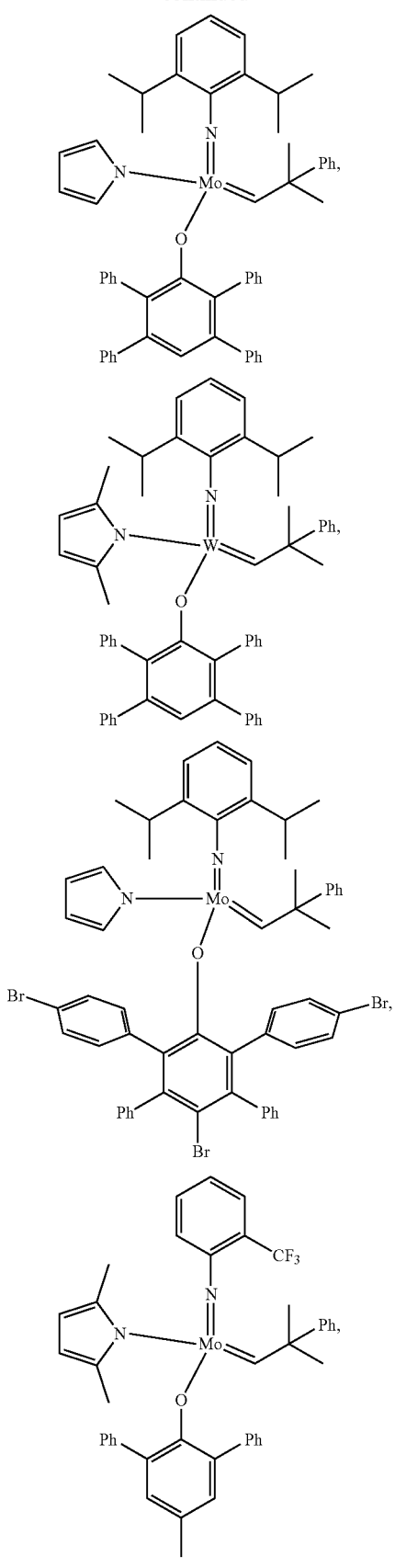
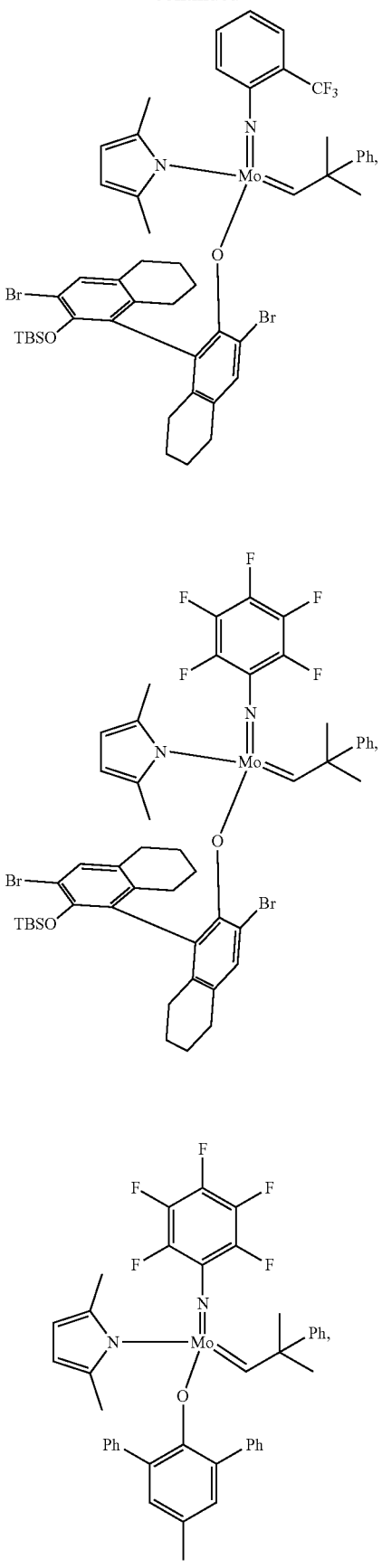

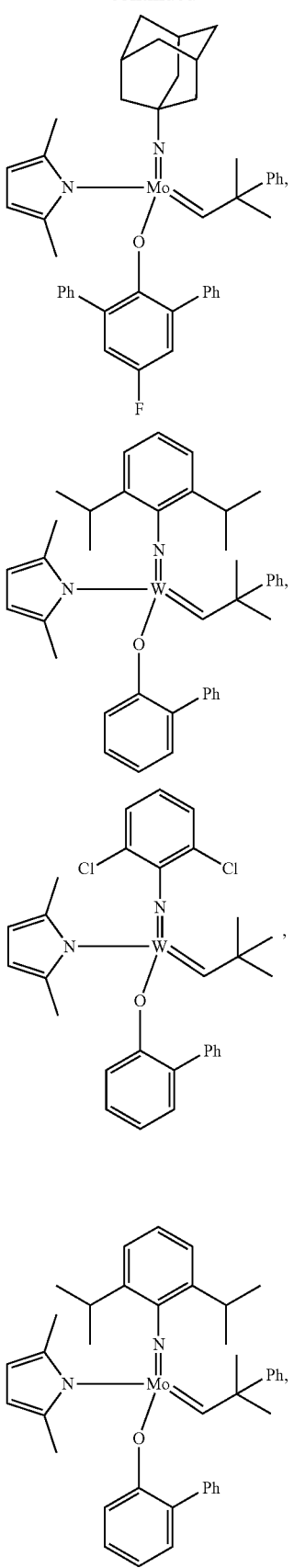
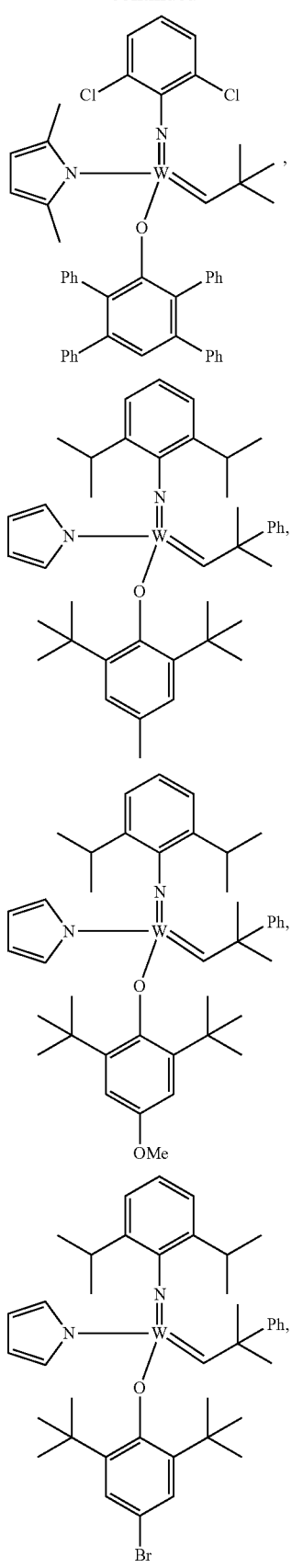

117
-continued
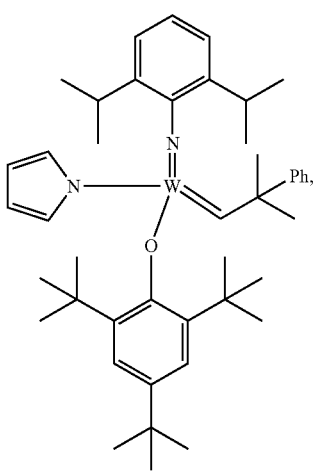
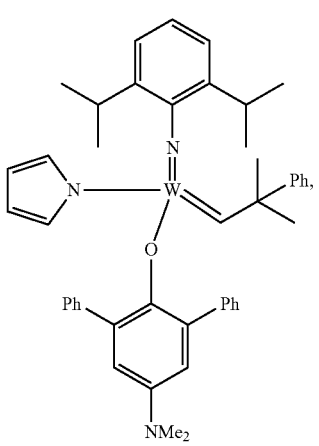
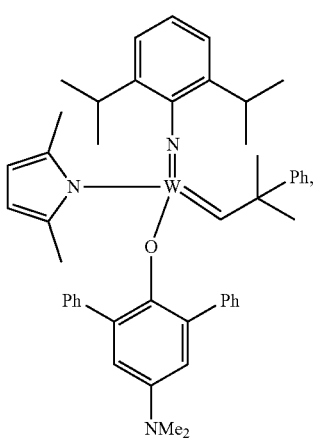
118
-continued
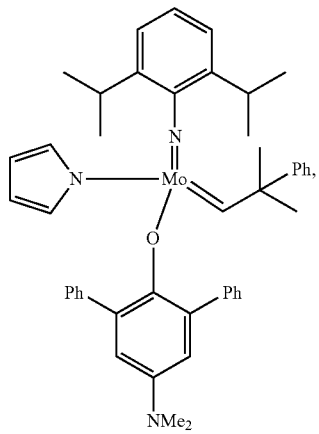
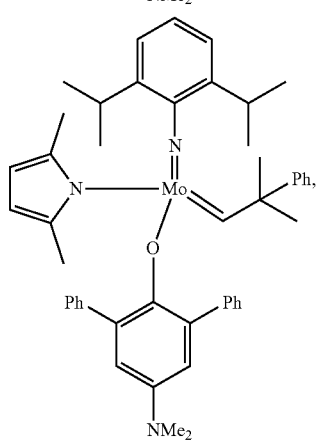
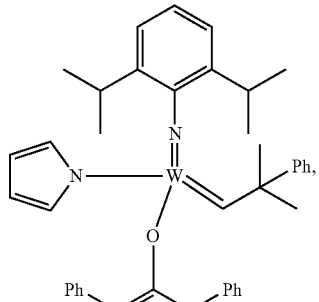
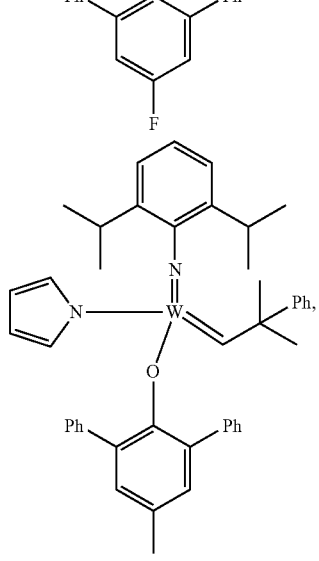

-continued
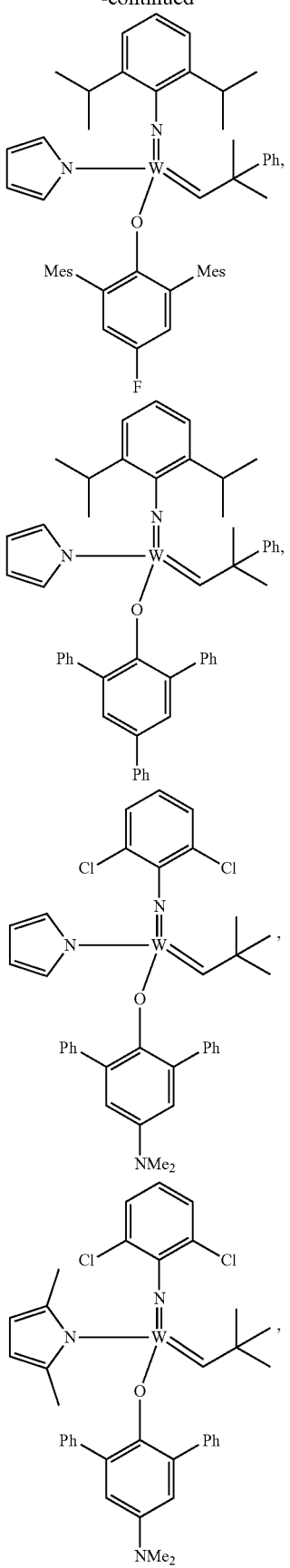
-continued
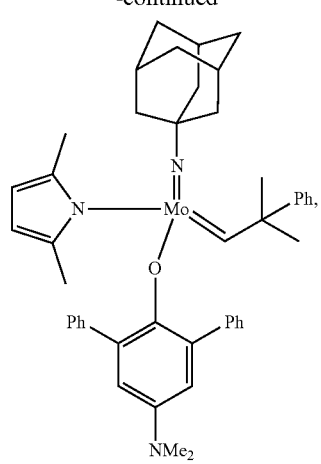

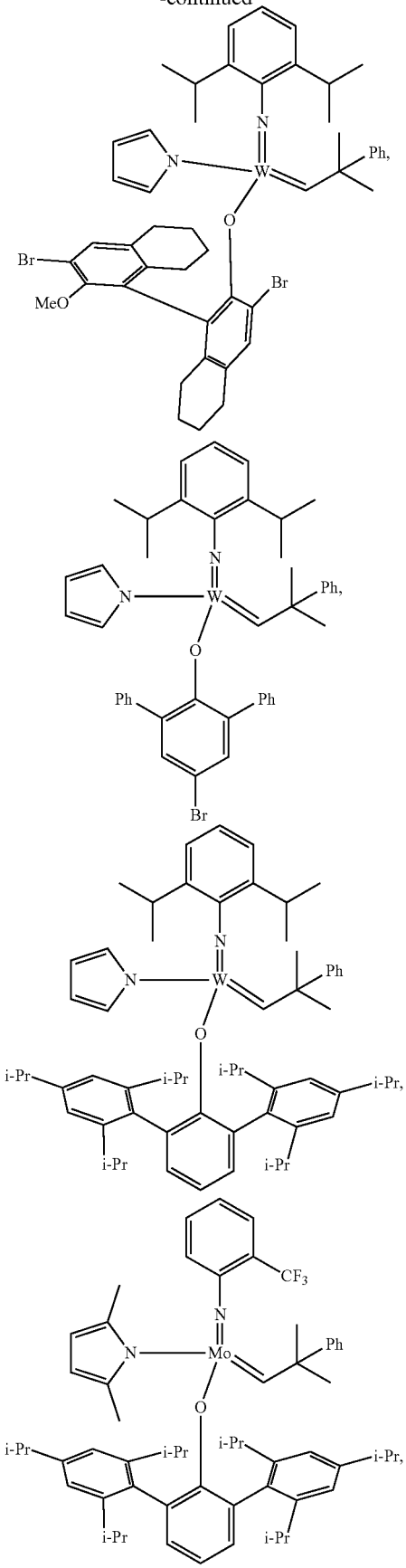
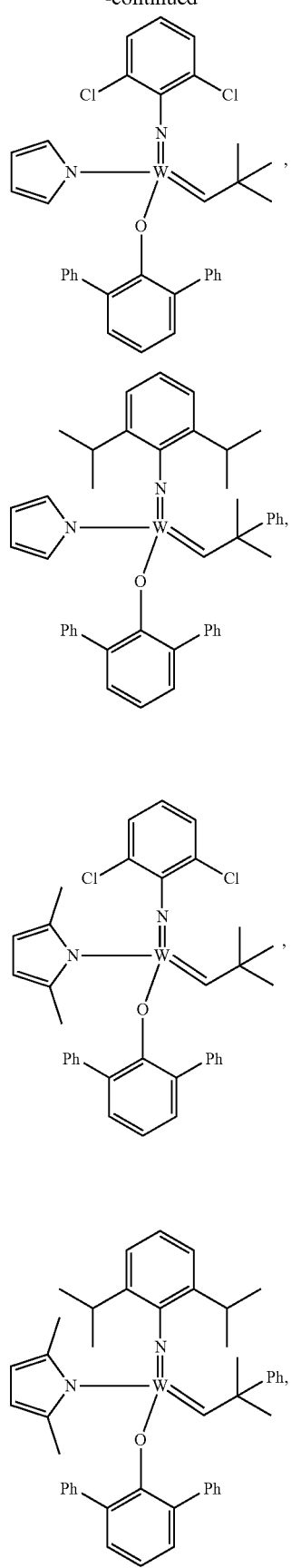

123
-continued
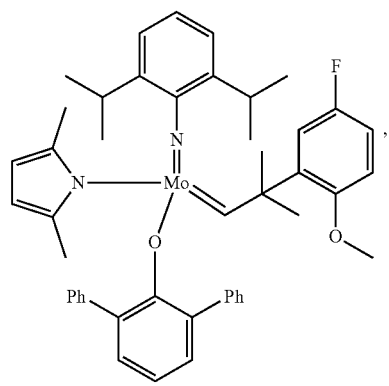
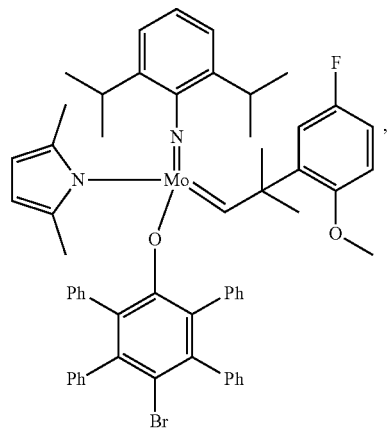
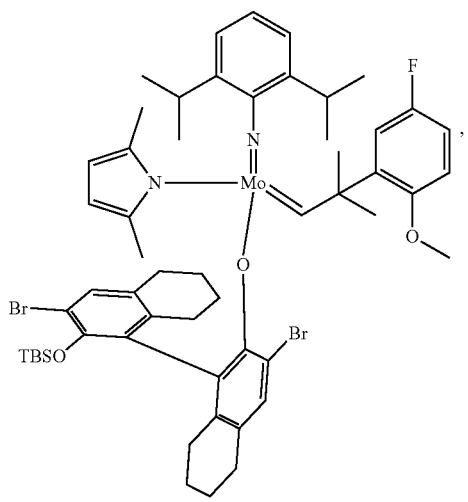
124
-continued
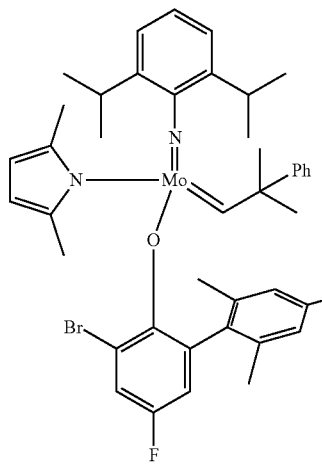
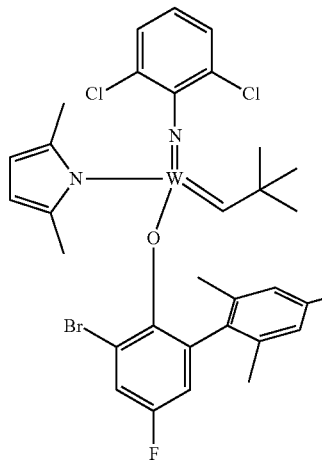
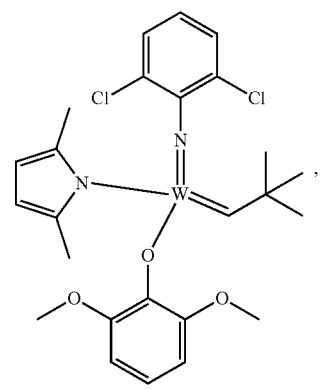
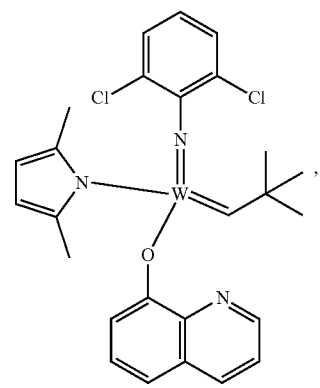

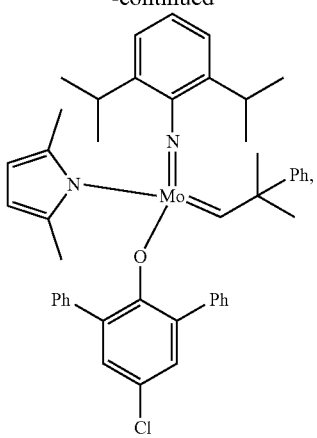
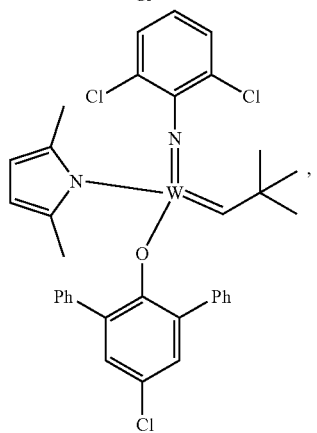
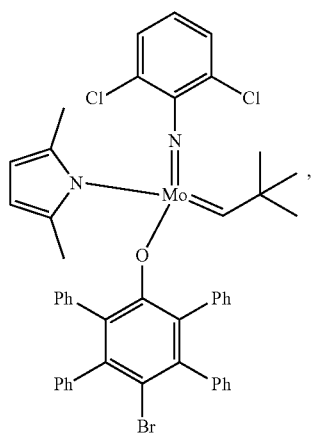
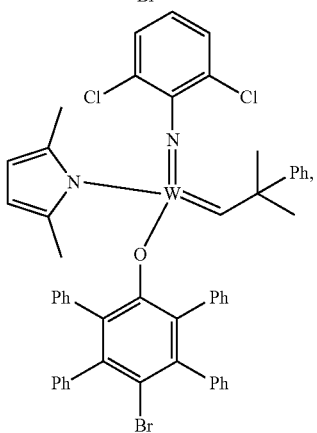
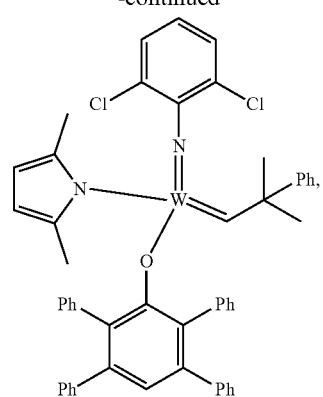
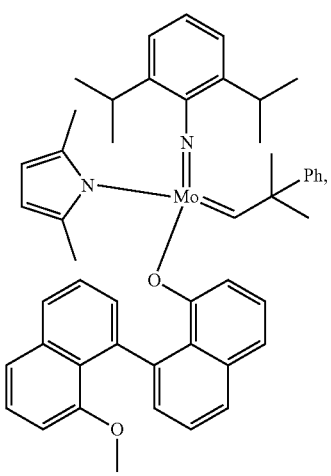
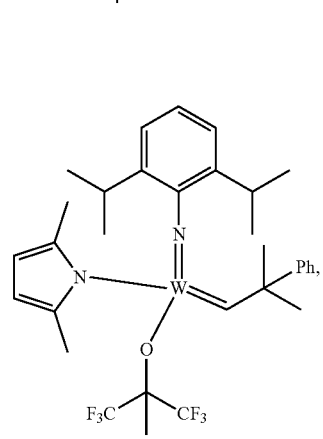
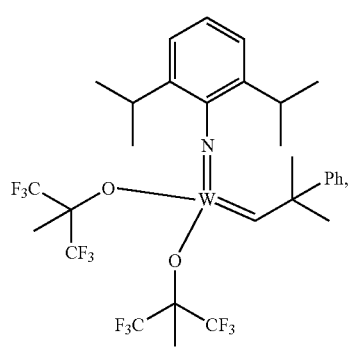

-continued
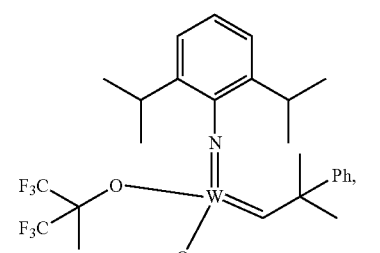
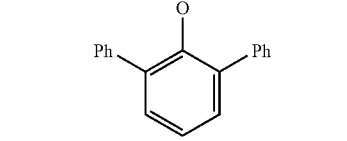
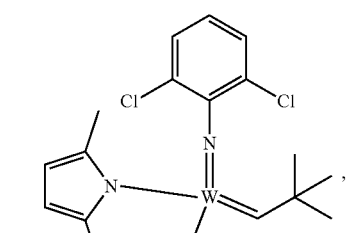
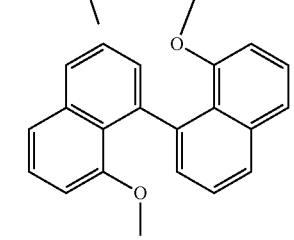
-continued
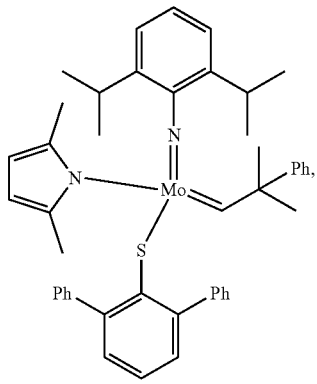
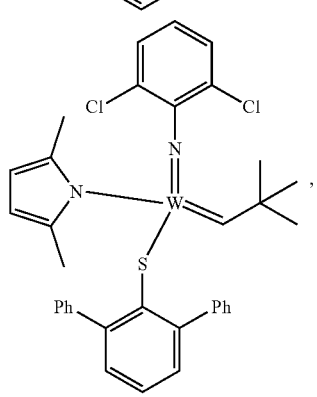
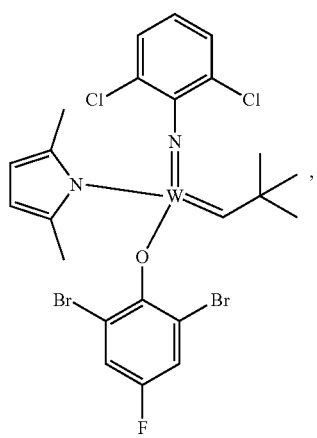
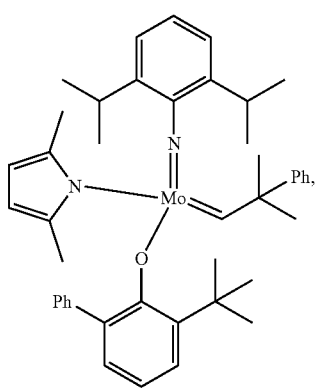

129
-continued
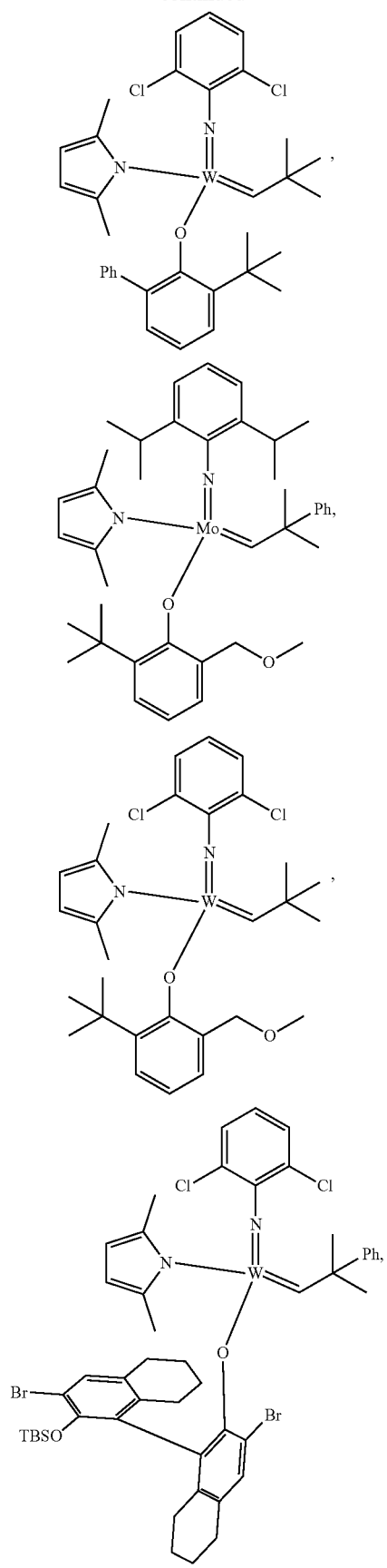
130
-continued
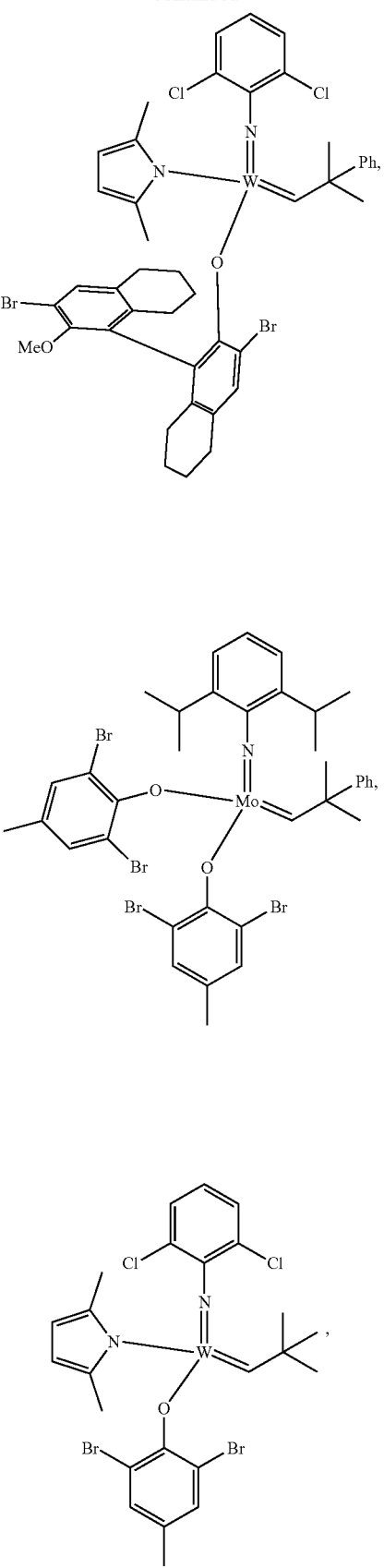

131
-continued
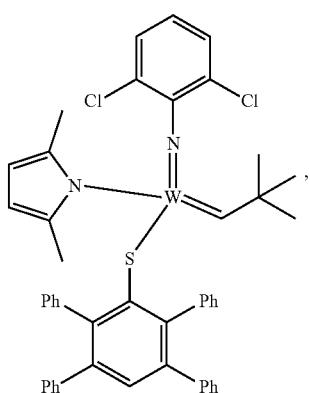
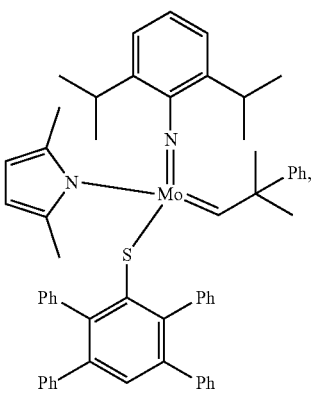
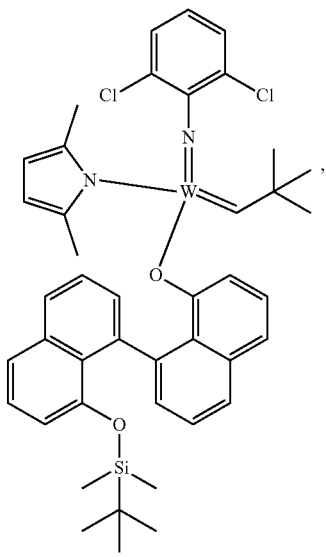
132
-continued
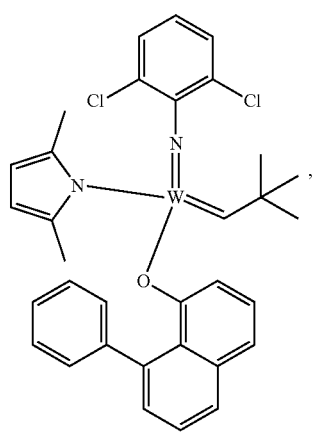
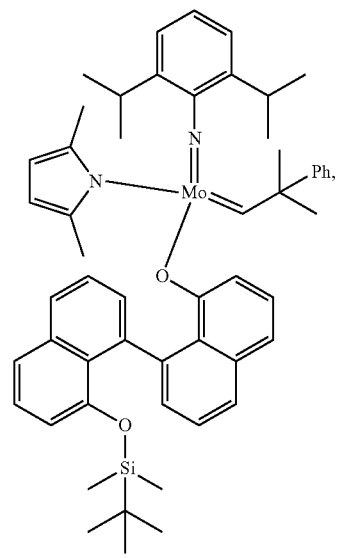
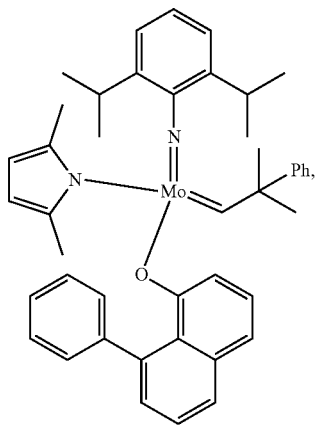

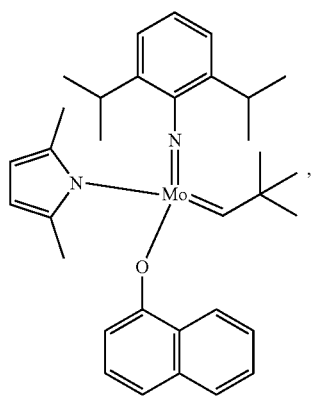
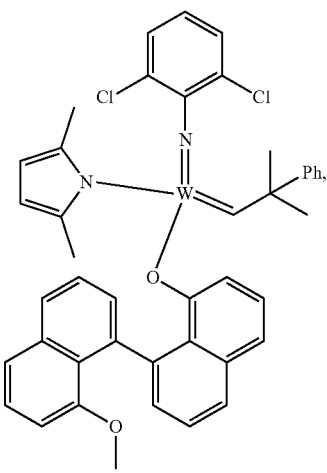
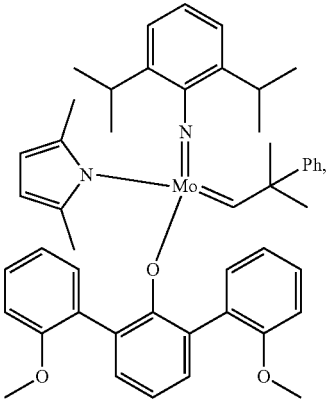
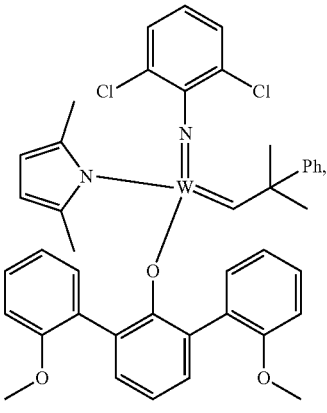
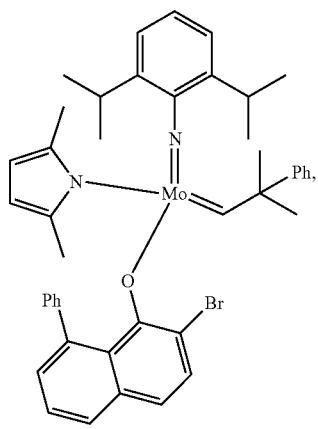
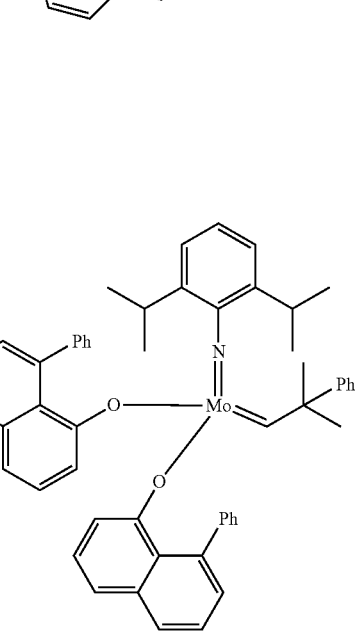
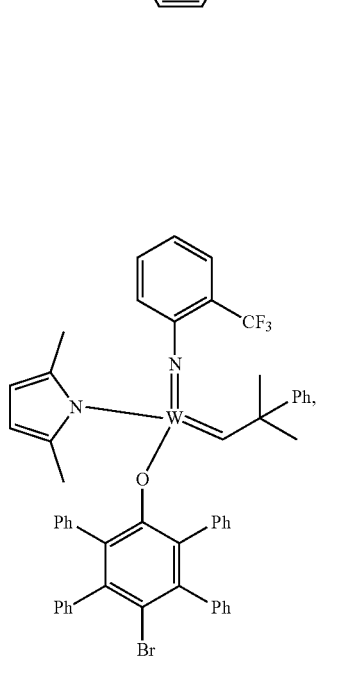

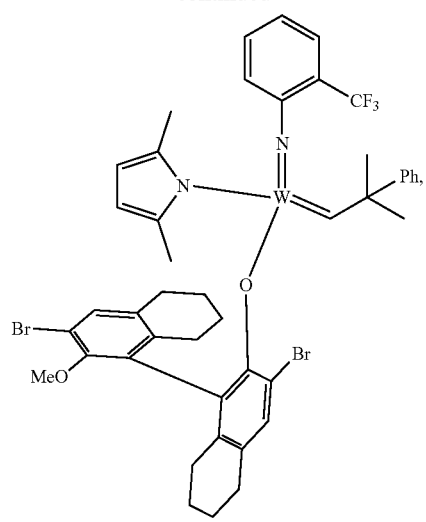
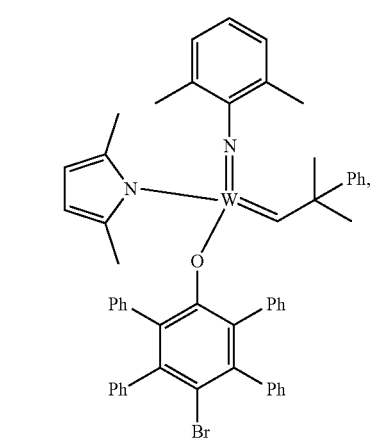
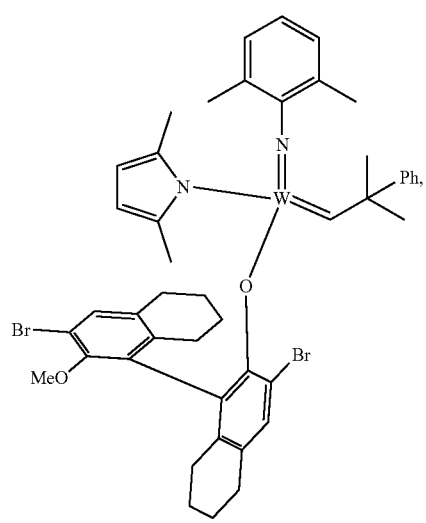
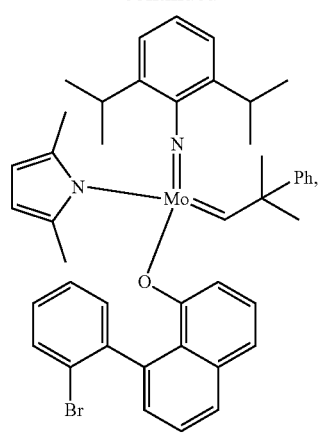
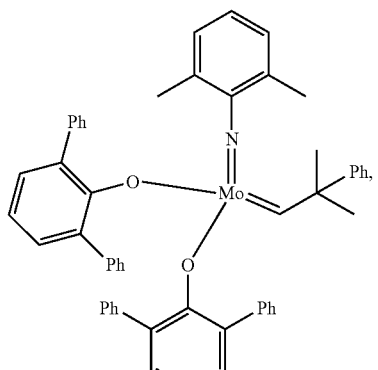
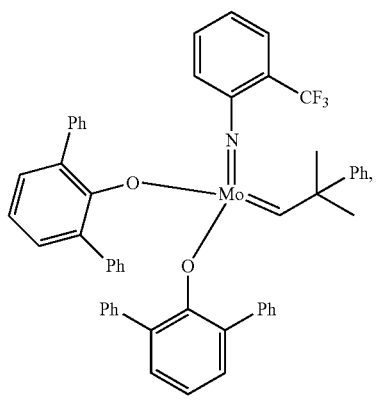
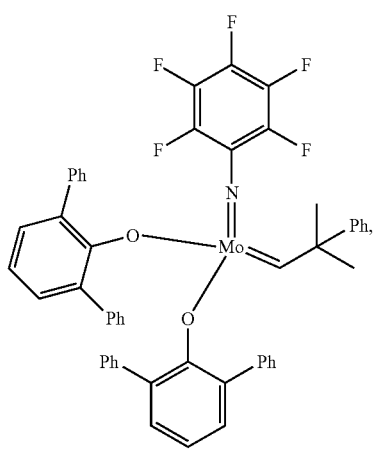

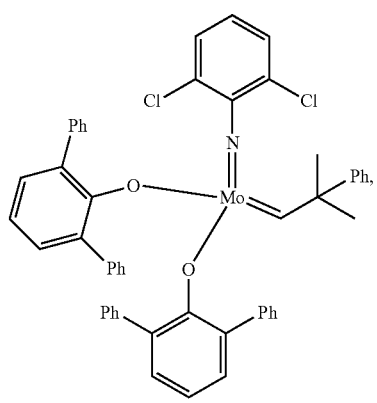
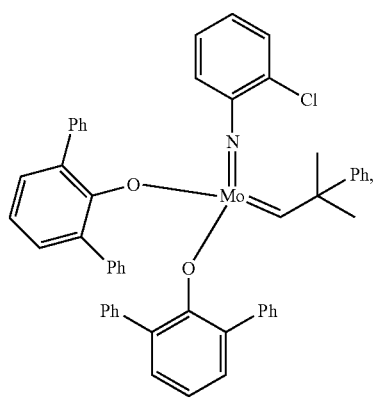
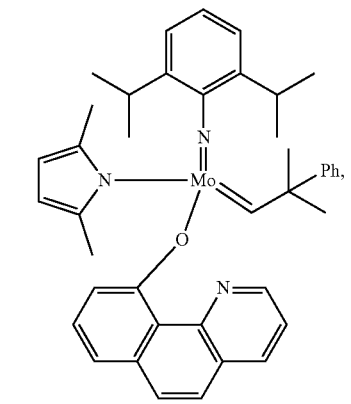
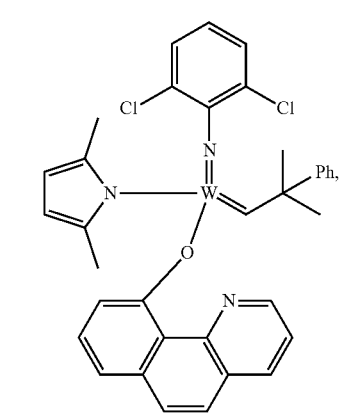
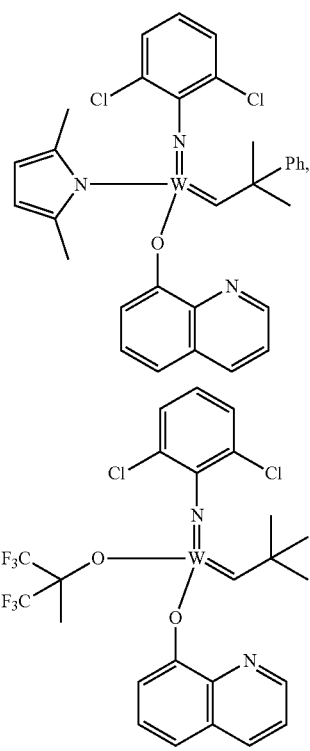
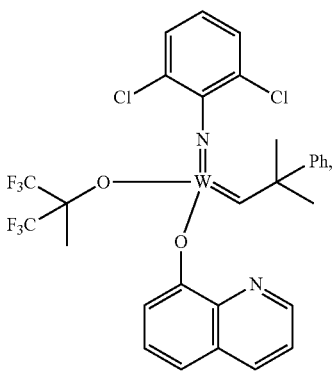
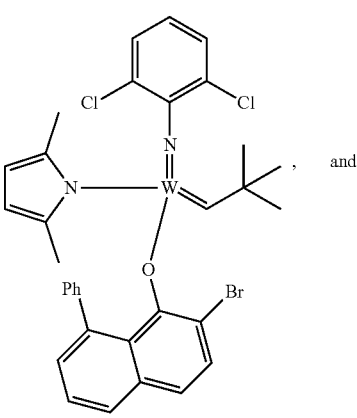

-continued

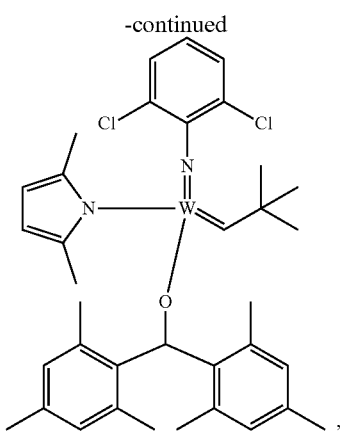

wherein "Me" is methyl, "Ph" is phenyl, "i-Pr" is isopropyl, "Mes" is mesityl (i.e., 2,4,6-trimethylphenyl), and "TBS" is tert-butyldimethylsilyl.

In some embodiments, the metathesis catalyst is

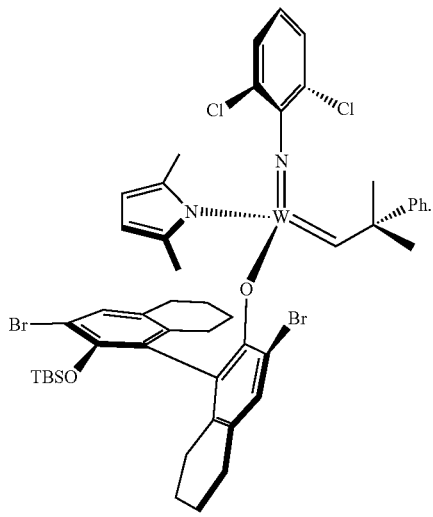

In some embodiments, the catalyst is a compound of Formula 3:

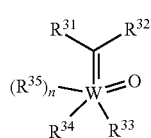

(3)

wherein:
each of $R^{31}$ and $R^{32}$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R;
each of $R^{33}$ and $R^{34}$ is independently halogen, R, —N(R)$_2$, —NRC(O)R, —NRC(O)OR, —NRC(O)N(R)$_2$, —NRSO$_2$R, —NRSO$_2$N(R)$_2$, —NROR, NR$_3$, —OR, a phosphorus-containing ligand, or an optionally substituted group selected from:
a 5-6 membered monocyclic heteroaryl ring having at least one nitrogen and 0-3 additional heteroatoms independently selected from nitrogen, oxygen, or sulfur,
a 4-7 membered saturated or partially unsaturated heterocyclic ring having at least one nitrogen and 0-2 additional heteroatoms independently selected from nitrogen, oxygen, or sulfur,
a 7-10 membered bicyclic saturated or partially unsaturated heterocyclic ring having at least one nitrogen and 0-4 additional heteroatoms independently selected from nitrogen, oxygen, or sulfur, and
an 8-10 membered bicyclic heteroaryl ring having at least one nitrogen and 0-4 additional heteroatoms independently selected from nitrogen, oxygen, or sulfur;

each R is independently hydrogen or an optionally substituted group selected from:
phenyl,
ferrocene,
$C_{1-20}$ aliphatic,
$C_{1-20}$ heteroaliphatic having 1-3 heteroatoms independently selected from nitrogen, oxygen, or sulfur,
a 3-7 membered saturated or partially unsaturated carbocyclic ring,
an 8-10 membered bicyclic saturated, partially unsaturated or aryl ring,
a 5-6 membered monocyclic heteroaryl ring having 1-4 heteroatoms independently selected from nitrogen, oxygen, or sulfur,
a 4-7 membered saturated or partially unsaturated heterocyclic ring having 1-3 heteroatoms independently selected from nitrogen, oxygen, or sulfur,
a 7-10 membered bicyclic saturated or partially unsaturated heterocyclic ring having 1-5 heteroatoms independently selected from nitrogen, oxygen, or sulfur; and
an 8-10 membered bicyclic heteroaryl ring having 1-5 heteroatoms independently selected from nitrogen, oxygen, or sulfur;
or two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur;
or two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;
n is 0, 1, or 2;
each $R^{35}$ is independently a monodentate ligand, or two $R^{35}$ are taken together with their intervening atoms to form an optionally substituted bidentate group; and
two or more of $R^{31}$, $R^{32}$, $R^{33}$, $R^{34}$ and $R^{35}$ may be taken together with their intervening atoms to form an optionally substituted polydentate ligand.

In some embodiments, the metathesis catalyst has a structure according to Formula 3 and the metathesis product comprises a Z olefin.

In some embodiments, the catalyst is selected from:

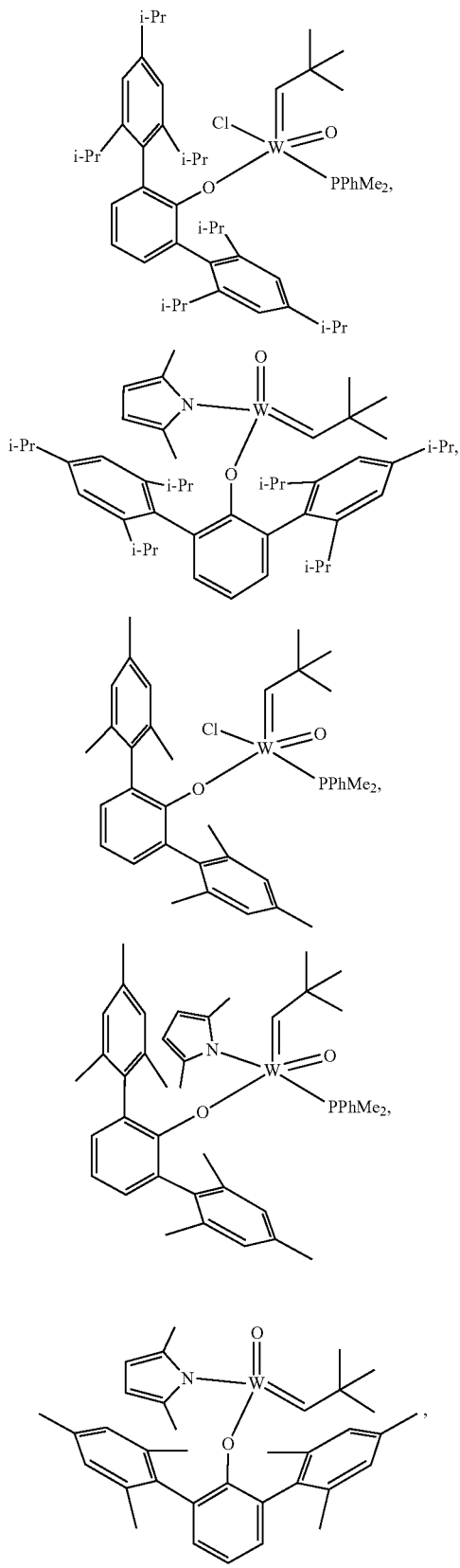

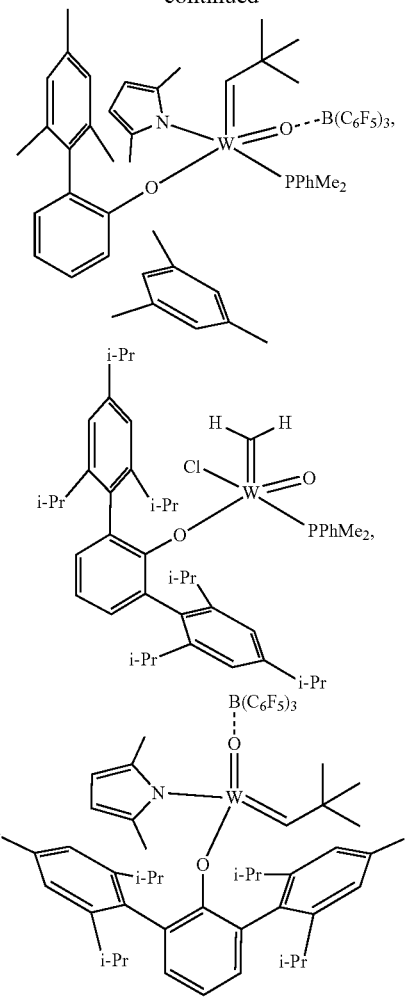

W(O)(CH-t-Bu)(Ph₂Pyr)(OHMT); W(O)(CH-t-Bu)(Ph₂Pyr)(OHIPT); W(O)(CH-t-Bu) [N(C₆F₅)₂](OHMT)(PPhMe₂); W(O)(CH-t-Bu)(PMe₃)₂Cl₂; W(O)(CH-t-Bu)(O-2,6-Ph₂C₆H₃)₂(PMe₃); W(O)(CH-t-Bu)(Cl)(OHIPT); W(O)(CH-t-Bu)(PMe₂Ph)₂Cl₂; W(O) (CHCMe₂Ph)Cl₂(PMe₂Ph)₂; W[OB(C₆F₅)₃](CH-t-Bu)(Me₂Pyr)(OHMT); W(O)(CH-t-Bu)[N—(C₆F₅)₂](OHMT); W(O)(CH-t-BU)(OHMT)(; W(O)(CH-t-BU)(OHIPT)₂; W(O)(CH-t-Bu)(Me₂Pyr)(DFTO)(PPhMte); W(O)(CH-t-Bu)(Me₂Pyr)(DFTO); W(O)(CHCMe₂Ph) (Me₂Pyr)(DFTO)(PPhMe); W(O)(CHCMe₂Ph)(Me₂Pyr)(DFTO); W(O)(CH-t-Bu)[N—(C₆F₅)₂](DFTO); and W(O)(CH-t-Bu)(DFTO)₂; wherein OHMT is O-2,6-dimesitylphenoxide; OHIPT is O-2,6-(2,4,6-triisopropylphenyl)₂C₆H₃; DFTO is 2,6-pentafluorophenylphenoxide; Ph₂Pyr is 2,5-diphenylpyrrol-1-yl; and Me₂Pyr is 2,5-dimethylpyrrol-1-yl.

Other metathesis catalysts can be used in the methods of the invention. In general, any metathesis catalyst stable under the reaction conditions and nonreactive with the functional groups present on the reactant shown in Schemes 3 through 8 may be used with the present invention. Such catalysts are, for example, those described by Grubbs (Grubbs, R. H., "Synthesis of large and small molecules using olefin metathesis catalysts." *PMSE Prepr.*, 2012), herein incorporated by reference in its entirety. Depending on the desired isomer of die olefin, a cis-selective metathesis catalyst may be used, for example one of those described by Shahane et al. (Shahane, S., et al. *Chem Cat Chem*, 2013. 5(12): p. 3436-3459), herein incorporated by reference in its entirety. Specific catalysts 1-5 exhibiting cis-selectivity are shown below (Scheme 5) and have been described previously (Khan, R. K., et al. *J. Am. Chem. Soc.*, 2013. 135(28): p. 10258-61; Hartung, J. et al. *J. Am. Chem. Soc.*, 2013. 135(28): p. 10183-5; Rosebrugh, L. E., et al. *J. Am. Chem. Soc.*, 2013. 135(4): p. 1276-9; Marx, V. M., et al. *J. Am. Chem. Soc.*, 2013. 135(1): p. 94-7; Herbert, M. B., et al. *Angew. Chem. Int. Ed. Engl.*, 2013. 52(1): p. 310-4; Keitz, B. K., et al. *J. Am. Chem. Soc.*, 2012. 134(4): p. 2040-3; Keitz, B. K., et al. *J. Am. Chem. Soc.*, 2012. 134(1): p. 693-9; Endo, K. et al. *J. Am. Chem. Soc.*, 2011. 133(22): p. 8525-7).

Scheme 5

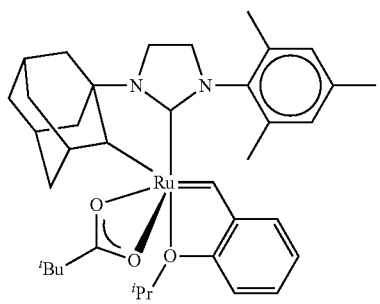

1

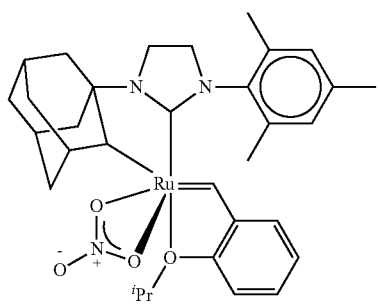

2

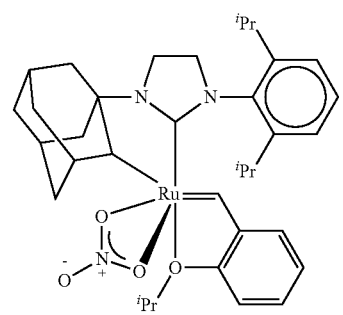

3

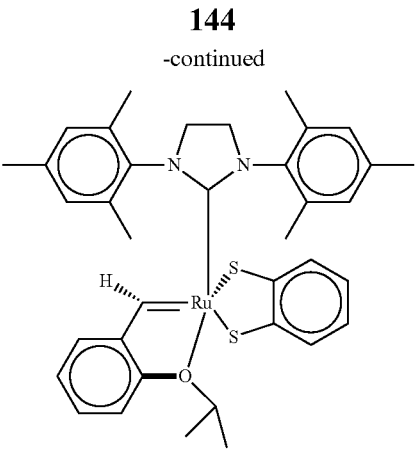

4

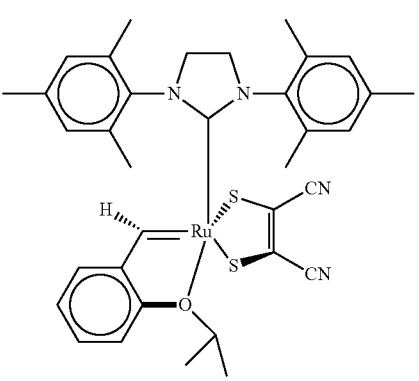

5

Additional Z-selective catalysts are described in (Cannon and Grubbs 2013; Bronner et al. 2014; Hartung et al. 2014; Pribisko et al. 2014; Quigley and Grubbs 2014) and are herein incorporated by reference in their entirety. Such metathesis catalysts include, but are not limited to, neutral ruthenium or osmium metal carbene complexes that possess metal centers that are formally in the +2 oxidation state, have an electron count of 16, are penta-coordinated, and are of the general formula LL'AA'M=$R_b R_c$ or LL'AA'M=C=)$_n C R_b R_c$ (Pederson and Grubbs 2002); wherein M is ruthenium or osmium;

L and L' are each independently any neutral electron donor ligand and preferably selected from phosphine, sulfonated phosphine, phosphite, phosphinite, phosphonite, arsine, stibnite, ether, amine, amide, imine, sulfoxide, carboxyl, nitrosyl, pyridine, thioether, or heterocyclic carbenes; and A and A' are anionic ligands independently selected from halogen, hydrogen, $C_1$-$C_{20}$ alkyl, aryl, $C_1$-$C_{20}$ alkoxide, aryloxide, $C_2$-$C_{20}$ alkoxycarbonyl, arylcarboxylate, $C_1$-$C_{20}$ carboxylate, arylsulfonyl, $C_1$-$C_{20}$ alkylsulfonyl, $C_1$-$C_{20}$ alkylsulfinyl; each ligand optionally being substituted with $C_1$-$C_5$ alkyl, halogen, $C_1$-$C_5$ alkoxy; or with a phenyl group that is optionally substituted with halogen, $C_1$-$C_5$ alkyl, or $C_1$-$C_5$ alkoxy; and A and A' together may optionally comprise a bidentate ligand; and $R_b$ and $R_c$ are independently selected from hydrogen, $C_1$-$C_{20}$ alkyl, aryl, $C_1$-$C_{20}$ carboxylate, $C_1$-$C_{20}$ alkoxy, aryloxy, $C_1$-$C_{20}$ alkoxy carbonyl, $C_1$-$C_{20}$ alkylthio, $C_1$-$C_{20}$ alkylsulfonyl and $C_1$-$C_{20}$ alkylsulfinyl, each of $R_b$ and $R_c$ optionally substituted with $C_1$-$C_5$ alkyl, halogen, $C_1$-$C_5$ alkoxy or with a phenyl group that is optionally substituted with halogen, $C_1$-$C_5$ alkyl, or $C_1$-$C_5$ alkoxy.

Other metathesis catalysts such as "well defined catalysts" can also be used. Such catalysts include, but are not limited to, Schrock's molybdenum metathesis catalyst, 2,6-diisopropylphenylimido neophylidenemolybdenum (VI) bis(hexafluoro-t-butoxide), described by Grubbs et al. (*Tetrahedron* 1998, 54: 4413-4450) and Basset's tungsten metathesis catalyst described by Couturier, J. L. et al. (*Angew. Chem. Int. Ed. Engl.* 1992, 31: 628).

Catalysts useful in the methods of the invention also include those described by Peryshkov, et al. *J. Am. Chem. Soc.* 2011, 133: 20754-20757; Wang, et al. *Angewandte Chemie*, 2013, 52: 1939-1943; Yu, et al. *J. Am. Chem. Soc.*, 2012, 134: 2788-2799; Halford. *Chem. Eng. News*, 2011, 89 (45): 11; Yu, et al. *Nature*, 2011, 479: 88-93; Lee. *Nature*, 2011, 471: 452-453; Meek, et al. *Nature*, 2011: 471, 461-466; Flook, et al. *J. Am. Chem. Soc.* 2011, 133: 1784-1786; Zhao, et al. *Org Lett.*, 2011, 13(4): 784-787; Ondi, et al. "High activity, stabilized formulations, efficient synthesis and industrial use of Mo- and W-based metathesis catalysts" *XiMo Technology Updates*, 2015: http://www.ximo-inc.com/files/ximo/uploads/download/Summary_3.11.15.pdf; Schrock, et al. *Macromolecules*, 2010: 43, 7515-7522; Peryshkov, et al. *Organometallics* 2013: 32, 5256-5259; Gerber, et al. *Organometallics* 2013: 32, 5573-5580; Marinescu, et al. *Organometallics* 2012: 31, 6336-6343; Wang, et al. *Angew. Chem. Int. Ed.* 2013: 52, 1939-1943; Wang, et al. *Chem. Eur. J.* 2013: 19, 2726-2740; Townsend et al. *J. Am. Chem. Soc.* 2012: 134, 11334-11337; and Johns et al. *Org. Lett.* 2016: 18, 772-775.

Catalysts useful in the methods of the invention also include those described in International Pub. No. WO 2014/155185; International Pub. No. WO 2014/172534; U.S. Pat. Appl. Pub. No. 2014/0330018; International Pub. No. WO 2015/003815; and International Pub. No. WO 2015/003814.

Catalysts useful in the methods of the invention also include those described in U.S. Pat. Nos. 4,231,947; 4,245,131; 4,427,595; 4,681,956; 4,727,215; International Pub. No. WO 1991/009825; U.S. Pat. Nos. 5,087,710; 5,142,073; 5,146,033; International Pub. No. WO 1992/019631; U.S. Pat. Nos. 6,121,473; 6,346,652; 8,987,531; U.S. Pat. Appl. Pub. No. 2008/0119678; International Pub. No. WO 2008/066754; International Pub. No. WO 2009/094201; U.S. Pat. Appl. Pub. No. 2011/0015430; U.S. Pat. Appl. Pub. No. 2011/0065915; U.S. Pat. Appl. Pub. No. 2011/0077421; International Pub. No. WO 2011/040963; International Pub. No. WO 2011/097642; U.S. Pat. Appl. Pub. No. 2011/0237815; U.S. Pat. Appl. Pub. No. 2012/0302710; International Pub. No. WO 2012/167171; U.S. Pat. Appl. Pub. No. 2012/0323000; U.S. Pat. Appl. Pub. No. 2013/0116434; International Pub. No. WO 2013/070725; U.S. Pat. Appl. Pub. No. 2013/0274482; U.S. Pat. Appl. Pub. No. 2013/0281706; International Pub. No. WO 2014/139679; International Pub. No. WO 2014/169014; U.S. Pat. Appl. Pub. No. 2014/0330018; and U.S. Pat. Appl. Pub. No. 2014/0378637.

Catalysts useful in the methods of the invention also include those described in International Pub. No. WO 2007/075427; U.S. Pat. Appl. Pub. No. 2007/0282148; International Pub. No. WO 2009/126831; International Pub. No. WO 2011/069134; U.S. Pat. Appl. Pub. No. 2012/0123133; U.S. Pat. Appl. Pub. No. 2013/0261312; U.S. Pat. Appl. Pub. No. 2013/0296511; International Pub. No. WO 2014/134333; and U.S. Pat. Appl. Pub. No. 2015/0018557.

Catalysts useful in the methods of the invention also include those set forth in the following table:

| Structure | Name |
|---|---|
| 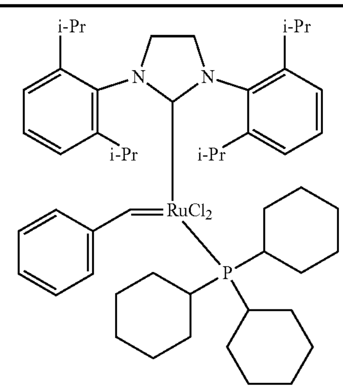 | dichloro[1,3-bis(2,6-isopropylphenyl)-2-imidazolidinylidene](benzylidene)(tricyclohexylphosphine)ruthenium(II) |
| 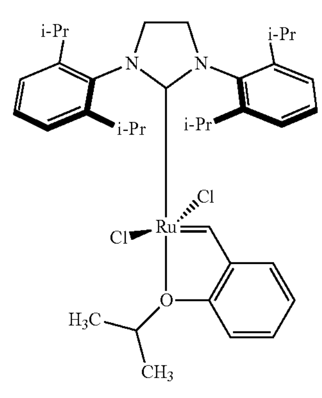 | dichloro[1,3-bis(2,6-isopropylphenyl)-2-imidazolidinylidene](2-isopropoxyphenylmethylene)ruthenium(II) |

| Structure | Name |
|---|---|
| 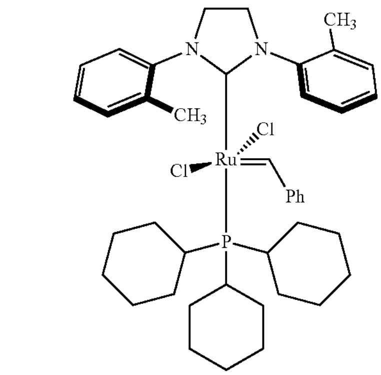 | dichloro[1,3-Bis(2-methylphenyl)-2-imidazolidinylidene](benzylidene)(tricyclohexylphosphine)ruthenium(II) |
| 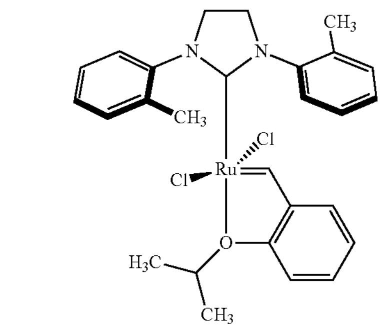 | dichloro[1,3-bis(2-methylphenyl)-2-imidazolidinylidene](2-isopropoxyphenylmethylene)ruthenium(II) |
| 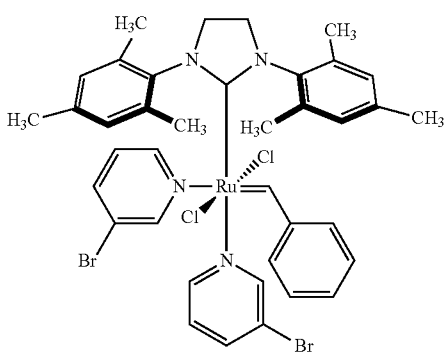 | dichloro[1,3-bis(2,4,6-trimethylphenyl)-2-imidazolidinylidene](benzylidene)bis(3-bromopyridine)ruthenium(II) |
| 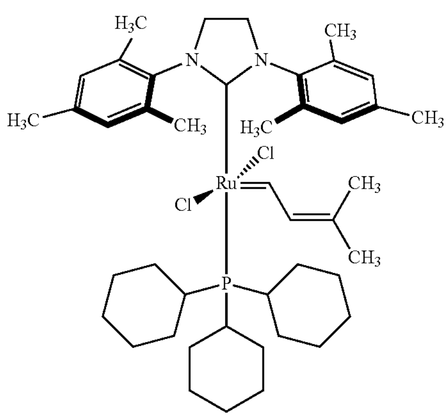 | dichloro[1,3-bis(2,4,6-trimethylphenyl)-2-imidazolidinylidene](3-methyl-2-butenylidene)(tricyclohexylphosphine)ruthenium(II) |

| Structure | Name |
|---|---|
| 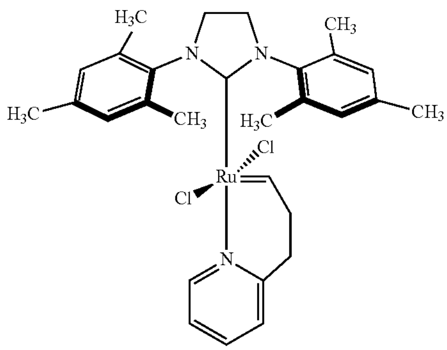 | dichloro[1,3-bis(2,4,6-trimethylphenyl)-2-imidazolidinylidene][3-(2-pyridinyl)propylidene]ruthenium(II) |
| 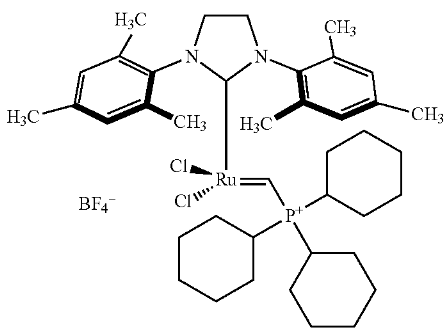 | dichloro[1,3-bis(2,4,6-trimethylphenyl)-2-imidazolidinylidene][(tricyclohexylphosphoranyl)methylidene]ruthenium(II) tetrafluoroborate |
| 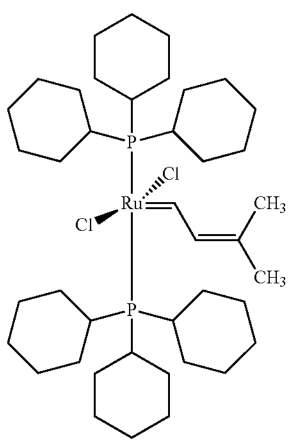 | dichloro(3-methyl-2-butenylidene)bis(tricyclohexylphosphine)ruthenium(II) |
| 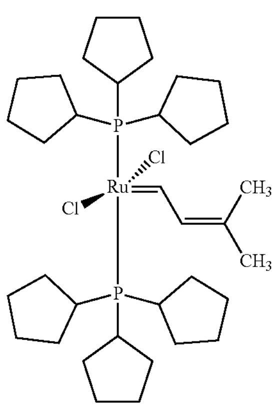 | dichloro(3-methyl-2-butenylidene)bis(tricyclopentylphosphine)ruthenium(II) |

| Structure | Name |
|---|---|
| 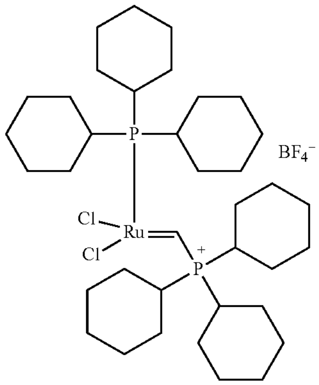 | dichloro(tricyclohexylphosphine)[(tricyclohexylphosphoranyl)methylidene]ruthenium(II) tetrafluoroborate |
| 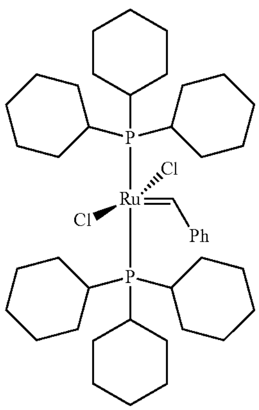 | bis(tricyclohexylphosphine)benzylidine ruthenium(IV)dichloride |
| 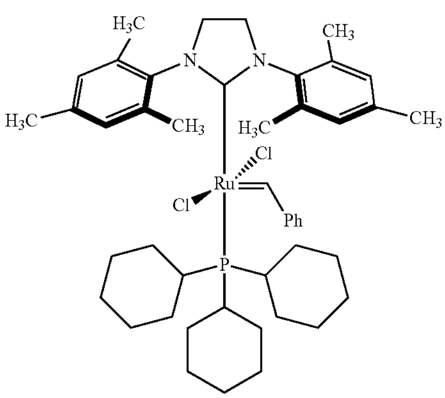 | [1,3-bis-(2,4,6-trimethylphenyl)-2-imidazolidinylidene]dichloro(phenylmethylene)(tricyclohexylphosphine)ruthenium |
| 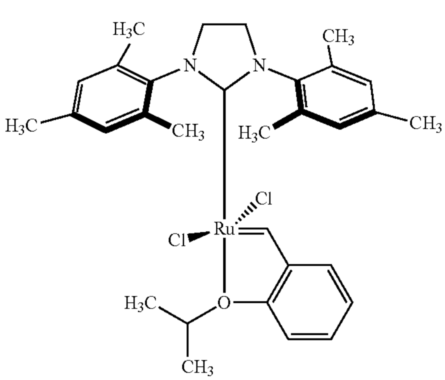 | (1,3-bis-(2,4,6-trimethylphenyl)-2-imidazolidinylidene)dichloro(o-isopropoxyphenylmethylene)ruthenium |

-continued

| Structure | Name |
|---|---|
| 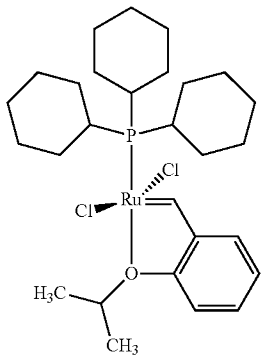 | dichloro(o-isopropoxyphenylmethylene)(tricyclohexylphosphine)ruthenium(II) |
| 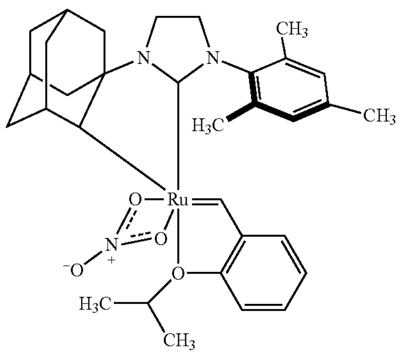 | [2-(1-methylethoxy-O)phenylmethyl-C](nitrato-O,O'){rel-(2R,5R,7R)-adamantane-2,1-diyl[3-(2,4,6-trimethylphenyl)-1-imidazolidinyl-2-ylidene]}ruthenium |

In some embodiments, the metathesis product comprises an E olefin, and the metathesis catalyst is selected from the group consisting of:

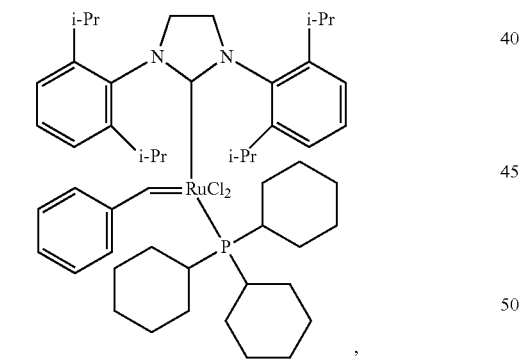

,

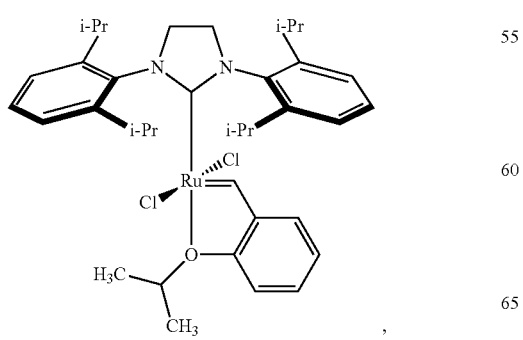

,

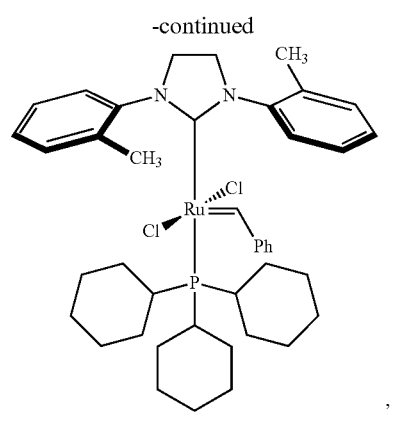

,

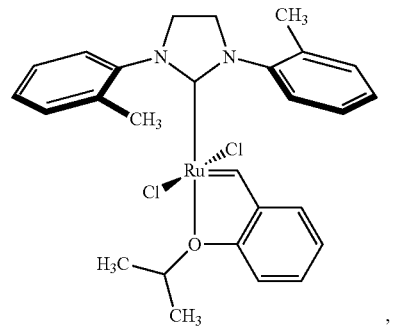

,

155
-continued
156
-continued
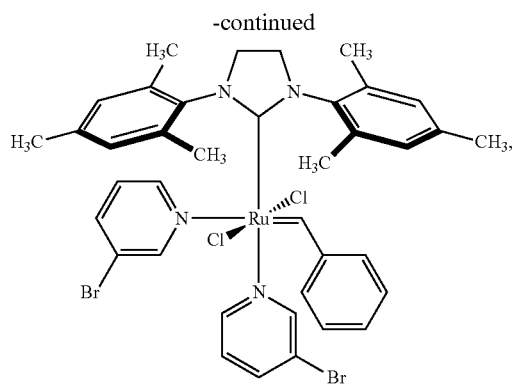
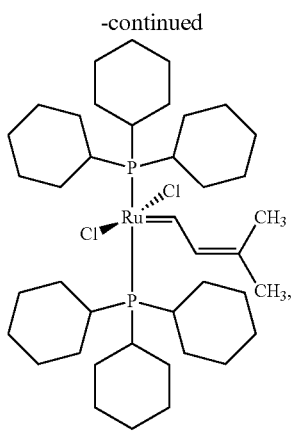
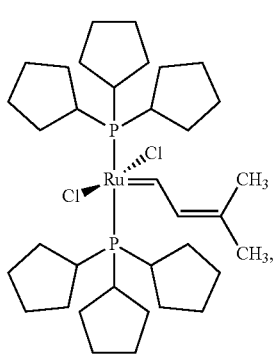
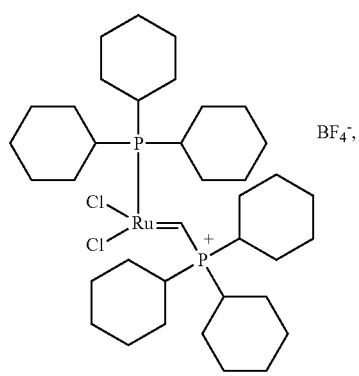

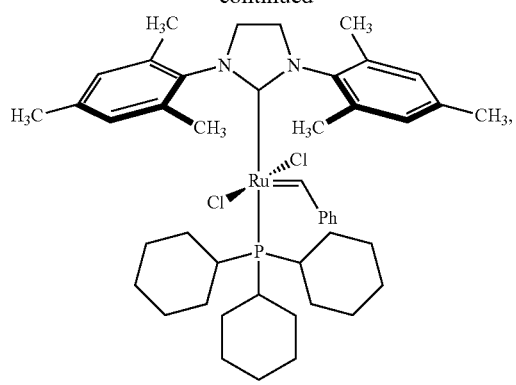
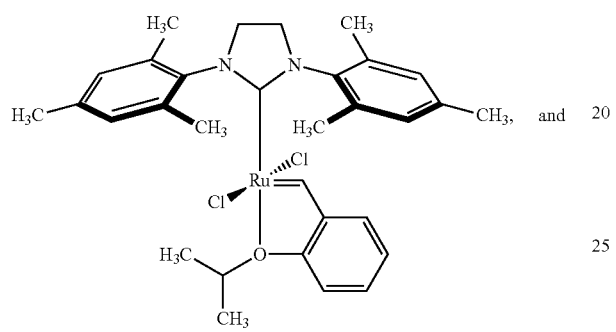
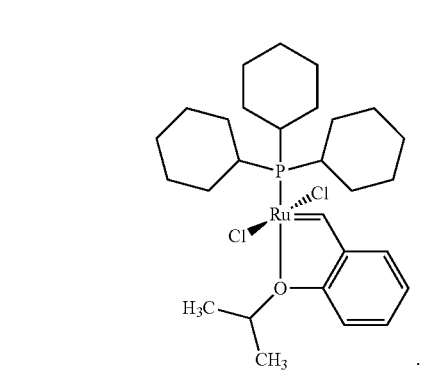
In some embodiments, the metathesis product comprises an E olefin, and the metathesis catalyst is selected from the group consisting of:
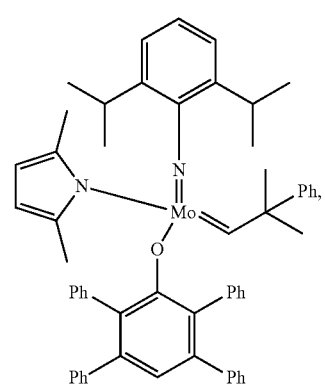
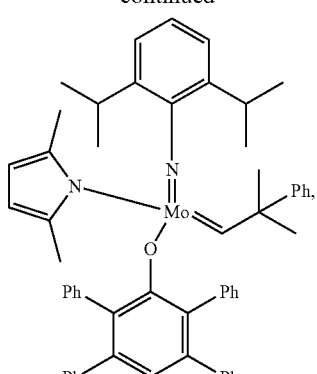
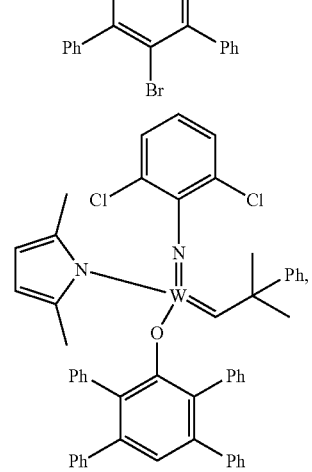
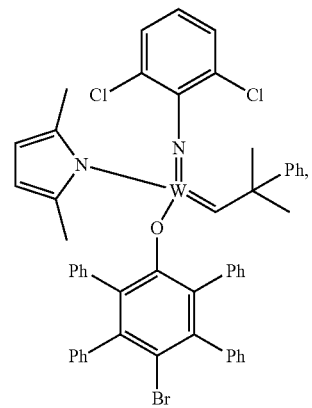
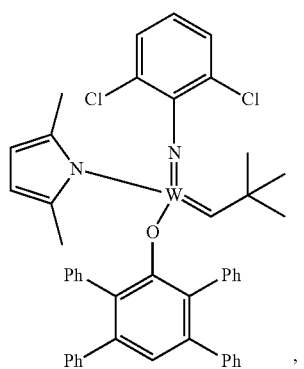

-continued

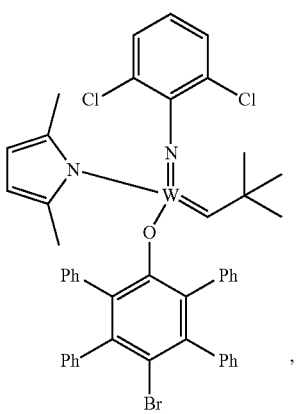

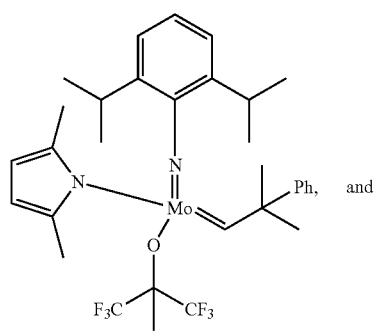

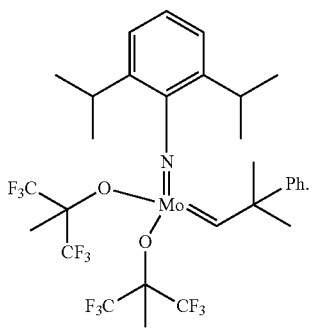

In some embodiments, the metathesis product comprises an E olefin, and the metathesis catalyst is selected from the group consisting of:

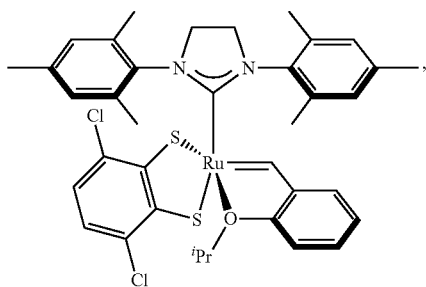

-continued

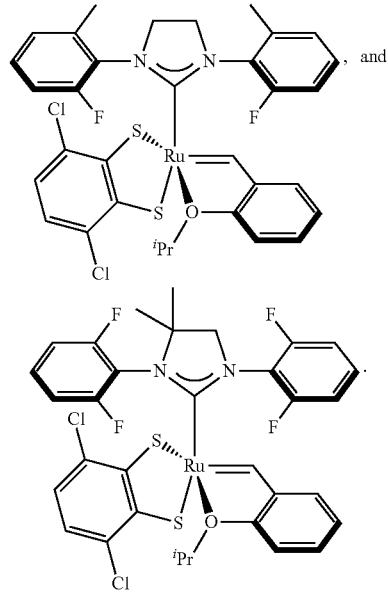

Catalysts useful in the methods of the invention also include those described in U.S. Pat. Appl. Pub. No. 2008/0009598; U.S. Pat. Appl. Pub. No. 2008/0207911; U.S. Pat. Appl. Pub. No. 2008/0275247; U.S. Pat. Appl. Pub. No. 2011/0040099; U.S. Pat. Appl. Pub. No. 2011/0282068; and U.S. Pat. Appl. Pub. No. 2015/0038723.

Catalysts useful in the methods of the invention include those described in International Pub. No. WO 2007/140954; U.S. Pat. Appl. Pub. No. 2008/0221345; International Pub. No. WO 2010/037550; U.S. Pat. Appl. Pub. No. 2010/0087644; U.S. Pat. Appl. Pub. No. 2010/0113795; U.S. Pat. Appl. Pub. No. 2010/0174068; International Pub. No. WO 2011/091980; International Pub. No. WO 2012/168183; U.S. Pat. Appl. Pub. No. 2013/0079515; U.S. Pat. Appl. Pub. No. 2013/0144060; U.S. Pat. Appl. Pub. No. 2013/0211096; International Pub. No. WO 2013/135776; International Pub. No. WO 2014/001291; International Pub. No. WO 2014/067767; U.S. Pat. Appl. Pub. No. 2014/0171607; and U.S. Pat. Appl. Pub. No. 2015/0045558.

Metathesis Reaction Conditions

The catalyst is typically provided in the reaction mixture in a sub-stoichiometric amount (e.g., catalytic amount). In certain embodiments, that amount is in the range of about 0.001 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, less than about 0.1 mol %, less than about 0.015 mol %, less than about 0.01 mol %, less than about 0.0015 mol %, or less, relative to the limiting reagent. In some embodiments, the catalyst is present in the range of about 2.5 mol % to about 5 mol %, relative to the limiting reagent. In some embodiments, the reaction mixture contains about 0.5 mol % catalyst. In the case where the molecular formula of the catalyst complex includes more than one metal, the amount of the catalyst complex used in the reaction may be adjusted accordingly.

In some cases, the methods described herein can be performed in the absence of solvent (e.g., neat). In some cases, the methods can include the use of one or more solvents. Examples of solvents that may be suitable for use in the invention include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the method is performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the method is performed at a pressure of about less than 760 torr. In some embodiments, the method is performed at a pressure of about less than 700 torr. In some embodiments, the method is performed at a pressure of about less than 650 torr. In some embodiments, the method is performed at a pressure of about less than 600 torr. In some embodiments, the method is performed at a pressure of about less than 550 torr. In some embodiments, the method is performed at a pressure of about less than 500 torr. In some embodiments, the method is performed at a pressure of about less than 450 torr. In some embodiments, the method is performed at a pressure of about less than 400 torr. In some embodiments, the method is performed at a pressure of about less than 350 torr. In some embodiments, the method is performed at a pressure of about less than 300 torr. In some embodiments, the method is performed at a pressure of about less than 250 torr. In some embodiments, the method is performed at a pressure of about less than 200 torr. In some embodiments, the method is performed at a pressure of about less than 150 torr. In some embodiments, the method is performed at a pressure of about less than 100 torr. In some embodiments, the method is performed at a pressure of about less than 90 torr. In some embodiments, the method is performed at a pressure of about less than 80 torr. In some embodiments, the method is performed at a pressure of about less than 70 torr. In some embodiments, the method is performed at a pressure of about less than 60 torr. In some embodiments, the method is performed at a pressure of about less than 50 torr. In some embodiments, the method is performed at a pressure of about less than 40 torr. In some embodiments, the method is performed at a pressure of about less than 30 torr. In some embodiments, the method is performed at a pressure of about less than 20 torr. In some embodiments, the method is performed at a pressure of about 20 torr.

In some embodiments, the method is performed at a pressure of about 19 torr. In some embodiments, the method is performed at a pressure of about 18 torr. In some embodiments, the method is performed at a pressure of about 17 torr. In some embodiments, the method is performed at a pressure of about 16 torr. In some embodiments, the method is performed at a pressure of about 15 torr. In some embodiments, the method is performed at a pressure of about 14 torr. In some embodiments, the method is performed at a pressure of about 13 torr. In some embodiments, the method is performed at a pressure of about 12 torr. In some embodiments, the method is performed at a pressure of about 11 torr. In some embodiments, the method is performed at a pressure of about 10 torr. In some embodiments, the method is performed at a pressure of about 10 torr. In some embodiments, the method is performed at a pressure of about 9 torr. In some embodiments, the method is performed at a pressure of about 8 torr. In some embodiments, the method is performed at a pressure of about 7 torr. In some embodiments, the method is performed at a pressure of about 6 torr. In some embodiments, the method is performed at a pressure of about 5 torr. In some embodiments, the method is performed at a pressure of about 4 torr. In some embodiments, the method is performed at a pressure of about 3 torr. In some embodiments, the method is performed at a pressure of about 2 torr. In some embodiments, the method is performed at a pressure of about 1 torr. In some embodiments, the method is performed at a pressure of less than about 1 torr.

In some embodiments, the two metathesis reactants are present in equimolar amounts. In some embodiments, the two metathesis reactants are not present in equimolar amounts. In certain embodiments, the two reactants are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the two reactants are present in a molar ratio of about 10:1. In certain embodiments, the two reactants are present in a molar ratio of about 7:1. In certain embodiments, the two reactants are present in a molar ratio of about 5:1. In certain embodiments, the two reactants are present in a molar ratio of about 2:1. In certain embodiments, the two reactants are present in a molar ratio of about 1:10. In certain embodiments, the two reactants are present in a molar ratio of about 1:7. In certain embodiments, the two reactants are present in a molar ratio of about 1:5. In certain embodiments, the two reactants are present in a molar ratio of 1:2.

In some embodiments, one molar equivalent of the olefin is contacted with one molar equivalent of the metathesis reaction partner. In some embodiments, about 1.5, 2, 2.5, or 3 molar equivalents of the olefin is contacted with one molar equivalent of the metathesis reaction partner. In some embodiments, about 1.5 molar equivalents of the olefin is contacted with one molar equivalent of the metathesis reaction partner.

In general, the reactions with many of the metathesis catalysts disclosed herein provide yields better than 15%, e.g., better than 50%, better than 75%, or better than 90%. In addition, the reactants and products are chosen to provide at least a 5° C. difference, e.g., a greater than 20° C. difference, or a greater than 40° C. difference in boiling points. Additionally, the use of metathesis catalysts allows for much faster product formation than byproduct, and it can be desirable to run these reactions as quickly as practical. In particular, the reactions are performed in less than about 24 hours, e.g., less than 12 hours, or less than 8 hours, or less than 4 hours. Advantageously, the methods of the invention provide metathesis products on a scale ranging from a few milligrams to hundreds of kilograms or more. For example, the methods can be conducted using around 1-10 grams of the olefin according to Formula I, or around 10-100 grams of the olefin according to Formula I, or around 100-500 grams of the olefin according to Formula I, or around 500-1000 grams of the olefin according to Formula I. The methods can be conducted using at least 1, 5, 10, 25, 50, 100, or 1,000 kilograms of starting material. The metathesis reactions can be conducted using a metathesis reactor as described, for example, in WO 2011/046872, which reactor can be operated in conjunction with one or more downstream separation units for separating and/or recycling particular product or byproduct streams (e.g., an olefin stream, a $C_2$-$C_3$ compound stream, or a $C_3$-$C_5$ compound stream). The metathesis reactor and separation unit(s) can be operated in conjunction with one or more adsorbent beds to facilitate the separation of the metathesized products from the catalyst, as well as washing and drying units for purification of desired products. The metathesis, reduction, and acylation reactions can be conducted to provide products on the scale of metric tons.

One of skill in the art will appreciate that the time, temperature and solvent can depend on each other, and that changing one can require changing the others to prepare the metathesis products in the methods of the invention. The metathesis steps can proceed at a variety of temperatures and times. In general, reactions in the methods of the invention are conducted using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, reactions in the methods of the invention are conducted at a temperature of from about 0° C. to about 200° C. For example, reactions can be conducted at 15-100° C. In some embodiments, reaction can be conducted at 20-80° C. In some embodiments, reactions can be conducted at 100-150° C.

The olefins, fatty alcohols, fatty acid esters, and other materials used in the methods of the invention can be obtained from any suitable source. In some embodiments, the metathesis reaction partners used in the methods of the invention are obtained from a natural oil and/or a derivative thereof. Representative examples of natural oils for use in accordance with the present teachings include but are not limited to vegetable oils, algal oils, animal fats, tall oils (e.g., by-products of wood pulp manufacture), derivatives of these oils, and the like, and combinations thereof. Representative examples of vegetable oils for use in accordance with the present teachings include but are not limited to canola oil, rapeseed oil, coconut oil, corn oil, cottonseed oil, olive oil, palm oil, peanut oil, safflower oil, sesame oil, soybean oil, sunflower oil, high oleic sunflower oil, linseed oil, palm kernel oil, tung oil, jatropha oil, jojoba oil, mustard oil, pennycress oil, camelina oil, hemp oil, castor oil, and the like, and combinations thereof. Representative examples of animal fats for use in accordance with the present teachings include but are not limited to lard, tallow, poultry fat, yellow grease, brown grease, fish oil, and the like, and combinations thereof. The natural oil can be refined, bleached, and/or deodorized.

Representative examples of natural oil derivatives for use in accordance with the method of the invention include, but are not limited to, gums, phospholipids, soapstock, acidulated soapstock, distillate or distillate sludge, fatty acids, fatty acid esters (e.g., non-limiting examples such as 2-ethylhexyl ester, etc.), hydroxy-substituted variations thereof, and the like, and combinations thereof. In some embodiments, the natural oil derivative comprises an ester. In some embodiments, the derivative is selected from the group consisting of a monoacylglyceride (MAG), a diacylglyceride (DAG), a triacylglyceride (TAG), and combinations thereof. In some embodiments, the natural oil derivative comprises a fatty acid methyl ester (FAME) derived from the glyceride of the natural oil.

In some embodiments, a feedstock includes canola or soybean oil, e.g., refined, bleached, and/or deodorized soybean oil (i.e., RBD soybean oil). Soybean oil typically contains about 95% weight or greater (e.g., 99% weight or greater) triglycerides of fatty acids. Major fatty acids in the polyol esters of soybean oil include saturated fatty acids, including palmitic acid (hexadecanoic acid) and stearic acid (octadecanoic acid), and unsaturated fatly acids, including oleic acid (9-octadecenoic acid), linoleic acid (9, 12-octadecadienoic acid), and linolenic acid (9, 12, 15-octadecatrienoic acid).

In some embodiments, materials to be reacted in a metathesis reaction—including those derived from natural oils—will containing one or more contaminants with the potential to adversely affect the performance of a metathesis catalyst. Such contaminants can be referred to as "catalyst poisons" or "catalyst poisoning contaminants." The contaminant levels can be reduced according to the methods described herein. In some embodiments, the material comprises a plurality of contaminants and the method comprises reducing levels of two or more of the contaminants. In some embodiments, the material comprises a plurality of contaminants and the method comprises reducing levels of three or more of the contaminants. In some embodiments, the material comprises a plurality of contaminants and the method comprises reducing levels of four or more of the contaminants. In some embodiments, the material comprises a plurality of contaminants and the method comprises reducing levels of five or more of the contaminants.

Representative contaminants include but are not limited to water, peroxides, peroxide decomposition products, hydroperoxides, protic materials, polar materials, Lewis basic catalyst poisons, and the like, and combinations thereof. It is to be understood that some contaminants may properly be classified in multiple categories (e.g., an alcohol can be considered both a protic material and a polar material). It is to be further understood that different catalysts may have different susceptibilities to a particular contaminant, and that a contaminant that adversely affects the performance of one catalyst (e.g., a ruthenium-based catalyst) may or may not affect (to a similar extent or to any extent whatsoever) a different catalyst (e.g., a molybdenum-based catalyst).

Representative protic materials that may be found as contaminants in a substrate that is to be reacted in a metathesis reaction include but are not limited to materials having a hydrogen atom bonded to oxygen (e.g., carboxylic acids, alcohols, and the like) and/or a hydrogen atom bonded to nitrogen (e.g., primary amines, secondary amines, and the like). In some embodiments, particularly though not exclusively in natural oil substrates, a protic material contaminant may comprise a carboxylic acid functional group, a hydroxyl functional group, or a combination thereof. In some embodiments, the protic material is selected from the group consisting of free fatty acids, hydroxyl-containing materials, MAGs, DAGs, and the like, and combinations thereof.

Representative polar materials that may be found as contaminants in a substrate that is to be reacted in a metathesis reaction include but are not limited to heteroatom-containing materials such as oxygenates. In some embodiments, the polar material is selected from the group consisting of alcohols, aldehydes, ethers, and the like, and combinations thereof.

Representative Lewis basic catalyst poisons that may be found as contaminants in a substrate that is to be reacted in a metathesis reaction include but are not limited to heteroatom-containing materials. In some embodiments, the Lewis basic catalyst poisons are selected from the group consisting of N-containing materials, P-containing materials, S-containing materials, and the like, and combinations thereof.

Reaction materials containing contaminants can be treated with one or more conditioning agents that mitigate potentially adverse effects of one or more of the contaminants. Conditioning agents that can be used in the methods of the invention (individually, or in combination sequentially or simultaneously) include heat, molecular sieves, alumina (aluminum oxide), silica gel, montmorillonite clay, fuller's earth, bleaching clay, diatomaceous earth, zeolites, kaolin, activated metals (e.g., Cu, Mg, and the like), acid anhydrides (e.g., acetic anhydride and the like), activated carbon (i.e., activated charcoal), soda ash, metal hydrides (e.g., alkaline earth metal hydrides such as $CaH_2$ and the like), metal sulfates (e.g., alkaline earth metal sulfates such as calcium sulfate, magnesium sulfate, and the like; alkali metal sulfates such as potassium sulfate, sodium sulfate, and the like; and other metal sulfates such as aluminum sulfate, potassium magnesium sulfate, and the like), metal halides (e.g., alkali earth metal halides such as potassium chloride and the like), metal carbonates (e.g., calcium carbonate, sodium carbonate, and the like), metal silicates (e.g., magnesium silicate and the like), phosphorous pentoxide, metal aluminum hydrides (e.g., alkali metal aluminum hydrides such as $LiAlH_4$, $NaAlH_4$, and the like), alkyl aluminum hydrides (e.g., DIBALH), metal borohydrides (e.g., alkali metal borohydrides such as $LiBH_4$, $NaBH_4$, and the like), organometallic reagents (e.g., Grignard reagents; organolithium reagents such as n-butyl lithium, t-butyl lithium, sec-butyl lithium; trialkyl aluminums such as triethyl aluminum, tributyl aluminum, triisobutyl aluminum, triisopropyl aluminum, trioctyl aluminum, and the like, metal amides (e.g., lithium diisopropyl amide, metal bis(trimethylsilyl) amides such as KHMDS, and the like), palladium on carbon (Pd/C) catalysts, and combinations thereof.

In some embodiments, the conditioning agent is a metal alkyl compound. In some embodiments, the metal, M, can be lithium, sodium, potassium, magnesium, calcium, zinc, cadmium, aluminum, or gallium Examples of suitable alkyl radicals, R, include, but are not limited to, methyl, ethyl, butyl, hexyl, decyl, tetradecyl, and eicosyl. Examples of metal alkyl compounds include, but are not limited to, $Mg(CH_3)_2$, $Mg(C_2H_5)_2$, $Mg(C_2H_5)(C_4H_9)$, $Mg(C_4H_9)_2$, $Mg(C_6H_{13})_2$, $Mg(C_{12}H_{25})_2$, $Zn(CH_3)_2$, $Zn(C_2H_5)_2$, $Zn(C_4H_5)_2$, $Zn(C_4H_9)(C_8H_{17})$, $Zn(C_6H_{13})_2$, $Zn(C_6H_5)_2$, $Al(C_2H_5)_3$, $Al(CH_3)_3$, $Al(n-C_4H_9)_3$, $Al(C_8H_{17})_3$, $Al(iso-C_4H_9)_3$, $Al(C_{12}H_{25})_3$, and combinations thereof. Metal alkyl compounds also include substances having one or more halogen or hydride groups, such as ethylaluminum dichloride, diethylaluminum chloride, diethylaluminum hydride, Grignard reagents, diisobutylaluminum hydride, and the like.

In some embodiments, the treating of the metathesis reaction material (e.g., a natural oil or a natural oil derivative) can include contacting the reaction material with a metal alkyl compound and, either simultaneously or separately, contacting the reaction material with a hydride-containing compound. In some embodiments, where the reaction material is contacted simultaneously with the metal alkyl compound and the hydride-containing compound, the hydride-containing compounds can be included in the metal alkyl compound. For example, in some instances, processes used to make certain metal alkyl compounds, such as trialkyl aluminum compounds, can lead to the formation of a certain concentration of hydride-containing compounds. In other embodiments, however, the metal alkyl compounds can be combined with one or more hydride-containing compounds. Or, in some embodiments, the metathesis reaction material can be treated by the hydride-containing compounds in a separate treatment step, which can be performed before, after, or both before and after, treatment of the reaction material with the metal alkyl compounds.

Any suitable hydride-containing compounds can be used. In some embodiments, the hydride-containing compounds are selected from the group consisting of metal aluminum hydrides (e.g., alkali metal aluminum hydrides such as $LiAlH_4$, $NaAlH_4$, and the like), alkyl aluminum hydrides (e.g., DIBALH), and combinations thereof. In some embodiments, the hydride-containing compound is an alkyl aluminum hydride, such as DIBALH.

In some embodiments, contacting the metathesis reaction material with the hydride-containing compound occurs in the same step as contacting the reaction material with the metal alkyl compound. In some embodiments, the weight-to-weight ratio of the metal alkyl compound to the hydride-containing compound in the treatment composition is from 2:1, or from 5:1, or from 10:1, or from 15:1, or from 20:1 to 1000:1. In some embodiments, the weight-to-weight ratio of the metal alkyl compound to the hydride-containing compound in the treatment composition is at least 2:1, or at least 5:1, or at least 10:1, or at least 15:1, or at least 20:1.

In certain instances, the efficacy of the metathesis catalyst can be improved (e.g., the turnover number can be increased or the overall catalyst loading may be decreased) through slow addition of the catalyst to a substrate. The overall catalyst loading can be decreased by at least 10%, at least 20%, or at least 30% when administered slowly to achieve the same turnover number as a single, full batch loading. The slow addition of overall catalyst loading can include adding fractional catalyst loadings to the reaction materials at an average rate of approximately 10 ppm by weight of catalyst per hour (ppmwt/hr), 5 ppmwt/hr, 1 ppmwt/hr, 0.5 ppmwt/hr, 0.1 ppmwt/hr, 0.05 ppmwt/hr, or 0.01 ppmwt/hr. In some embodiments, the catalyst is slowly added at a rate of between about 0.01-10 ppmwt/hr, 0.05-ppmwt/hr, or 0.1-1 ppmwt/hr. The slow addition of the catalyst can be conducted in batch loadings at frequencies of every 5 minutes, 15 minutes, 30 minutes, 1 hour, 2 hours, 4 hours, 12 hours, or 1 day. In other embodiments, the slow addition is conducted in a continuous addition process.

Pheromone Products

As described above, a number of the fatty olefin derivatives obtained via the methods of the invention can be used as insect pheromones or pheromone precursor materials. The precursor materials and pheromone products include, for example, the compounds listed in Table 1 and Table 6. The method can be used for synthesizing one or more of the pheromones listed in Table 7.

TABLE 7

Pheromone products.

| Name | Name | Name |
| --- | --- | --- |
| (E)-2-Decen-1-ol | (Z,Z)-5,9-Tridecadienyl acetate | (Z)-10-Hexadecenal |
| (E)-2-Decenyl acetate | (Z,Z)-7,11-Tridecadienyl acetate | (E)-11-Hexadecen-1-ol |
| (E)-2-Decenal | (E,Z,Z)-4,7,10-Tridecatrienyl acetate | (E)-11-Hexadecenyl acetate |
| (Z)-2-Decen-1-ol | (E)-3-Tetradecen-1-ol | (E)-11-Hexadecenal |
| (Z)-2-Decenyl acetate | (E)-3-Tetradecenyl acetate | (Z)-11-Hexadecen-1-ol |

TABLE 7-continued

Pheromone products.

| Name | Name | Name |
|---|---|---|
| (Z)-2-Decenal | (Z)-3-Tetradecen-1-ol | (Z)-11-Hexadecenyl acetate |
| (E)-3-Decen-1-ol | (Z)-3-Tetradecenyl acetate | (Z)-11-Hexadecenal |
| (Z)-3-Decenyl acetate | (E)-5-Tetradecen-1-ol | (Z)-12-Hexadecenyl acetate |
| (Z)-3-Decen-1-ol | (E)-5-Tetradecenyl acetate | (Z)-12-Hexadecenal |
| (Z)-4-Decen-1-ol | (E)-5-Tetradecenal | (E)-14-Hexadecenal |
| (E)-4-Decenyl acetate | (Z)-5-Tetradecen-1-ol | (Z)-14-Hexadecenyl acetate |
| (Z)-4-Decenyl acetate | (Z)-5-Tetradecenyl acetate | (E,E)-1,3-Hexadecadien-1-ol |
| (Z)-4-Decenal | (Z)-5-Tetradecenal | (E,Z)-4,6-Hexadecadien-1-ol |
| (E)-5-Decen-1-ol | (E)-6-Tetradecenyl acetate | (E,Z)-4,6-Hexadecadienyl acetate |
| (E)-5-Decenyl acetate | (Z)-6-Tetradecenyl acetate | (E,Z)-4,6-Hexadecadienal |
| (Z)-5-Decen-1-ol | (E)-7-Tetradecen-1-ol | (E,Z)-6,11-Hexadecadienyl acetate |
| (Z)-5-Decenyl acetate | (E)-7-Tetradecenyl acetate | (E,Z)-6,11-Hexadecadienal |
| (Z)-5-Decenal | (Z)-7-Tetradecen-1-ol | (Z,Z)-7,10-Hexadecadien-1-ol |
| (E)-7-Decenyl acetate | (Z)-7-Tetradecenyl acetate | (Z,Z)-7,10-Hexadecadienyl acetate |
| (Z)-7-Decenyl acetate | (Z)-7-Tetradecenal | (Z,E)-7,11-Hexadecadien-1-ol |
| (E)-8-Decen-1-ol | (E)-8-Tetradecenyl acetate | (Z,E)-7,11-Hexadecadienyl acetate |
| (E,E)-2,4-Decadienal | (Z)-8-Tetradecen-1-ol | (Z,E)-7,11-Hexadecadienal |
| (E,Z)-2,4-Decadienal | (Z)-8-Tetradecenyl acetate | (Z,Z)-7,11-Hexadecadien-1-ol |
| (Z,Z)-2,4-Decadienal | (Z)-8-Tetradecenal | (Z,Z)-7,11-Hexadecadienyl acetate |
| (E,E)-3,5-Decadienyl acetate | (E)-9-Tetradecen-1-ol | (Z,Z)-7,11-Hexadecadienal |
| (Z,E)-3,5-Decadienyl acetate | (E)-9-Tetradecenyl acetate | (Z,Z)-8,10-Hexadecadienyl acetate |
| (Z,Z)-4,7-Decadien-1-ol | (Z)-9-Tetradecen-1-ol | (E,Z)-8,11-Hexadecadienal |
| (Z,Z)-4,7-Decadienyl acetate | (Z)-9-Tetradecenyl acetate | (E,E)-9,11-Hexadecadienal |
| (E)-2-Undecenyl acetate | (Z)-9-Tetradecenal | (E,Z)-9,11-Hexadecadienyl acetate |
| (E)-2-Undecenal | (E)-10-Tetradecenyl acetate | (E,Z)-9,11-Hexadecadienal |
| (Z)-5-Undecenyl acetate | (Z)-10-Tetradecenyl acetate | (Z,E)-9,11-Hexadecadienal |
| (Z)-7-Undecenyl acetate | (E)-11-Tetradecen-1-ol | (Z,Z)-9,11-Hexadecadienal |
| (Z)-8-Undecenyl acetate | (E)-11-Tetradecenyl acetate | (E,E)-10,12-Hexadecadien-1-ol |
| (Z)-9-Undecenyl acetate | (E)-11-Tetradecenal | (E,E)-10,12-Hexadecadienyl acetate |
| (E)-2-Dodecenal | (Z)-11-Tetradecen-1-ol | (E,Z)-10,12-Hexadecadienal |
| (Z)-3-Dodecen-1-ol | (Z)-11-Tetradecenyl acetate | (E,Z)-10,12-Hexadecadien-1-ol |
| (E)-3-Dodecenyl acetate | (Z)-11-Tetradecenal | (E,Z)-10,12-Hexadecadienyl acetate |
| (Z)-3-Dodecenyl acetate | (E)-12-Tetradecenyl acetate | (E,Z)-10,12-Hexadecadienal |
| (E)-4-Dodecenyl acetate | (Z)-12-Tetradecenyl acetate | (Z,E)-10,12-Hexadecadienyl acetate |
| (E)-5-Dodecen-1-ol | (E,E)-2,4-Tetradecadienal | (Z,E)-10,12-Hexadecadienal |
| (E)-5-Dodecenyl acetate | (E,E)-3,5-Tetradecadienyl acetate | (Z,Z)-10,12-Hexadecadienal |
| (Z)-5-Dodecen-1-ol | (E,Z)-3,5-Tetradecadienyl acetate | (E,E)-11,13-Hexadecadien-1-ol |
| (Z)-5-Dodecenyl acetate | (Z,E)-3,5-Tetradecadienyl acetate | (E,E)-11,13-Hexadecadienyl acetate |
| (Z)-5-Dodecenal | (E,Z)-3,7-Tetradecadienyl acetate | (E,E)-11,13-Hexadecadienal |
| (E)-6-Dodecen-1-ol | (E,Z)-3,8-Tetradecadienyl acetate | (E,Z)-11,13-Hexadecadien-1-ol |
| (Z)-6-Dodecenyl acetate | (E,Z)-4,9-Tetradecadienyl acetate | (E,Z)-11,13-Hexadecadienyl acetate |
| (E)-6-Dodecenal | (E,Z)-4,9-Tetradecadienal | (E,Z)-11,13-Hexadecadienal |
| (E)-7-Dodecen-1-ol | (E,Z)-4,10-Tetradecadienyl acetate | (Z,E)-11,13-Hexadecadien-1-ol |
| (E)-7-Dodecenyl acetate | (E,E)-5,8-Tetradecadienyl acetate | (Z,E)-11,13-Hexadecadienyl acetate |
| (E)-7-Dodecenal | (Z,Z)-5,8-Tetradecadien-1-ol | (Z,E)-11,13-Hexadecadienal |
| (Z)-7-Dodecen-1-ol | (Z,Z)-5,8-Tetradecadienyl acetate | (Z,Z)-11,13-Hexadecadien-1-ol |
| (Z)-7-Dodecenyl acetate | (Z,Z)-5,8-Tetradecadienal | (Z,Z)-11,13-Hexadecadienyl acetate |
| (Z)-7-Dodecenal | (E,E)-8,10-Tetradecadien-1-ol | (Z,Z)-11,13-Hexadecadienal |
| (E)-8-Dodecen-1-ol | (E,E)-8,10-Tetradecadienyl acetate | (E,E)-10,14-Hexadecadienal |
| (E)-8-Dodecenyl acetate | (E,E)-8,10-Tetradecadienal | (Z,E)-11,14-Hexadecadienyl acetate |
| (E)-8-Dodecenal | (E,Z)-8,10-Tetradecadienyl acetate | (E,E,Z)-4,6,10-Hexadecatrien-1-ol |
| (Z)-8-Dodecen-1-ol | (E,Z)-8,10-Tetradecadienal | (E,E,Z)-4,6,10-Hexadecatrienyl acetate |
| (Z)-8-Dodecenyl | (Z,E)-8,10-Tetradecadien-1-ol | (E,Z,Z)-4,6,10-Hexadecatrien-1-ol |
| (E)-9-Dodecen-1-ol | (Z,E)-8,10-Tetradecadienyl acetate | (E,Z,Z)-4,6,10-Hexadecatrienyl acetate |
| (E)-9-Dodecenyl acetate | (Z,Z)-8,10-Tetradecadienyl acetate | (E,E,Z)-4,6,11-Hexadecatrienyl acetate |
| (E)-9-Dodecenal | (E,E)-9,11-Tetradecadienyl acetate | (E,E,Z)-4,6,11-Hexadecatrienal |
| (Z)-9-Dodecen-1-ol | (E,Z)-9,11-Tetradecadienyl acetate | (Z,Z,E)-7,11,13-Hexadecatrienal |
| (Z)-9-Dodecenyl acetate | (Z,E)-9,11-Tetradecadien-1-ol | (E,E,E)-10,12,14-Hexadecatrienyl acetate |
| (Z)-9-Dodecenal | (Z,E)-9,11-Tetradecadienyl acetate | (E,E,E)-10,12,14-Hexadecatrienal |
| (E)-10-Dodecen-1-ol | (Z,E)-9,11-Tetradecadienal | (E,E,Z)-10,12,14-Hexadecatrienyl acetate |
| (E)-10-Dodecenyl acetate | (Z,Z)-9,11-Tetradecadien-1-ol | (E,Z,Z)-10,12,14-Hexadecatrienal |
| (E)-10-Dodecenal | (Z,Z)-9,11-Tetradecadienyl acetate | (E,E,Z,Z)-4,6,11,13-Hexadecatetraenal |
| (Z)-10-Dodecen-1-ol | (Z,Z)-9,11-Tetradecadienal | (E)-2-Heptadecenal |
| (Z)-10-Dodecenyl acetate | (E,E)-9,12-Tetradecadienyl acetate | (Z)-2-Heptadecenal |
| (E,Z)-3,5-Dodecadienyl acetate | (Z,E)-9,12-Tetradecadien-1-ol | (E)-8-Heptadecen-1-ol |
| (Z,E)-3,5-Dodecadienyl acetate | (Z,E)-9,12-Tetradecadienyl acetate | (E)-8-Heptadecenyl acetate |
| (Z,Z)-3,6-Dodecadien-1-ol | (Z,E)-9,12-Tetradecadienal | (Z)-8-Heptadecen-1-ol |
| (E,E)-4,10-Dodecadienyl acetate | (Z,Z)-9,12-Tetradecadien-1-ol | (Z)-9-Heptadecenal |
| (E,E)-5,7- | (Z,Z)-9,12-Tetradecadienyl | (E)-10-Heptadecenyl |

TABLE 7-continued

Pheromone products.

| Name | Name | Name |
|------|------|------|
| Dodecadien-1-ol | acetate | acetate |
| (E,E)-5,7-Dodecadienyl acetate | (E,E)-10,12-Tetradecadien-1-ol | (Z)-11-Heptadecen-1-ol |
| (E,Z)-5,7-Dodecadien-1-ol | (E,E)-10,12-Tetradecadienyl acetate | (Z)-11-Heptadecenyl acetate |
| (E,Z)-5,7-Dodecadienyl acetate | (E,E)-10,12-Tetradecadienal | (E,E)-4,8-Heptadecadienyl acetate |
| (E,Z)-5,7-Dodecadienal | (E,Z)-10,12-Tetradecadienyl acetate | (Z,Z)-8,10-Heptadecadien-1-ol |
| (Z,E)-5,7-Dodecadien-1-ol | (Z,E)-10,12-Tetradecadienyl acetate | (Z,Z)-8,11-Heptadecadienyl acetate |
| (Z,E)-5,7-Dodecadienyl acetate | (Z,Z)-10,12-Tetradecadien-1-ol | (E)-2-Octadecenyl acetate |
| (Z,E)-5,7-Dodecadienal | (Z,Z)-10,12-Tetradecadienyl acetate | (E)-2-Octadecenal |
| (Z,Z)-5,7-Dodecadienyl acetate | (E,Z,Z)-3,8,11-Tetradecatrienyl acetate | (Z)-2-Octadecenyl acetate |
| (Z,Z)-5,7-Dodecadienal | (E)-8-Pentadecen-1-ol | (Z)-2-Octadecenal |
| (E,E)-7,9-Dodecadienyl acetate | (E)-8-Pentadecenyl acetate | (E)-9-Octadecen-1-ol |
| (E,Z)-7,9-Dodecadien-1-ol | (Z)-8-Pentadecen-1-ol | (E)-9-Octadecenyl acetate |
| (E,Z)-7,9-Dodecadienyl acetate | (Z)-8-Pentadecenyl acetate | (E)-9-Octadecenal |
| (E,Z)-7,9-Dodecadienal | (Z)-9-Pentadecenyl acetate | (Z)-9-Octadecen-1-ol |
| (Z,E)-7,9-Dodecadien-1-ol | (E)-9-Pentadecenyl acetate | (Z)-9-Octadecenyl acetate |
| (Z,E)-7,9-Dodecadienyl acetate | (Z)-10-Pentadecenyl acetate | (Z)-9-Octadecenal |
| (Z,Z)-7,9-Dodecadien-1-ol | (Z)-10-Pentadecenal | (E)-11-Octadecen-1-ol |
| (Z,Z)-7,9-Dodecadienyl acetate | (E)-12-Pentadecenyl acetate | (E)-11-Octadecenal |
| (E,E)-8,10-Dodecadien-1-ol | (Z)-12-Pentadecenyl acetate | (Z)-11-Octadecen-1-ol |
| (E,E)-8,10-Dodecadienyl acetate | (Z,Z)-6,9-Pentadecadien-1-ol | (Z)-11-Octadecenyl acetate |
| (E,E)-8,10-Dodecadienal | (Z,Z)-6,9-Pentadecadienyl acetate | (Z)-11-Octadecenal |
| (E,Z)-8,10-Dodecadien-1-ol | (Z,Z)-6,9-Pentadecadienal | (E)-13-Octadecenyl acetate |
| (E,Z)-8,10-Dodecadienyl acetate | (E,E)-8,10-Pentadecadienyl acetate | (E)-13-Octadecenal |
| (E,Z)-8,10-Dodecadienal | (E,Z)-8,10-Pentadecadien-1-ol | (Z)-13-Octadecen-1-ol |
| (Z,E)-8,10-Dodecadien-1-ol | (E,Z)-8,10-Pentadecadienyl acetate | (Z)-13-Octadecenyl acetate |
| (Z,E)-8,10-Dodecadienyl acetate | (Z,E)-8,10-Pentadecadienyl acetate | (Z)-13-Octadecenal |
| (Z,E)-8,10-Dodecadienal | (Z,Z)-8,10-Pentadecadienyl acetate | (E)-14-Octadecenal |
| (Z,Z)-8,10-Dodecadien-1-ol | (E,Z)-9,11-Pentadecadienal | (E,Z)-2,13-Octadecadien-1-ol |
| (Z,Z)-8,10-Dodecadienyl acetate | (Z,Z)-9,11-Pentadecadienal | (E,Z)-2,13-Octadecadienyl acetate |
| (Z,E,E)-3,6,8-Dodecatrien-1-ol | (E)-3-Hexadecenyl acetate | (E,Z)-2,13-Octadecadienal |
| (Z,Z,E)-3,6,8-Dodecatrien-1-ol | (E)-5-Hexadecen-1-ol | (Z,E)-2,13-Octadecadienyl acetate |
| (E)-2-Tridecenyl acetate | (E)-5-Hexadecenyl acetate | (Z,Z)-2,13-Octadecadien-1-ol |
| (Z)-2-Tridecenyl acetate | (Z)-5-Hexadecen-1-ol | (Z,Z)-2,13-Octadecadienyl acetate |
| (E)-3-Tridecenyl acetate | (Z)-5-Hexadecenyl acetate | (E,E)-3,13-Octadecadienyl acetate |
| (E)-4-Tridecenyl acetate | (E)-6-Hexadecenyl acetate | (E,Z)-3,13-Octadecadienyl acetate |
| (Z)-4-Tridecenyl acetate | (E)-7-Hexadecen-1-ol | (E,Z)-3,13-Octadecadienal |
| (Z)-4-Tridecenal | (E)-7-Hexadecenyl acetate | (Z,E)-3,13-Octadecadienyl acetate |
| (E)-6-Tridecenyl acetate | (E)-7-Hexadecenal | (Z,Z)-3,13-Octadecadienyl acetate |
| (Z)-7-Tridecenyl acetate | (Z)-7-Hexadecen-1-ol | (Z,Z)-3,13-Octadecadienal |
| (E)-8-Tridecenyl acetate | (Z)-7-Hexadecenyl acetate | (E,E)-5,9-Octadecadien-1-ol |
| (Z)-8-Tridecenyl acetate | (Z)-7-Hexadecenal | (E,E)-5,9-Octadecadienyl acetate |
| (E)-9-Tridecenyl acetate | (E)-8-Hexadecenyl acetate | (E,E)-9,12-Octadecadien-1-ol |
| (Z)-9-Tridecenyl acetate | (E)-9-Hexadecen-1-ol | (Z,Z)-9,12-Octadecadienyl acetate |
| (Z)-10-Tridecenyl acetate | (E)-9-Hexadecenyl acetate | (Z,Z)-9,12-Octadecadienal |
| (E)-11-Tridecenyl acetate | (E)-9-Hexadecenal | (Z,Z)-11,13-Octadecadienal |
| (Z)-11-Tridecenyl acetate | (Z)-9-Hexadecen-1-ol | (E,E)-11,14-Octadecadienal |
| (E,Z)-4,7-Tridecadienyl acetate | (Z)-9-Hexadecenyl acetate | (Z,Z)-13,15-Octadecadienal |
| (Z,Z)-4,7-Tridecadien-1-ol | (Z)-9-Hexadecenal | (Z,Z,Z)-3,6,9-Octadecatrienyl acetate |
| (Z,Z)-4,7-Tridecadienyl acetate | (E)-10-Hexadecenyl acetate | (E,E,E)-9,12,15-Octadecatrien-1-ol |
| (E,Z)-5,9-Tridecadienyl acetate | (E)-10-Hexadecenal | (Z,Z,Z)-9,12,15-Octadecatrienyl acetate |
| (Z,E)-5,9-Tridecadienyl acetate | (Z)-10-Hexadecenyl acetate | (Z,Z,Z)-9,12,15-Octadecatrienal |

In certain embodiments, the invention provides a method for synthesizing a fatty olefin derivative as described above wherein the fatty olefin derivative is selected from (E)-7-dodecenal; (Z)-10-dodecenyl acetate; (Z)-10-hexadecenyl acetate; (Z)-10-pentadecenal; (Z)-10-pentadecenyl acetate; (Z)-10-tetradecenyl acetate; (Z)-10-tridecenyl acetate; (Z)-7-decenyl acetate; (Z)-7-dodecenyl acetate; (Z)-7-hexadecenal; (Z)-7-hexadecenyl acetate; (Z)-7-tetradecenal; (Z)-7-tetradecenyl acetate; (Z)-7-undecenyl acetate; (Z)-9-dodecenal; (Z)-9-dodecenyl acetate; (Z)-9-hexadecenal; (Z)-9-hexadecenyl acetate; (Z)-9-pentadecenyl acetate; (Z)-9-tetradecenal; (Z)-9-tetradecenyl acetate; (Z)-9-tetradecenyl formate; (Z)-9-tetradecenyl nitrate; (Z)-9-tridecenyl acetate; (Z)-9-undecenyl acetate; (E)-11-tetradecen-1-ol; (E)-11-tetradecenyl acetate; (E)-5-decen-1-ol; (E)-5-decenyl acetate; (E)-8-dodecen-1-ol; (E)-8-dodecenyl acetate; (Z)-11-hexadecen-1-ol; (Z)-11-hexadecenal; (Z)-11-hexadecenyl acetate; (Z)-11-tetraceden-1-ol; (Z)-11-tetracedenyl acetate; (Z)-13-octadecen-1-ol; (Z)-13-octadecenal; (Z)-3- hexanol; (Z)-3-nonen-1-ol; (Z)-5-decen-1-ol; (Z)-5-decenyl acetate; (Z)-7-dodecen-1-ol; (Z)-7-hexadecen-1-ol; (Z)-8-dodecen-1-ol; (Z)-8-dodecenyl acetate; (Z)-9-dodecen-1-ol; (Z)-9-hexadecen-1-ol; and (Z)-9-tetradecen-1-ol. In some such embodiments, the fatty olefin derivative is a pheromone.

In some embodiments, the fatty olefin derivative is selected from (E)-7-dodecenal; (Z)-10-dodecenyl acetate; (Z)-10-hexadecenyl acetate; (Z)-10-pentadecenal; (Z)-10-pentadecenyl acetate; (Z)-10-tetradecenyl acetate; (Z)-10-tridecenyl acetate; (Z)-7-decenyl acetate; (Z)-7-dodecenyl acetate; (Z)-7-hexadecenal; (Z)-7-hexadecenyl acetate; (Z)-7-tetradecenal; (Z)-7-tetradecenyl acetate; (Z)-7-undecenyl acetate; (Z)-9-dodecenal; (Z)-9-dodecenyl acetate; (Z)-9-hexadecenal; (Z)-9-hexadecenyl acetate; (Z)-9-pentadecenyl acetate; (Z)-9-tetradecenal; (Z)-9-tetradecenyl acetate; (Z)-9-tetradecenyl formate; (Z)-9-tetradecenyl nitrate; (Z)-9-tridecenyl acetate; and (Z)-9-undecenyl acetate. In some such embodiments, the fatty olefin derivative is a pheromone.

In some embodiments, the fatty olefin derivative is selected from (E)-7-dodecenal; (Z)-10-dodecenyl acetate; (Z)-10-hexadecenyl acetate; (Z)-10-pentadecenal; (Z)-10-pentadecenyl acetate; (Z)-10-tetradecenyl acetate; (Z)-10-Tridecenyl acetate; (Z)-7-decenyl acetate; (Z)-7-hexadecenyl acetate; (Z)-7-tetradecenal; (Z)-7-tetradecenyl acetate; (Z)-7-undecenyl acetate; (Z)-9-dodecenal; (Z)-9-pentadecenyl acetate; (Z)-9-tetradecenal; (Z)-9-tetradecenyl formate; (Z)-9-tetradecenyl nitrate; (Z)-9-tridecenyl acetate; and (Z)-9-undecenyl acetate. In some such embodiments, the fatty olefin derivative is a pheromone.

As described above, the methods of the invention can also be used for the synthesis of polyene derivatives, including polyene pheromones. See, for example, Scheme 6.

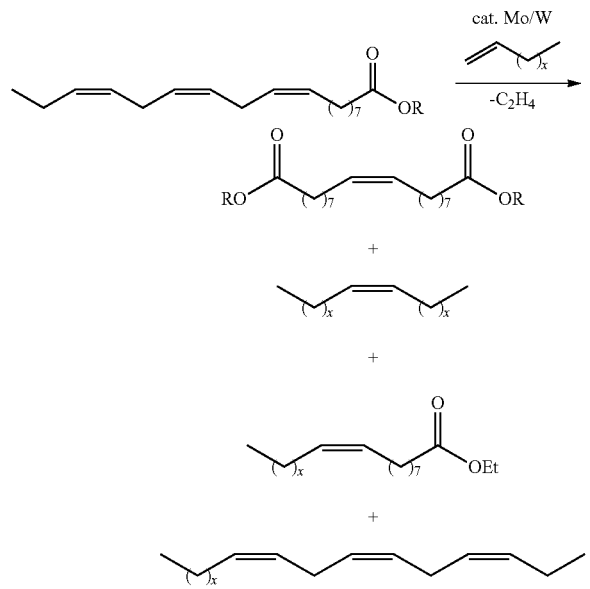

Polyene derivatives include dienes, trienes, and tetraenes. The double bonds in the polyenes can be Z double bonds or E double bonds. Dienes that can be prepared using the methods of the invention include, but are not limited to, (6Z,9Z)-heptadeca-6,9-diene; (6Z,9Z)-octadeca-6,9-diene; (6Z,9Z)-nonadeca-6,9-diene; (6Z,9Z)-eicosa-6,9-diene; (6Z,9Z)-henicosa-6,9-diene; (6Z,9Z)-docosa-6,9-diene; and (6Z,9Z)-tricosa-6,9-diene. The dienes can be used as pheromones.

Trienes that can be prepared using the methods of the invention include, but are not limited to, (3Z,6Z,9Z)-heptadeca-3,6,9-triene; (3Z,6Z,9Z)-octadeca-3,6,9-triene; (3Z,6Z,9Z)-nonadeca-3,6,9-triene; (3Z,6Z,9Z)-eicosa-3,6,9-triene; (3Z,6Z,9Z)-henicosa-3,6,9-triene; (3Z,6Z,9Z)-docosa-3,6,9-triene; (3Z,6Z,9Z)-tricosa-3,6,9-triene; (4E,6Z,9Z)-heptadeca-4,6,9-triene; (4E,6Z,9Z)-octadeca-4,6,9-triene; (4E,6Z,9Z)-nonadeca-4,6,9-triene; (4E,6Z,9Z)-eicosa-4,6,9-triene; (4E,6Z,9Z)-henicosa-4,6,9-triene; (4E,6Z,9Z)-docosa-4,6,9-triene; and (4E,6Z,9Z)-tricosa-4,6,9-triene. The trienes can be used as pheromones.

Tetraenes that can be prepared using the methods of the invention include, but are not limited to, (3Z,6Z,9Z)-heptadeca-1,3,6,9-tetraene; (3Z,6Z,9Z)-octadeca-1,3,6,9-tetraene; (3Z,6Z,9Z)-nonadeca-1,3,6,9-tetraene; (3Z,6Z,9Z)-eicosa-1,3,6,9-tetraene; (3Z,6Z,9Z)-henicosa-1,3,6,9-tetraene; (3Z,6Z,9Z)-docosa-1,3,6,9-tetraene; (3Z,6Z,9Z)-tricosa-1,3,6,9-tetraene; (3Z,6Z,9Z,11E/Z)-heptadeca-3,6,9,11-tetraene; (3Z,6Z,9Z,11E/Z)-octadeca-3,6,9,11-tetraene; (3Z,6Z,9Z,11E/Z)-nonadeca-3,6,9,11-tetraene; (3Z,6Z,9Z,11E/Z)-eicosa-3,6,9,11-tetraene; (3Z,6Z,9Z,11E/Z)-henicosa-3,6,9,11-tetraene; (3Z,6Z,9Z,11E/Z)-docosa-3,6,9,11-tetraene; and (3Z,6Z,9Z,11E/Z)-tricosa-3,6,9,11-tetraene. The tetraenes can be used as pheromones.

Polyene derivatives include oxidized polyenes such as ketones and epoxides. Examples of ketone polyene derivatives include, but are not limited to: (6Z,9Z)-heptadeca-6,9-dien-3-one; (6Z,9Z)-octadeca-6,9-dien-3-one; (6Z,9Z)-nonadeca-6,9-dien-3-one; (6Z,9Z)-eicosa-6,9-dien-3-one; (6Z,9Z)-henicosa-6,9-dien-3-one; (6Z,9Z)-docosa-6,9-dien-3-one; and (6E,9E)-tricosa-6,9-dien-3-one. Examples of polyene epoxide derivatives include, but are not limited to 3Z,6Z-9R,10S-epoxy-heneicosadiene, 3Z,6Z-9R,10S-epoxy-docosadiene, and the like. The ketone polyene derivatives and the polyene epoxide derivatives can be used as pheromones. The structure, taxonomic distribution, mechanisms of action, and biosynthetic pathways of polyene pheromones (including polyene epoxides) are described by Millar (*Annu. Rev. Entomol.* 2000. 45:575-604).

Pheromone Compositions and Uses Thereof

Pheromones prepared according to the methods of the invention can be formulated for use as insect control compositions. The pheromone compositions can include a carrier, and/or be contained in a dispenser. The carrier can be, but is not limited to, an inert liquid or solid.

Examples of solid carriers include but are not limited to fillers such as kaolin, bentonite, dolomite, calcium carbonate, talc, powdered magnesia, Fuller's earth, wax, gypsum, diatomaceous earth, rubber, plastic, silica and China clay. Examples of liquid carriers include, but are not limited to, water; alcohols, such as ethanol, butanol or glycol, as well as their ethers or esters, such as methylglycol acetate; ketones, such as acetone, cyclohexanone, methylethyl ketone, methylisobutylketone, or isophorone; alkanes such as hexane, pentane, or heptanes; aromatic hydrocarbons, such as xylenes or alkyl naphthalenes; mineral or vegetable oils; aliphatic chlorinated hydrocarbons, such as trichloroethane or methylene chloride; aromatic chlorinated hydrocarbons, such as chlorobenzenes; water-soluble or strongly polar solvents such as dimethylformamide, dimethyl sulfoxide, or N-methylpyrrolidone; liquefied gases; and mixtures thereof. Baits or feeding stimulants can also be added to the carrier.

Pheromone compositions can be formulated so as to provide slow release into the atmosphere, and/or so as to be protected from degradation following release. For example, the pheromone compositions can be included in carriers such as microcapsules, biodegradable flakes and paraffin wax-based matrices.

Pheromone compositions can contain other pheromones or attractants provided that the other compounds do not substantially interfere with the activity of the composition. The pheromone compositions can also include insecticides. Examples of suitable insecticides include, but are not limited to, buprofezin, pyriproxyfen, flonicamid, acetamiprid, dinotefuran, clothianidin, acephate, malathion, quinolphos, chloropyriphos, profenophos, bendiocarb, bifenthrin, chlorpyrifos, cyfluthrin, diazinon, pyrethrum, fenpropathrin, kinoprene, insecticidal soap or oil, and mixtures thereof.

Pheromone compositions can be used in conjunction with a dispenser for release of the composition in a particular environment. Any suitable dispenser known in the art can be used. Examples of such dispensers include but are not limited to bubble caps comprising a reservoir with a permeable barrier through which pheromones are slowly released, pads, beads, tubes rods, spirals or balls composed of rubber, plastic, leather, cotton, cotton wool, wood or wood products that are impregnated with the pheromone composition. For example, polyvinyl chloride laminates, pellets, granules, ropes or spirals from which the pheromone composition evaporates, or rubber septa One of skill in the art will be able to select suitable carriers and/or dispensers for the desired mode of application, storage, transport or handling.

A variety of pheromones, including those set forth in Table 1 can be prepared according to the methods of the invention and formulated as described above. For example, the methods of the invention can be used to prepare peach twig borer (PTB) sex pheromone, which is a mixture of (E)-dec-5-en-1-ol (17%) and (E)-dec-5-en-1-yl acetate (83%). The PTB sex pheromone can be used in conjunction with a sustained pheromone release device having a polymer container containing a mixture of the PTB sex pheromone and a fatty acid ester (such as a sebacate, laurate, palmitate, stearate or arachidate ester) or a fatty alcohol (such as undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol). The polymer container can be a tube, an ampule, or a bag made of a polyolefin or an olefin component-containing copolymer. Sex pheromones of other pest insects such the cotton bollworm (*Helicoverpa armigerd*), fall army worm (*Spodoptera frugiperda*), oriental fruit moth (*Grapholita molesta*) and leaf roller (*Tortricidae*) can be used in this type of sustained pheromone release device. The sex pheromones typically include one or more aliphatic acetate compounds having from 10 to 16 carbon atoms (e.g., decyl acetate, decenyl acetate, decadienyl acetate, undecyl acetate, undecenyl acetate, dodecyl acetate, dodecenyl acetate, dodecadienyl acetate, tridecyl acetate, tridecenyl acetate, tridecadienyl acetate, tetradecyl acetate, tetradecenyl acetate, tetradecadienyl acetate, and the like) and/or one or more aliphatic aldehyde compounds having from 10 to 16 carbon atoms (e.g., 7-hexadecenal, 11-hexadecenal, 13-octadecenal, and the like).

Pheromones prepared according to the methods of the invention, as well as compositions containing the pheromones, can be used to control the behavior and/or growth of insects in various environments. The pheromones can be used, for example, to attract or repel male or female insects to or from a particular target area. The pheromones can be used to attract insects away from vulnerable crop areas. The pheromones can also be used example to attract insects as part of a strategy for insect monitoring, mass trapping, lure/attract-and-kill or mating disruption.

Mass trapping involves placing a high density of traps in a crop to be protected so that a high proportion of the insects are removed before the crop is damaged. Lure/attract-and-kill techniques are similar except once the insect is attracted to a lure, it is subjected to a killing agent. Where the killing agent is an insecticide, a dispenser can also contain a bait or feeding stimulant that will entice the insects to ingest an effective amount of the insecticide.

It will be appreciated by a person skilled in the art that a variety of different traps are possible. Suitable examples of such traps include water traps, sticky traps, and one-way traps. Sticky traps come in many varieties. One example of a sticky trap is of cardboard construction, triangular or wedge-shaped in cross-section, where the interior surfaces are coated with a non-drying sticky substance. The insects contact the sticky surface and are caught. Water traps include pans of water and detergent that are used to trap insects. The detergent destroys the surface tension of the water, causing insects that are attracted to the pan, to drown in the water. One-way traps allow an insect to enter the trap but prevent it from exiting. The traps of the invention can be colored brightly, to provide additional attraction for the insects.

The trap is positioned in an area infested (or potentially infested) with insects. Generally, the trap is placed on or close to a tree or large plant and the pheromone attracts the insects to the trap. The insects can then be caught, immobilized and/or killed within the trap, for example, by the killing agent present in the trap.

Pheromones prepared according to the methods of the invention can also be used to disrupt mating. Strategies of mating disruption include confusion, trail-masking and false-trail following. Constant exposure of insects to a high concentration of a pheromone can prevent male insects from responding to normal levels of the pheromone released by female insects. Trail-masking uses a pheromone to destroy the trail of pheromones released by females. False-trail following is carried out by laying numerous spots of a pheromone in high concentration to present the male with many false trails to follow. When released in sufficiently high quantities, the male insects are unable to find the natural source of the sex pheromones (the female insects) so that mating cannot occur.

Insect populations can be surveyed or monitored by counting the number of insects in a target area (e.g., the number of insects caught in a trap). Inspection by a horticulturist can provide information about the life stage of a population. Knowing where insects are, how many of them there are, and their life stage enables informed decisions to be made as to where and when insecticides or other treatments are warranted. For example, a discovery of a high insect population can necessitate the use of methods for removal of the insect. Early warning of an infestation in a new habitat can allow action to be taken before the population becomes unmanageable. Conversely, a discovery of a low insect population can lead to a decision that it is sufficient to continue monitoring the population. Insect populations can be monitored regularly so that the insects are only controlled when they reach a certain threshold. This provides cost-effective control of the insects and reduces the environmental impact of the use of insecticides.

As will be apparent to one of skill in the art, the amount of a pheromone or pheromone composition used for a particular application can vary depending on several factors such as the type and level of infestation; the type of composition used; the concentration of the active components; how the composition is provided, for example, the type of dispenser used; the type of location to be treated; the length of time the method is to be used for; and environmental factors such as temperature, wind speed and direction, rainfall and humidity. Those of skill in the art will be able to determine an effective amount of a pheromone or pheromone composition for use in a given application.

IV. Examples

Example 1. Cross-metathesis of Dec-9-en-1-yl Acetate with Hex-1-ene

Prior to introduction of the metathesis catalyst, dec-9-en-1-ylacetate (CAS #50816-18-7) and hex-1-ene (CAS #592-41-6) are treated with either aluminum oxide ($Al_2O_3$) or a trialkylaluminum as described in U.S. Pat. No. 9,388,097 to reduce moisture, peroxides, and other potential catalyst poisons to a level suitable for conducting the metathesis reaction. In a nitrogen-filled glovebox, a 20 mL scintillation vial is charged with a magnetic stir bar, 1.00 g of pretreated dece-9-en-1-yl acetate and 1.27 g of pretreated hex-1-ene. The vial is closed with a perforated septum and placed in an aluminum heating block regulated at 40° C. atop a hotplate/magnetic stirrer where the stirring rate is fixed at 500 rpm. A solution of 1-({3,3'-dibromo-2'-[(tert-butyldimethylsilyl)oxy]-5H,5'H,6H,6'H,7H,7'H,8H,8'H-[1,1'-binaphthalene]-2-yl}oxy)-1-(2,5-dimethylpyrrol-1-yl)-1-(2-methyl-2-phenylpropylidene)-N-phenyltungstenimine (CAS #1628041-76-8) catalyst in dry and degassed toluene is prepared by weighing 10 mg of the catalyst into a 1 mL volumetric flask and diluting to the calibration mark with solvent. Using a gas tight microliter syringe, 57 µL of the catalyst solution (0.57 mg, 0.025 wt %, 0.0025 mol %) is withdrawn from the volumetric flask and added to the reaction mixture. After four hours, the vial is removed from the glovebox and the reaction mixture is analyzed by GC-MS. The GC-MS data indicates that (Z)-tetradec-9-en-1-yl acetate is formed in high yield.

Example 2. Cross-Metathesis of Methyl Dec-9-enoate with Oct-1-ene

Prior to introduction of the metathesis catalyst, methyl dec-9-enoate (CAS #25601-41-6) and oct-1-ene (CAS #111-66-0) are treated to reduce moisture, peroxides and other potential catalyst poisons to a level suitable for conducting the metathesis reaction as described in U.S. Pat. No. 9,388,097. In a nitrogen-filled glovebox, a 20 mL scintillation vial is charged with a magnetic stir bar, 1.00 g of pretreated methyl dec-9-enoate and 1.83 g of pretreated oct-1-ene. The vial is closed with a perforated septum and placed in an aluminum heating block regulated at 40° C. atop a hotplate/magnetic stirrer where the stirring rate is fixed at 500 rpm A solution of 1-({3,3'-dibromo-2'-[(tert-butyldimethylsilyl)oxy]-5H,5H,6H,6'H,7H,7'H,8H,8'H-[1,1'-binaphthalene]-2-yl}oxy)-1-(2,5-dimethylpyrrol-1-yl)-1-(2-methyl-2-phenylpropylidene)-N-phenyltungstenimine (CAS #1628041-76-8) catalyst in dry and degassed toluene is prepared by weighing 10 mg of the catalyst into a 1 mL volumetric flask and diluting to the calibration mark with solvent. Using a gas tight microliter syringe, 71 µL of the catalyst solution (0.71 mg cat., 0.025 wt %, 0.0029 mol %) is withdrawn from the volumetric flask and added reaction mixture. After four hours the vial is removed from the glovebox and the reaction mixture is analyzed by GC-MS. The GC-MS data indicates that methyl (Z)-hexadec-9-enoate is formed in high yield.

Example 3. Reduction of Methyl Hexadec-9-enoate with Sodium Bis(2-methoxyethoxy) Aluminumhydride In an oven-dried, nitrogen-flushed flask sealed with a rubber septum and containing a magnetic stir bar is added 0.47 g JV-methylpiperazine (CAS #109-01-3) and 10 mL of dry, degassed toluene. The flask is submerged in an ice bath and, with magnetic stirring, 1.48 g of a 70% solution of sodium bis(2-methoxyethoxy)aluminumhydride (CAS #22722-98-1) in toluene is added dropwise. In a separate oven dried, nitrogen-flushed flask sealed with a rubber septum is added 1.00 g of methyl hexadec-9-enoate, prepared through the process detailed in Example 2, and 20 mL of dry, degassed toluene. The flask is then submerged in an ice bath and stirrer via an external magnetic stirrer. After stirring for one hour, the N-methylpiperazine/sodium bis(2-methoxyethoxy)aluminumhydride mixture is added dropwise via a cannula to the toluene solution of ester. The resulting mixture is stirred at ice-bath temperature for one hour and then brought to ambient temperature and stirred for an additional hour. The reaction is quenched by addition of 20 mL of deionized water and then extracted with 20 mL of EtOAc. The organic layer is washed with 20 mL of deionized water, dried over sodium sulfated and then concentrated in vacuo. The product is analyzed by GC-MS, indicating that (Z)-hexadec-9-enal is formed in high yield.

Example 4. Preparation of Eicosa-3.6.9-triene, a Polyene Pheromone

Prior to introduction of metathesis catalysts, linseed oil (CAS #8001-26-1) and dodec-1-ene (CAS #112-41-4) are treated to reduce moisture, peroxides and other potential catalyst poisons to the desired level. In a nitrogen-filled glovebox, a 20 mL scintillation vial is charged with a magnetic stir bar, 1.00 g of pretreated linseed oil and 0.481 g of pretreated dec-1-ene. The vial is closed with a perforated septum and placed in an aluminum heating block regulated at 40° C. atop a hotplate/magnetic stirrer where the stirring rate is fixed at 500 rpm. A solution of 1-({3,3'-dibromo-2'-[(tert-butyldimethylsilyl)oxy]-5H,5'H,6H,6'H,7H,7'H,8H,8'H-[1,1'-binaphthalene]-2-yl}oxy)-1-(2,5-dimethylpyrrol-1-yl)-1-(2-methyl-2-phenylpropylidene)-N-phenyltungstenimine (CAS #1628041-76-8) in dry and degassed toluene is prepared by weighing 10 mg of the catalyst into a 1 mL volumetric flask and diluting to the calibration mark with solvent. Using a gas tight microliter syringe, 37 µL (0.37 mg cat., 0.025 wt %, 0.0071 mol %) of the catalyst solution is withdrawn from the volumetric flask and added reaction mixture. After one hour the vial is removed from the glovebox. The reaction mixture is transesterified with methanol using sodium methoxide as a catalyst prior to analysis by GC-MS. The transesterified reaction mixture contains the desired eicosa-3,6,9-triene product (CAS #134370-60-8), as well as small amounts of 1,18-dimethyl octadec-9-enedioate (CAS #13481-97-5), methyl eicos-9-enoate (CAS #10340-21-3), docos-11-ene (CAS #62978-77-2), and cyclohexa-1,4-diene (CAS #628-41-1).

Example 5. Metathesis Catalyst Screening for the Z-Selective Cross-Metathesis of Methyl Dec-9-enoate and Hex-1-ene In a nitrogen-filled glovebox, a 30 mL glass vial was charged a with a magnetic stir bar and 2.70 g of an equimolar mixture of methyl dec-9-enoate and hex-1-ene previously treated with activated basic alumina to reduce levels of moisture, peroxide and protic impurities in the method described in U.S. Ser. No. 14/209,686. To the olefin mixture was added 0.0025 mol % of a molybdenum or tungsten metathesis catalysts as a toluene solution. The vial was then closed with a perforated cap and the reaction mixtures were stirred by means of a magnetic hotplate stirrer for a total of four hours after the addition of catalyst. Aliquots of the reaction mixture were taken at one and four hours after the addition of catalyst and analyzed to determine 9-DAME conversion (%) and methyl (Z)-tetradec-9-enoate selectivity (%) (Table 8) by GC-MS/FID after using the equations below in conjunction with external calibration curves obtained for the analytes of interest. GC chromatograms were recorded using a Shimadzu GC2010 Plus instrument equipped with an Agilent DB-23 capillary column with a length of 30 m, an inner diameter of 0.25 mm and a film thickness of 0.25 μm. Nitrogen was used as the carrier gas and the total flow of gas through the column was 61.9 mL/min. Injections were split at a 1:30 ratio with the carrier gas and the injector of the instrument was maintained at a constant temperature of 240° C. The oven temperature was held at 35° C. during the injection and for the following five minutes, then raised to 100° C. at a rate of 35° C./min, raised further to 130° C. at a rate of 7° C./min, raised again to 240° C. at a rate of 35° C./min and finally held at this terminal temperature for 3.71 minutes for a total run length of approx. 18 minutes.

Methyl Dec-9-enoate Conversion (%) =

$$1 - \left(\frac{\text{Final mol Methyl Dec-9-enoate}}{\text{Initial mol Methyl Dec-9-enoate}}\right) \times 100$$

Methyl (Z)-Tetradec-9-enoate Selectivity (%) =

$$\left(\frac{\text{mol Methyl (Z)-Tetradec-9-enoate}}{\text{mol Methyl (Z)-Tetradec-9-enoate} + \text{mol Methyl (E)-Tetradec-9-enoate}}\right) \times 100$$

TABLE 8

|  | 4 Hour Reaction Length | | 24 Hour Reaction Length | |
| --- | --- | --- | --- | --- |
| Catalyst | Methyl Dec-9-enoate Conversion (%) | Methyl (Z)-Tetradec-9-enoate Selectivity (%) | Methyl Dec-9-enoate Conversion (%) | Methyl (Z)-Tetradec-9-enoate Selectivity (%) |
| 1 | 40 | 91 | 73 | 90 |
| 2 | 56 | 94 | 70 | 93 |
| 3 | 67 | 95 | 68 | 95 |
| 4 | 51 | 16 | 52 | 16 |
| 5 | 21 | 95 | 28 | 94 |
| 6 | 47 | 94 | 54 | 94 |
| 7 | <0.1 | Not Determined | <0.1 | Not Determined |
| 8 | <0.1 | Not Determined | <0.1 | Not Determined |
| 9 | 15 | 95 | 17 | 95 |
| 10 | 52 | 93 | 60 | 93 |

| Catalyst | Structure | Formula |
| --- | --- | --- |
| 1 | 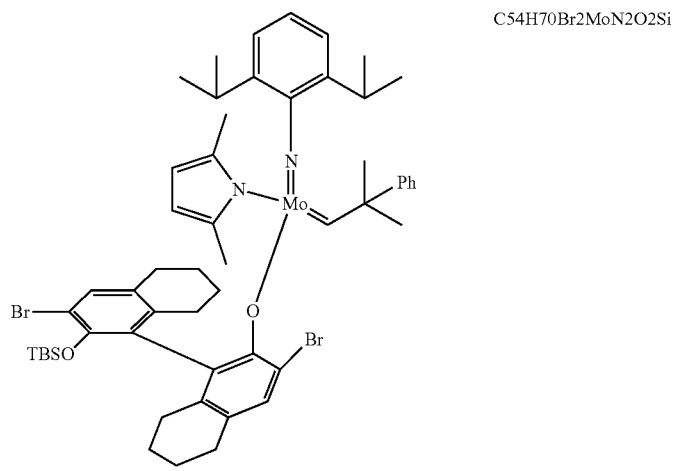 | C54H70Br2MoN2O2Si |

TABLE 8-continued
2 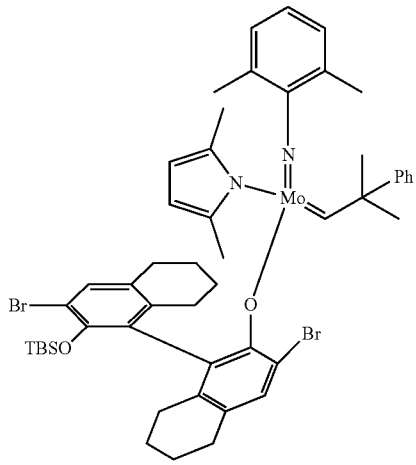 C50H62Br2MoN2O2Si
3 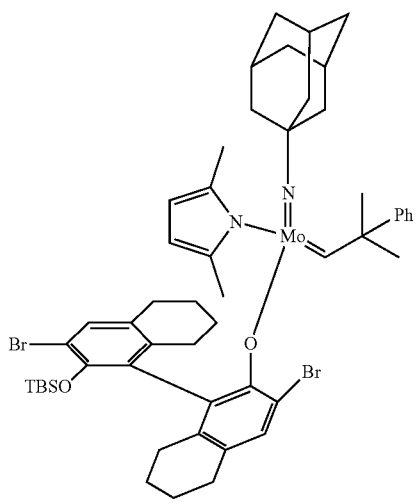 C52H68Br2MoN2O2Si
4 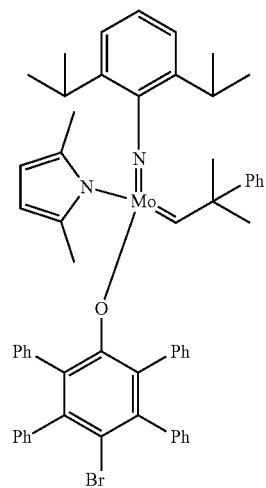 C52H68Br2MoN2OSi TABLE 8-continued
| | | |
|---|---|---|
| 5 | 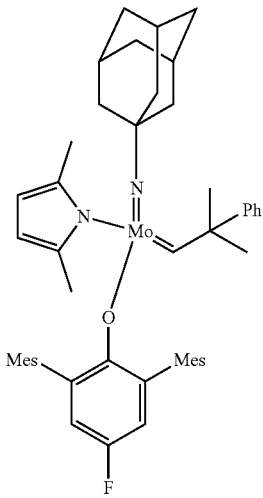 | C50H59FMoN2O |
| 6 | 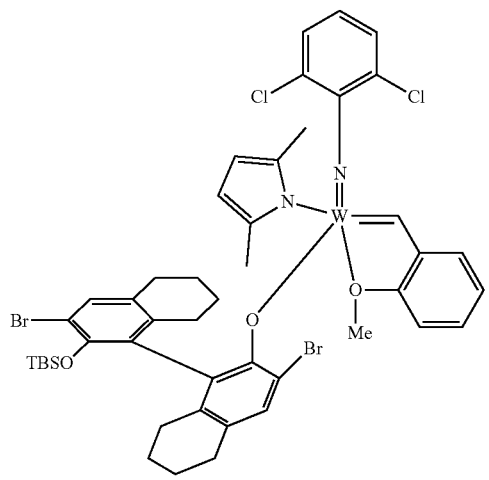 | C46H52Br2Cl2N2O3SiW |
| 7 | 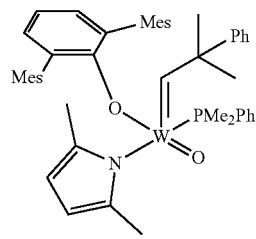 | C48H56NO2PW |
| 8 | 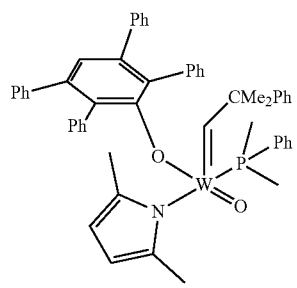 | C54H52NO2PW |

TABLE 8-continued

| 9 | 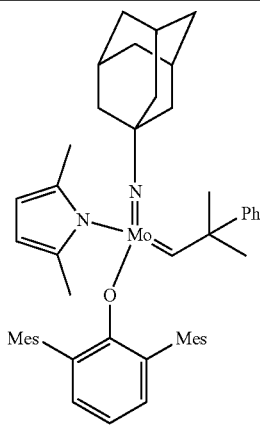 | C50H60MoN2O |
|---|---|---|
| 10 | | C54H50N2OW |

Ph = phenyl, C6H5;
Mes = 2,4,6-trimethylphenyl, 2,4,6-Me3C6H2;
TBS = tert-butyldimethylsilyl, SiMe2(t-Bu)

Example 6. Synthesis and Isolation of Methyl (Z)-Tetradec-9-enoate Via Cross-Metathesis of Methyl Dec-9-enoate and Hex-1-ene Into a glass vessel equipped with an agitator, thermometer and reflux condenser, were charged 500 g of methyl dec-9-enoate (2.71 mol) and 480 g of hex-1-ene (5.70 mol). To the thoroughly homogenized feedstocks a solution of triethylaluminum in toluene (3.82 g, 0.0335 mol, 0.389 mol %) was added in one portion. After agitating at 500 rpm for an hour at 23-25° C., the temperature of the feedstock was raised to 40-41° C. 0.121 g (0.00128 mol %, 123 ppmwt) of tungsten, [(1R)-3,3'-dibromo-2'-[[(1,1-dimethylethyl)dimethylsilyl]oxy]-5,5', 6,6',7,7',8,8'-octahydro[1,1'-binaphthalen]-2-olato-κO][2,6-dichlorobenzenaminato(2-)-κN](2, 5-dimethyl-1H-pyrrol-1-yl)[(2-methoxyphenyl)methylene]-, (T-4)-(CAS #1817807-15-0) was added in four portions to control the rate of ethylene generation and the reaction was allowed to proceed for three hours. After that time GC-FID analysis showed the reaction proceed in 57% Methyl Dec-9-enoate Conversion and 96% Methyl (Z)-tetradec-9-enoate Selectivity. To the cooled (25-30° C.) reaction mixture was added 10 mL of methanol (H$_2$O=0.035-0.038 w %). The mixture was stirred at ambient temperature for 15-20 minutes. The aliquot was then removed from the reactor and filtered through a plug comprising a lower 0.5 cm layer of diatomaceous earth and an upper 1.0 cm layer of silica gel. The filter cake was washed with 7×100 mL MTBE. The volume of the colorless and clear filtrate was concentrated under reduced pressure in a 45° C. water bath at a pressure of 40 mbar to obtain the crude product as a colorless liquid. The crude material was vacuum distilled (0.2-1 mbar) using a short path distillation apparatus and 166 g (25% overall yield) of methyl (Z)-tetradec-9-enoate was collected at a head temperature of 95-97° C. and pressure of 0.4 mbar.

Example 7. Reduction of Methyl (Z)-tetradec-9-enoate to (Z)-tetradec-9-en-1-ol Using Sodium Bis (2-methoxyethoxy) Aluminumhydride In an oven dried, nitrogen-flushed flask sealed with a rubber septum and containing a magnetic stir bar was added 240 g (0.831 mol 'AlH$_2$', 1.2 eq.) of a 70% solution of sodium bis(2-methoxyethoxy)aluminumhydride (CAS #22722-98-1) in toluene. The flask is then submerged in an ice bath and stirred via an external magnetic stirrer and 166 g (0.691 mol) of methyl (Z)-tetradec-9-enoate, prepared through the process detailed in Example 6, was slowly added. The resulting mixture is stirred at ice-bath temperature for one hour and then brought to ambient temperature and stirred for an additional hour. The reaction mixture was then quenched with 10 mL deionized water and acidified with 15 w/w % aqueous sulfuric acid until the pH of the aqueous layer was 4. The obtained slurry was filtered through diatomaceous earth and the filter cake was rinsed with 2×150 mL of toluene. The two phases of the mother liquor were separated. The aqueous layer was washed with additional 300 mL of toluene. The combined organic phases were washed with 1500 mL deionized water. All volatile components were removed by in vacuo and the product dried via azeotropic distillation with additional toluene to yield 144 g (0.678 mol, 98% yield).

Example 8. Synthesis of (Z)-tetradec-9-en-1-yl Acetate Through Esterification of (Z)-tetradec-9-en-1-ol to with Acetic Anhydride In an oven dried, nitrogen-flushed flask sealed with a rubber septum and containing a magnetic stir bar was added 144 g (0.678 mol) of (Z)-tetradec-9-en-1-ol, prepared through the method detailed in Example 7, 75.9 g of acetic anhydride (0.743 mol) and 5.50 g of sodium acetate (0.067 mol, 0.1 eq.). The reaction mixture was then heated to 60° C. for one hour, cooled and then washed consecutively with water and a sodium carbonate solution, yielding 160 g (0.629 mol, 92% yield) of (Z)-tetradec-9-en-1-yl acetate as a colorless liquid.

Example 9. Acetylation of 7-octen-1-ol with Acetic Anhydride 7-octen-1-ol (46.49 g, 363 mmol), first purified via vacuum distillation (72° C./8 mbar), was charged into a three-necked, round-bottomed flask equipped with a thermometer, a reflux condenser and a magnetic stirrer bar. The top of the condenser was connected to a Schlenk line and the whole apparatus was flushed with nitrogen. Acetic anhydride (44.29 g, 434 mmol) and anhydrous sodium acetate (3.25 g, 39.7 mmol) were added to the flask. The mixture was stirred at 68° C. for 4 hours. GC showed complete conversion. 200 mL of DCM was added to the reaction mixture and mixed with water (100 mL). NaHCO$_3$ (25 g) was carefully and portion-wise added to adjust the pH of the aqueous phase to 6. The organic phase was separated and extracted with saturated solution of NaHCO$_3$ (pH~8-9) then with 100 mL of water (pH~7). The separated DCM fraction was dried over Na$_2$SO$_4$ (60 g) and Na$_2$CO$_3$ (6 g) for one night. Organic phase was collected filtered, solid was washed with DCM and hexane. Volatiles were removed on rotary evaporator and the crude product further dried at 60° C./10 mbar for 4 hours. The material was then vacuum distilled a (79-80° C./10 mbar) to yield 51.53 g (83% yield) of a colorless liquid was obtained.

Example 10. Cross-Metathesis of Oct-7-en-1-yl Acetate with Hex-1-ene

In a nitrogen-filled glovebox, a 20 mL scintillation vial was charged with a magnetic stir bar, 1.315 g of oct-7-en-1-yl acetate (CAS #5048-35-1) and finally 0.685 g of hex-1-ene (1.05 equivalents). The vial was then closed with a perforated septum. The feedstock was treated with 69 μL of a 25 wt % solution of triethylaluminum in toluene (14.4 mg AlEt$_3$, 0.720 wt %, 0.803 mol %) and the mixture stirred via an external magnetic stirrer at room temperature for four hours. To the mixture was then added 0.002 mol % (0.35 mg, 0.0177 wt %) of tungsten [(1R)-3,3'-dibromo-2'-[[(1,1-dimethylethyl)dimethylsilyl]oxy]-5,5', 6,6',7,7',8,8'-octahydro [1,1'-binaphthalen]-2-olato-κO][2,6-dichlorobenzenaminato (2-)-κN](2, 5-dimethyl-1H-pyrrol-1-yl)[(2-methoxyphenyl) methylene]-, (T-4)-(CAS #1817807-15-0) as a solution in benzene. At the time after the additional of catalyst specified in the table below, an aliquot of the reaction mixture was removed from the glovebox and analyzed by GC-MS/FID. The results of the GC-MS/FID analysis of these samples is presented in the table below:

| Time After Catalyst Addition (h) | Approximate Conversion of Oct-7-en-1-yl Acetate to Dodec-7-en-1-yl Acetate (%) | Approximate (Z)-Dodec-7-en-1-yl Acetate Content (%) |
| --- | --- | --- |
| 1 | 34 | 97 |
| 4 | 37 | 97 |
| 6 | 38 | 97 |
| 24 | 38 | 97 |

Example 11. Cross-Metathesis of Oct-7-en-1-yl Acetate with Hex-1-ene

Prior to conducting the procedure below, the oct-7-en-1-yl acetate was further purified through a second vacuum distillation to remove additional catalyst deactivating impurities. In a nitrogen-filled glovebox, a 20 mL scintillation vial was charged with a magnetic stir bar, 1.338 g of oct-7-en-1-yl acetate (CAS #5048-35-1) and finally 0.662 g of hex-1-ene. The vial was then closed with a perforated septum. The feedstock was treated with 7.4 μL of a 25 wt % solution of triethylaluminum in toluene (1.54 mg AlEt$_3$, 0.0769 wt %, 0.0857 mol %) and the mixture stirred via an external magnetic stirrer at room temperature for four hours. To the mixture was then added 0.002 mol % (0.35 mg, 0.0177 wt %) of tungsten [(1R)-3,3'-dibromo-2'-[[(1,1-dimethylethyl)dimethylsilyl]oxy]-5,5',6,6',7,7', 8,8'-octahydro [1,1'-binaphthalen]-2-olato-κO][2,6-dichlorobenzenaminato (2-)-κN](2,5-dimethyl-1H-pyrrol-1-yl)[(2-methoxyphenyl) methylene]-, (T-4)-(CAS #1817807-15-0) was added as a solution in benzene. At the time after the additional of catalyst specified in the table below, an aliquot of the reaction mixture was removed from the glovebox and analyzed by GC-MS/FID. The results of the GC-MS/FID analysis of these samples is presented in the table below:

| Time After Catalyst Addition (h) | Approximate Conversion of Oct-7-en-1-yl Acetate to Dodec-7-en-1-yl Acetate (%) | Approximate (Z)-Dodec-7-en-1-yl Acetate Content (%) |
| --- | --- | --- |
| 1 | 47 | 97 |
| 2 | 62 | 97 |
| 4 | 72 | 96 |
| 8 | 80 | 96 |
| 72 | 83 | 96 |

Example 12. Reduction of Methyl Dec-9-enoate to Dec-9-en-1-ol Using Sodium Bis(2-methoxyethoxy) Aluminumhydride In an oven dried, nitrogen-flushed flask sealed with a rubber septum and containing a magnetic stir bar was added 96.0 mL (353 mmol 'AlH$_2$', 1.3 eq.) of a 70% solution of sodium bis(2-methoxyethoxy)aluminumhydride (CAS #22722-98-1) in toluene. The flask is then submerged in an ice bath and stirred via an external magnetic stirrer and 50 g (271 mmol) of methyl dec-9-enoate was slowly added so as to maintain the temperature of the reaction mixture below 15° C. The resulting mixture is stirred at ice-bath temperature for one hour and then brought to ambient temperature and stirred for an additional hour. The reaction mixture was then quenched with 10 mL deionized water and acidified with 15 w/w % aqueous sulfuric acid until the pH of the aqueous layer was 4. The obtained slurry was filtered through diatomaceous earth and the filter cake was rinsed with 2×50 mL of toluene. The two phases of the mother liquor were separated. The aqueous layer was washed with additional 100 mL of toluene. The combined organic phases were washed with 50 mL deionized water. All volatile components were removed by in vacuo and the product dried via azeotropic distillation with additional toluene to yield 42.9 g of a colorless oil. This oil was later determined to contain 96.0 wt % of dec-9-en-ol (97.1% yield) by GC-MS/FID analysis.

Example 13. Acetylation of 9-decen-1-ol

9-Decen-1-ol (50.0 g, 320 mmol), prepared through the method of Example 13, was charged into a three-necked, round-bottomed flask equipped with a thermometer, a reflux condenser and a magnetic stirrer bar. The top of the condenser was connected to a Schlenk line and the whole apparatus was flushed with nitrogen. Acetic anhydride (33 mL, 352 mmol, 1.1 eq.) and anhydrous sodium acetate 2.6 g, 32 mmol) were added to the flask. The mixture was stirred at 68° C. for 4 hours. GC showed complete conversion. 100 mL of DCM was added to the reaction mixture and mixed with water (100 mL). NaHCO$_3$ (25 g) was carefully and portion-wise added to adjust the pH of the aqueous phase to 6. The organic phase was separated and extracted with saturated solution of NaHCO$_3$ (pH~8-9) then with 100 mL of water (pH~7). The separated DCM fraction was dried over Na$_2$SO$_4$ (60 g) and Na$_2$CO$_3$ (6 g) for one night. Organic phase was collected filtered, solid was washed with DCM and hexane. All volatile components were removed on rotary evaporator to yield 63.6 g of a colorless oil. This oil was later determined to contain 95.8 wt % of dec-9-en-ol (95.6% yield).

Example 14. Cross-Metathesis of Dec-9-en-1-yl Acetate with Hex-1-ene

In a nitrogen-filled glovebox, a 20 mL scintillation vial was charged with a magnetic stir bar, 1.404 g of dec-9-en-1-yl acetate prepared through the method of Example 14 and finally 0.5% g of hex-1-ene. The vial was then closed with a perforated septum. The feedstock was treated with 42.7 μL of a 25 wt % solution of triethylaluminum in toluene (0.9 mg AlEt$_3$, 0.444 wt %, 0.541 mol %) and the mixture stirred via an external magnetic stirrer at room temperature for four hours. To the mixture was then added 0.002 mol % (0.32 mg, 0.0159 wt %) of tungsten [(1R)-3,3'-dibromo-2'-[[(1,1-dimethylethyl)dimethylsilyl]oxy]-5,5', 6,6',7,7',8,8'-octahydro[1,1'-binaphthalen]-2-olato-κO][2,6-dichlorobenzenaminato(2-)-κN](2, 5-dimethyl-1H-pyrrol-1-yl)[(2-methoxyphenyl)methylene]-, (T-4)-(CAS #1817807-15-0) as a solution in benzene. At the time after the additional of catalyst specified in the table below, an aliquot of the reaction mixture was removed from the glovebox and analyzed by GC-MS/FID. The GC-MS/FID data indicated that 23.9% of the starting dec-9-en-1-yl acetate was converted to tetradec-9-en-1-yl acetate and in an E/Z ratio of 3/97.

Example 15. Effect of Metathesis Catalyst Loading on the Z-Selective Cross-Metathesis of Methyl Dec-9-enoate and Hex-1-ene In a nitrogen-filled glovebox, five 30 mL scintillation vial wer charged with a magnetic stir bar, 2.70 g of an equimolar mixture of methyl dec-9-enoate and hex-1-ene. The vial was then closed with a perforated septum. The feedstock was treated with 11 μL of a 25 wt % solution of triethylaluminum in toluene (2.3 mg AlEt$_3$, 0.085 wt %, 0.1 mol %) and the mixture stirred via an external magnetic stirrer at room temperature for 18 hours. To the mixture was added the amount of tungsten [(1R)-3,3'-dibromo-2'-[[(1,1-dimethylethyl) dimethylsilyl]oxy]-5,5',6,6',7,7',8,8'-octahydro[1,1'-binaphthalen]-2-olato-κO][2,6-dichlorobenzenaminato(2-)-κN](2,5-dimethyl-1H-pyrrol-1-yl)[(2-methoxyphenyl)methylene]-, (T-4)-(CAS #1817807-15-0) listed in the table below as a solution in benzene. At the time after the addition of catalyst specified in the table below, an aliquot of the reaction mixture was removed from the glovebox and analyzed by GC-MS/FID to determine '9-DAME Conversion (%)' and 'Methyl (Z)-tetradec-9-enoate Selectivity (%)' as described in Example 5.

| Catalyst Loading (mol %) | Time (h) | Methyl Dec-9-enoate Conversion (%) | Methyl (Z)-Tetradec-9-enoate Selectivity (%) |
|---|---|---|---|
| 0.0005 | 1 | 31 | 99 |
|  | 4 | 58 | 98 |
|  | 8 | 59 | 97 |
| 0.001 | 1 | 38 | 98 |
|  | 4 | 76 | 97 |
|  | 8 | 76 | 96 |
| 0.0015 | 1 | 54 | 98 |
|  | 4 | 72 | 95 |
|  | 8 | 75 | 94 |
| 0.002 | 1 | 66 | 98 |
|  | 4 | 82 | 93 |
|  | 8 | 84 | 90 |
| 0.0025 | 1 | 72 | 97 |
|  | 4 | 84 | 91 |
|  | 8 | 88 | 88 |

Example 16. Cross-Metathesis of Oct-7-en-1-yl Acetate with Oct-1-ene

Using the method of Example 1, an equimolar amount of oct-7-en-1-yl acetate and oct-1-ene are charged into a 20 mL glass scintillation vial equipped with a magnetic stir bar inside of a nitrogen-filled glovebox. The mixture is then stirred by means of an external hotplate stirrer and is then treated with an alkyl aluminum reagent to reduce levels of moisture, peroxide and protic impurities as described in U.S. Pat. No. 9,388,097. After sufficient time to ensure the removal of catalyst deactivating impurities to the desired level, the temperature of the substrate mixture is raised to the desired level and a sufficient quantity of a Z-selective group 6 metathesis catalyst to generate the desired level of 'Methyl Dec-9-enoate Conversion (%)', as defined in Example 5, is added to the pretreated substrates. After the required amount of time, the vial is removed from the glovebox and the reaction mixture is analyzed by GC-MS. The GC-MS data indicates that (Z)-tetradec-7-en-1-v 1 acetate is formed in high yield.

Example 17. Cross-Metathesis of Oct-7-en-1-yl Acetate with But-1-ene

Using the method of Example 1, an equimolar amount of oct-7-en-1-yl acetate and but-1-ene are charged into a glass pressure vessel equipped with a magnetic stir bar. The mixture is then stirred by means of an external hotplate stirrer and treated with an alkyl aluminum reagent to reduce levels of moisture, peroxide and protic impurities as described in U.S. Pat. No. 9,388,097. After sufficient time to ensure the removal of catalyst deactivating impurities to the desired level, the temperature of the substrate mixture is raised to the appropriate temperature and a sufficient quantity of a Z-selective group 6 metathesis catalyst to generate the desired level of 'Methyl Dec-9-enoate Conversion (%)', as defined in Example 5, is added to the pretreated substrates. After the required amount of time, the vial is removed from the glovebox and the reaction mixture is analyzed by GC-MS. The GC-MS data indicates that (Z)-dec-7-en-1-yl acetate is formed in high yield.

Example 18. Cross-Metathesis of Dec-9-en-1-yl Acetate with Oct-1-ene

Using the method of Example 1, an equimolar amount of dec-9-en-1-yl acetate and oct-1-ene are charged into a 20 mL glass scintillation vial equipped with a magnetic stir bar inside of a nitrogen-filled glovebox. The mixture is then stirred by means of an external hotplate stirrer and is then treated with an alkyl aluminum reagent to reduce levels of moisture, peroxide and protic impurities as described in U.S. Pat. No. 9,388,097. After sufficient time to ensure the removal of catalyst deactivating impurities to the desired level, the temperature of the substrate mixture is raised to the desired level and a sufficient quantity of a Z-selective group 6 metathesis catalyst to generate the desired level of 'Methyl Dec-9-enoate Conversion (%)', as defined in Example 5, is added to the pretreated substrates. After the required amount of time, the vial is removed from the glovebox and the reaction mixture is analyzed by GC-MS. The GC-MS data indicates that (Z)-hexadec-9-en-1-yl acetate is formed in high yield.

Example 19. Cross-Metathesis of Dec-9-en-1-yl Acetate with But-1-ene

Using the method of Example 1, an equimolar amount of dec-9-en-1-yl acetate and but-1-ene are charged into a glass pressure vessel equipped with a magnetic stir bar. The mixture is then stirred by means of an external hotplate stirrer and treated with an alkyl aluminum reagent to reduce levels of moisture, peroxide and protic impurities as described in U.S. Pat. No. 9,388,097. After sufficient time to ensure the removal of catalyst deactivating impurities to the desired level, the temperature of the substrate mixture is raised to the desired level and a sufficient quantity of a Z-selective group 6 metathesis catalyst to generate the desired level of 'Methyl Dec-9-enoate Conversion (%)', as defined in Example 5, is added to the pretreated substrates. After the required amount of time, the vial is removed from the glovebox and the reaction mixture is analyzed by GC-MS. The GC-MS data indicates that (Z)-dodec-9-en-1-yl acetate is formed in high yield.

V. Exemplary Embodiments

Exemplary embodiments provided in accordance with the presently disclosed subject matter include, but are not limited to, the claims and the following embodiments:

1. A method for synthesizing a fatty olefin derivative, the method comprising:
a) contacting an olefin according to Formula I

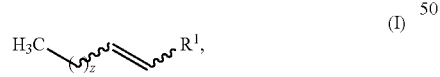
(I)

with a metathesis reaction partner according to Formula IIb

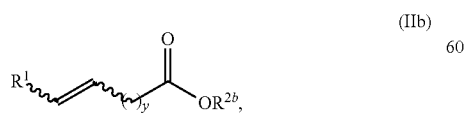
(IIb)

in the presence of a metathesis catalyst under conditions sufficient to form a metathesis product according to Formula IIIb:

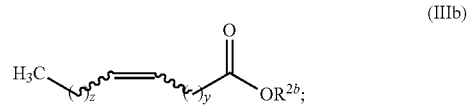
(IIIb)

b) converting the metathesis product to the fatty olefin derivative;
wherein:
each $R^1$ is independently selected from the group consisting of H, $C_{1-18}$ alkyl, and $C_{2-18}$ alkenyl;
$R^{2b}$ is $C_{1-8}$ alkyl;
subscript y is an integer ranging from 0 to 17; and
subscript z is an integer ranging from 0 to 17.
2. The method of embodiment 1, wherein converting the metathesis product to the fatty olefin derivative comprises reducing the metathesis product to form an alkenol according to Formula Vb:

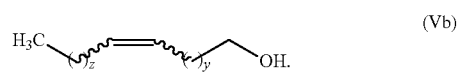
(Vb)

3. The method of embodiment 2, wherein the alkenol is the fatty olefin derivative.
4. The method of embodiment 2, wherein converting the metathesis product to the fatty olefin derivative further comprises acylating the alkenol, thereby forming a fatty olefin derivative according to Formula VIb:

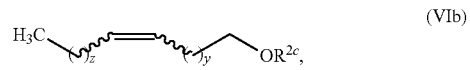
(VIb)

wherein $R^{2c}$ is $C_{1-6}$ acyl.
5. The method of any one of embodiments 1-3, wherein $R^1$ is H, $R^{2b}$ is methyl, subscript y is 7, and subscript z is 3.
6. The method of embodiment 4, wherein $R^1$ is H, $R^{2b}$ is methyl, subscript y is 7, subscript z is 3, and $R^{2c}$ is acetyl.
7. The method of embodiment 2, wherein converting the metathesis product to the fatty olefin derivative further comprises oxidizing the alkenol, thereby forming a fatty olefin derivative according to Formula VIIb:

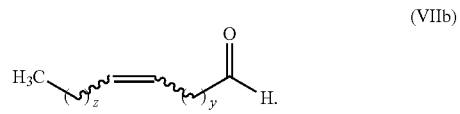
(VIIb)

8. The method of embodiment 1, wherein converting the metathesis product to the fatty olefin derivative further comprises reducing the metathesis product, thereby forming a fatty olefin derivative according to Formula VIIb:

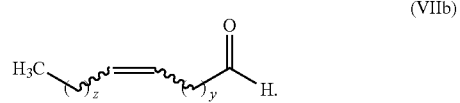
(VIIb)

9. The method of embodiment 7 or embodiment 8, wherein $R^1$ is H, $R^{2b}$ is methyl, subscript y is 7, and subscript z is 3.

10. The method of any one of embodiments 1-9, wherein the olefin has a structure according to Formula Ia:

(Ia)

11. The method of embodiment 10, wherein subscript z is 3.

12. The method of any one of embodiments 1-11, wherein the metathesis product comprises a Z olefin.

13. The method of embodiment 12, wherein at least about 80% of the olefin is a Z olefin.

14. The method of embodiment 12, wherein at least about 90% of the olefin is a Z olefin.

15. The method of any one of embodiments 12-14, wherein the metathesis catalyst is a Z-selective molybdenum catalyst or a Z-selective tungsten catalyst.

16. The method of embodiment 15, wherein the metathesis catalyst has a structure according to Formula 2:

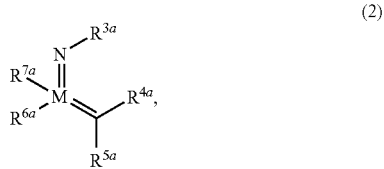

(2)

wherein:

M is Mo or W;

$R^{3a}$ is selected from the group consisting of aryl, heteroaryl, alkyl, heteroalkyl, cycloalkyl, and heterocycloalkyl, each of which is optionally substituted;

$R^{4a}$ and $R^{5a}$ are independently selected from the group consisting of hydrogen, optionally substituted alkyl, optionally substituted alkenyl, optionally substituted heteroalkyl, optionally substituted heteroalkenyl, optionally substituted aryl, and optionally substituted heteroaryl;

$R^{7a}$ is selected from the group consisting of alkyl, alkoxy, heteroalkyl, aryl, aryloxy, heteroaryl, silylalkyl, and silyloxy, each of which is optionally substituted; and $R^{6a}$ is $R^{8a}$—X—, wherein X is O or S and $R^{8a}$ is optionally substituted aryl; or X is O and $R^{8a}$ is $SiR^{9a}R^{10a}R^{11a}$ or $CR^{12a}R^{13a}R^{14a}$, wherein $R^{9a}$, $R^{10a}$, $R^{11a}$, $R^{12a}$, $R^{13a}$, and $R^{14a}$ are independently selected from the group consisting of optionally substituted alkyl and optionally substituted phenyl; or $R^{6a}$ and $R^{7a}$ are linked together and are bonded to M via oxygen.

17. The method of embodiment 16, wherein:

$R^{7a}$ is selected from the group consisting of alkyl, alkoxy, heteroalkyl, aryl, aryloxy, and heteroaryl, each of which is optionally substituted; and X is O or S and $R^{8a}$ is optionally substituted aryl; or X is O and $R^{8a}$ is $CR^{12a}R^{13a}R^{14a}$.

18. The method of embodiment 16, wherein $R^{3a}$ is selected from the group consisting of 2,6-dimethylphenyl; 2,6-diisopropylphenyl; 2,6-dichlorophenyl; and adamant-1-yl;

$R^{4a}$ is selected from the group consisting of —C(CH$_3$)$_2$C$_6$H$_5$ and —C(CH$_3$)$_3$; $R^{5a}$ is H;

$R^{7a}$ is selected from the group consisting of pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenyl-phenoxy; and t-butyloxy; and $R^{6a}$ is $R^{8a}$—X—, wherein X=O and $R^{8a}$ is phenyl which bears two substituents in the ortho positions with respect to O, or which bears at least three substituents, from which two substituents are in the ortho positions with respect to O and one substituent is in the para position with respect to O; or $R^{8a}$ is selected from the group consisting of optionally substituted 8-(naphthalene-1-yl)-naphthalene-1-yl; optionally substituted 8-phenyl naphthalene-1-yl; optionally substituted quinoline-8-yl; triphenylsilyl; triisopropylsilyl; triphenylmethyl; tri(4-methylphenyl)methy 1; 9-phenyl-fluorene-9-yl; 2-phenyl-1,1,1,3,3,3-hexafluoro-prop-2-yl; 2-methyl-1,1,1,3,3,3-hexafluoro-prop-2-yl; and t-butyl.

19. The method of embodiment 18, wherein;

$R^{7a}$ is selected from the group consisting of pyrrol-1-yl; 2,5-dimethyl-pyrrol-1-yl; and $R^{8a}$ is phenyl which bears two substituents in the ortho positions with respect to O, or which bears at least three substituents, from which two substituents are in the ortho positions with respect to O and one substituent is in the para position with respect to O; or $R^{8a}$ is selected from the group consisting of optionally substituted 8-(naphthalene-1-yl)-naphthalene-1-yl and optionally substituted 8-phenlynaphthalene-1-yl.

20. The method of embodiment 16, wherein the metathesis catalyst has a structure according to Formula 2a:

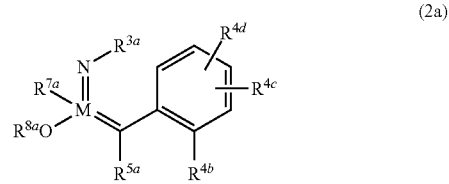

(2a)

wherein:

$R^{3a}$ is aryl, heteroaryl, alkyl, or cycloalkyl, each of which is optionally substituted;

$R^{7a}$ is pyrrolyl, imidazolyl, indolyl, pyrazolyl, azaindolyl, or indazolyl, each of which is optionally substituted;

$R^{8a}$ is optionally substituted aryl;

$R^{5a}$ is a hydrogen atom, alkyl, or alkoxy;

$R^{4b}$ is a hydrogen atom, —O—(C$_{1-6}$ alkyl), —CH$_2$—O—(C$_{1-6}$ alkyl), heteroalkoxy, or —N(C$_{1-6}$ alkyl)$_2$; and $R^{4c}$ and $R^{4d}$ are independently a hydrogen atom, C$_{1-6}$ alkyl, C$_{1-6}$ alkoxy, a halogen atom, —NO$_2$, an amide, or a sulfonamide.

21. The method of embodiment 20, wherein:

$R^{7a}$ is pyrrolyl, imidazolyl, pyrazolyl, azaindolyl, or indazolyl, each of which is optionally substituted; and $R^{5a}$ is a hydrogen atom 22. The method of embodiment 20, wherein $R^{3a}$ is phenyl, 2,6-dichlorophenyl, 2,6-dimethylphenyl, 2,6-diisopropylphenyl, 2-trifluoromethylphenyl, pentafluorophenyl, tert-butyl, or 1-adamantyl.

23. The method of embodiment 20 or embodiment 22, wherein $R^{8a}$ is
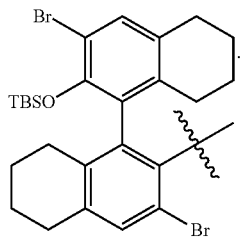 [SMILES: *c1c(Br)cc2c(c1-c1c3c(cc(Br)c1O[Si](C)(C)C(C)(C)C)CCCC3)CCCC2]
24. The method of any one of embodiments 20-23, wherein $R^{4a}$ is methoxy, $R^{4c}$ is hydrogen, and $R^{4a}$ is hydrogen.
25. The method of embodiment 15, wherein the metathesis catalyst is selected from the group consisting of
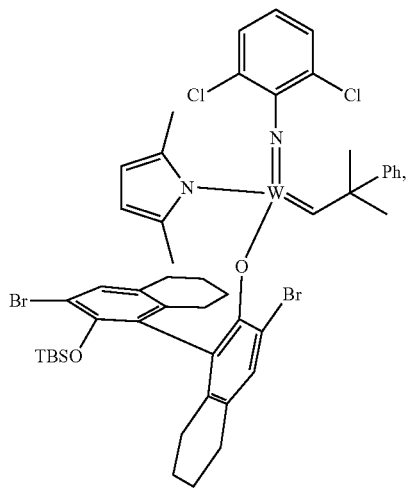
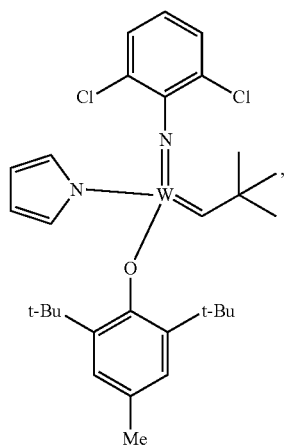
-continued
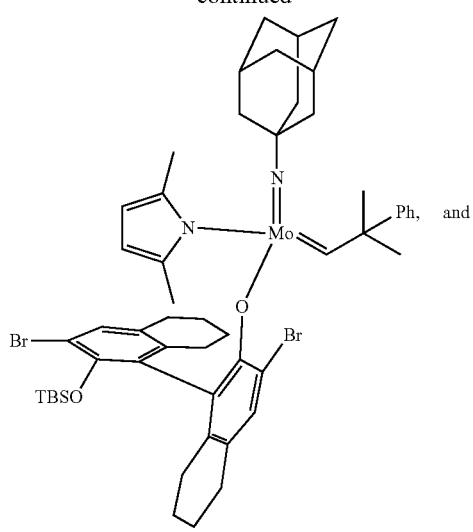
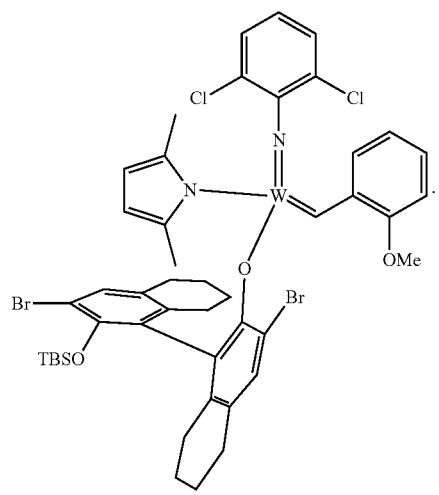
26. The method of embodiment 25, wherein the metathesis catalyst is
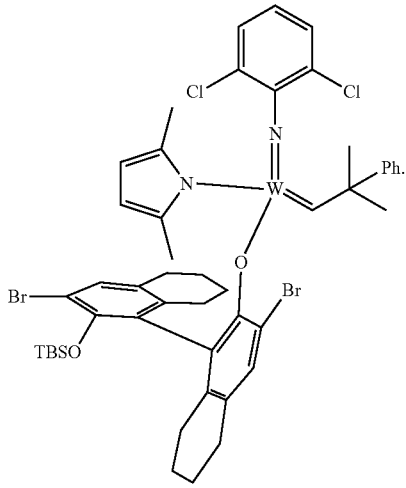

27. The method of embodiment 25, wherein the metathesis catalyst is

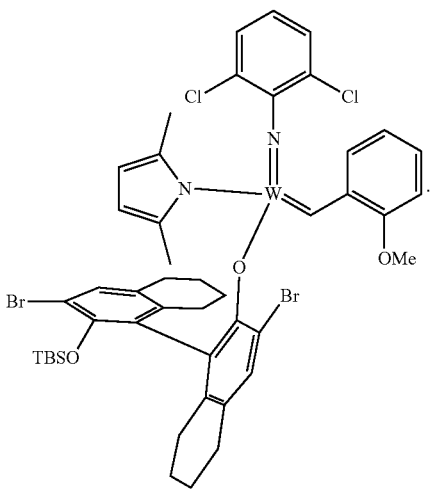

28. The method of any one of embodiments 15-27, wherein the catalyst is present in an amount less than 0.01 mol % with respect to the olefin or to the metathesis reaction partner.
29. The method of any one of embodiments 1-10, wherein the metathesis product comprises an E olefin.
30. The method of embodiment 29, wherein greater than about 85% of the olefin is an E olefin.
31. The method of embodiment 29, wherein at least about 90% of the olefin is an E olefin.
32. The method of any one of embodiments 29-31, wherein the metathesis catalyst is an E-selective ruthenium catalyst.
33. The method of any one of embodiments 1-32, wherein the molar ratio of the olefin to the metathesis reaction partner ranges from about 1:1 to about 5:1.
34. The method of any one of embodiments 33, wherein the molar ratio of the olefin to the metathesis reaction partner ranges from about 2:1 to about 3:1
35. The method of any one of embodiments 1-34, wherein the metathesis reaction partner is derived from a natural oil.
36. The method of embodiment 35, wherein the natural oil is selected from the group consisting of canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, jojoba oil, mustard oil, pennycress oil, camelina oil, castor oil, and combinations thereof.
37. The method of embodiment 35 or 36, wherein the metathesis reaction partner comprises one or more catalyst-poisoning contaminants.
38. The method of embodiment 37, further comprising treating the metathesis reaction partner with a metal alkyl compound under conditions sufficient to reduce the concentration of at least one of the catalyst-poisoning contaminants, wherein the treating is conducted prior to contacting the olefin with the metathesis reaction partner.
39. The method of embodiment 1, wherein
the olefin according to Formula I is a linear $C_3$-$C_{12}$ alpha olefin,
the metathesis reaction partner according to Formula IIb is a $\Delta^9$-unsaturated fatty acid alkyl ester,
the metathesis catalyst is a Z-selective metathesis catalyst, and the metathesis product according to Formula IIIb is a $C_{11}$-$C_{20}$ (Z)-9-unsaturated fatty acid alkyl ester.
40. The method of embodiment 39, wherein converting the metathesis product to the fatty olefin derivative comprises contacting the $C_{11}$-$C_{20}$ (Z)-9-unsaturated fatty acid alkyl ester with a reducing agent under conditions sufficient to form a $C_{11}$-$C_{20}$ (Z)-9-fatty alcohol.
41. The method of embodiment 40, wherein the reducing agent is sodium bis(2-methoxyethoxy)aluminum hydride.
42. The method of embodiment 40, wherein converting the metathesis product to the fatty olefin derivative further comprises contacting the $C_{11}$-$C_{20}$ (Z)-9-fatty alcohol with an acylating agent in the presence of a base under conditions sufficient to form an acetate ester of the $C_{11}$-$C_{20}$ (Z)-9-fatty alcohol.
43. The method of embodiment 42, wherein the acylating agent is acetic anhydride.
44. The method of embodiment 40, wherein converting the metathesis product to the fatty olefin derivative further comprises oxidizing the $C_{11}$-$C_{20}$ (Z)-9-fatty alcohol to form a $C_{11}$-$C_{20}$ (Z)-9-alkenal.
45. The method of embodiment 39, wherein converting the metathesis product to the fatty olefin derivative comprises contacting the $C_{11}$-$C_{20}$ (Z)-9-fatty acid alkyl ester with a reducing agent under conditions sufficient to form a $C_{11}$-$C_{20}$ (Z)-9-alkenal.
46. The method of embodiment 45, wherein the reducing agent is amine-modified sodium bis(2-methoxyethoxy) aluminumhydride.
47. The method of embodiment 1, wherein:
the fatty acid derivative is (Z)-tetradec-9-en-1-yl acetate;
the olefin according to Formula I is hex-1-ene,
the metathesis reaction partner according to Formula IIb is a $\Delta^9$-unsaturated fatty acid alkyl ester,
the metathesis catalyst is a Z-selective metathesis catalyst, and
the metathesis product according to Formula IIIb is an alkyl ester of (Z)-9-tetradec-9-enoate; and
wherein converting the metathesis product to the fatty olefin derivative comprises:
contacting the alkyl ester of (Z)-9-tetradec-9-enoate with a reducing agent under conditions sufficient to form (Z)-tetradec-9-en-1-ol, and
acylating the (Z)-tetradec-9-en-1-ol to form the (Z)-tetradec-9-en-1-yl acetate.
48. The method of embodiment 47, wherein the metathesis reaction partner according to Formula IIb is methyl 9-decenoate and the metathesis product is methyl (Z)-tetradec-9-enoate.
49. The method of embodiment 47, wherein the reducing agent is sodium bis(2-methoxy ethoxy)aluminumhydride.
50. The method of embodiment 47, wherein acylating the (Z)-tetradec-9-en-1-ol comprises contacting the (Z)-tetradec-9-en-1-ol with an acylating agent in the presence of a base under conditions sufficient to form (Z)-tetradec-9-en-1-yl acetate.
51. The method of embodiment 50, wherein the acylating agent is acetic anhydride.
52. The method of any one of embodiments 47-51, wherein the metathesis reaction partner according to Formula IIb is methyl 9-decenoate and the metathesis product is methyl (Z)-tetradec-9-enoate.

53. The method of embodiment 1, wherein:
the fatty acid derivative is (Z)-tetradec-9-enal,
the olefin according to Formula I is hex-1-ene,
the metathesis reaction partner according to Formula IIb is a $\Delta^9$-unsaturated fatty acid alkyl ester,
the metathesis catalyst is a Z-selective metathesis catalyst, and
the metathesis product according to Formula IIIb is an alkyl ester of (Z)-9-tetradec-9-enoate; and
wherein converting the metathesis product to the fatty olefin derivative comprises contacting the alkyl ester of (Z)-9-tetradec-9-enoate with a reducing agent under conditions sufficient to form the (Z)-tetradec-9-enal.

54. The method of embodiment 53, wherein the reducing agent is amine-modified sodium bis(2-methoxyethoxy)aluminumhydride.

55. The method of embodiment 53 or embodiment 54, wherein the $\Delta^9$-unsaturated fatty acid alkyl ester according to Formula IIg is methyl 9-decenoate and the metathesis product is methyl (Z)-tetradec-9-enoate.

56. The method of embodiment 1, wherein:
the fatty acid derivative is (Z)-tetradec-9-enal,
the olefin according to Formula I is hex-1-ene,
the metathesis reaction partner according to Formula IIb is a $\Delta^9$-unsaturated fatty acid alkyl ester,
the metathesis catalyst is a Z-selective metathesis catalyst, and
the metathesis product according to Formula IIIb is an alkyl ester of (Z)-9-tetradec-9-enoate; and
wherein converting the metathesis product to the fatty olefin derivative comprises
contacting the alkyl ester of (Z)-9-tetradec-9-enoate with a reducing agent under conditions sufficient to form (Z)-tetradec-9-en-1-ol, and
oxidizing the (Z)-tetradec-9-en-1-ol to form the (Z)-tetradec-9-enal.

57. The method of embodiment 56, wherein the reducing agent is sodium bis(2-methoxyethoxy)aluminumhydride.

58. The method of embodiment 56 or embodiment 57, wherein the $\Delta^9$-unsaturated fatty acid alkyl ester according to Formula IIg is methyl 9-decenoate and the metathesis product is methyl (Z)-tetradec-9-enoate.

59. The method of any one of embodiments 39-58, wherein the metathesis catalyst has a structure according to Formula 2a:

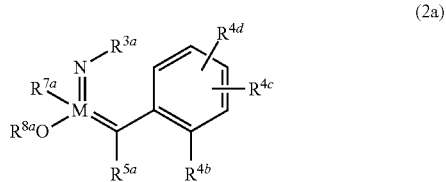

wherein:
M is Mo or W;
$R^{3a}$ is aryl, heteroaryl, alkyl, or cycloalkyl, each of which is optionally substituted;
$R^{7a}$ is pyrrolyl, imidazolyl, indolyl, pyrazolyl, azaindolyl, or indazolyl, each of which is optionally substituted;
$R^{8a}$ is optionally substituted aryl;
$R^{5a}$ is a hydrogen atom, alkyl, or alkoxy;

$R^{4b}$ is a hydrogen atom, —O—($C_{1-6}$ alkyl), —$CH_2$—O—($C_{1-6}$ alkyl), heteroalkoxy, or —N($C_{1-6}$ alkyl)$_2$; and $R^{4c}$ and $R^{4d}$ are independently a hydrogen atom, $C_{1-6}$ alkyl, $C_{1-6}$ alkoxy, a halogen atom, —$NO_2$, an amide, or a sulfonamide.

60. The method of embodiment 59, wherein the metathesis catalyst is selected from the group consisting of:

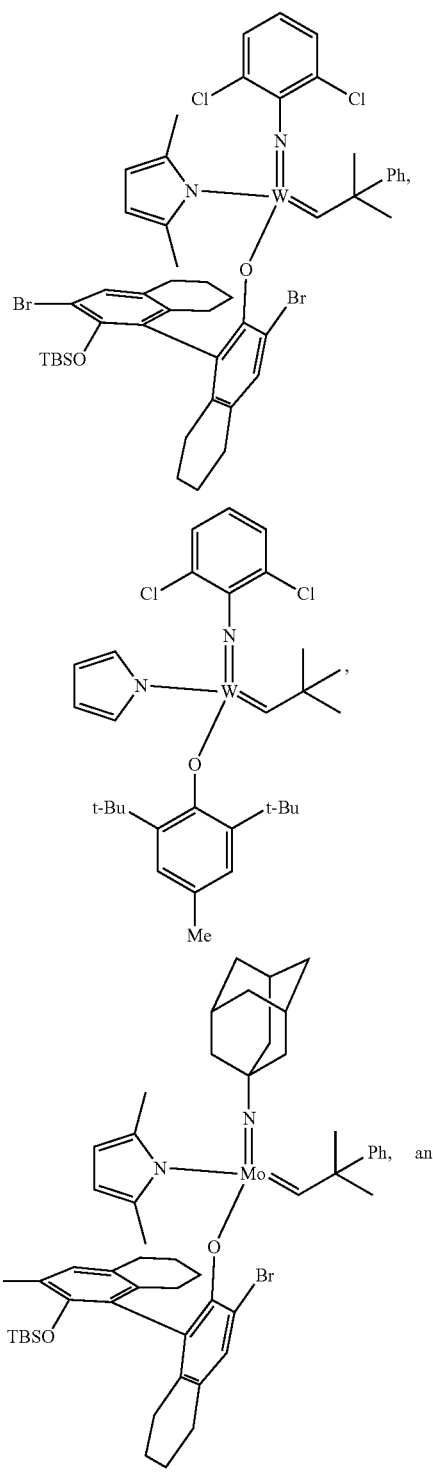

-continued

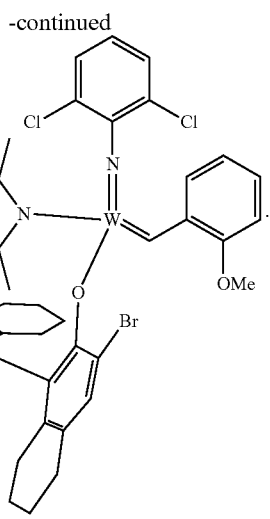

61. A fatty olefin derivative synthesized according to the method of any one of embodiments 1-60.
62. The fatty olefin derivative of embodiment 61, which is an insect pheromone.
63. A method for synthesizing a fatty olefin derivative according to Formula VIb:

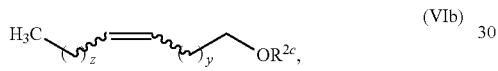

the method comprising:
i) reducing an alkyl ester according to Formula IIb

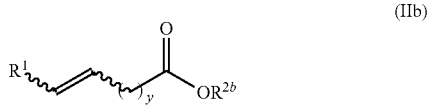

to form an alkenol according to Formula VIII

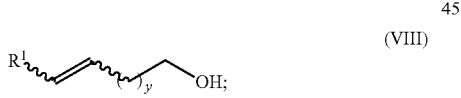

ii) acylating the alkenol to form an acylated alkenol according to Formula IX

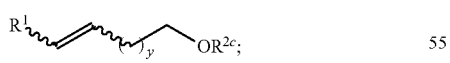

iii) contacting the acylated alkenol with an olefin according to Formula I

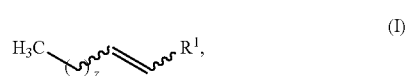

in the presence of a metathesis catalyst under conditions sufficient to form the fatty olefin derivative; wherein:

$R^1$ is selected from the group consisting of H, $C_{1-18}$ alkyl, and $C_{2-18}$ alkenyl;
$R^{2b}$ is $C_{1-8}$ alkyl,
$R^{2c}$ is $C_{1-6}$ acyl,
subscript y is an integer ranging from 0 to 17;
subscript z is an integer ranging from 0 to 17; and
the metathesis catalyst is a tungsten catalyst or a molybdenum catalyst.
64. The method of embodiment 63, wherein $R^1$ is H, $R^{21a}$ is methyl, $R^{2c}$ is acetyl, subscript y is 7, and subscript z is 3.
65. The method of embodiment 63 or embodiment 64, wherein the metathesis product comprises an E olefin.
66. The method of embodiment 63 or embodiment 64, wherein the metathesis product comprises a Z olefin.
67. The method of embodiment 66, wherein the metathesis catalyst is a Z-selective molybdenum catalyst or a Z-selective tungsten catalyst.
68. The method of embodiment 67, wherein the metathesis catalyst has a structure according to Formula 2:

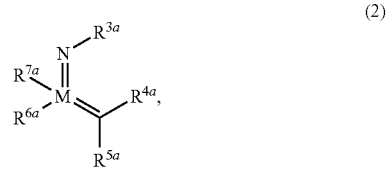

wherein:
M is Mo or W;
$R^{3a}$ is selected from the group consisting of aryl, heteroaryl, alkyl, heteroalkyl, cycloalkyl, and heterocycloalkyl, each of which is optionally substituted;
$R^{4a}$ and $R^{5a}$ are independently selected from the group consisting of hydrogen, optionally substituted alkyl, optionally substituted alkenyl, optionally substituted heteroalkyl, optionally substituted heteroalkenyl, optionally substituted aryl, and optionally substituted heteroaryl;
$R^{7a}$ is selected from the group consisting of alkyl, alkoxy, heteroalkyl, aryl, aryloxy, heteroaryl, silylalkyl, and silyloxy, each of which is optionally substituted; and
$R^{6a}$ is $R^{8a}$—X—, wherein
X is O or S and $R^{8a}$ is optionally substituted aryl; or
X is O and $R^{8a}$ is $SiR^{9a}R^{10a}R^{11a}$ or $CR^{12a}R^{13a}R^{14a}$, wherein $R^{9a}$, $R^{10a}$, $R^{11a}$, $R^{12a}$, $R^{13a}$, and $R^{14a}$ are independently selected from the group consisting of optionally substituted alkyl and optionally substituted phenyl; or
$R^{6a}$ and $R^{7a}$ are linked together and are bonded to M via oxygen.
69. The method of embodiment 68, wherein the metathesis catalyst has a structure according to Formula 2a:

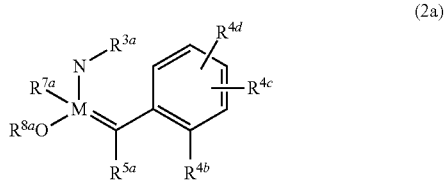

wherein:

$R^{3a}$ is aryl, heteroaryl, alkyl, or cycloalkyl, each of which is optionally substituted;

$R^{7a}$ is pyrrolyl, imidazolyl, indolyl, pyrazolyl, azaindolyl, or indazolyl, each of which is optionally substituted;

$R^{8a}$ is optionally substituted aryl;

$R^{5a}$ is a hydrogen atom, alkyl, or alkoxy;

$R^{4b}$ is a hydrogen atom, —O—($C_{1-6}$ alkyl), —$CH_2$—O—($C_{1-6}$alkyl), heteroalkoxy, or —N($C_{1-6}$ alkyl)$_2$; and $R^{4c}$ and $R^{4d}$ are independently a hydrogen atom, $C_{1-6}$ alkyl, $C_{1-6}$ alkoxy, a halogen atom, —$NO_2$, an amide, or a sulfonamide.

70. The method of embodiment 68 or embodiment 69, wherein the metathesis catalyst is selected from the group consisting of:

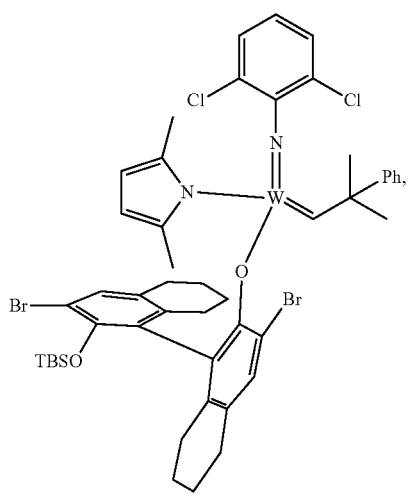

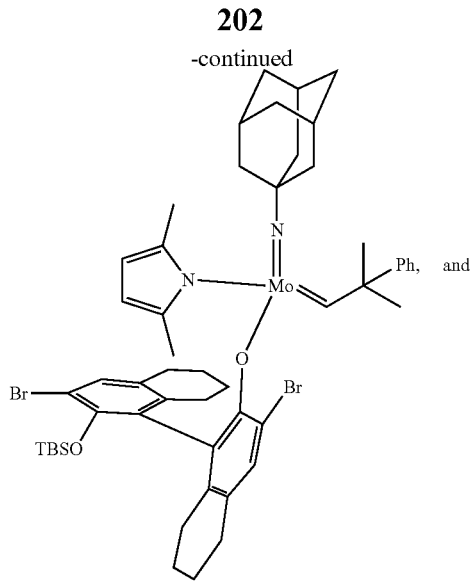

-continued

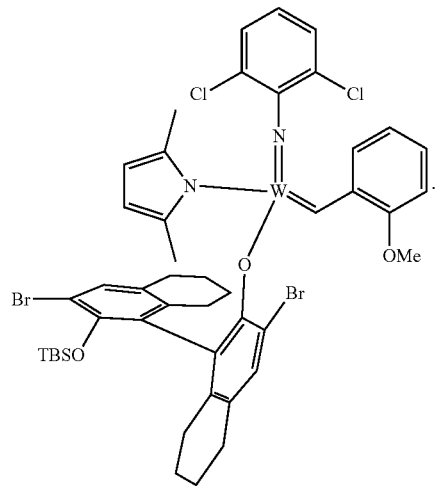

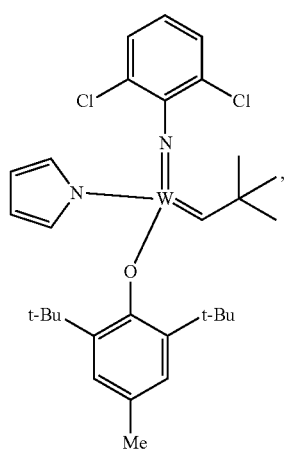

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

What is claimed is:

1. A method for synthesizing a fatty olefin derivative, the method comprising:

a) contacting an olefin according to Formula I

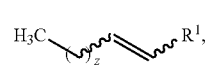 (I)

wherein $R^1$ is $C_{1-18}$ alkyl, and subscript z is an integer ranging from 0 to 17, with a metathesis reaction partner according to Formula IIb

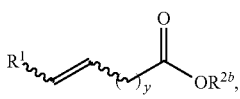

(IIb)

wherein
R$^1$ is selected from the group consisting of H, C$_{1-18}$ alkyl, and C$_{2-18}$ alkenyl,
R$^{2b}$ is C$_{1-8}$ alkyl, and
subscript y is an integer ranging from 0 to 17,
in the presence of a Z-selective metathesis catalyst to form a metathesis product according to Formula IIIc:

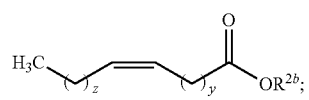

(IIIc)

and
b) converting the metathesis product to the fatty olefin derivative;
wherein the fatty olefin derivative is selected from the group consisting of an unsaturated fatty alcohol, an unsaturated fatty alcohol acetate, an unsaturated fatty aldehyde, and an unsaturated fatty acid ester; and
wherein:
  (i) the Z-selective metathesis catalyst has a structure according to Formula 2:

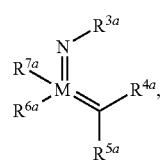

(2)

wherein:
M is Mo or W;
R$^{3a}$ is selected from the group consisting of aryl, heteroaryl, alkyl, heteroalkyl, cycloalkyl, and heterocycloalkyl, each of which is optionally substituted;
R$^{4a}$ and R$^{5a}$ are independently selected from the group consisting of hydrogen, optionally substituted alkyl, optionally substituted alkenyl, optionally substituted heteroalkyl, optionally substituted heteroalkenyl, optionally substituted aryl, and optionally substituted heteroaryl;
R$^{7a}$ is selected from the group consisting of alkyl, alkoxy, heteroalkyl, aryl, aryloxy, heteroaryl, silylalkyl, and silyloxy, each of which is optionally substituted; and
R$^{6a}$ is R$^{8a}$—X—, wherein
X is O or S and lea is optionally substituted aryl; or
X is O and R$^{8a}$ is SiR$^{9a}$R$^{10a}$R$^{11a}$ or CR$^{12a}$R$^{13a}$R$^{14a}$, wherein R$^{9a}$, R$^{10a}$, R$^{11a}$, R$^{12a}$, R$^{13a}$, and R$^{14a}$ are independently selected from the group consisting of optionally substituted alkyl and optionally substituted phenyl; or
R$^{6a}$ and R$^{7a}$ are linked together and are bonded to M via oxygen; or
  (ii) the Z-selective metathesis catalyst is selected from the group consisting of

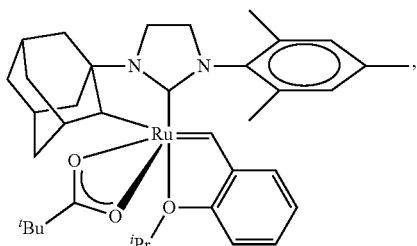

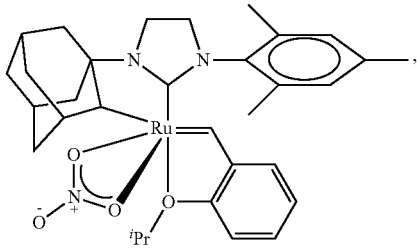

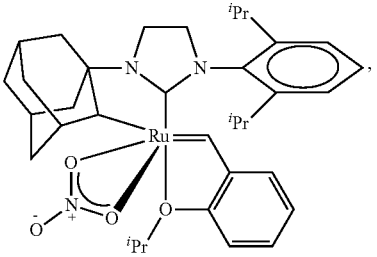

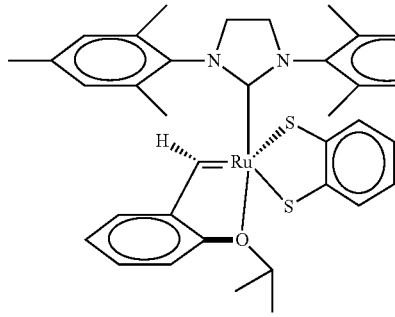

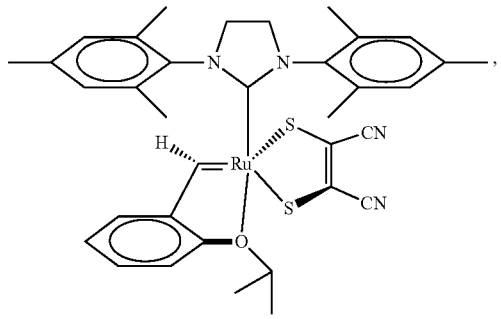

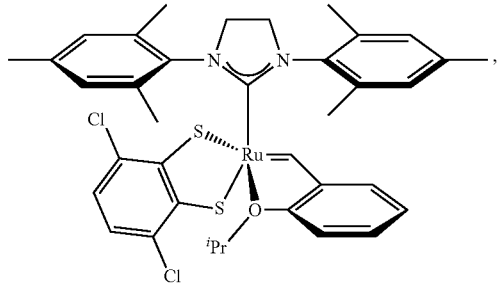

-continued

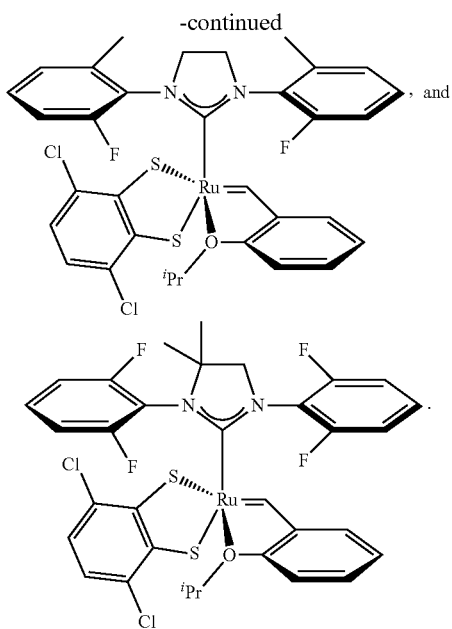
, and

2. The method of claim 1, wherein converting the metathesis product to the fatty olefin derivative comprises reducing the metathesis product to form an unsaturated fatty alcohol according to Formula Vc:

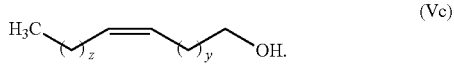
(Vc)

3. The method of claim 2, wherein the unsaturated fatty alcohol is the fatty olefin derivative.

4. The method of claim 3, wherein $R^{2b}$ is methyl, subscript y is 7, and subscript z is 3.

5. The method of claim 2, wherein converting the metathesis product to the fatty olefin derivative further comprises acylating the unsaturated fatty alcohol, thereby forming an unsaturated fatty alcohol acetate according to Formula VIc:

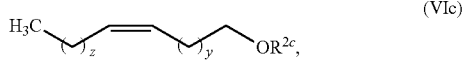
(VIc)

wherein $R^{2c}$ is $C_{1-6}$ acyl, and
wherein the unsaturated fatty alcohol acetate is the fatty olefin derivative.

6. The method of claim 5, wherein $R^{2b}$ is methyl, subscript y is 7, subscript z is 3, and $R^{2c}$ is acetyl.

7. The method of claim 2, wherein converting the metathesis product to the fatty olefin derivative further comprises oxidizing the unsaturated fatty alcohol, thereby forming an unsaturated fatty aldehyde according to Formula VIIc:

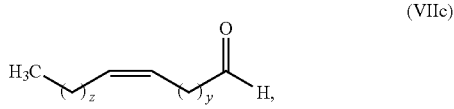
(VIIc)

wherein the unsaturated fatty aldehyde is the fatty olefin derivative.

8. The method of claim 1, wherein converting the metathesis product to the fatty olefin derivative further comprises reducing the metathesis product, thereby forming a fatty olefin derivative according to Formula VIIc:

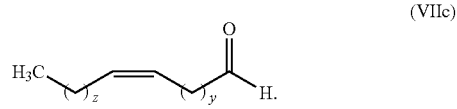
(VIIc)

9. The method of claim 8, wherein $R^1$ is H, $R^{2b}$ is methyl, subscript y is 7, and subscript z is 3.

10. The method of claim 1, wherein:
   $R^{7a}$ is selected from the group consisting of alkyl, alkoxy, heteroalkyl, aryl, aryloxy, and heteroaryl, each of which is optionally substituted; and
   X is O or S and $R^{8a}$ is optionally substituted aryl; or
   X is O and $R^{8a}$ is $CR^{12a}R^{13a}R^{14a}$.

11. The method of claim 1, wherein
   $R^{3a}$ is selected from the group consisting of 2,6-dimethylphenyl; 2,6-diisopropylphenyl; 2,6-dichlorophenyl; and adamant-1-yl;
   $R^{4a}$ is selected from the group consisting of —C(CH$_3$)$_2$C$_6$H$_5$ and —C(CH$_3$)$_3$;
   $R^{5a}$ is H;
   $R^{7a}$ is selected from the group consisting of pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenyl-phenoxy; and t-butyloxy; and
   $R^{6a}$ is $R^{8a}$—X—, wherein
   X=O and
   $R^{8a}$ is phenyl which bears two substituents in the ortho positions with respect to O, or which bears at least three substituents, from which two substituents are in the ortho positions with respect to O and one substituent is in the para position with respect to O; or
   $R^{8a}$ is selected from the group consisting of optionally substituted 8-(naphthalene-1-yl)-naphthalene-1-yl; optionally substituted 8-phenlynaphthalene-1-yl; optionally substituted quinoline-8-yl; triphenylsilyl; triisopropylsilyl; triphenylmethyl; tri(4-methylphenyl)methyl; 9-phenyl-fluorene-9-yl; 2-phenyl-1,1,1,3,3,3-hexafluoro-prop-2-yl; 2-methyl-1,1,1,3,3,3-hexafluoro-prop-2-yl; and t-butyl.

12. The method of claim 11, wherein:
   $R^{7a}$ is selected from the group consisting of pyrrol-1-yl; 2,5-dimethyl-pyrrol-1-yl; and
   $R^{8a}$ is phenyl which bears two substituents in the ortho positions with respect to O, or which bears at least three substituents, from which two substituents are in the ortho positions with respect to O and one substituent is in the para position with respect to O; or
   $R^{8a}$ is selected from the group consisting of optionally substituted 8-(naphthalene-1-yl)-naphthalene-1-yl and optionally substituted 8-phenlynaphthalene-1-yl.

13. The method of claim 1, wherein the Z-selective metathesis catalyst according to Formula 2 has a structure according to Formula 2a:

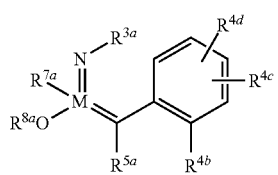
(2a)

wherein:

$R^{3a}$ is aryl, heteroaryl, alkyl, or cycloalkyl, each of which is optionally substituted;

$R^{7a}$ is pyrrolyl, imidazolyl, indolyl, pyrazolyl, azaindolyl, or indazolyl, each of which is optionally substituted;

$R^{8a}$ is optionally substituted aryl;

$R^{5a}$ is a hydrogen atom, alkyl, or alkoxy;

$R^{4b}$ is a hydrogen atom, —O—($C_{1-6}$ alkyl), —CH$_2$—O—($C_{1-6}$ alkyl), heteroalkoxy, or —N($C_{1-6}$ alkyl)$_2$; and $R^{4c}$ and $R^{4d}$ are independently a hydrogen atom, $C_{1-6}$ alkyl, $C_{1-6}$ alkoxy, a halogen atom, —NO$_2$, an amide, or a sulfonamide.

14. The method of claim 13, wherein:

$R^{7a}$ is pyrrolyl, imidazolyl, pyrazolyl, azaindolyl, or indazolyl, each of which is optionally substituted; and $R^{5a}$ is a hydrogen atom.

15. The method of claim 13, wherein $R^{3a}$ is phenyl, 2,6-dichlorophenyl, 2,6-dimethylphenyl, 2,6-diisopropylphenyl, 2-trifluoromethylphenyl, pentafluorophenyl, tert-butyl, or 1-adamantyl.

16. The method of claim 15, wherein $R^{8a}$ is

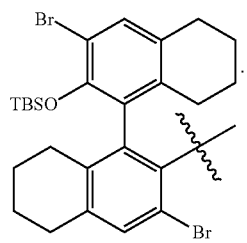 [SMILES: *c1c(Br)cc2c(c1-c1c3c(cc(Br)c1O[Si](C)(C)C(C)(C)C)CCCC3)CCCC2]

17. The method of claim 16, wherein $R^{4b}$ is methoxy, $R^{4c}$ is hydrogen, and $R^{4d}$ is hydrogen.

18. The method of claim 1, wherein the Z-selective metathesis catalyst according to Formula 2 is selected from the group consisting of

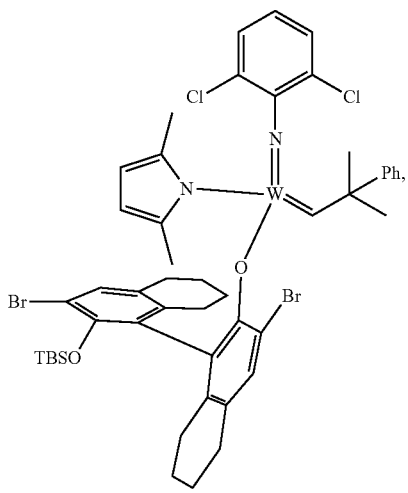

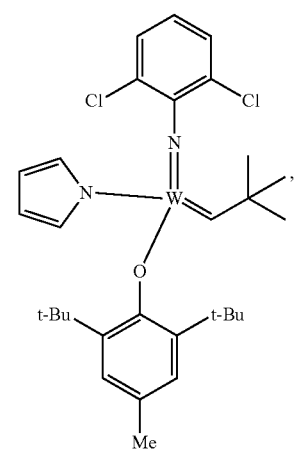

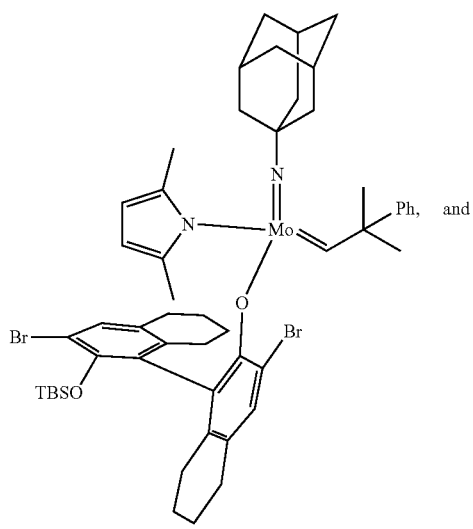

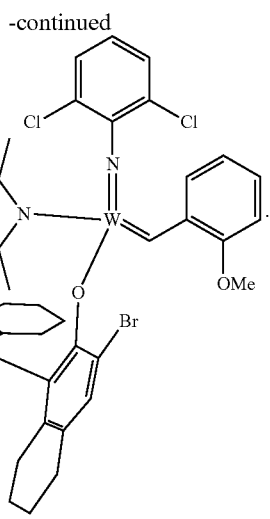

19. The method of claim 1, wherein the catalyst is present in an amount less than 0.01 mol % with respect to the olefin or to the metathesis reaction partner.

20. The method of claim 1, wherein $R^1$ is H, $R^{2b}$ is methyl, subscript y is 7, and subscript z is 5.

21. The method of claim 1, wherein the fatty olefin derivative is a $C_{11}$-$C_{20}$ (Z)-9-fatty alcohol.

22. The method of claim 5, wherein the unsaturated fatty alcohol acetate is an acetate ester of the $C_{11}$-$C_{20}$ (Z)-9-fatty alcohol.

23. The method of claim 7, wherein the unsaturated fatty aldehyde is an $C_{11}$-$C_{20}$ (Z)-9-alkenal.

24. The method of claim 1, wherein the olefin according to Formula I is a linear $C_3$-$C_{12}$ olefin and the alkyl ester according to Formula IIb is a $\Delta^9$-unsaturated fatty acid alkyl ester.

25. The method of claim 1, wherein the fatty olefin derivative is selected from the group consisting of (Z)-11-hexadecen-1-ol; (Z)-11-tetradecen-1-ol; and (Z)-13-octadecen-1-ol.

26. The method of claim 5, wherein the unsaturated fatty alcohol acetate is selected from the group consisting of (Z)-10-dodecenyl acetate; (Z)-10-hexadecenyl acetate; (Z)-10-pentadecenal; (Z)-10-pentadecenyl acetate; (Z)-10-tetradecenyl acetate; (Z)-10-tridecenyl acetate; (Z)-7-decenyl acetate; (Z)-7-dodecenyl acetate; (Z)-7-hexadecenyl acetate; (Z)-7-tetradecenyl acetate; (Z)-7-undecenyl acetate; (Z)-9-dodecenyl acetate; (Z)-9-hexadecenyl acetate; (Z)-9-pentadecenyl acetate; (Z)-9-tetradecenyl acetate; (Z)-9-tridecenyl acetate; (Z)-9-undecenyl acetate; (Z)-11-hexadecenyl acetate; and (Z)-11-tetradecenyl acetate.

27. The method of claim 7, wherein the unsaturated fatty aldehyde is selected from the group consisting of (E)-7-dodecenal; (Z)-9-hexadecenal; (Z)-7-hexadecenal; (Z)-9-tetradecenal; (Z)-7-tetradecenal; (Z)-9-dodecenal; (Z)-11-hexadecenal; and (Z)-13-octadecenal.

28. The method of claim 1, wherein the fatty olefin derivative is an insect pheromone.

\* \* \* \* \*